(12) United States Patent
Johnstone et al.

(10) Patent No.: US 7,745,475 B2
(45) Date of Patent: Jun. 29, 2010

(54) HETEROARYL BENZAMIDE DERIVATIVES AS GLK ACTIVATORS

(75) Inventors: Craig Johnstone, Macclesfield (GB); Darren McKerrecher, Macclesfield (GB); Kurt Gordon Pike, Macclesfield (GB); Michael James Waring, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 303 days.

(21) Appl. No.: 11/628,448

(22) PCT Filed: Jun. 1, 2005

(86) PCT No.: PCT/GB2005/002166

§ 371 (c)(1),
(2), (4) Date: Dec. 4, 2006

(87) PCT Pub. No.: WO2005/121110

PCT Pub. Date: Dec. 12, 2005

(65) Prior Publication Data

US 2008/0015203 A1    Jan. 17, 2008

(30) Foreign Application Priority Data

Jun. 5, 2004 (GB) .................. 0412602.5
Oct. 16, 2004 (GB) .................. 0423041.3
Feb. 12, 2005 (GB) .................. 0502961.6

(51) Int. Cl.
*A01N 43/56* (2006.01)
*C07D 233/00* (2006.01)

(52) U.S. Cl. .................. 514/403; 548/335.1; 548/300.1; 514/183; 514/359

(58) Field of Classification Search .......... None
See application file for complete search history.

(56) References Cited

U.S. PATENT DOCUMENTS

| | | |
|---|---|---|
| 2,750,393 A | 6/1956 | Elpern |
| 2,967,194 A | 1/1961 | Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,255,335 B1 | 7/2001 | Himmler et al. |

(Continued)

FOREIGN PATENT DOCUMENTS

CA    2605738    11/2006

(Continued)

OTHER PUBLICATIONS

Brenner et al. "Imino-bridged heterocycles. VII. (1) N-aminobenzocycloheptapyridinimines" J. Heterocyclic Chem. 23:1331-1332 (1986).

(Continued)

*Primary Examiner*—James D Anderson
*Assistant Examiner*—Meghan Finn
(74) *Attorney, Agent, or Firm*—Morgan, Lewis & Bockius LLP

(57) ABSTRACT

Compounds of Formula (I) wherein: $R^1$ is hydroxymethyl; $R^2$ is selected from $-C(O)NR^4R^5$, $SO_2NR^4R^5$, $S(O)_pR^4$ and HET-2; HET-1 is a 5- or 6-membered, optionally substituted C-linked heteroaryl ring; HET-2 is a 4-, 5- or 6-membered, C- or N-linked optionally substituted heterocyclyl ring; $R^3$ is selected from halo, fluoromethyl, difluoromethyl, trifluoromethyl, methyl, methoxy and cyano; $R^4$ is selected from for example hydrogen, optionally substituted (1-4C)alkyl and HET-2; $R^5$ is hydrogen or (1-4C)alkyl; or $R^4$ and $R^5$ together with the nitrogen atom to which they are attached may form a heterocyclyl ring system as defined by HET-3; HET-3 is for example an optionally substituted N-linked, 4, 5 or 6 membered, saturated or partially unsaturated heterocyclyl ring; p is (independently at each occurrence) 0, 1 or 2; m is 0 or 1; n is 0, 1 or 2; provided that when m is 0, then n is 1 or 2; or a salt, pro drug or solvate thereof, are described. Their use as GLK activators, pharmaceutical compositions containing them, and processes for their preparation are also described.

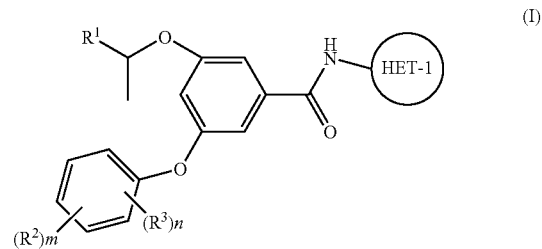

3 Claims, No Drawings

U.S. PATENT DOCUMENTS

| | | |
|---|---|---|
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 7,390,908 B2 | 6/2008 | Boyd et al. |
| 7,524,957 B2 | 4/2009 | Boyd et al. |
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |
| 2003/0228982 A1 | 12/2003 | Helmke et al. |
| 2004/0014968 A1 | 1/2004 | Bizzarro et al. |
| 2004/0077555 A1 | 4/2004 | Ishihara et al. |
| 2004/0214868 A1 | 10/2004 | Hayter et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0058353 A1 | 3/2006 | Mckerrecher et al. |
| 2006/0167053 A1 | 7/2006 | Iino et al. |
| 2006/0258728 A1 | 11/2006 | Tani et al. |
| 2007/0093535 A1 | 4/2007 | Hayter et al. |
| 2007/0112040 A1 | 5/2007 | Hayter et al. |
| 2007/0255062 A1 | 11/2007 | Johnstone et al. |
| 2007/0287693 A1 | 12/2007 | Johnstone et al. |
| 2008/0057074 A1 | 3/2008 | Takaoka et al. |
| 2008/0153800 A1 | 6/2008 | McCabe et al. |
| 2008/0171734 A1 | 7/2008 | Campbell et al. |
| 2008/0200694 A1 | 8/2008 | Cornwall et al. |
| 2008/0234273 A1 | 9/2008 | McKerrecher et al. |
| 2008/0280872 A1 | 11/2008 | Johnstone et al. |
| 2008/0280874 A1 | 11/2008 | Johnstone et al. |
| 2008/0300412 A1 | 12/2008 | Hopes et al. |
| 2008/0312207 A1 | 12/2008 | Johnstone et al. |
| 2008/0318968 A1 | 12/2008 | Martin et al. |
| 2009/0018157 A1 | 1/2009 | Johnstone et al. |
| 2009/0029905 A1 | 1/2009 | McKerrecher et al. |
| 2009/0062351 A1 | 3/2009 | Caulkett et al. |
| 2009/0105214 A1 | 4/2009 | McKerrecher et al. |
| 2009/0105263 A1 | 4/2009 | Caulkett et al. |
| 2009/0111790 A1 | 4/2009 | Mckerrecher et al. |
| 2009/0118159 A1 | 5/2009 | McKerrecher et al. |
| 2009/0227592 A1 | 9/2009 | Boyd et al. |
| 2009/0253676 A1 | 10/2009 | Johnstone et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1790637 | 5/2005 |
| EP | 1541563 | 6/2005 |
| EP | 1600442 | 11/2005 |
| EP | 1604981 | 12/2005 |
| EP | 1702919 | 9/2006 |
| EP | 1995246 | 11/2008 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 11/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |

| | | |
|---|---|---|
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/79145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 94/04525 | 3/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/105637 | 9/2007 |
| WO | WO 2008/050101 | 5/2008 |
| WO | WO 2008/050117 | 5/2008 |
| WO | WO 2008/075073 | 6/2008 |

OTHER PUBLICATIONS

Coghlan et al. "Glucokinase activators in diabetes management" Expert Opin. Investig. Drugs 17(2):145-167 (2008).
Leighton, "Pre-clinical disease models—challenges and success stories"44th Drug Information Association Annual Meeting, Boston, MA, US (2008).
Lith, "Evaluation of the effects on whole body glucose metabolism after single doses of X2000—A glucose lowering agent" Poster presentation, Master thesis in Pharmaceutical Bioscience, Goteborgs University (2008).
Ralph et al. "Glucose Modulation of Glucokinase Activation by Small Molecules" Biochemistry 47(17):5028-5036 (2008).
Robertson et al. "Structure-activity relationships of arylimidazopyridine cardiotonics: discovery and inotropic activity of 2-[2-methoxy-4-(methylsulfinyl)pheny;]-1H-imidazo[4,5-c]pyridine" Journal of Medicinal Chemistry 28:717-727 (1985).
Sarabu et al., "Glucokinase activators as new type 2 diabetes therapeutic agents" Expert Opinion on Therapeutic Patents 18(7):759-768 (2008).
Shorvon, "Pyrrolidone derivatives" Lancet 358(9296):1885-1892 (2001).
Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.
West, Anthony R., "Solid State Chemistry and its Applications" Wiley, New York, pp. 358 and 365 (1988).
Wolff, Manfred E. "Burger's Medicinal Chemistry", 5th Edition, Part I, John Wiley & Sons, pp. 975-977 (1995).
Alvarez et al. "Evidence that glucokinase regulatory protein is expressed and interacts with glucokinase in rat brain" J. Neurochem. 80(1):45-53 (2002).
Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the Pyrido[2,3-d]pyrimidine series" J. Org. Chem. 42(6):993-996 (1977).

Ando et al. "Fluoride salts on alumina as reagents for alkylation of phenols and alcohols" Bull. Chem. Soc. Jpn., 55:2504-2507 (1982).
Atwell, G. J. et al. "Potential antitumor agents. VI. Bisquaternary salts" J. Med. Chem. 11(2):295-300 (1968).
Baker, R. et al. "Structure and synthesis of Pallescansin E utilizing a modified Wadsworth-Emmons reaction" J. Chem. Soc., Perkin Trans. 1, 12, pp. 3087-3091 (1981).
Baker, R. et al. "Synthesis of Pallescensin-E: use of crown ether in the Wadsworth procedure for olefin formation" Tetrahedron Lett. 22, pp. 161-162 (1981).
Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry No. 6511458 (Apr. 18, 1994), [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42:3514-3518 (1977).
Berl et al. "Induced fit selection of a barbiturate receptor from a dynamic structural and conformational/configurational library" European J. Org. Chem. (11):3089-3094 (1999).
Berl et al. "Template-induced and molecular recognition directed hierarchical generation of supramolecular assemblies from molecular strands" Chem. Eur. J., 6(11): 1938-1946 (2000).
Bonina, F. et al. "Synthesis and pharmacologic activity of 2-arylethenylthiazol-4-acetic and 4-carboxylic acids" Farmaco, 40(11), p. 875-884 (1985).
Boucherle et al. "Recherches dans la serie des cetones polyphenoliques IV. Thiazoles" Chimica. Therapeutica., 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brocklehurst et al. "Stimulation of Hepatocyte Glucose Metabolism by Novel Small Molecule Glucokinase Activators" Diabetes 53:535-541 (2004).
Caro et al. "Liver glucokinase: decreased activity in patients with type II diabetes" Horm. Metab. Res., 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem., 44(17): 2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica, 13(6): 539-543 (1978) (Translation enclosed).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2001).
Chemical Abstracts Service, Columbus, Ohio, US: CAS Registry No. 354767-66-1 (Sep. 5, 2001).

Christesen et al. "The second activating glucokinase mutation (A456V): Implications for glucose homeostasis and diabetes therapy" Diabetes, 51(4):1240-1246 (2002).
Ciaceri et al. "Analgesic, antipyretic and anti-inflammatory action of some new acids of the phenylethylenethiazole series" Minerva Medica 63(42):2409-2413 (1972).
Coburn et al. "Mesoionic purinone analogs. IV. Synthesis and in vitro antibacterial properties of mesoionic thiazolo(3,2-a)pyrimidin-5,7-diones and mesoionic 1,3,4-thiadizolo(3,2-a)pyrimidin-5,7-diones" J. Pharm. Sciences. 62(11):1785-1789 (1973).
Coghlan "Small molecule Glucokinase Activators (GKAs) as novel anti-diabetic agents" CIDEM seminar (May 2005).
Coghlan "Small molecule Glucokinase Activators (GKAs) as novel anti-diabetic agents" Society for Medicines Research Seminar (Jun. 2004).
Coope et al. "Predictive blood glucose lowering efficacy by Glucokinase activators in high fat fed female Zucker rats", Br. J. Pharmacol., 149(3):328-335 (2006).
Corbett "Glucokinase activators: Discovery of novel, orally active glucose lowering agents" *Abstract*, Cambridge Healthtech Institute's Eleventh Annual Molecular Medicine Tri-Conference, Moscone West Convention Center, San Francisco, CA (Mar. 24-26, 2004).
Corbett "Glucokinase activators: Discovery of novel, orally active glucose lowering agents" *Presentation Slides*, Cambridge Healthtech Institute's Eleventh Annual Molecular Medicine Tri-Conference, Moscone West Convention Center, San Francisco, CA (Mar. 24-26, 2004).
Cushman et al. "Synthesis and evaluation of new protein-tyrosine kinase inhibitors. Part 1. pyridine-containing stilbenes and amides" Bioorganic & Medicinal Chemistry Letters, 1(4):211-214 (1991).
DeFronzo et al. "The triumvirate: β-cell, muscle, liver. A collusion responsible for NIDDM" Diabetes 37:667-687 (1988).
DeJohn, et al., "Functionalization of Substituted 2(1H)- and 4(1H)-Pyridones. III. The Preparation of Substituted 6-Vinyl-1,2-dihydro-2-oxo-- and 1,4-Dihydro-4-oxo-3-pyridinecarboxylic Acids through the Chemistry of Pyridone Dianions", J. Heterocyclic Chem., 20(5), p. 1295-1302 (1983).
De Paulis, T. et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem., 25: 507-517 (1990).
Desai et al. "Phenotypic correction of diabetic mice by adenovirus-mediated glucokinase expression" Diabetes 50:2287-2295 (2001).
Edmont et al. "Synthesis and evaluation of quinoline carboxyguanidines as antidiabetic agents" Bioorg. Med. Chem. Lett. 10(16):1831-1834 (2000).
Elpern et al. "Iodinated Benzamidotetrazoles" J. Org. Chem., 22: 1686 (1957).
Ferre et al. "Correction of diabetic alterations by glucokinase" PNAS USA. 93(14): 7225-7230 (1996).
Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem., 29(4):538-549 (1986).
Froguel et al. "Familial hyperglycemia due to mutations in glucokinase—Definition of a subtype of diabetes mellitus" New Engl. J. Med., 328:697-702 (1993).
Fujimoto et al. "Administration of D-glucosamine into the third cerebroventricle induced feeding accompanied by hyperglycemia in rats" Life Sciences 37(26):2475-2482 (1985).
Gill et al. "Stimulation of insulin release by a small molecule glucokinase activator" EASD Islet Study Group Abstract (Nov. 2005).
Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).
Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine, 338(4):226-230 (1998).

Gorman et al. "Effect of high-fat diet on glucose homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: potential role in diabetes therapy" Science 301(5631):370-373 (2003).

Guertin et al. "Small Molecule Glucokinase Activators as Glucose Lowering Agents: A New Paradigm for Diabetes Therapy" Current Medicinal Chemistry, 13(15): 1839-1843 (2006).

Hashimoto, Y. et al. "Evaluation of differentiation-inducing activity of retinoids on human leukemia cell lines HL-60 and NB4", Biol. Pharm. Bull., 19(10): 1322-1328 (1996).

Hirst, S. et al. "Molecular recognition of phosphate esters: a balance of hydrogen bonding and proton transfer interactions" Israel Journal of Chemistry, 32: 105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. Synthesis of a 2,3,4,4a,5,6-hexahydrobenzo[f]quinoline system by "aryne substitution" Bull Chem Soc France, vol. 11, 4463-4467 (1968) (Translation enclosed).

Kamata, T. et al. "Pyroelectricity of noncentrosymmetric Langmuir-Blodgett films of phenylpyrazine derivatives" Jpn. J. Appl. Phys., 33(2), p. 1074-1078 (1994).

Kar A. "Cinchophen analogues as potential CNS agents" J Pharm Sci., 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of Heptanedioic Acid to a Threefold Pyridine Arylamide Receptor. Enhancement of the Stability of Supramolecular Solution Structures by Multiple Binding Sites" J. Org. Chem., 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron, 55:13159-13170 (1999).

Kurata et al. "D-Glucose suppression of eating after intra-third ventricle infusion in rat" Physiology & Behavior, 37:615-620 (1986).

Kurata et al. "Structural evaluation of glucose analogues on feeding elicitation in rat" Metabolism, 38(1):46-51 (1989).

Lai et al. "Formation of columnar arrangements in copper(ii) complexes of 2-phenylazomethinopyridine derivatives" J. Materials Chemistry, 8(11):2379-2383 (1998).

Leighton et al. "Small molecule glucokinase activators as novel antidiabetic agents" Biochem Soc Trans., 33(Pt 2):371-374 (Apr. 2005).

Leighton et al. "Improved Glycemic Control After Sub-acute Administration of A Glucokinase Activator To Male Zucker (fa/fa) Rats" abstract of the oral presentation, American Diabetes Association, Jun. 2007.

Levin et al. "Brain glucose sensing and body energy homeostasis: role in obesity and diabetes" Am. J. Physiol., 276(5 Pt 2):R1223-R1231 (1999).

Levin et al. "Differential effects of diet and obesity on high and low affinity sulfonylurea binding sites in the rat brain" Brain Research, 739(1-2):293-300 (1996).

Levin et al. "In vivo and in vitro regulation of [3H]glyburide binding to brain sulfonylurea receptors in obesity-prone and resistant rats by glucose" Brain Research, 776(1-2):146-153 (1997).

Levin et al. "Reduced glucose-induced neuronal activation in the hypothalamus of diet-induced obese rats" Brain Research, 808(2):317-319 (1998).

Levin, B. E. "Glucosensing neurons do more than just sense glucose" International Journal of Obesity, 25, suppl 5: S68-S72 (2001).

Levkoev et al. "Research on cyanide dyes 11. 7,7'-Dimethylthiacarbocyanines" Zhurnal Obshchei Khimii, 27:3097-3107 (1957) (Translation enclosed).

Lynch et al. "Localization of glucokinase gene expression in the rat brain" Diabetes, 49(5):693-700 (2000).

Mastafanova et al. "Features of the catalytic reduction of 4-(3-oxoquinuclidyl-2-methylene)-6-methoxyquinoline and its ethyleneketal" Kim Geterotsiki Soedin., (1):86-94 (1989) (Translation enclosed).

Mastafanova et al., "Synthesis, Anti-Inflammatory and Analgesic Activity of 1,6-Disubstituted Pipecolic and 6-Substituted Picolinic Acids," Khim Farm ZH, 22(4) 428-431 (1988).

Mastafanova, et al. "Synthesis and study of the antihypertensive activity of substituted N-acetylmercaptopropionyl-6-[2'-phenylethyl]pipecolinic acids" Khim Farm ZH., 22(3), p. 294-302 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie (International ed. in English), 39(3):551-554 (2000).

McKerrecher "Design and synthesis of novel glucokinase activators" 13th RSC-SCI Medicinal Chemistry Symposium, Churchill College Cambridge (Sep. 2005).

McKerrecher et al. "Design and synthesis of novel glucokinase activators as potential treatment for type 2 diabetes" Frontiers in Medicinal Chemistry, Frankfurt (Mar. 2006).

McKerrecher et al. "Design of a potent, soluble glucokinase activator with excellent in vivo efficacy" Bioorg. Med. Chem. Left., 16(10):2705-2709 (May 15, 2006) Epub Feb 28, 2006.

McKerrecher et al. "Discovery, synthesis and biological evaluation of novel glucokinase activators" Bioorg Med Chem Lett., 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

McKerrecher et al. "Design & Synthesis of Novel Glucokinase Activators as Potential Treatments for Type 2 Diabetes" 233rd ACS National Meeting, Chicago, IL, Mar. 25-29, 2007.

Meijer et al "Chiral amplification in supramolecular stacks" Polymer Preprints (Am Chem Soc, divn Polymer chemistry) 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab., 281(4):E649-E654 (2001).

Moore et al. "Acute fructose administration improves oral glucose tolerance in adults with type 2 diabetes" Diabetes Care, 24(11):1882-1887 (2001).

Motesharei et al. "Molecular Recognition in Membrane Mimics: A Fluorescence Probe" J. Am. Chem. Soc., 116(16):7413-7414 (1994).

Motesharei et al. "Molecular Recognition on Functionalized Self-Assembled Monolayers of Alkanethiols on Gold" J. Am. Chem. Soc., 120(29): 7328-7336 (1998).

Palmans "Extended-core discotic liquid crystals based on the intramolecular H-bonding in N-acylated 2,2'-bipyridine-3,3'-diamine moieties" Chemistry, 3(2):300-307 (1997).

Plieninger et al. "Synthesis of 7,8-dihydro-5,6-benzoquinoline-(3)-carboxylic acid" Chem. Ber., 87:882-887 (1954) (Translation enclosed).

Printz et al. "Mammalian glucokinase" Annu. Rev. Nutr., 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by Streptomyces purpurogenisclerotics and Nocardia vaccinii" J. Antibiot (Tokyo), 52(3):245-255 (1999).

Rivalle, C. et al. "Furannes et pyrroles disubstitues en 2,3-XVIII : Synthese et rearrangement de 4H-dihydro-9,10 benzo[4,5]cyclohepta[1,2-b]furannones-4" Tetrahedron, 32(7), p. 829-834 (1976).

Rogers et al. "Mesoionic purinone analogues as inhibitors of cyclic-AMP phosphodiesterase: a comparison of several ring systems" J. Med. Chem., 24(11):1284-1287 (1981).

Roncero et al. "Functional glucokinase isoforms are expressed in rat brain" J. Neurochem., 74(5):1848-1857 (2000).

Rowe et al. "Potassium channel dysfunction in hypothalamic glucose-receptive neurones of obese Zucker rats" Journal of Physiology, 497.2:365-377 (1996).

Schuit et al. "Glucose sensing in pancreatic β-Cells. A model for the study of other glucose-regulated cells in gut, pancreas, and hypothalamus" Diabetes, 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem., 274(45):31833-31838 (1999).

Shiota et al. "Glucokinase gene locus transgenic mice are resistant to the development of obesity-induced type 2 diabetes" Diabetes, 50(3):622-629 (2001).

Spanswick et al. "Insulin activates ATP-sensitive K+ channels in hypothalamic neurons of lean, but not obese rats" Nature Neuroscience, 3(8):757-758 (2000).

Spanswick et al. "Leptin inhibits hypothalamic neurons by activation of ATP-sensitive potassium channels" Nature, 390(6659):521-525 (1997).

Stout et al. "Synthesis and antiarrhythmic and parasympatholytic properties of substituted phenols. 3. Modifications to the linkage region (region 3)" J. Med. Chem., 28(3):295-298 (1985).

Suhua et al. "Synthesis and biological activity of tyrosine protein kinase inhibitors" Acta Pharmaceutica Sinica, 32(7):515-523 (1997).

Tecilla, P. et al. "Hydrogen-bonding self-assembly of multichromophore structures" J. Am. Chem. Soc., 112: 9408-9411 (1990).

Tecilla, P. et al. "Transition-state stabilization and molecular recognition: acceleration of phosphoryl-transfer reactions by an artificial receptor" J. Am. Chem. Soc., 112: 9586-9590 (1990).

Tecilla et al. "Synthetic hydrogen bonding receptors as models of transacylase enzymes" Tetrahedron, 51(2):435-448 (1995).

Tornetta et al. "Arylvinylthiazole derivatives with anti-inflammatory, analgesic and anti-pyretic activity" Boll Sedute Accad Giovenia Sci. Nat. Catanica, 11(9-10):89-95 (1973) (Translation enclosed).

Tucker, H. et al. "Novel Inhibitors of prolyl 4-hydroxylase. 2. 5-amide substituted pyridine-2-carboxylic acids" J. Med. Chem., 35, p. 804-807 (1992).

Van Gorp et al. "C3-symmetrical supramolecular architectures: fibers and organic gels from discotic trisamides and trisureas" J Am. Chem. Soc., 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest..,98(8):1755-1761 (1996).

Vertigan et al. "Impact of cell glycogen content on modulation of hepatocyte glucose metabolism by pharmacological agents" Diabetologia, 47 Supp 1, A214, 589 (2004).

Williams et al. "Meeting the Needs of Type 2 Diabetes Patients" Highlights from the society for medicines research symposium type 2 diabetes: mechanisms and emerging therapeutic targets, held Jun. 17, 2004, in London, United Kingdom, Drug News and Perspectives, 17(8) (Oct. 1-4, 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007).

Winzell et al. "Glucokinase Activation Reduces Glycemia and Improves Glucose Tolerance in Mice with High-fat Diet-induced Insulin Resistance", Diabetes, vol. 56 (Supplement 1) 1482-P (2007).

Yakushijin, K. et al. "Intramolecular ring formation of phenyl azide and furan" Heterocycles, 12(8), pp. 1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes, 48(9):1763-1772 (1999).

Yoshina, S. et al. "Studies of heterocyclic compounds. II. Synthesis of 2-furylvinyl-benzenes and studies of polarography" Yakugaku Zasshi, 88(4), p. 398-404 (1968).

Yoshina, S. et al. "Studies of heterocyclic compounds. III. Synthesis of methyl 5-(2-phenylvinyl)2-furoate" Yakugaku Zasshi, 88(4), p. 405-409 (1968).

Yoshina, S. et al. "Studies of heterocyclic compounds. IV. Ultraviolet spectra of 2-(2-furyl)vinylbenzenes and 2-(2- furyl)vinylfurans" Yakugaku Zasshi, 88(4), p. 410-416 (1968).

Yoshina, S. et al. "Studies of heterocyclic compounds. VI. 2-(Carbomethoxy-2-furyl)vinyl benzenes and their ultraviolet spectra" Yakugaku Zasshi, 88(4), p. 977-983 (1968).

Youssefyeh et al. "Development of high-affinity 5-HT3 receptor antagonists. 1. Initial structure-activity relationship of novel benzamides" J. Med. Chem., 35(5): 895-903 (1992).

Zhang et al. "Synthesis based on affinity separation (SAS): separation of products having barbituric acid tag from untagged compounds by using hydrogen bond interaction" Synlett, 5:590-596 (2001).

Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984), Only Abstract Provided and Considered.

HETEROARYL BENZAMIDE DERIVATIVES AS GLK ACTIVATORS

The present invention relates to a group of benzoyl amino heterocyclyl compounds which are useful in the treatment or prevention of a disease or medical condition mediated through glucokinase (GLK or GK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising said compounds and to methods of treatment of diseases mediated by GLK using said compounds.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Maturity-Onset Diabetes of the Young Type 2 (MODY-2), the diabetes is caused by GLK loss of function mutations [3,4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 6a, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is dominant in the post-absorptive state whereas F1P predominates in the post-prandial state. In contrast to the hepatocyte, the pancreatic β-cell expresses GLK in the absence of GLKRP. Therefore, β-cell GLK activity is regulated extensively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act selectively in the liver. However, compounds with either profile are predicted to be of therapeutic benefit in treating Type 2 diabetes as this disease is characterised by defective glucose utilisation in both tissues.

GLK, GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively (32, 33, 34). Therefore, small molecule activators of GLK may have additional beneficial effects on insulin secretion, b-cell function and survival and body weight as a consequence of stimulating GIP and GLP-1 secretion from these entero-endocrine cells.

In WO00/58293 and WO01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described hereinafter. Compounds of the present invention may activate GLK directly or may activate GLK by inhibiting the interaction of GLKRP with GLK.

Further GLK activators have been described in WO03/095438 (substituted phenylacetamides, Roche), WO03/055482 (carboxamide and sulphonamide derivatives, Novo Nordisk), WO2004/002481 (arylcarbonyl derivatives, Novo Nordisk), and in WO03/080585 (amino-substituted benzoylaminoheterocycles, Banyu).

Our International application Number: WO03/000267 describes a group of benzoyl amino pyridyl carboxylic acids which are activators of the enzyme glucokinase (GLK).

Our International application Number: WO03/015774 describes compounds of the Formula (A):

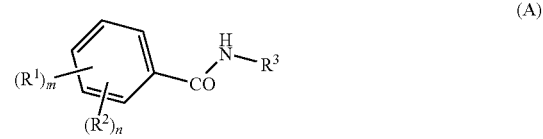

(A)

wherein $R^3$ is a substituted heterocycle other than a carboxylic acid substituted pyridyl.

International application WO2004/076420 (Banyu) describes compounds which are generally a subset of those described in WO03/015774, wherein for example R¹ is an (substituted) alkyl ether and R² is (substituted) phenoxy.

We have surprisingly found a small group of compounds, generally a selected subgroup of those described in WO 03/015774, which have generally superior potency for the GLK enzyme, and more advantageous physical properties, including, for example, higher aqueous solubility, higher permeability, and/or lower plasma protein binding. Consequently, such compounds having a balance of these properties would be expected to display higher plasma free drug levels and superior in vivo efficacy after oral dosing as determined, for example, by activity in Oral Glucose Tolerance Tests (OGTTs). Therefore this group of compounds would be expected to provide superior oral exposure at a lower dose and thereby be particularly suitable for use in the treatment or prevention of a disease or medical condition mediated through GLK.

Thus, according to the first aspect of the invention there is provided a compound of Formula (I):

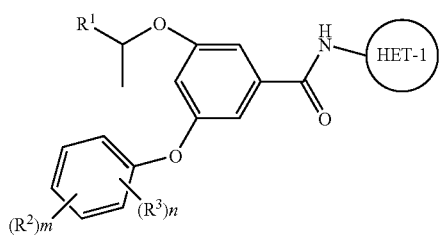

wherein:

R¹ is hydroxymethyl;

R² is selected from —C(O)NR⁴R⁵, —SO₂NR⁴R⁵, —S(O)$_p$R⁴ and HET-2;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from R⁶;

HET-2 is a 4-, 5- or 6-membered, C- or N-linked heterocyclyl ring containing 1, 2, 3 or 4 heteroatoms independently selected from O, N and S, wherein a —CH₂— group can optionally be replaced by a —C(O)—, and wherein a sulphur atom in the heterocyclic ring may optionally be oxidised to a S(O) or S(O)₂ group, which ring is optionally substituted on an available carbon or nitrogen atom by 1 or 2 substituents independently selected from R⁷;

R³ is selected from halo, fluoromethyl, difluoromethyl, trifluoromethyl, methyl, methoxy and cyano;

R⁴ is selected from hydrogen, (1-4C)alkyl [optionally substituted by 1 or 2 substituents independently selected from HET-2, —OR⁵, —SO₂R⁵, (3-6C)cycloalkyl (optionally substituted with 1 group selected from R⁷) and —C(O)NR⁵R⁵], (3-6C)cycloalkyl (optionally substituted with 1 group selected from R⁷) and HET-2;

R⁵ is hydrogen or (1-4C)alkyl;

or R⁴ and R⁵ together with the nitrogen atom to which they are attached may form a heterocyclyl ring system as defined by HET-3;

R⁶ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

R⁷ is selected from —OR⁵, (1-4C)alkyl, —C(O)(1-4C)alkyl, —C(O)NR⁴R⁵, (1-4C)alkoxy(1-4C)alkyl, hydroxy(1-4C)alkyl and —S(O)$_p$R⁵;

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —CH₂— group can optionally be replaced by a —C(O)— and wherein a sulphur atom in the ring may optionally be oxidised to a S(O) or S(O)₂ group; which ring is optionally substituted on an available carbon or nitrogen atom by 1 or 2 substituents independently selected from R⁸; or HET-3 is an N-linked, 7 membered, saturated or partially unsaturated heterocyclyl ring, optionally containing 1 further heteroatom (in addition to the linking N atom) independently selected from O, S and N, wherein a —CH₂— group can optionally be replaced by a —C(O)— group and wherein a sulphur atom in the ring may optionally be oxidised to a S(O) or S(O)₂ group; which ring is optionally substituted on an available carbon or nitrogen atom by 1 or 2 substituents independently selected from R⁸; or HET-3 is an 6-10 membered bicyclic saturated or partially unsaturated heterocyclyl ring, optionally containing 1 further nitrogen atom (in addition to the linking N atom), wherein a —CH₂— group can optionally be replaced by a —C(O)—; which ring is optionally substituted on an available carbon or nitrogen atom by 1 substituent selected from hydroxy and R³;

R⁸ is selected from —OR⁵, (1-4C)alkyl, —C(O)(1-4C)alkyl, —C(O)NR⁴R⁵, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_p$R⁵;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when in is 0, then n is 1 or 2;

or a salt, pro-drug or solvate thereof.

In a further aspect of the invention there is provided a compound of formula (I), or a salt, pro-drug or solvate thereof as hereinbefore defined, with the proviso that compounds exemplified in WO2004/076420, which would otherwise fall within the scope of this invention, are excluded.

In a further aspect of the invention there is provided a compound of formula (I), or a salt, pro-drug or solvate thereof as hereinbefore, defined, wherein:

R¹ is hydroxymethyl;

R² is selected from —C(O)NR⁴R⁵, —SO₂NR⁴R⁵, —S(O)$_p$R⁴ and HET-2;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;

HET-2 is a 4-, 5- or 6-membered, C- or N-linked heterocyclyl ring containing 1, 2, 3 or 4 heteroatoms independently selected from O, N and S, wherein a —$CH_2$— group can optionally be replaced by a —C(O)—, and wherein a sulphur atom in the heterocyclic ring may optionally be oxidised to a S(O) or $S(O)_2$ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from hydrogen, (1-4C)alkyl [optionally substituted by 1 or 2 substituents independently selected from HET-2, —$OR^5$, —$SO_2R^5$, (3-6C)cycloalkyl (optionally substituted with 1 group selected from $R^7$) and —C(O)$NR^5R^5$] and HET-2;

$R^5$ is hydrogen or (1-4C)alkyl;

or $R^4$ and $R^5$ together with the nitrogen atom to which they are attached may form a heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —$OR^5$, (1-4C)alkyl, —C(O)(1-4C)alkyl, —C(O)$NR^4R^5$, (1-4C)alkoxy(1-4C)alkyl, hydroxy(1-4C)alkyl and —S(O)$_pR^5$, HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —$CH_2$— group can optionally be replaced by a —C(O)— and wherein a sulphur atom in the ring may optionally be oxidised to a S(O) or $S(O)_2$ group; which ring is optionally substituted on an available carbon or nitrogen atom by 1 or 2 substituents independently selected from $R^8$; or HET-3 is an N-linked, 7 membered, saturated or partially unsaturated heterocyclyl ring, optionally containing 1 further heteroatom (in addition to the linking N atom) independently selected from O, S and N, wherein a —$CH_2$— group can optionally be replaced by a —C(O)— group and wherein a sulphur atom in the ring may optionally be oxidised to a S(O) or $S(O)_2$ group; which ring is optionally substituted on an available carbon or nitrogen atom by 1 or 2 substituents independently selected from $R^8$; or HET-3 is an 6-10 membered bicyclic saturated or partially unsaturated heterocyclyl ring, optionally containing 1 further nitrogen atom (in addition to the linking N atom), wherein a —$CH_2$— group can optionally be replaced by a —C(O)—; which ring is optionally substituted on an available carbon or nitrogen atom by 1 substituent selected from $R^3$;

$R^8$ is selected from —$OR^5$, (1-4C)alkyl, —C(O)(1-4C)alkyl, —C(O)$NR^4R^5$, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_pR^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In another aspect of the invention, there is provided a compound of the formula (I) as hereinbefore defined, wherein $R^1$ is hydroxymethyl;

$R^2$ is selected from —C(O)—HET-3 and —$SO_2$—HET-3;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;

HET-2 is a 4-, 5- or 6-membered, C- or N-linked heterocyclyl ring containing 1, 2, 3 or 4 heteroatoms independently selected from O, N and S, wherein a —$CH_2$— group can optionally be replaced by a —C(O)—, and wherein a sulphur atom in the heterocyclic ring may optionally be oxidised to a S(O) or $S(O)_2$ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from hydrogen, (1-4C)alkyl [optionally substituted by 1 or 2 substituents independently selected from HET-2, —$OR^5$, —$SO_2R^5$, (3-6C)cycloalkyl (optionally substituted with 1 group-selected from $R^7$) and —C(O)$NR^5R^5$], (3-6C)cycloalkyl (optionally substituted with 1 group selected from $R^7$) and HET-2;

$R^5$ is hydrogen or (1-4C)alkyl; or $R^4$ and $R^5$ together with the nitrogen atom to which they are attached may form a heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —$OR^5$, (1-4C)alkyl, —C(O)(1-4C)alkyl, —C(O)$NR^4R^5$, (1-4C)alkoxy(1-4C)alkyl, hydroxy(1-4C)alkyl and —S(O)$_pR^5$;

HET-3 is an N-linked, 4, 5 or 6 membered, saturated or partially unsaturated heterocyclyl ring, optionally containing 1 or 2 further heteroatoms (in addition to the linking N atom) independently selected from O, N and S, wherein a —$CH_2$— group can optionally be replaced by a —C(O)— and wherein a sulphur atom in the ring may optionally be oxidised to a S(O) or $S(O)_2$ group; which ring is optionally substituted on an available carbon or nitrogen atom by 1 or 2 substituents independently selected from $R^8$; or HET-3 is an N-linked, 7 membered, saturated or partially unsaturated heterocyclyl ring, optionally containing 1 further heteroatom (in addition to the linking N atom) independently selected from O, S and N, wherein a —CH$_2$— group can optionally be replaced by a —C(O)— group and wherein a sulphur atom in the ring may optionally be oxidised to a S(O) or S(O)$_2$ group; which ring is optionally substituted on an available carbon or nitrogen atom by 1 or 2 substituents independently selected from R$^8$; or HET-3 is an 6-10 membered bicyclic saturated or partially unsaturated heterocyclyl ring, optionally containing 1 further nitrogen atom (in addition to the linking N atom) wherein a —CH$_2$— group can optionally be replaced by a —C(O)—; which ring is optionally substituted on an available carbon or nitrogen atom by 1 substituent selected from hydroxy and R$^3$;

R$^8$ is selected from —OR$^5$, (1-4C)alkyl, —C(O)(1-4C)alkyl, —C(O)NR$^4$R$^5$, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_p$R$^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In a further aspect of the invention there is provided a compound of the formula (I), as hereinbefore defined or a salt, pro-drug or solvate thereof, wherein:

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon or nitrogen atom by 1 or 2 substituents independently selected from R$^8$.

In another aspect of the invention, there is provided a compounds of the formula (I) as hereinbefore defined, wherein R$^1$ is hydroxymethyl;

R$^2$ is selected from —C(O)NR$^{41}$R$^{51}$, —SO$_2$NR$^{41}$R$^{51}$ and —S(O)$_p$R$^{41}$;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from R$^6$;

HET-2 is a 4-, 5- or 6-membered, C- or N-linked heterocyclyl ring containing 1, 2, 3 or 4 heteroatoms independently selected from O, N and S, wherein a —CH$_2$— group can optionally be replaced by a —C(O)—, and wherein a sulphur atom in the heterocyclic ring may optionally be oxidised to a S(O) or S(O)$_2$ group, which ring is optionally substituted on an available carbon or nitrogen atom by 1 or 2 substituents independently selected from R$^7$;

R$^3$ is selected from halo, fluoromethyl, difluoromethyl, trifluoromethyl, methyl, methoxy and cyano;

R$^{41}$ is selected from (1-4C)alkyl [substituted by 1 or 2 substituents independently selected from HET-2, —OR$^5$, —SO$_2$R$^5$, (3-6C)cycloalkyl (optionally substituted with 1 group selected from R$^7$) and —C(O)NR$^5$R$^5$], (3-6C)cycloalkyl (optionally substituted with 1 group selected from R$^7$) and HET-2;

R$^{51}$ is hydrogen or (1-4C)alkyl;

R$^4$ is selected from (1-4C)alkyl [optionally substituted by 1 or 2 substituents independently selected from HET-2, —OR$^5$, —SO$_2$R$^5$, (3-6C)cycloalkyl (optionally substituted with 1 group selected from R$^7$) and —C(O)NR$^5$R$^5$], (3-6C)cycloalkyl (optionally substituted with 1 group selected from R$^7$) and HET-2;

R$^5$ is hydrogen or (1-4C)alkyl;

or R$^4$ and R$^5$ together with the nitrogen atom to which they are attached may form a heterocyclyl ring system as defined by HET-3;

R$^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

R$^7$ is selected from —OR$^5$, (1-4C)alkyl, —C(O)(1-4C)alkyl, —C(O)NR$^4$R$^5$, (1-4C)alkoxy(1-4C)alkyl, hydroxy(1-4C)alkyl and —S(O)$_p$R$^5$;

HET-3 is an N-linked, 4, 5 or 6 membered, saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon or nitrogen atom by 1 or 2 substituents independently selected from R$^8$; or HET-3 is an N-linked, 7 membered, saturated or partially unsaturated heterocyclyl ring, optionally containing 1 further heteroatom (in addition to the linking N atom) independently selected from O, S and N, wherein a —CH$_2$— group can optionally be replaced by a —C(O)— group and wherein a sulphur atom in the ring may optionally be oxidised to a S(O) or S(O)$_2$ group; which ring is optionally substituted on an available carbon or nitrogen atom by 1 or 2 substituents independently selected from R$^8$; or HET-3 is an 6-10 membered bicyclic saturated or partially unsaturated heterocyclyl ring, optionally containing 1 further nitrogen atom (in addition to the linking N atom) wherein a —CH$_2$— group can optionally be replaced by a —C(O)—; which ring is optionally substituted on an available carbon or nitrogen atom by 1 substituent selected from hydroxy and R$^3$;

R$^8$ is selected from —OR$^5$, (1-4C)alkyl, —C(O)(1-4C)alkyl, —C(O)NR$^4$R$^5$, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_p$R$^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In a further aspect of the invention there is provided a compound of the formula (I) as hereinbefore defined, or a salt, pro-drug or solvate thereof, wherein:

$R^4$ is selected from hydrogen, (1-4C)alkyl [optionally substituted by 1 or 2 substituents independently selected from HET-2, —$OR^5$, —$SO_2R^5$, (3-6C)cycloalkyl (optionally substituted with 1 group selected from $R^7$) and —C(O)$NR^5R^5$], and HET-2;

HET-3 as an 6-10 membered bicyclic saturated or partially unsaturated heterocyclyl ring, optionally containing 1 further nitrogen atom (in addition to the linking N atom) wherein a —$CH_2$— group can optionally be replaced by a —C(O)—, is optionally substituted on an available carbon or nitrogen atom by 1 substituent selected from $R^3$.

In another aspect of the invention, there is provided a compound of the formula (I) as hereinbefore defined, wherein $R^1$ is hydroxymethyl;

$R^2$ is HET-2;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;

HET-2 is a 4-, 5- or 6-membered, C- or N-linked heterocyclyl ring containing 1, 2, 3 or 4 heteroatoms independently selected from O, N and S, wherein a —$CH_2$— group can optionally be replaced by a —C(O)—, and wherein a sulphur atom in the heterocyclic ring may optionally be oxidised to a S(O) or $S(O)_2$ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from hydrogen, (1-4C)alkyl [optionally substituted by 1 or 2 substituents independently selected from HET-2, —$OR^5$, —$SO_2R^5$, (3-6C)cycloalkyl (optionally substituted with 1 group selected from $R^7$) and —C(O)$NR^5R^5$], (3-6C)cycloalkyl (optionally substituted with 1 group selected from $R^7$) and HET-2;

$R^5$ is hydrogen or (1-4C)alkyl;

or $R^4$ and $R^5$ together with the nitrogen atom to which they are attached may form a heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —$OR^5$, (1-4C)alkyl, —C(O)(1-4C)alkyl, —C(O)$NR^4R^5$, (1-4C)alkoxy(1-4C)alkyl, hydroxy(1-4C)alkyl and —S(O)$_pR^5$;

HET-3 is an N-linked, 4, 5 or 6 membered, saturated or partially unsaturated heterocyclyl ring, optionally containing 1 or 2 further heteroatoms (in addition to the linking N atom) independently selected from O, N and S, wherein a —$CH_2$— group can optionally be replaced by a —C(O)— and wherein a sulphur atom in the ring may optionally be oxidised to a S(O) or $S(O)_2$ group; which ring is optionally substituted on an available carbon or nitrogen atom by 1 or 2 substituents independently selected from $R^8$; or HET-3 is an N-linked, 7 membered, saturated or partially unsaturated heterocyclyl ring, optionally containing 1 further heteroatom (in addition to the linking N atom) independently selected from O, S and N, wherein a —$CH_2$— group can optionally be replaced by a —C(O)— group and wherein a sulphur atom in the ring may optionally be oxidised to a S(O) or $S(O)_2$ group; which ring is optionally substituted on an available carbon or nitrogen atom by 1 or 2 substituents independently selected from $R^8$; or HET-3 is an 6-10 membered bicyclic saturated or partially unsaturated heterocyclyl ring, optionally containing 1 further nitrogen atom (in addition to the linking N atom) wherein a —$CH_2$— group can optionally be replaced by a —C(O)—; which ring is optionally substituted on an available carbon or nitrogen atom by 1 substituent selected from hydroxy and $R^3$;

$R^8$ is selected from —$OR^5$, (1-4C)alkyl, —C(O)(1-4C)alkyl, —C(O)$NR^4R^5$, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_pR^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

It will be understood that when $R^4$ is —C(O)$NR^5R^5$, each $R^5$ is independently selected from hydrogen and (1-4C)alkyl, and therefore this definition of $R^4$ includes (but is not limited to) —$CONH_2$, —CONHMe, —$CONMe_2$ and —CONMeEt.

It will be understood that where a compound of the formula (I) contains more than one HET-2 ring, they may be the same or different.

It will be understood that where a compound of the formula (I) contains more than one group $R^4$, they may be the same or different.

It will be understood that where a compound of the formula (I) contains more than one group $R^5$, they may be the same or different.

It will be understood that where a compound of the formula (I) contains more than one group $R^8$, they may be the same or different.

A similar convention applies for all other groups and substituents on a compound of formula (I) as hereinbefore defined.

Compounds of Formula (I) may form salts which are within the ambit of the invention. Pharmaceutically acceptable salts are preferred although other salts may be useful in, for example, isolating or purifying compounds.

In another aspect, the invention relates to compounds of formula (I) as hereinabove defined or to a pharmaceutically acceptable salt.

In another aspect, the invention relates to compounds of formula (I) as hereinabove defined or to a pro-drug thereof. Suitable examples of pro-drugs of compounds of formula (I) are in-vivo hydrolysable esters of compounds of formula (I). Therefore in another aspect, the invention relates to compounds of formula (I) as hereinabove defined or to an in-vivo hydrolysable ester thereof.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

For the avoidance of doubt, reference to the group HET-1 containing a nitrogen in the 2-position, is intended to refer to the 2-position relative to the amide nitrogen atom to which the group is attached. For example, the following structures are encompassed (but not limited to):

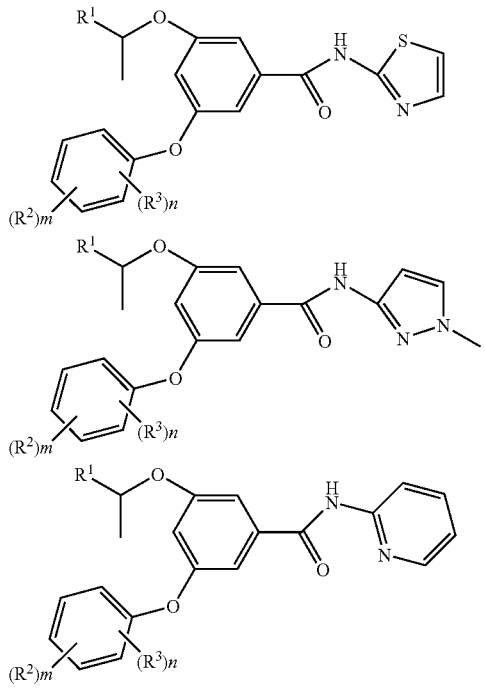

Suitable examples of HET-1 as a 5- or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

It will be understood that HET-2 can be a saturated, or partially or fully unsaturated ring.

Suitable examples of HET-2 include azetidinyl, furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, morpholino, morpholinyl, piperidinyl, piperazinyl, morpholinyl, thiomorpholinyl, pyrrolyl, pyrrolidinyl, pyrrolidonyl, 2,5-dioxopyrrolidinyl, 1,1-dioxotetrahydrothienyl, 2-oxoimidazolidinyl, 2,4-dioxoimidazolidinyl, 2-oxo-1,3,4-(4-triazolinyl), 2-oxazolidinonyl, 2-oxotetrahydrofuranyl, tetrahydrofuranyl, tetrahydropyranyl, 1,1-dioxothiomorpholino, 1,3-dioxolanyl, 1,2,4-triazolyl, 1,2,3-triazolyl, pyranyl, and 4-pyridonyl.

It will be understood that HET-2 may be linked by any appropriate available C or N atom, therefore for example, for HET-2 as "imidazolyl" includes 1-, 2-, 4- and 5-imidazolyl.

Suitable examples of HET-3 as a 4-6 membered saturated or partially unsaturated heterocyclic ring are morpholino, piperidinyl, piperazinyl, pyrrolidinyl and azetidinyl.

A suitable example of HET-3 as a 7-membered saturated or partially unsaturated heterocyclic ring is homopiperazinyl, homo-morpholino, homo-thiomorpholino (and versions thereof wherein the sulfur is oxidised to an SO or $S(O)_2$ group) and homo-piperidinyl.

Suitable examples of HET-3 as an 6-10 membered bicyclic-heterocyclic ring are bicyclic saturated or partially unsaturated heterocyclyl ring such as those illustrated by the structures shown below (wherein the dotted line indicates the point of attachment to the rest of the molecule):

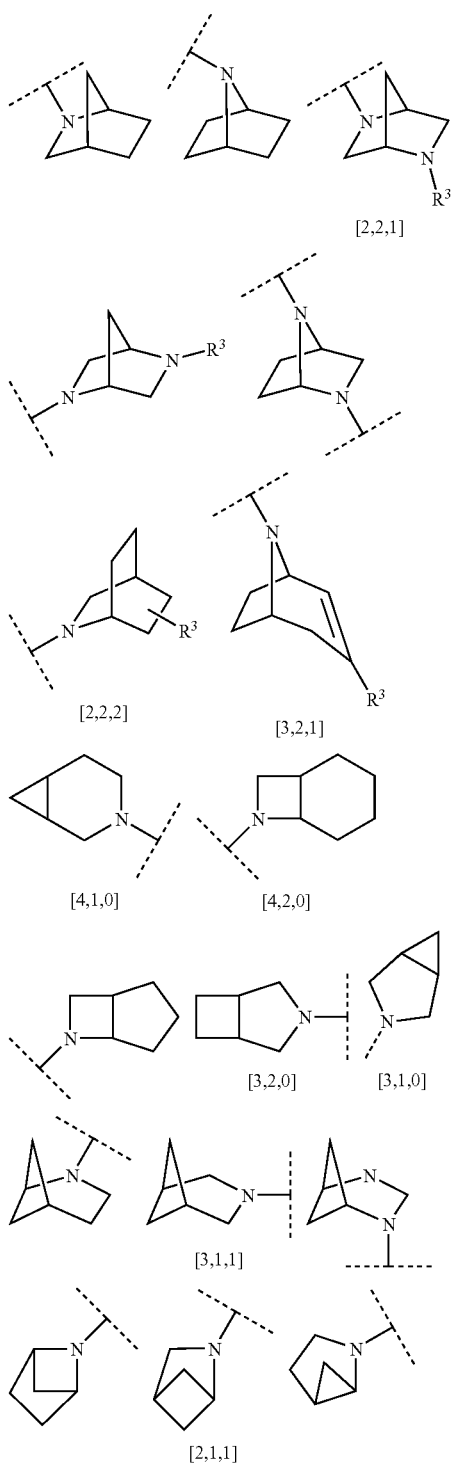

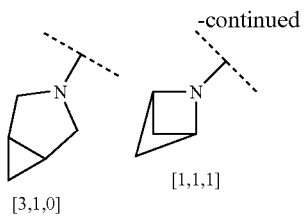

[3,1,0]   [1,1,1]

In particular HET-3 is a [2,2,1] system such as

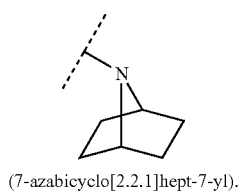

(7-azabicyclo[2.2.1]hept-7-yl).

In another embodiment, HET-3 is a [2.1.1] system such as

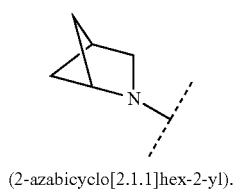

(2-azabicyclo[2.1.1]hex-2-yl).

Suitable examples of HET-4 are furyl, pyrrolyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl and triazolyl.

It will be appreciated that, where definitions of heterocyclyl groups HET-1 to HET-4 encompass heteroaryl or heterocyclyl rings which may be substituted on nitrogen, such substitution may not result in charged quaternary nitrogen atoms or unstable structures (such as N-halo compounds). It will be appreciated that the definitions of HET-1 to HET-4 are not intended to include any O—O, O—S or S—S bonds. It will be appreciated that the definitions of HET-1 to HET-4 are not intended to include unstable structures.

Examples of (1-4C)alkyl include methyl, ethyl, propyl, isopropyl, butyl and tert-butyl; examples of (3-6C)cycloalkyl include cyclopropyl, cyclobutyl, cyclopentyl and cyclohexyl; examples of halo include fluoro, chloro, bromo and iodo; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; examples of (1-4C)alkylS(O)$_p$(1-4C)alkyl include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of amino(1-4C)alkyl include aminomethyl, aminoethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino)butyl; examples of di(1-4C)alkylamino(1-4C)alkyl include dimethylaminomethyl, methyl(ethyl)aminomethyl, methyl(ethyl)aminoethyl, (N,N-diethyl)aminoethyl, (N,N-dimethyl)aminopropyl and (N,N-dimethyl)aminobutyl; examples of (1-4C)alkylamino include methylamino, ethylamino, propylamino, isopropylamino, butylamino and tert-butylamino; examples of di(1-4C)alkylamino include dimethylamino, methyl(ethyl)amino, diethylamino, dipropylamino, di-isopropylamino and dibutylamino; examples of —C(O)(1-4C)alkyl include methylcarbonyl, ethylcarbonyl, propylcarbonyl and tert-butyl carbonyl.

It is to be understood that, insofar as certain of the compounds of Formula (I) defined above may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

In one embodiment of the invention are provided compounds of formula (I), in an alternative embodiment are provided pharmaceutically-acceptable salts of compounds of formula (I); in a further alternative embodiment are provided in-vivo hydrolysable esters of compounds of formula (I), and in a further alternative embodiment are provided pharmaceutically-acceptable salts of in-vivo hydrolysable esters of compounds of formula (I).

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I). Further, each of the following values may be used in combination with one or more of the other following values to limit the broadest definition of formula (I).

(1) $R^1$ is hydroxymethyl and the configuration is preferably (S), that is:

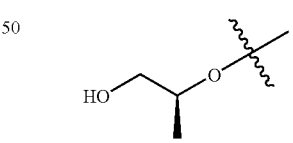

(2) $R^2$ is —C(O)NR$^4$R$^5$ (3) $R^2$ is —SO$_2$NR$^4$R$^5$ (4) $R^2$ is —S(O)$_p$R$^4$ (5) $R^2$ is HET-2

(6) m is 1 and preferably $R^2$ is in the para position relative to the ether linkage (7) m is 1 and n is 0 or 1

(8) m is 1 and n is 0

(9) m is 1, n is 0 and $R^2$ is in the para position relative to the ether linkage

(10) m is 1, n is 1, $R^2$ is in the para position relative to the ether linkage, $R^3$ is in the ortho position relative to the ether linkage

(11) m is 1, n is 1, $R^2$ is in the para position relative to the ether linkage, $R^3$ is in the meta position relative to the ether linkage

(12) n is 0

(13) n is 1

(14) n is 2

(15) n is 2 and both $R^3$ are halo

(16) n is 2 and each $R^3$ is independently halo or methoxy

(17) m is 1, n is 2 and $R^2$ is in the para position relative to the ether linkage

(18) m is 1, n is 2, $R^2$ is in the para position relative to the ether linkage and each $R^3$ is in an ortho position relative to the ether linkage

(19) m is 1, n is 2, both $R^3$ are halo, $R^2$ is in the para position relative to the ether linkage and each $R^3$ is in an ortho position relative to the ether linkage

(20) m is 1, n is 2, both $R^3$ are halo, $R^2$ is in the para position relative to the ether linkage and one $R^3$ is in an ortho position relative to the ether linkage and the other $R^3$ is in a meta position relative to the ether linkage

(21) $R^3$ is fluoromethyl or difluoromethyl

(22) $R^3$ is halo or trifluoromethyl

(23) $R^3$ is halo

(24) $R^3$ is chloro or fluoro

(25) $R^3$ is fluoro

(26) $R^3$ is methoxy

(27) n is 2 and both $R^3$ are fluoro

(28) n is 2 and one $R^3$ is fluoro and the other is chloro

(29) n is 2, both $R^3$ are fluoro and are in the 3- and 5-positions (meta-positions) relative to the ether linkage

(30) m is 1, n is 2, $R^2$ is in the para position relative to the ether linkage, both $R^3$ are fluoro and are in the 3- and 5-positions relative to the ether linkage

(31) p is 0

(32) p is 1

(33) p is 2

(34) HET-1 is a 5-membered heteroaryl ring

(35) HET-1 is a 6-membered heteroaryl ring

(36) HET-1 is substituted with 1 or 2 substituents independently selected from $R^6$

(37) HET-1 is substituted with 1 substituent selected from $R^6$

(38) HET-1 is unsubstituted

(39) HET-1 is selected from thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, and triazolyl

(40) HET-1 is selected from thiazolyl, isothiazolyl, thiadiazolyl, pyrazolyl, imidazolyl, oxazolyl, isoxazolyl and oxadiazolyl

(41) HET-1 is selected from pyridyl, pyrazinyl, pyridazinyl and pyrimidinyl

(42) HET-1 is selected from thiazolyl, pyrazolyl and oxazolyl

(43) HET-1 is selected from thiadiazolyl and oxadiazolyl

(44) HET-1 is selected from 1,3,4-thiadiazolyl and 1,3,4-oxadiazolyl

(45) HET-1 is selected from 1,2,4-oxadiazolyl and 1,2,4-oxadiazolyl

(46) HET-1 is pyrazolyl

(47) HET-1 is pyridyl or pyrazinyl

(48) HET-1 is pyrazinyl

(49) HET-1 is selected from thiazolyl, pyrazolyl, thiadiazolyl and pyrazinyl;

(50) $R^6$ is selected from (1-4C)alkyl, halo, hydroxy(1-4C)alkyl, di(1-4C)alkylamino(1-4C)alkyl and HET-4

(51) $R^6$ is selected from methyl, ethyl, bromo, chloro, fluoro, hydroxymethyl, methoxymethyl, aminomethyl, N-methylaminomethyl, dimethylaminomethyl

(52) $R^6$ is selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, and di(1-4C)alkylamino(1-4C)alkyl

(53) $R^6$ is selected from methyl, ethyl, bromo, chloro, fluoro, aminomethyl, N-methylaminomethyl, and dimethylaminomethyl

(54) $R^6$ is selected from methyl, ethyl, bromo, chloro, fluoro, hydroxymethyl and methoxymethyl

(55) $R^6$ is selected from methyl, ethyl, bromo, chloro and fluoro

(56) $R^6$ is methyl

(57) $R^6$ is selected from methyl, ethyl, bromo, chloro, fluoro, aminomethyl, N-methylaminomethyl, dimethylaminomethyl, hydroxymethyl and methoxymethyl

(58) $R^6$ is selected from methyl, ethyl, aminomethyl, N-methylaminomethyl, dimethylaminomethyl, hydroxymethyl and methoxymethyl

(59) $R^6$ is selected from (1-4C)alkyl and (1-4C)alkoxy(1-4C)alkyl.

(60) $R^6$ is selected from methyl, ethyl, isopropyl and methoxymethyl

(61) when 2 substituents $R^6$ are present, both are selected from methyl, ethyl, bromo, chloro and fluoro; preferably both are methyl

(62) $R^6$ is selected from (1-4C)alkylS(O)$_p$(1-4C)alkyl, (1-4C)alkylamino(1-4C)alkyl, di(1-4C)alkylamino(1-4C)alkyl and HET-4

(63) $R^6$ is HET-4

(64) HET-4 is selected from furyl, pyrrolyl and thienyl

(65) HET-4 is furyl

(66) $R^4$ is hydrogen

(67) $R^4$ is (1-4C)alkyl [substituted by 1 or 2 substituents independently selected from HET-2, —OR$^5$, —SO$_2$R$^5$, (3-6C)cycloalkyl (optionally substituted with 1 group selected from R$^7$) and —C(O)NR$^5$R$^5$]

(68) $R^4$ is (1-4C)alkyl [substituted by 1 substituent selected from HET-2, —$OR^5$, —$SO_2R^5$, (3-6C)cycloalkyl and —$C(O)NR^5R^5$]

(69) $R^4$ is (1-4C)alkyl

(70) $R^4$ is (1-4C)alkyl substituted by —$OR^5$

(71) $R^4$ is (1-4C)alkyl substituted by HET-2

(72) $R^4$ is (3-6C)cycloalkyl, particularly cyclopropyl or cyclobutyl

(73) $R^4$ is (3-6C)cycloalkyl substituted by a group selected from $R^7$

(74) $R^4$ is (3-6C)cycloalkyl substituted by a group selected from —$OR^5$ and (1-4C)alkyl

(75) $R^4$ is selected from (1-4C)alkyl and (3-6C)cycloalkyl.

(76) $R^4$ is selected from methyl, ethyl, cyclopropyl and cyclobutyl

(77) $R^4$ is HET-2

(78) $R^4$ is selected from hydrogen, (1-4C)alkyl, and (1-4C)alkyl substituted with —$OR^5$

(79) HET-2 is unsubstituted

(80) HET-2 is substituted with 1 or 2 substituents independently selected from (1-4C)alkyl, hydroxy and (1-4C)alkoxy

(81) HET-2 is a fully saturated ring system

(82) HET-2 is a fully unsaturated ring system

(83) HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl,

(84) HET-2 is selected from azetidinyl, morpholino, morpholinyl, piperidinyl, piperazinyl, pyrrolidinyl, thiomorpholinyl, tetrahydrofuranyl, and tetrahydropyranyl

(85) HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl

(86) HET-2 is selected from furyl, thienyl, thiazolyl, isothiazolyl, thiadiazolyl, pyridyl, imidazolyl, pyrimidinyl, oxazolyl, isoxazolyl, oxadiazolyl, piperidinyl, piperazinyl, 3-oxopiperazinyl, pyrrolidinyl, pyrrolidonyl, 2-oxazolidinonyl, tetrahydrofuranyl, tetrahydropyranyl, 1,1-dioxotetrahydrothienyl, and 2-oxoimidazolidinyl

(87) HET-2 is selected from morpholino, furyl, imidazolyl, oxazolyl, isoxazolyl, oxadiazolyl, piperidinyl, piperazinyl, 3-oxopiperazinyl, pyrrolidinyl, 2-pyrrolidonyl, 2-oxazolidinonyl, tetrahydrofuranyl, tetrahydropyranyl, 1,1-dioxotetrahydrothienyl, and 2-oxoimidazolidinyl

(88) HET-2 is selected from morpholino, furyl, imidazolyl, isoxazolyl, oxadiazolyl, piperidinyl, piperazinyl, 3-oxopiperazinyl, pyrrolidinyl, 2-pyrrolidonyl, tetrahydropyranyl, 1,1-dioxotetrahydrothienyl, and 2-oxoimidazolidinyl

(89) HET-3 is oxadiazolyl or pyrazolyl

(90) $R^5$ is hydrogen

(91) $R^5$ is (1-4)alkyl, preferably methyl

(92) $R^5$ is hydrogen or methyl

(93) $R^7$ is selected from —$OR^5$, (1-4C)alkyl, —C(O)(1-4C)alkyl, —$C(O)NR^4R^5$, (1-4C)alkoxy(1-4C)alkyl, and hydroxy(1-4C)alkyl

(94) $R^7$ is selected from —$OR^5$, (1-4C)alkyl, —C(O)(1-4C)alkyl, —$C(O)NR^4R^5$, and hydroxy(1-4C)alkyl

(95) $R^7$ is selected from hydroxy, methoxy, —COMe, —$CONH_2$, —CONHMe, —$CONMe_2$, and hydroxymethyl

(96) $R^7$ is selected from (1-4C)alkyl, hydroxy and (1-4C)alkoxy

(97) $R^7$ is selected from methyl, ethyl, methoxy and hydroxy

(98) $R^7$ is methyl

(99) $R^8$ is selected from methyl, hydroxy, methoxy, —COMe, —$CONH_2$, —CONHMe, —$CONMe_2$, hydroxymethyl, hydroxyethyl, —NHMe and —$NMe_2$(100) $R^8$ is selected from morpholino, piperidinyl, piperazinyl, pyrrolidinyl and azetidinyl (101) $R^8$ is selected from methyl, —COMe, —$CONH_2$, hydroxyethyl and hydroxy (102) $R^8$ is selected from (1-4C)alkyl and (1-4C)alkoxy (103) $R^8$ is selected from methyl, methoxy and isopropoxy (104) $R^8$ is methyl (105) HET-3 is a fully saturated ring (106) HET-3 is selected from morpholino, piperidinyl, piperazinyl, pyrrolidinyl and azetidinyl (107) $R^4$ and $R^5$ together with the nitrogen to which they are attached form a ring as defined by HET-3

(108) HET-3 is selected from pyrrolidinyl and azetidinyl (109) HET-3 is azetidinyl (110) HET-3 is a 4 to 6-membered saturated or partially unsaturated heterocyclic ring as herein before defined (111) HET-3 is a 7-membered saturated or partially unsaturated heterocyclic ring as hereinbefore defined (112) HET-3 is an 6 to 10-membered bicyclic saturated or partially unsaturated heterocyclic ring as hereinbefore defined (113) HET-3 is 7-azabicyclo[2.2.1]hept-7-yl (114) HET-3 is 7-azabicyclo[2.2.1]hept-7-yl or 2-azabicyclo[2.1.1]hex-2-yl (115) HET-3 is selected from morpholino, piperidinyl, piperazinyl, pyrrolidinyl and azetidinyl (116) HET-3 is unsubstituted (117) HET-3 is substituted by methyl, methoxy or isopropoxy According to a further feature of the invention there is provided the following preferred groups of compounds of the invention:

In a further aspect of the invention there is provided a compound of Formula (I) as hereinbefore defined, wherein $R^4$ is selected from hydrogen, (1-4C)alkyl [optionally substituted by 1 or 2 substituents independently selected from HET-2, —$OR^5$, —$SO_2R^5$, (3-6C)cycloalkyl (optionally substituted with 1 group selected from $R^7$) and —$C(O)NR^5R^5$] and HET-2.

In a further aspect of the invention there is provided a compound of Formula (I) wherein:

$R^1$ is hydroxymethyl;

$R^2$ is selected from —C(O)NR$^4$R$^5$, —SO$_2$NR$^4$R$^5$, —S(O)$_p$R$^4$ and HET-2;

HET-1 is a 5- or 6-membered, C-linked heteroaryl ring containing a nitrogen atom in the 2-position and optionally 1, 2 or 3 further ring heteroatoms independently selected from O, N and S; which ring is optionally substituted on an available carbon atom, or on a ring nitrogen atom provided it is not thereby quaternised, with 1 or 2 substituents independently selected from $R^6$;

HET-2 is a 5- or 6-membered, C- or N-linked heterocyclyl ring containing 1, 2, 3 or 4 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from hydrogen, (1-4C)alkyl, [optionally substituted by —OR$^5$] and HET-2;

$R^5$ is hydrogen or (1-4C)alkyl;

or $R^4$ and $R^5$ together with the nitrogen atom to which they are attached may form a 4-6 membered heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —OR$^5$ and (1-4C)alkyl;

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to an S(O) or S(O)$_2$ group; which ring is optionally substituted on an available carbon or nitrogen atom by 1 or 2 substituents independently selected from $R^8$;

$R^8$ is selected from —OR$^5$ and (1-4C)alkyl;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In a further aspect of the invention there is provided a compound of Formula (I) wherein:

$R^1$ is hydroxymethyl;

$R^2$ is selected from —C(O)NR$^4$R$^5$, —SO$_2$NR$^4$R$^5$, —S(O)$_p$R$^4$ and HET-2;

HET-1 is a 5- or 6-membered, C-linked heteroaryl ring containing a nitrogen atom in the 2-position and optionally 1, 2 or 3 further ring heteroatoms independently selected from O, N and S; which ring is optionally substituted on an available carbon atom, or on a ring nitrogen atom provided it is not thereby quaternised; with 1 or 2 substituents independently selected from $R^6$;

HET-2 is a 5- or 6-membered, C- or N-linked heterocyclyl ring containing 1, 2, 3 or 4 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from hydrogen, (1-4C)alkyl, [optionally substituted by —OR$^5$] and HET-2;

$R^5$ is hydrogen or (1-4C)alkyl;

or $R^4$ and $R^5$ together with the nitrogen atom to which they are attached may form a heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —OR$^5$ and (1-4C)alkyl;

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to an S(O) or S(O)$_2$ group; which ring is optionally substituted on an available carbon or nitrogen atom by 1 or 2 substituents independently selected from $R^8$; or HET-3 is an N-linked, 7 membered, saturated or partially unsaturated heterocyclyl ring, optionally containing 1 further heteroatom (in addition to the linking N atom) independently selected from O, S and N, wherein a —CH$_2$— group can optionally be replaced by a —C(O)— group and wherein a sulphur atom in the ring may optionally be oxidised to an S(O) or S(O)$_2$ group; which ring is optionally substituted on an available carbon or nitrogen atom by 1 or 2 substituents independently selected from $R^8$; or HET-3 is an 6-10 membered bicyclic saturated or partially unsaturated heterocyclyl ring, optionally containing 1 further nitrogen atom (in addition to the linking N atom), wherein a —CH$_2$— group can optionally be replaced by a —C(O)—; which ring is optionally substituted on an available carbon or nitrogen atom by 1 substituent selected from $R^3$;

$R^8$ is selected from —OR$^5$ and (1-4C)alkyl;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In a further aspect of the invention is provided a compound of the formula (I) as hereinbefore defined wherein:

$R^1$ is hydroxymethyl;

$R^2$ is selected from —C(O)NR$^4$R$^5$, —SO$_2$NR$^4$R$^5$, —S(O)$_p$R$^4$ and HET-2;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;

HET-2 is a 4-, 5- or 6-membered, C- or N-linked heterocyclyl ring containing 1, 2, 3 or 4 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available, carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from (1-4C)alkyl [substituted by 1 or 2 substituents independently selected from HET-2, —SO$_2$R$^5$, (3-6C)cycloalkyl (optionally substituted with 1 group selected from $R^7$) and —C(O)NR$^5$R$^5$];

$R^5$ is hydrogen or (1-4C)alkyl;

or $R^4$ and $R^5$ together with the nitrogen atom to which they are attached may form a 4-6 membered heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —C(O)(1-4C)alkyl, —C(O)NR$^4$R$^5$, (1-4C)alkoxy(1-4C)alkyl, hydroxy(1-4C)alkyl and —S(O)$_p$R$^5$;

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to an S(O) or S(O)$_2$ group; which ring is optionally substituted on an available carbon or nitrogen atom by 1 or 2 substituents independently selected from $R^8$;

$R^8$ is selected from —C(O)(1-4C)alkyl, —C(O)NR$^4$R$^5$, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_p$R$^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In a further aspect of the invention is provided a compound of the formula (I) as hereinbefore defined wherein:

$R^1$ is hydroxymethyl;

$R^2$ is selected from —C(O)NR$^4$R$^5$, —SO$_2$NR$^4$R$^5$, —S(O)$_p$R$^4$ and HET-2;

HET-1 is a 5- or 6-membered, C-linked heteroaryl ring containing a nitrogen atom in the 2-position and optionally 1 or 2 further ring heteroatoms independently selected from O, N and S; which ring is optionally substituted on an available carbon atom, or on a ring nitrogen atom provided it is not thereby quaternised, with 1 or 2 substituents independently selected from $R^6$;

HET-2 is a 4-, 5- or 6-membered, C- or N-linked heterocyclyl ring containing 1, 2, 3 or 4 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$;

$R^3$ is selected from halo, fluoromethyl, difluoromethyl, trifluoromethyl, methyl, methoxy and cyano;

$R^4$ is selected from (1-4C)alkyl [substituted by 1 or 2 substituents independently selected from HET-2, —SO$_2$R$^5$, (3-6C)cycloalkyl (optionally substituted with 1 group selected from $R^7$) and —C(O)NR$^5$R$^5$];

$R^5$ is hydrogen or (1-4C)alkyl;

or $R^4$ and $R^5$ together with the nitrogen atom to which they are attached may form a heterocyclyl ring system as defined by HET-3;

$R^6$ is independently selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl and HET-4;

$R^7$ is selected from —C(O)(1-4C)alkyl, —C(O)NR$^4$R$^5$, (1-4C)alkoxy(1-4C)alkyl, hydroxy(1-4C)alkyl and —S(O)$_p$R$^5$;

HET-3 is an N-linked, 4 to 6 membered, saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to an S(O) or S(O)$_2$ group; which ring is optionally substituted on an available carbon or nitrogen atom by 1 or 2 substituents independently selected from $R^8$; or HET-3 is an N-linked, 7 membered, saturated or partially unsaturated heterocyclyl ring, optionally containing 1 further heteroatom (in addition to the linking N atom) independently selected from O, S and N, wherein a —CH$_2$— group can optionally be replaced by a —C(O)— group and wherein a sulphur atom in the ring may optionally be oxidised to an S(O) or S(O)$_2$ group; which ring is optionally substituted on an available carbon or nitrogen atom by 1 or 2 substituents independently selected from $R^8$; or HET-3 is an 6-10 membered bicyclic saturated or partially unsaturated heterocyclyl ring, optionally containing 1 further nitrogen atom (in addition to the linking N atom), wherein a —CH$_2$— group can optionally be replaced by a —C(O)—;

which ring is optionally substituted on an available carbon or nitrogen atom by 1 substituent selected from $R^3$;

$R^8$ is selected from —C(O)(1-4C)alkyl, —C(O)NR$^4$R$^5$, (1-4C)alkylamino, di(1-4C)alkylamino, HET-3 (wherein said ring is unsubstituted), (1-4C)alkoxy(1-4C)alkyl, hydroxy(1-4C)alkyl and —S(O)$_p$R$^5$;

HET-4 is a 5- or 6-membered, C- or N-linked unsubstituted heteroaryl ring containing 1, 2 or 3 ring heteroatoms independently selected from O, N and S;

p is (independently at each occurrence) 0, 1 or 2;

m is 0 or 1;

n is 0, 1 or 2;

provided that when m is 0, then n is 1 or 2;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is a 5- or 6-membered heteroaryl ring, and is optionally substituted by 1 or 2 groups selected from $R^6$ $R^2$ is —CONR$^4$R$^5$ or —SO$_2$NR$^4$R$^5$;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl (optionally substituted with 1 group selected from $R^7$) and —C(O)NR$^5$R$^5$];

$R^5$ is hydrogen or methyl;

$R^6$ is selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl, di(1-4C)alkylamino(1-4C)alkyl;

HET-2 is a 5- or 6-membered heterocyclyl ring as hereinbefore defined, containing 1 or 2 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$; and $R^7$ is selected from —OR$^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is a 5- or 6-membered heteroaryl ring, and is optionally substituted by 1 or 2 groups selected from $R^6$ $R^2$ is —CONR$^4$R$^5$ or —SO$_2$NR$^4$R$^5$;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl (optionally substituted with 1 group selected from $R^7$) and —C(O)NR$^5$R$^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is a 5- or 6-membered heterocyclyl ring as hereinbefore defined, containing 1 or 2 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$; and $R^7$ is selected from —OR$^5$ and (1-4C)alkyl;

or a salt, pro-drug or solvate thereof;

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by 1 or 2 groups selected from $R^6$;

$R^2$ is —CONR$^4$R$^5$ or —SO$_2$NR$^4$R$^5$;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl and —C(O)NR$^5$R$^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, wherein HET-2 is optionally substituted by a substituent selected from $R^7$; and $R^7$ is selected from —OR$^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by 1 or 2 groups selected from $R^6$;

$R^2$ is —CONR$^4$R$^5$ or —SO$_2$NR$^4$R$^5$;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl and —C(O)NR$^5$R$^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, wherein HET-2 is optionally substituted by a substituent selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group selected from $R^6$;

$R^2$ is —$CONR^4R^5$ or —$SO_2NR^4R^5$;

$R^3$ is halo or trifluoromethyl;

$R^4$ is (1-4C)alkyl [optionally substituted by 1 or 2 substituents independently selected from HET-2, —$OR^5$, —$SO_2R^5$, (3-6C)cycloalkyl and —$C(O)NR^5R^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, wherein HET-2 is optionally substituted by a substituent selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group selected from $R^6$;

$R^2$ is —$CONR^4R^5$ or —$SO_2NR^4R^5$;

$R^3$ is halo or trifluoromethyl;

$R^4$ is (1-4C)alkyl [optionally substituted by 1 or 2 substituents independently selected from HET-2, —$OR^5$, —$SO_2R^5$, (3-6C)cycloalkyl and —$C(O)NR^5R^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, oxazolyl, isoxazolyl and oxadiazolyl, and is optionally substituted by a group selected from $R^6$;

$R^2$ is —$CONR^4R^5$ or —$SO_2NR^4R^5$;

$R^3$ is halo or trifluoromethyl; —$R^4$ is selected from hydrogen, (1-4C)alkyl [optionally substituted by —$OR^5$], (3-6C)cycloalkyl (optionally substituted with 1 group selected from $R^7$) and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from morpholino, furyl, imidazolyl, isoxazolyl, oxadiazolyl, piperidinyl, piperazinyl, 3-oxopiperazinyl, pyrrolidinyl, 2-pyrrolidonyl, tetrahydropyranyl, 1,1-dioxotetrahydrothienyl, and 2-oxoimidazolidinyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl and pyridazinyl, and is optionally substituted by a group selected from $R^6$;

$R^2$ is —$CONR^4R^5$ or —$SO_2NR^4R^5$;

$R^3$ is halo or trifluoromethyl;

$R^4$ is selected from hydrogen, (1-4C)alkyl [optionally substituted by —$OR^5$], (3-6C)cycloalkyl (optionally substituted with 1 group selected from $R^7$) and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from morpholino, furyl, imidazolyl, isoxazolyl, oxadiazolyl, piperidinyl, piperazinyl, 3-oxopiperazinyl, pyrrolidinyl, 2-pyrrolidonyl, tetrahydropyranyl, 1,1-dioxotetrahydrothienyl, and 2-oxoimidazolidinyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, oxazolyl, isoxazolyl and oxadiazolyl, and is optionally substituted by a group selected from $R^6$;

$R^2$ is —$CONR^4R^5$ or —$SO_2NR^4R^5$;

$R^3$ is halo or trifluoromethyl;

$R^4$ is selected from (1-4C)alkyl [optionally substituted by —$OR^5$], (3-6C)cycloalkyl (optionally substituted with 1 group selected from $R^7$) and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from piperidinyl, piperazinyl, 3-oxopiperazinyl, 2-pyrrolidonyl, 2,5-dioxopyrrolidinyl, 2-oxotetrahydrofuranyl, tetrahydrofuranyl, tetrahydropyranyl, 2-oxoimidazolidinyl, and 2,4-dioxoimidazolidinyl, optionally substituted by $R^7$; and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, oxazolyl, isoxazolyl and oxadiazolyl, and is optionally substituted by a group selected from $R^6$;

$R^2$ is —$CONR^4R^5$ or —$SO_2NR^4R^5$;

$R^3$ is halo or trifluoromethyl;

$R^4$ is selected from (1-4C)alkyl [optionally substituted by —$OR^5$], (3-6C)cycloalkyl (optionally substituted with 1 group selected from $R^7$) and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is piperidinyl or piperazinyl, and is optionally substituted by $R^7$; and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl and pyrazolyl, and is optionally substituted by a group selected from $R^6$;

$R^2$ is —$CONR^4R^5$;

$R^4$ is piperidinyl, optionally substituted with methyl;

$R^5$ is hydrogen or methyl;

$R^6$ is methyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl and pyridazinyl, and is optionally substituted by a group selected from $R^6$;

$R^2$ is —$CONR^4R^5$ or —$SO_2NR^4R^5$;

$R^3$ is halo or trifluoromethyl;

$R^4$ is selected from (1-4C)alkyl [optionally substituted by —$OR^5$] and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from piperidinyl, piperazinyl, 3-oxopiperazinyl, 2-pyrrolidonyl, 2,5-dioxopyrrolidinyl, 2-oxazolidinonyl, 2-oxotetrahydrofuranyl, tetrahydrofuranyl, tetrahydropyranyl, 2-oxoimidazolidinyl, and 2,4-dioxoimidazolidinyl, and is optionally substituted by $R^7$; and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl and pyridazinyl, and is optionally substituted by a group selected from $R^6$ $R^2$ is —$CONR^4R^5$ or —$SO_2NR^4R^5$;

$R^3$ is halo or trifluoromethyl;

$R^4$ is selected from (1-4C)alkyl [optionally substituted by —$OR^5$] and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is piperidinyl or piperazinyl, optionally substituted by $R^7$; and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, oxazolyl, isoxazolyl and oxadiazolyl, and is optionally substituted by a group selected from $R^6$;

$R^2$ is —$CONR^4R^5$ or —$SO_2NR^4R^5$;

$R^3$ is halo or trifluoromethyl;

$R^4$ and $R^5$ together with the nitrogen to which they are attached form a morpholino, piperidinyl, piperazinyl, pyrrolidinyl or azetidinyl ring, which ring is optionally substituted on a carbon or nitrogen atom by $R^8$;

$R^6$ is selected from methyl, ethyl, bromo, chloro, fluoro, hydroxymethyl, methoxymethyl, aminomethyl, N-methylaminomethyl, and dimethylaminomethyl;

$R^8$ is selected from hydroxy, (1-4C)alkoxy and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, oxazolyl, isoxazolyl and oxadiazolyl, and is optionally substituted by a group selected from $R^6$;

$R^2$ is —CONR$^4$R$^5$ or —SO$_2$NR$^4$R$^5$;

$R^3$ is halo or trifluoromethyl;

$R^4$ and $R^5$ together with the nitrogen to which they are attached form a morpholino, piperidinyl, piperazinyl, pyrrolidinyl or azetidinyl ring, which ring is optionally substituted on a carbon or nitrogen atom by $R^8$;

$R^6$ is selected from methyl, ethyl, bromo, chloro, fluoro, hydroxymethyl, methoxymethyl, aminomethyl, N-methylaminomethyl, and dimethylaminomethyl;

$R^8$ is pyrrolidine or piperidine;

or a salt, pro-drug or solvate thereof.

In a further aspect of the invention is provided a compound of the formula (I) as hereinbefore defined wherein $R^1$ is hydroxymethyl;

m is 1 and n is or 1;

HET-1 is selected from thiazolyl, isothiazolyl, thiadiazolyl, pyrazolyl, oxazolyl, isoxazolyl and oxadiazolyl, and is optionally substituted by a group selected from $R^6$, $R^2$ is —CONR$^4$R$^5$ or —SO$_2$NR$^4$R$^5$;

$R^3$ is halo or trifluoromethyl;

$R^4$ and $R^5$ together with the nitrogen to which they are attached form a morpholino, piperidinyl, piperazinyl, pyrrolidinyl or azetidinyl ring, which ring is optionally substituted on a carbon or nitrogen atom by (1-4C)alkyl;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl and pyridazinyl, optionally substituted by a group selected from $R^6$;

$R^2$ is —CONR$^4$R$^5$ or —SO$_2$NR$^4$R$^5$;

$R^3$ is halo or trifluoromethyl;

$R^4$ and $R^5$ together with the nitrogen to which they are attached form a morpholino, piperidinyl, piperazinyl, pyrrolidinyl or azetidinyl ring, which ring is optionally substituted on a carbon or nitrogen atom by (1-4C)alkyl;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl and pyrazolyl, and is optionally substituted by a group selected from $R^6$;

$R^2$ is —CONR$^4$R$^5$;

$R^4$ and $R^5$ together with the nitrogen to which they are attached form a piperidinyl, or piperazinyl ring, which ring is optionally substituted on a carbon or nitrogen atom by (1-4C)alkyl or by a pyrrolidinyl ring;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl and pyrazolyl, and is optionally substituted by a group selected from $R^6$;

$R^2$ is —CONR$^4$R$^5$;

$R^4$ and $R^5$ together with the nitrogen to which they are attached form an azetidinyl ring which ring is optionally substituted on a carbon atom by hydroxy;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl, pyrazolyl and pyrazinyl, and is optionally substituted by a group selected from $R^6$;

$R^2$ is —CONR$^4$R$^5$;

$R^4$ and $R^5$ together with the nitrogen to which they are attached form an azetidinyl ring which ring is optionally substituted on a carbon atom by methyl, methoxy or isopropoxy;

$R^6$ is selected from methyl, ethyl, isopropyl and methoxymethyl;

or a salt, pro-drug or solvate thereof.

In a further aspect of the invention is provided a compound of the formula (I) as hereinbefore defined wherein $R^1$ is hydroxymethyl;

m is 1 and n is 1;

HET-1 is selected from thiazolyl, thiadiazolyl and pyrazolyl, and is optionally substituted by a group selected from $R^6$;

$R^2$ is —CONR$^4$R$^5$;

$R^3$ is chloro or fluoro;

$R^4$ and $R^5$ together with the nitrogen to which they are attached form an azetidinyl ring which ring is optionally substituted on a carbon atom by hydroxy;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl and pyrazolyl, and is optionally substituted by a group selected from $R^6$;

$R^2$ is —CONR$^4$R$^5$;

$R^4$ and $R^5$ together with the nitrogen to which they are attached form a 7-membered ring HET-3 which ring is optionally substituted on a carbon or nitrogen atom by methyl;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from, thiazolyl, thiadiazolyl and pyrazolyl, and is optionally substituted by a group selected from $R^6$;

$R^2$ is —CONR$^4$R$^5$;

$R^4$ and $R^5$, together with the nitrogen to which they are attached form a 6-10 membered bicyclic heterocyclic ring HET-3 as hereinbefore defined, which ring is optionally substituted by hydroxy or methyl;

$R^6$ is selected from methyl, ethyl, bromo, chloro, fluoro; hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is a 5- or 6-membered heteroaryl ring, optionally substituted by 1 or 2 groups independently selected from $R^6$;

$R^2$ is —S(O)$_p$R$^4$;

p is 1 or 2;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl (optionally substituted with 1 group selected from $R^7$) and —C(O)NR$^5$R$^5$];

$R^5$ is hydrogen or methyl;

$R^6$ is selected from (1-4C)alkyl, halo, hydroxy(1-4C)alkyl, (1-4C)alkoxy(1-4C)alkyl, (1-4C)alkylS(O)$_p$(1-4C)alkyl, amino(1-4C)alkyl, (1-4C)alkylamino(1-4C)alkyl and di(1-4C)alkylamino(1-4C)alkyl;

HET-2 is a 5- or 6-membered heterocyclyl ring, containing 1 or 2 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$; and $R^7$ is selected from —OR$^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is a 5- or 6-membered heteroaryl ring, optionally substituted by 1 or 2 groups independently selected from $R^6$;

$R^2$ is —S(O)$_p$R$^4$;

p is 1 or 2;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl (optionally substituted with 1 group selected from $R^7$) and —C(O)NR$^5$R$^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is a 5- or 6-membered heterocyclyl ring, containing 1 or 2 heteroatoms independently selected from O, N and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by 1 or 2 substituents independently selected from $R^7$; and $R^7$ is selected from —OR$^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group selected from $R^6$;

$R^2$ is —S(O)$_p$R$^4$;

p is 1 or 2;

$R^3$ is halo or trifluoromethyl;

$R^4$ is (1-4C)alkyl [optionally substituted by 1 or 2 substituents independently selected from HET-2, —OR$^5$, —SO$_2$R$^5$, (3-6C)cycloalkyl and —C(O)NR$^5$R$^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group selected from $R^6$;

$R^2$ is —$S(O)_pR^4$;

p is 1 or 2;

$R^3$ is halo or trifluoromethyl;

$R^4$ is selected from hydrogen, (1-4C)alkyl [optionally substituted by —$OR^5$], (3-6C)cycloalkyl (optionally substituted with 1 group selected from $R^7$) and HET-2;

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group selected from $R^6$;

$R^2$ is —$S(O)_pR^4$;

p is 1 or 2;

$R^3$ is halo or trifluoromethyl;

$R^4$ is (1-4C)alkyl [optionally substituted by 1 or 2 substituents independently selected from HET-2, —$OR^5$, —$SO_2R^5$, (3-6C)cycloalkyl and —$C(O)NR^5R^5$];

$R^5$ is hydrogen or methyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group selected from $R^6$;

$R^2$ is —$S(O)_pR^4$;

p is 1 or 2;

$R^3$ is halo or trifluoromethyl;

$R^4$ is selected from hydrogen, (1-4C)alkyl [optionally substituted by —$OR^5$], (3-6C)cycloalkyl (optionally substituted with 1 group selected from $R^7$) and HET-2;

$R^5$ is hydrogen or methyl;

$R^6$ is selected from methyl, ethyl, bromo, chloro, fluoro, aminomethyl, N-methylaminomethyl, and dimethylaminomethyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group selected from $R^6$;

$R^2$ is —$S(O)_pR^4$;

p is 1 or 2;

$R^3$ is halo or trifluoromethyl;

$R^4$ is (1-4C)alkyl;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl and pyrazolyl, and is optionally substituted by $R^6$;

$R^2$ is —$S(O)_pR^4$;

p is 1 or 2;

$R^4$ is (1-4C)alkyl;

$R^6$ is methyl;

or a salt, pro-drug or solvate thereof.

In a further aspect of the invention is provided a compound of the formula (I) as hereinbefore defined wherein $R^1$ is hydroxymethyl;

m is 1 and n is 0;

HET-1 is selected from thiazolyl, thiadiazolyl and pyrazolyl, and is optionally substituted by $R^6$;

$R^2$ is —$S(O)_pR^4$;

p is 1 or 2;

$R^4$ is (3-6C)cycloalkyl;

$R^6$ is methyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group selected from $R^6$;

$R^2$ is —$S(O)_pR^4$;

p is 1 or 2;

$R^3$ is halo or trifluoromethyl;

$R^4$ is (1-4C)alkyl;

$R^6$ is selected from methyl, ethyl, bromo, chloro, fluoro, hydroxymethyl, methoxymethyl, aminomethyl, N-methylaminomethyl, and dimethylaminomethyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is a 5- or 6-membered heteroaryl ring, and is optionally substituted by a group selected from $R^6$;

$R^2$ is HET-2;

$R^3$ is halo or trifluoromethyl;

$R^5$ is hydrogen or (1-4C)alkyl;

$R^6$ is methyl;

HET-2 is a 5- or 6-membered heterocyclyl ring, containing 1 or 2 heteroatoms independently selected from O, N and S, wherein a —$CH_2$— group can optionally be replaced by a —C(O)—, and wherein a sulphur atom in the heterocyclic ring may optionally be oxidised to an S(O) or $S(O)_2$ group, which ring is optionally substituted on an available carbon or nitrogen atom by 1 or 2 substituents independently selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group $R^6$;

$R^2$ is HET-2;

$R^3$ is halo or trifluoromethyl;

$R^5$ is hydrogen or methyl;

$R^6$ is methyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group $R^6$;

$R^2$ is HET-2;

$R^3$ is halo or trifluoromethyl;

$R^5$ is hydrogen or methyl;

$R^6$ is methyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group $R^6$;

$R^2$ is HET-2;

$R^3$ is halo or trifluoromethyl;

$R^5$ is hydrogen or methyl;

$R^6$ is methyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group $R^6$;

$R^2$ is HET-2;

$R^3$ is halo or trifluoromethyl;

$R^5$ is hydrogen or methyl;

$R^6$ is methyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group selected from $R^7$; and $R^7$ is selected from —$OR^5$ and (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group selected from $R^6$;

$R^2$ is HET-2;

$R^3$ is halo or trifluoromethyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, and is optionally substituted by a group $R^7$; and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thiazolyl, isothiazolyl, thiadiazolyl, pyrazolyl, imidazolyl, oxazolyl, isoxazolyl and oxadiazolyl, and is optionally substituted by a group selected from $R^6$;

$R^2$ is HET-2;

$R^3$ is halo or trifluoromethyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group $R^7$; and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from pyridyl, pyrazinyl, pyridazinyl and pyrimidinyl, and is optionally substituted by a group selected from $R^6$;

$R^2$ is HET-2;

$R^3$ is halo or trifluoromethyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from azetidinyl, morpholino, morpholinyl, piperidinyl, piperazinyl, 3-oxopiperazinyl, thiomorpholinyl, pyrrolidinyl, pyrrolidonyl, 2,5-dioxopyrrolidinyl, 1,1-dioxotetrahydrothienyl, 2-oxazolidinonyl, 2-oxotetrahydrofuranyl, tetrahydrofuranyl, tetrahydropyranyl, 1,1-dioxothiomorpholino, 1,3-dioxolanyl, 2-oxoimidazolidinyl, 2,4-dioxoimidazolidinyl, pyranyl and 4-pyridonyl, and is optionally substituted by a group selected from $R^7$; and $R^7$ is (1-4C)alkyl;

or a salt, pro-drug or solvate thereof.

In a further aspect of the invention is provided a compound of the formula (I) as hereinbefore defined wherein $R^1$; is hydroxymethyl;

m is 1 and n is 0 or 1;

HET-1 is selected from pyridyl, pyrazinyl, pyridazinyl and pyrimidinyl, and is optionally substituted by a group selected from $R^6$;

$R^2$ is HET-2;

$R^3$ is halo or trifluoromethyl;

$R^6$ is selected from methyl, ethyl, bromo, chloro, fluoro, hydroxymethyl, methoxymethyl, aminomethyl, N-methylaminomethyl, and dimethylaminomethyl;

HET-2 is selected from furyl, thienyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, pyrrolyl, 1,2,4-triazolyl and 1,2,3-triazolyl, and is optionally substituted by a group $R^7$ and $R^7$ is (1-4C)alkyl;

or a salt, pro-drug or solvate thereof.

In a further aspect of the invention is provided a compound of the formula (I) as hereinbefore defined wherein $R^1$ is hydroxymethyl;

m is 1 and n is 0 or 1;

HET-1 is selected from thienyl, pyrazolyl, thiadiazolyl and pyrazinyl, and is optionally substituted by a group selected from $R^6$;

$R^6$ is selected from methyl, ethyl, isopropyl and methoxymethyl;

$R^2$ is selected from methylsulfonyl, azetidinylcarbonyl, dimethylaminocarbonyl, ethylsulfonyl, dimethylaminosulfonyl and pyrrolidinylcarbonyl;

$R^3$ is selected from fluoro, chloro and methoxy;

or a salt, pro-drug or solvate thereof.

In a further aspect of the invention is provided a compound of the formula (I) as hereinbefore defined wherein $R^1$ is hydroxymethyl;

m is 1 and n is 0, 1 or 2;

HET-1 is selected from thienyl, pyrazolyl, thiadiazolyl and pyrazinyl, and is optionally substituted by a group selected from $R^6$;

$R^6$ is selected from methyl, ethyl, isopropyl and methoxymethyl;

$R^2$ is selected from methylsulfonyl, azetidinylcarbonyl, dimethylaminocarbonyl, ethylsulfonyl, dimethylaminosulfonyl, methylazetidinylcarbonyl, methoxyazetidinylcarbonyl, isopropoxyazetidinylcarbonyl, azetidinylsulfonyl, cyclobutylsulfonyl, cyclopropylsulfonyl, 7-azabicyclo[2.2.1]hept-7-ylcarbonyl, 2-azabicyclo[2.1.1]hex-2-ylcarbonyl and pyrrolidinylcarbonyl;

$R^3$ is selected from fluoro, chloro and methoxy;

or a salt, pro-drug or solvate thereof.

In a further aspect of the invention is provided a compound of the formula (I) as hereinbefore defined wherein $R^1$ is hydroxymethyl;

m is 1 and n is 0, 1 or 2;

HET-1 is selected from thienyl, pyrazolyl, thiadiazolyl and pyrazinyl, and is optionally substituted by a group selected from $R^6$;

$R^6$ is selected from methyl, ethyl, isopropyl and methoxymethyl;

$R^2$ is selected from methylsulfonyl, azetidinylcarbonyl, dimethylaminocarbonyl, ethylsulfonyl, dimethylaminosulfonyl, methylazetidinylcarbonyl, methoxyazetidinylcarbonyl, isopropoxyazetidinylcarbonyl, azetidinylsulfonyl, cyclobutylsulfonyl, cyclopropylsulfonyl and pyrrolidinylcarbonyl;

$R^3$ is selected from fluoro, chloro and methoxy;

or a salt, pro-drug or solvate thereof.

In a further aspect of the invention is provided a compound of the formula (I) as hereinbefore defined wherein $R^1$ is hydroxymethyl;

m is 0 and n is 1 or 2;

HET-1 is selected from thienyl, pyrazolyl, thiadiazolyl and pyrazinyl, and is optionally substituted by a group selected from $R^6$;

$R^6$ is selected from methyl, ethyl, isopropyl and methoxymethyl;

$R^3$ is selected from fluoro, chloro and methoxy;

or a salt, pro-drug or solvate thereof.

Further preferred compounds of the invention are each of the Examples and/or Reference Examples, each of which provides a further independent aspect of the invention. In further aspects, the present invention also comprises any two or more compounds of the Examples and/or Reference Examples.

In one aspect, particular compounds of the invention comprise any one or more of:

3-[(1S)-2-hydroxy-1-methylethoxy]-5-[4-(methylsulfonyl)phenoxy]-N-1,3-thiazol-2-ylbenzamide;

3-[(1S)-2-hydroxy-1-methylethoxy]-N-[4-(methoxymethyl)-1,3-thiazol-2-yl]-5-[4-(methylsulfonyl)phenoxy]benzamide;

3-[(1S)-2-hydroxy-1-methylethoxy]-5-[4-(methylsulfonyl)phenoxy]-N-(4-methyl-1,3-thiazol-2-yl)benzamide;

3-[(1S)-2-hydroxy-1-methylethoxy]-5-[4-(methylsulfonyl)phenoxy]-N-(5-methyl-1,3-thiazol-2-yl)benzamide;

3-[(1S)-2-hydroxy-1-methylethoxy]-N-(5-methyl-1H-pyrazol-3-yl)-5-[4-(methylsulfonyl)phenoxy]benzamide;

3-[(1S)-2-hydroxy-1-methylethoxy]-N-(1-methyl-1H-pyrazol-3-yl)-5-[4-(methylsulfonyl)phenoxy]benzamide;

3-[(1S)-2-hydroxy-1 methylethoxy]-5-[4-(methylsulfonyl)phenoxy]-N-(3-methyl-1,2,4-thiadiazol-5-yl)benzamide;

3-[(1S)-2-hydroxy-1-methylethoxy]-5-[4-(methylsulfonyl)phenoxy]-N-1H-pyrazol-3-ylbenzamide;

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-[(3,5-difluorophenyl)oxy]-5-{[(1S)-2-hydroxy-1-methylethyl]oxy}-N-(1-methyl-1H-pyrazol-3-yl)benzamide;

3-{[4-(azetidin-1-ylcarbonyl)-2-chlorophenyl]oxy}-5-{[(1S)-2-hydroxy-1-methylethyl]oxy}-N-(1-methyl-1H-pyrazol-3-yl)benzamide;

3-chloro-4-(3-[(1S)-2-hydroxy-1-methylethoxy]-5-{[(1-methyl-1H-pyrazol-3-yl)amino]carbonyl}phenoxy)-N,N-dimethylbenzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide; and 3-({4-[(dimethylamino)carbonyl]phenyl}oxy)-5-{[(1S)-2-hydroxy-1-methylethyl]oxy}-N-(1-methyl-1H-pyrazol-3-yl)benzamide;

or a salt, pro-drug or solvate thereof.

In one aspect, particular compounds of the invention comprise any one or more of:

3-[(1S)-2-hydroxy-1-methylethoxy]-5-[4-(methylsulfonyl)phenoxy]-N-1,3-thiazol-2-ylbenzamide;

3-[(1S)-2-hydroxy-1-methylethoxy]-N-[4-(methoxymethyl)-1,3-thiazol-2-yl]-5-[4-(methylsulfonyl)phenoxy]benzamide;

3-[(1S)-2-hydroxy-1-methylethoxy]-5-[4-(methylsulfonyl)phenoxy]-N-(4-methyl-1,3-thiazol-2-yl)benzamide;

3-[(1S)-2-hydroxy-1-methylethoxy]-5-[4-(methylsulfonyl)phenoxy]-N-(5-methyl-1,3-thiazol-2-yl)benzamide;

3-[(1S)-2-hydroxy-1-methylethoxy]-N-(5-methyl-1H-pyrazol-3-yl)-5-[4-(methylsulfonyl)phenoxy]benzamide;

3-[(1S)-2-hydroxy-1-methylethoxy]-N-(1-methyl-1H-pyrazol-3-yl)-5-[4-(methylsulfonyl)phenoxy]benzamide;

3-[(1S)-2-hydroxy-1-methylethoxy]-5-[4-(methylsulfonyl)phenoxy]-N-(3-methyl-1,2,4-thiadiazol-5-yl)benzamide;

3-[(1S)-2-hydroxy-1-methylethoxy]-5-[4-(methylsulfonyl)phenoxy]-N-1H-pyrazol-3-ylbenzamide;

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-[(3,5-difluorophenyl)oxy]-5-{[(1S)-2-hydroxy-1-methylethyl]oxy}-N-(1-methyl-1H-pyrazol-3-yl)benzamide;

3-{[4-(azetidin-1-ylcarbonyl)-2-chlorophenyl]oxy}-5-{[(1S)-2-hydroxy-1-methylethyl]oxy}-N-(1-methyl-1H-pyrazol-3-yl)benzamide;

3-chloro-4-[(3-{[(1S)-2-hydroxy-1-methylethyl]oxy}-5-{[(1-methyl-1H-pyrazol-3-yl)amino]carbonyl}phenyl)oxy]-N,N-dimethylbenzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

3-({4-[(dimethylamino)carbonyl]phenyl}oxy)-5-{[(1S)-2-hydroxy-1-methylethyl]oxy}-N-(1-methyl-1H-pyrazol-3-yl)benzamide;

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)-2-chlorophenoxy]-N-(1-ethyl-1H-pyrazol-3-yl)-5-[(1S)-2-hydroxy-1-methylethoxy]benzamide;

N-(1-ethyl-1H-pyrazol-3-yl)-3-[4-(ethylsulfonyl)-2-fluorophenoxy]-5-[(1S)-2-hydroxy-1-methylethoxy]benzamide;

3-chloro-4-{3-{[(1-ethyl-1H-pyrazol-3-yl)amino]carbonyl}-5-[(1S)-2-hydroxy-1-methylethoxy]phenoxy}-N,N-dimethylbenzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-{4-[(dimethylamino)carbonyl]phenoxy}-N-(1-ethyl-1H-pyrazol-3-yl)-5-[(1S)-2-hydroxy-1-methylethoxy]benzamide;

3-(3-fluoro-4-methoxyphenoxy)-5-[(1S)-2-hydroxy-1-methylethoxy]-N-(1-methyl-1H-pyrazol-3-yl)benzamide;

3-(3,4-dimethoxyphenoxy)-5-[(1S)-2-hydroxy-1-methylethoxy]-N-(1-methyl-1H-pyrazol-3-yl)benzamide;

3-fluoro-4-[(3-{[(1S)-2-hydroxy-1-methylethyl]oxy}-5-{[(1-methyl-1H-pyrazol-3-yl)amino]carbonyl}phenyl)oxy]-N,N-dimethylbenzamide;

3-[2-chloro-4-(ethylsulfinyl)phenoxy]-5-[(1S)-2-hydroxy-1-methylethoxy]-N-(1-methyl-1H-pyrazol-3-yl)benzamide;

3-[2-fluoro-4-(pyrrolidin-1-ylcarbonyl)phenoxy]-5-[(1S)-2-hydroxy-1-methylethoxy]-N-(1-methyl-1H-pyrazol-3-yl)benzamide;

3-[4-(azetidin-1-ylcarbonyl)-2-chlorophenoxy]-5-[(1S)-2-hydroxy-1-methylethoxy]-N-(1-isopropyl-1H-pyrazol-3-yl)benzamide;

3-fluoro-4-(3-[(1S)-2-hydroxy-1-methylethoxy]-5-{[(1-isopropyl-1H-pyrazol-3-yl)amino]carbonyl}phenoxy)-N,N-dimethylbenzamide;

3-[(1S)-2-hydroxy-1-methylethoxy]-N-(1-isopropyl-1H-pyrazol-3-yl)-5-[4-(methylsulfonyl)phenoxy]benzamide;

3-[4-(azetidin-1-ylcarbonyl)-2-fluorophenoxy]-5-[(1S)-2-hydroxy-1-methylethoxy]-N-(1-isopropyl-1H-pyrazol-3-yl)benzamide;

3-[2-chloro-4-(ethylsulfonyl)phenoxy]-5-[(1S)-2-hydroxy-1-methylethoxy]-N-(1-isopropyl-1H-pyrazol-3-yl)benzamide;

3-[4-(azetidin-1-ylcarbonyl)phenoxy]-5-[(1S)-2-hydroxy-1-methylethoxy]-N-(1-isopropyl-1H-pyrazol-3-yl)benzamide;

3-[4-(ethylsulfonyl)phenoxy]-5-[(1S)-2-hydroxy-1-methylethoxy]-N-(1-isopropyl-1H-pyrazol-3-yl)benzamide; and 3-{4-[(dimethylamino)sulfonyl]phenoxy}-5-[(1S)-2-hydroxy-1-methylethoxy]-N-(1-methyl-1H-pyrazol-3-yl)benzamide; and/or N-(1-ethyl-1H-pyrazol-3-yl)-3-[2-fluoro-4-(pyrrolidin-1-ylcarbonyl)phenoxy]-5-[(1S)-2-hydroxy-1-methylethoxy]benzamide;

3-[2-chloro-4-(pyrrolidin-1-ylcarbonyl)phenoxy]-N-(1-ethyl-1H-pyrazol-3-yl)-5-[(1S)-2-hydroxy-1-methylethoxy]benzamide;

3-[2-chloro-4-(ethylsulfinyl)phenoxy]-5-[(1S)-2-hydroxy-1-methylethoxy]-N-(1-methyl-1H-pyrazol-3-yl)benzamide;

3-[2-chloro-4-(ethylsulfinyl)phenoxy]-5-[(1S)-2-hydroxy-1-methylethoxy]-N-(1-methyl-1H-pyrazol-3-yl)benzamide;

3-[4-(azetidin-1-ylcarbonyl)phenoxy]-5-[(1S)-2-hydroxy-1-methylethoxy]-N-1H-pyrazol-3-ylbenzamide;

3-[5-chloro-2-fluoro-4-(methylsulfonyl)phenoxy]-5-[(1S)-2-hydroxy-1-methylethoxy]-N-(1-methyl-1H-pyrazol-3-yl)benzamide;

3-[2,5-difluoro-4-(methylsulfonyl)phenoxy]-5-[(1S)-2-hydroxy-1-methylethoxy]-N-(1-methyl-1H-pyrazol-3-yl)benzamide;

3-[(1S)-2-hydroxy-1-methylethoxy]-N-(1-methyl-1H-pyrazol-3-yl)-5-[4-(1,2,4-oxadiazol-3-yl)phenoxy]benzamide; and 3-[4-(azetidin-1-ylcarbonyl)phenoxy]-5-[(1S)-2-hydroxy-1-methylethoxy]-N-(5-methylpyrazin-2-yl)benzamide; and/or 3-[4-(azetidin-1-ylcarbonyl)-2-fluorophenoxy]-5-[(1S)-2-hydroxy-1-methylethoxy]-N-(5-methyl-1,3-thiazol-2-yl)benzamide;

3-[4-(azetidin-1-ylcarbonyl)-2-fluorophenoxy]-5-[(1S)-2-hydroxy-1-methylethoxy]-N-(4-methyl-1,3-thiazol-2-yl)benzamide;

3-[4-(azetidin-1-ylcarbonyl)-2-fluorophenoxy]-5-[(1S)-2-hydroxy-1-methylethoxy]-N-[4-(methoxymethyl)-1,3-thiazol-2-yl]benzamide;

3-[(1S)-2-hydroxy-1-methylethoxy]-N-(1-methyl-1H-pyrazol-3-yl)-5-[4-(piperidin-1-ylcarbonyl)phenoxy]benzamide;

3-[(1S)-2-hydroxy-1-methylethoxy]-N-(1-methyl-1H-pyrazol-3-yl)-5-[4-(morpholin-4-ylcarbonyl)phenoxy]benzamide;

3-[(1S)-2-hydroxy-1-methylethoxy]-5-{4-[(4-methylpiperazin-1-yl)carbonyl]phenoxy}-N-(1-methyl-1H-pyrazol-3-yl)benzamide;

3-{4-[(cyclopropylamino)carbonyl]phenoxy}-5-[(1S)-2-hydroxy-1-methylethoxy]-N-(1-methyl-1H-pyrazol-3-yl)benzamide;

3-[4-(7-azabicyclo[2.2.1]hept-7-ylcarbonyl)phenoxy]-5-[(1S)-2-hydroxy-1-methylethoxy]-N-(1-methyl-1H-pyrazol-3-yl)benzamide;

3-[2-fluoro-4-(piperidin-1-ylcarbonyl)phenoxy]-5-[(1S)-2-hydroxy-1-methylethoxy]-N-(1-methyl-1H-pyrazol-3-yl)benzamide;

3-[2-fluoro-4-(morpholin-4-ylcarbonyl)phenoxy]-5-[(1S)-2-hydroxy-1-methylethoxy]-N-(1-methyl-1H-pyrazol-3-yl)benzamide;

3-{2-fluoro-4-[(4-methylpiperazin-1-yl)carbonyl]phenoxy}-5-[(1S)-2-hydroxy-1-methylethoxy]-N-(1-methyl-1H-pyrazol-3-yl)benzamide;

N-cyclopropyl-3-fluoro-4-(3-[(1S)-2-hydroxy-1-methylethoxy]-5-{[(1-methyl-1H-pyrazol-3-yl)amino]carbonyl}phenoxy)benzamide;

3-[4-(7-azabicyclo[2.2.1]hept-7-ylcarbonyl)-2-fluorophenoxy]-5-[(1S)-2-hydroxy-1-methylethoxy]-N-(1-methyl-1H-pyrazol-3-yl)benzamide;

3-{2-fluoro-4-[(2-methylazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-methoxyazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-isopropoxyazetidin-1-yl)carbonyl]phenoxy}-5-[(1S)-2-hydroxy-1-methylethoxy]-N-(1-methyl-1H-pyrazol-3-yl)benzamide;

3-[(1S)-2-hydroxy-1-methylethoxy]-5-{4-[(2-methylazetidin-1-yl)carbonyl]phenoxy}-N-(5-methylpyrazin-2-yl)benzamide;

3-[(1S)-2-hydroxy-1-methylethoxy]-5-{4-[(3-methoxyazetidin-1-yl)carbonyl]phenoxy}-N-(5-methylpyrazin-2-yl)benzamide;

3-[4-(azetidin-1-ylcarbonyl)-2-fluorophenoxy]-5-[(1R)-2-hydroxy-1-methylethoxy]-N-(1-methyl-1H-pyrazol-3-yl)benzamide;

3-[4-(azetidin-1-ylcarbonyl)phenoxy]-5-[(1R)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-(3-methyl-1,2,4-thiadiazol-5-yl)benzamide;

3-[4-(azetidin-1-ylcarbonyl)phenoxy]-5-[(1S)-2-hydroxy-1-methylethoxy]-N-(3-methyl-1,2,4-thiadiazol-5-yl)benzamide;

3-[4-(azetidin-1-ylsulfonyl)phenoxy]-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-1H-pyrazol-3-ylbenzamide;

3-[4-(cyclobutylsulfonyl)phenoxy]-5-[(1S)-2-hydroxy-1-methylethoxy]-N-(1-methyl-1H-pyrazol-3-yl)benzamide;

3-[4-(cyclopropylsulfonyl)phenoxy]-5-[(1S)-2-hydroxy-1-methylethoxy]-N-(1-methyl-1H-pyrazol-3-yl)benzamide;

3-[(1S)-2-hydroxy-1-methylethoxy]-N-(1-methyl-1H-pyrazol-3-yl)-5-[4-(1H-pyrazol-3-yl)phenoxy]benzamide;

2-chloro-5-fluoro-4-(3-[(1S)-2-hydroxy-1-methylethoxy]-5-{[(1-methyl-1H-pyrazol-3-yl)amino]carbonyl}phenoxy)-N,N-dimethylbenzamide;

2,5-difluoro-4-(3-[(1S)-2-hydroxy-1-methylethoxy]-5-{[(1-methyl-1H-pyrazol-3-yl)amino]carbonyl}phenoxy)-N,N-dimethylbenzamide;

3-[4-(azetidin-1-ylcarbonyl)-2,5-difluorophenoxy]-5-[(1S)-2-hydroxy-1-methylethoxy]-N-(1-methyl-1H-pyrazol-3-yl)benzamide;

3-[4-(azetidin-1-ylcarbonyl)-2-chloro-3-fluorophenoxy]-5-[(1S)-2-hydroxy-1-methylethoxy]-N-(1-methyl-1H-pyrazol-3-yl)benzamide;

3-[4-(azetidin-1-ylcarbonyl)-5-chloro-2-fluorophenoxy]-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-1,3-thiazol-2-ylbenzamide;

3-[4-(azetidin-1-ylcarbonyl)phenoxy]-5-[(1S)-2-hydroxy-1-methylethoxy]-N-1,3-thiazol-2-ylbenzamide;

3-[4-(azetidin-1-ylcarbonyl)-2-chlorophenoxy]-5-[(1S)-2-hydroxy-1-methylethoxy]-N-pyrazin-2-ylbenzamide;

3-[4-(azetidin-1-ylcarbonyl)phenoxy]-5-[(1S)-2-hydroxy-1-methylethoxy]-N-pyrazin-2-ylbenzamide;

3-[4-(azetidin-1-ylcarbonyl)-3-fluorophenoxy]-5-[(1S)-2-hydroxy-1-methylethoxy]-N-(1-methyl-1H-pyrazol-3-yl)benzamide;

3-[4-(2-azabicyclo[2.1.1]hex-2-ylcarbonyl)-2-fluorophenoxy]-5-[(1S)-2-hydroxy-1-methylethoxy]-N-(1-methyl-1H-pyrazol-3-yl)benzamide;

3-[4-(azetidin-1-ylcarbonyl)phenoxy]-N-(1,5-dimethyl-1H-pyrazol-3-yl)-5-[(1S)-2-hydroxy-1-methylethoxy]benzamide; and 3-[4-(azetidin-1-ylcarbonyl)-2-fluorophenoxy]-N-(1,5-dimethyl-1H-pyrazol-3-yl)-5-[(1S)-2-hydroxy-1-methylethoxy]benzamide;

or a salt, pro-drug or solvate thereof.

In another aspect, particular compounds of the invention comprise any one or more of:

3-[(1S)-2-hydroxy-1-methylethoxy]-5-[4-(methylsulfonyl)phenoxy]-N-(4-methyl-1,3-thiazol-2-yl)benzamide;

3-[(1S)-2-hydroxy-1-methylethoxy]-N-(5-methyl-1H-pyrazol-3-yl)-5-[4-(methylsulfonyl)phenoxy]benzamide;

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-[(3,5-difluorophenyl)oxy]-5-{[(1S)-2-hydroxy-1-methylethyl]oxy}-N-(1-methyl-1H-pyrazol-3-yl)benzamide;

3-{[4-(azetidin-1-ylcarbonyl)-2-chlorophenyl]oxy}-5-{[(1S)-2-hydroxy-1-methylethyl]oxy}-N-(1-methyl-1H-pyrazol-3-yl)benzamide;

3-chloro-4-[(3-{[(1S)-2-hydroxy-1-methylethyl]oxy}-5-{[(1-methyl-1H-pyrazol-3-yl)amino]carbonyl}phenyl)oxy]-N,N-dimethylbenzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)-2-chlorophenoxy]-N-(1-ethyl-1H-pyrazol-3-yl)-5-[(1S)-2-hydroxy-1-methylethoxy]benzamide;

N-(1-ethyl-1H-pyrazol-3-yl)-3-[4-(ethylsulfonyl)-2-fluorophenoxy]-5-[(1S)-2-hydroxy-1-methylethoxy]benzamide;

3-chloro-4-{3-{[(1-ethyl-1H-pyrazol-3-yl)amino]carbonyl}-5-[(1S)-2-hydroxy-1-methylethoxy]phenoxy}-N,N-dimethylbenzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-{4-[(dimethylamino)carbonyl]phenoxy}-N-(1-ethyl-1H-pyrazol-3-yl)-5-[(1S)-2-hydroxy-1-methylethoxy]benzamide;

3-(3-fluoro-4-methoxyphenoxy)-5-[(1S)-2-hydroxy-1-methylethoxy]-N-(1-methyl-1H-pyrazol-3-yl)benzamide;

3-(3,4-dimethoxyphenoxy)-5-[(1S)-2-hydroxy-1-methylethoxy]-N-(1-methyl-1H-pyrazol-3-yl)benzamide;

3-fluoro-4-[(3-{[(1S)-2-hydroxy-1-methylethyl]oxy}-5-{[(1-methyl-1H-pyrazol-3-yl)amino]carbonyl}phenyl)oxy]-N,N-dimethylbenzamide;

3-[2-chloro-4-(ethylsulfinyl)phenoxy]-5-[(1S)-2-hydroxy-1-methylethoxy]-N-(1-methyl-1H-pyrazol-3-yl)benzamide;

3-[2-fluoro-4-(pyrrolidin-1-ylcarbonyl)phenoxy]-5-[(1S)-2-hydroxy-1-methylethoxy]-N-(1-methyl-1H-pyrazol-3-yl)benzamide;

3-[4-(azetidin-1-ylcarbonyl)-2-chlorophenoxy]-5-[(1S)-2-hydroxy-1-methylethoxy]-N-(1-isopropyl-1H-pyrazol-3-yl)benzamide;

3-fluoro-4-(3-[(1S)-2-hydroxy-1-methylethoxy]-5-{[(1-isopropyl-1H-pyrazol-3-yl)amino]carbonyl}phenoxy)-N,N-dimethylbenzamide;

3-[(1S)-2-hydroxy-1-methylethoxy]-N-(1-isopropyl-1H-pyrazol-3-yl)-5-[4-(methylsulfonyl)phenoxy]benzamide;

3-[4-(azetidin-1-ylcarbonyl)-2-fluorophenoxy]-5-[(1S)-2-hydroxy-1-methylethoxy]-N-(1-isopropyl-1H-pyrazol-3-yl)benzamide;

3-[2-chloro-4-(ethylsulfonyl)phenoxy]-5-[(1S)-2-hydroxy-1-methylethoxy]-N-(1-isopropyl-1H-pyrazol-3-yl)benzamide;

3-[4-(azetidin-1-ylcarbonyl)phenoxy]-5-[(1S)-2-hydroxy-1-methylethoxy]-N-(1-isopropyl-1H-pyrazol-3-yl)benzamide;

3-[4-(ethylsulfonyl)phenoxy]-5-[(1S)-2-hydroxy-1-methylethoxy]-N-(1-isopropyl-1H-pyrazol-3-yl)benzamide; and 3-{4-[(dimethylamino)sulfonyl]phenoxy}-5-[(1S)-2-hydroxy-1-methylethoxy]-N-(1-methyl-1H-pyrazol-3-yl)benzamide; and/or N-(1-ethyl-1H-pyrazol-3-yl)-3-[2-fluoro-4-(pyrrolidin-1-ylcarbonyl)phenoxy]-5-[(1S)-2-hydroxy-1-methylethoxy]benzamide;

3-[2-chloro-4-(pyrrolidin-1-ylcarbonyl)phenoxy]-N-(1-ethyl-1H-pyrazol-3-yl)-5-[(1S)-2-hydroxy-1-methylethoxy]benzamide;

3-[2-chloro-4-(ethylsulfinyl)phenoxy]-5-[(1S)-2-hydroxy-1-methylethoxy]-N-(1-methyl-1H-pyrazol-3-yl)benzamide;

3-[2-chloro-4-(ethylsulfinyl)phenoxy]-5-[(1S)-2-hydroxy-1-methylethoxy]-N-(1-methyl-1H-pyrazol-3-yl)benzamide;

3-[4-(azetidin-1-ylcarbonyl)phenoxy]-5-[(1S)-2-hydroxy-1-methylethoxy]-N-1H-pyrazol-3-ylbenzamide;

3-[5-chloro-2-fluoro-4-(methylsulfonyl)phenoxy]-5-[(1S)-2-hydroxy-1-methylethoxy]-N-(1-methyl-1H-pyrazol-3-yl)benzamide;

3-[2,5-difluoro-4-(methylsulfonyl)phenoxy]-5-[(1S)-2-hydroxy-1-methylethoxy]-N-(1-methyl-1H-pyrazol-3-yl)benzamide;

3-[(1S)-2-hydroxy-1-methylethoxy]-N-(1-methyl-1H-pyrazol-3-yl)-5-[4-(1,2,4-oxadiazol-3-yl)phenoxy]benzamide; and 3-[4-(azetidin-1-ylcarbonyl)phenoxy]-5-[(1S)-2-hydroxy-1-methylethoxy]-N-(5-methylpyrazin-2-yl)benzamide; and/or 3-[4-(azetidin-1-ylcarbonyl)-2-fluorophenoxy]-5-[(1S)-2-hydroxy-1-methylethoxy]-N-(5-methyl-1,3-thiazol-2-yl)benzamide;

3-[4-(azetidin-1-ylcarbonyl)-2-fluorophenoxy]-5-[(1S)-2-hydroxy-1-methylethoxy]-N-(4-methyl-1,3-thiazol-2-yl)benzamide;

3-[4-(azetidin-1-ylcarbonyl)-2-fluorophenoxy]-5-[(1S)-2-hydroxy-1-methylethoxy]-N-[4-(methoxymethyl)-1,3-thiazol-2-yl]benzamide;

3-[(1S)-2-hydroxy-1-methylethoxy]-N-(1-methyl-1H-pyrazol-3-yl)-5-[4-(piperidin-1-ylcarbonyl)phenoxy]benzamide;

3-[(1S)-2-hydroxy-1-methylethoxy]-N-(1-methyl-1H-pyrazol-3-yl)-5-[4-(morpholin-4-ylcarbonyl)phenoxy]benzamide;

3-[(1S)-2-hydroxy-1-methylethoxy]-5-{4-[(4-methylpiperazin-1-yl)carbonyl]phenoxy}-N-(1-methyl-1H-pyrazol-3-yl)benzamide;

3-{4-[(cyclopropylamino)carbonyl]phenoxy}-5-[(1S)-2-hydroxy-1-methylethoxy]-N-(1-methyl-1H-pyrazol-3-yl)benzamide;

3-[4-(7-azabicyclo[2.2.1]hept-7-ylcarbonyl)phenoxy]-5-[(1S)-2-hydroxy-1-methylethoxy]-N-(1-methyl-1H-pyrazol-3-yl)benzamide;

3-[2-fluoro-4-(piperidin-1-ylcarbonyl)phenoxy]-5-[(1S)-2-hydroxy-1-methylethoxy]-N-(1-methyl-1H-pyrazol-3-yl)benzamide;

3-[2-fluoro-4-(morpholin-4-ylcarbonyl)phenoxy]-5-[(1S)-2-hydroxy-1-methylethoxy]-N-(1-methyl-1H-pyrazol-3-yl)benzamide;

3-{2-fluoro-4-[(4-methylpiperazin-1-yl)carbonyl]phenoxy}-5-[(1S)-2-hydroxy-1-methylethoxy]-N-(1-methyl-1H-pyrazol-3-yl)benzamide;

N-cyclopropyl-3-fluoro-4-(3-[(1S)-2-hydroxy-1-methylethoxy]-5-{[(1-methyl-1H-pyrazol-3-yl)amino]carbonyl}phenoxy)benzamide;

3-[4-(7-azabicyclo[2.2.1]hept-7-ylcarbonyl)-2-fluorophenoxy]-5-[(1S)-2-hydroxy-1-methylethoxy]-N-(1-methyl-1H-pyrazol-3-yl)benzamide;

3-{2-fluoro-4-[(2-methylazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-methoxyazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-isopropoxyazetidin-1-yl)carbonyl]phenoxy}-5-[(1S)-2-hydroxy-1-methylethoxy]-N-(1-methyl-1H-pyrazol-3-yl)benzamide;

3-[(1S)-2-hydroxy-1-methylethoxy]-5-{4-[(2-methylazetidin-1-yl)carbonyl]phenoxy}-N-(5-methylpyrazin-2-yl)benzamide;

3-[(1S)-2-hydroxy-1-methylethoxy]-5-{4-[(3-methoxyazetidin-1-yl)carbonyl]phenoxy}-N-(5-methylpyrazin-2-yl)benzamide;

3-[4-(azetidin-1-ylcarbonyl)-2-fluorophenoxy]-5-[(1R)-2-hydroxy-1-methylethoxy]-N-(1-methyl-1H-pyrazol-3-yl)benzamide;

3-[4-(azetidin-1-ylcarbonyl)phenoxy]-5-[(1R)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-(3-methyl-1,2,4-thiadiazol-5-yl)benzamide;

3-[4-(azetidin-1-ylcarbonyl)phenoxy]-5-[(1S)-2-hydroxy-1-methylethoxy]-N-(3-methyl-1,2,4-thiadiazol-5-yl)benzamide;

3-[4-(azetidin-1-ylsulfonyl)phenoxy]-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-1H-pyrazol-3-ylbenzamide;

3-[4-(cyclobutylsulfonyl)phenoxy]-5-[(1S)-2-hydroxy-1-methylethoxy]-N-(1-methyl-1H-pyrazol-3-yl)benzamide;

3-[4-(cyclopropylsulfonyl)phenoxy]-5-[(1S)-2-hydroxy-1-methylethoxy]-N-(1-methyl-1H-pyrazol-3-yl)benzamide;

3-[(1S)-2-hydroxy-1-methylethoxy]-N-(1-methyl-1H-pyrazol-3-yl)-5-[4-(1H-pyrazol-3-yl)phenoxy]benzamide;

2-chloro-5-fluoro-4-(3-[(1S)-2-hydroxy-1-methylethoxy]-5-{[(1-methyl-1H-pyrazol-3-yl)amino]carbonyl}phenoxy)-N,N-dimethylbenzamide;

2,5-difluoro-4-(3-[(1S)-2-hydroxy-1-methylethoxy]-5-{[(1-methyl-1H-pyrazol-3-yl)amino]carbonyl}phenoxy)-N,N-dimethylbenzamide;

3-[4-(azetidin-1-ylcarbonyl)-2,5-difluorophenoxy]-5-[(1S)-2-hydroxy-1-methylethoxy]-N-(1-methyl-1H-pyrazol-3-yl)benzamide;

3-[4-(azetidin-1-ylcarbonyl)-2-chloro-3-fluorophenoxy]-5-[(1S)-2-hydroxy-1-methylethoxy]-N-(1-methyl-1H-pyrazol-3-yl)benzamide;

3-[4-(azetidin-1-ylcarbonyl)-5-chloro-2-fluorophenoxy]-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-1,3-thiazol-2-ylbenzamide;

3-[4-(azetidin-1-ylcarbonyl)phenoxy]-5-[(1S)-2-hydroxy-1-methylethoxy]-N-1,3-thiazol-2-ylbenzamide;

3-[4-(azetidin-1-ylcarbonyl)-2-chlorophenoxy]-5-[(1S)-2-hydroxy-1-methylethoxy]-N-pyrazin-2-ylbenzamide;

3-[4-(azetidin-1-ylcarbonyl)phenoxy]-5-[(1S)-2-hydroxy-1-methylethoxy]-N-pyrazin-2-ylbenzamide;

3-[4-(azetidin-1-ylcarbonyl)-3-fluorophenoxy]-5-[(1S)-2-hydroxy-1-methylethoxy]-N-(1-methyl-1H-pyrazol-3-yl)benzamide;

3-[4-(2-azabicyclo[2.1.1]hex-2-ylcarbonyl)-2-fluorophenoxy]-5-[(1S)-2-hydroxy-1-methylethoxy]-N-(1-methyl-1H-pyrazol-3-yl)benzamide;

3-[4-(azetidin-1-ylcarbonyl)phenoxy]-N-(1,5-dimethyl-1H-pyrazol-3-yl)-5-[(1S)-2-hydroxy-1-methylethoxy]benzamide; and 3-[4-(azetidin-1-ylcarbonyl)-2-fluorophenoxy]-N-(1,5-dimethyl-1H-pyrazol-3-yl)-5-[(1S)-2-hydroxy-1-methylethoxy]benzamide;

or a salt, pro-drug or solvate thereof.

In another aspect, particular compounds of the invention comprise any one or more of:

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-{[4-(azetidin-1-ylcarbonyl)-2-chlorophenyl]oxy}-5-{[(1S)-2-hydroxy-1-methylethyl]oxy}-N-(1-methyl-1H-pyrazol-3-yl)benzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)-2-chlorophenoxy]-N-(1-ethyl-1H-pyrazol-3-yl)-5-[(1S)-2-hydroxy-1-methylethoxy]benzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-[2-fluoro-4-(pyrrolidin-1-ylcarbonyl)phenoxy]-5-[(1S)-2-hydroxy-1-methylethoxy]-N-(1-methyl-1H-pyrazol-3-yl)benzamide;

3-[4-(azetidin-1-ylcarbonyl)-2-chlorophenoxy]-5-[(1S)-2-hydroxy-1-methylethoxy]-N-(1-isopropyl-1H-pyrazol-3-yl)benzamide;

3-[4-(azetidin-1-ylcarbonyl)-2-fluorophenoxy]-5-[(1S)-2-hydroxy-1-methylethoxy]-N-(1-isopropyl-1H-pyrazol-3-yl)benzamide;

3-[4-(azetidin-1-ylcarbonyl)phenoxy]-5-[(1S)-2-hydroxy-1-methylethoxy]-N-(1-isopropyl-1H-pyrazol-3-yl)benzamide;

3-[2-chloro-4-(pyrrolidin-1-ylcarbonyl)phenoxy]-N-(1-ethyl-1H-pyrazol-3-yl)-5-[(1S)-2-hydroxy-1-methylethoxy]benzamide;

3-[4-(azetidin-1-ylcarbonyl)phenoxy]-5-[(1S)-2-hydroxy-1-methylethoxy]-N-1H-pyrazol-3-ylbenzamide; and 3-[4-(azetidin-1-ylcarbonyl)phenoxy]-5-[(1S)-2-hydroxy-1-methylethoxy]-N-(5-methylpyrazin-2-yl)benzamide; and/or 3-[4-(azetidin-1-ylcarbonyl)-2-fluorophenoxy]-5-[(1S)-2-hydroxy-1-methylethoxy]-N-(5-methyl-1,3-thiazol-2-yl)benzamide;

3-[4-(azetidin-1-ylcarbonyl)-2-fluorophenoxy]-5-[(1S)-2-hydroxy-1-methylethoxy]-N-(4-methyl-1,3-thiazol-2-yl)benzamide;

3-[4-(azetidin-1-ylcarbonyl)-2-fluorophenoxy]-5-[(1S)-2-hydroxy-1-methylethoxy]-N-[4-(methoxymethyl)-1,3-thiazol-2-yl]benzamide;

3-[(1S)-2-hydroxy-1-methylethoxy]-N-(1-methyl-1H-pyrazol-3-yl)-5-[4-(piperidin-1-ylcarbonyl)phenoxy]benzamide;

3-[(1S)-2-hydroxy-1-methylethoxy]-N-(1-methyl-1H-pyrazol-3-yl)-5-[4-(morpholin-4-ylcarbonyl)phenoxy]benzamide;

3-[(1S)-2-hydroxy-1-methylethoxy]-5-{4-[(4-methylpiperazin-1-yl)carbonyl]phenoxy}-N-(1-methyl-1H-pyrazol-3-yl)benzamide;

3-[4-(7-azabicyclo[2.2.1]hept-7-ylcarbonyl)phenoxy]-5-[(1S)-2-hydroxy-1-methylethoxy]-N-(1-methyl-1H-pyrazol-3-yl)benzamide;

3-[2-fluoro-4-(piperidin-1-ylcarbonyl)phenoxy]-5-[(1S)-2-hydroxy-1-methylethoxy]-N-(1-methyl-1H-pyrazol-3-yl)benzamide;

3-[2-fluoro-4-(morpholin-4-ylcarbonyl)phenoxy]-5-[(1S)-2-hydroxy-1-methylethoxy]-N-(1-methyl-1H-pyrazol-3-yl)benzamide;

3-{2-fluoro-4-[(4-methylpiperazin-1-yl)carbonyl]phenoxy}-5-[(1S)-2-hydroxy-1-methylethoxy]-N-(1-methyl-1H-pyrazol-3-yl)benzamide;

3-[4-(7-azabicyclo[2.2.1]hept-7-ylcarbonyl)-2-fluorophenoxy]-5-[(1S)-2-hydroxy-1-methylethoxy]-N-(1-methyl-1H-pyrazol-3-yl)benzamide;

3-{2-fluoro-4-[(2-methylazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-methoxyazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-isopropoxyazetidin-1-yl)carbonyl]phenoxy}-5-[(1S)-2-hydroxy-1-methylethoxy]-N-(1-methyl-1H-pyrazol-3-yl)benzamide;

3-[(1S)-2-hydroxy-1-methylethoxy]-5-{4-[(2-methylazetidin-1-yl)carbonyl]phenoxy}-N-(5-methylpyrazin-2-yl)benzamide;

3-[(1S)-2-hydroxy-1-methylethoxy]-5-{4-[(3-methoxyazetidin-1-yl)carbonyl]phenoxy}-N-(5-methylpyrazin-2-yl)benzamide;

3-[4-(azetidin-1-ylcarbonyl)-2-fluorophenoxy]-5-[(1R)-2-hydroxy-1-methylethoxy]-N-(1-methyl-1H-pyrazol-3-yl)benzamide;

3-[4-(azetidin-1-ylcarbonyl)phenoxy]-5-[(1R)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-(3-methyl-1,2,4-thiadiazol-5-yl)benzamide;

3-[4-(azetidin-1-ylcarbonyl)phenoxy]-5-[(1S)-2-hydroxy-1-methylethoxy]-N-(3-methyl-1,2,4-thiadiazol-5-yl)benzamide;

3-[4-(azetidin-1-ylsulfonyl)phenoxy]-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-1H-pyrazol-3-ylbenzamide;

3-[4-(azetidin-1-ylcarbonyl)-2,5-difluorophenoxy]-5-[(1S)-2-hydroxy-1-methylethoxy]-N-(1-methyl-1H-pyrazol-3-yl)benzamide;

3-[4-(azetidin-1-ylcarbonyl)-2-chloro-3-fluorophenoxy]-5-[(1S)-2-hydroxy-1-methylethoxy]-N-(1-methyl-1H-pyrazol-3-yl)benzamide;

3-[4-(azetidin-1-ylcarbonyl)-5-chloro-2-fluorophenoxy]-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-1,3-thiazol-2-ylbenzamide;

3-[4-(azetidin-1-ylcarbonyl)phenoxy]-5-[(1S)-2-hydroxy-1-methylethoxy]-N-1,3-thiazol-2-ylbenzamide;

3-[4-(azetidin-1-ylcarbonyl)-2-chlorophenoxy]-5-[(1S)-2-hydroxy-1-methylethoxy]-N-pyrazin-2-ylbenzamide;

3-[4-(azetidin-1-ylcarbonyl)phenoxy]-5-[(1S)-2-hydroxy-1-methylethoxy]-N-pyrazin-2-ylbenzamide;

3-[4-(azetidin-1-ylcarbonyl)-3-fluorophenoxy]-5-[(1S)-2-hydroxy-1-methylethoxy]-N-(1-methyl-1H-pyrazol-3-yl)benzamide;

3-[4-(2-azabicyclo[2.1.1]hex-2-ylcarbonyl)-2-fluorophenoxy]-5-[(1S)-2-hydroxy-1-methylethoxy]-N-(1-methyl-1H-pyrazol-3-yl)benzamide;

3-[4-(azetidin-1-ylcarbonyl)phenoxy]-N-(1,5-dimethyl-1H-pyrazol-3-yl)-5-[(1S)-2-hydroxy-1-methylethoxy]benzamide; and 3-[4-(azetidin-1-ylcarbonyl)-2-fluorophenoxy]-N-(1,5-dimethyl-1H-pyrazol-3-yl)-5-[(1S)-2-hydroxy-1-methylethoxy]benzamide;

or a salt, pro-drug or solvate thereof.

In another aspect, particular compounds of the invention comprise any one or more of:

3-[(1S)-2-hydroxy-1-methylethoxy]-N-(1-methyl-1H-pyrazol-3-yl)-5-[4-(methylsulfonyl)phenoxy]benzamide;

3-[(1S)-2-hydroxy-1-methylethoxy]-5-[4-(methylsulfonyl)phenoxy]-N-(3-methyl-1,2,4-thiadiazol-5-yl)benzamide;

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

3-({4-[(dimethylamino)carbonyl]phenyl}oxy)-5-{[(1S)-2-hydroxy-1-methylethyl]oxy}-N-(1-methyl-1H-pyrazol-3-yl)benzamide;

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)-2-chlorophenoxy]-N-(1-ethyl-1H-pyrazol-3-yl)-5-[(1S)-2-hydroxy-1-methylethoxy]benzamide;

N-(1-ethyl-1H-pyrazol-3-yl)-3-[4-(ethylsulfonyl)-2-fluorophenoxy]-5-[(1S)-2-hydroxy-1-methylethoxy]benzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-(3,4-dimethoxyphenoxy)-5-[(1S)-2-hydroxy-1-methylethoxy]-N-(1-methyl-1H-pyrazol-3-yl)benzamide;

3-[4-(azetidin-1-ylcarbonyl)phenoxy]-5-[(1S)-2-hydroxy-1-methylethoxy]-N-(5-methylpyrazin-2-yl)benzamide;

3-{2-fluoro-4-[(2-methylazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-methoxyazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-isopropoxyazetidin-1-yl)carbonyl]phenoxy}-5-[(1S)-2-hydroxy-1-methylethoxy]-N-(1-methyl-1H-pyrazol-3-yl)benzamide;

3-[(1S)-2-hydroxy-1-methylethoxy]-5-{4-[(2-methylazetidin-1-yl)carbonyl]phenoxy}-N-(5-methylpyrazin-2-yl)benzamide;

3-[(1S)-2-hydroxy-1-methylethoxy]-5-{4-[(3-methoxyazetidin-1-yl)carbonyl]phenoxy}-N-(5-methylpyrazin-2-yl)benzamide;

3-[4-(azetidin-1-ylcarbonyl)-2-fluorophenoxy]-5-[(1S)-2-hydroxy-1-methylethoxy]-N-(3-methyl-1,2,4-thiadiazol-5-yl)benzamide;

3-[4-(azetidin-1-ylcarbonyl)phenoxy]-5-[(1S)-2-hydroxy-1-methylethoxy]-N-(3-methyl-1,2,4-thiadiazol-5-yl)benzamide;

3-[4-(cyclobutylsulfonyl)phenoxy]-5-[(1S)-2-hydroxy-1-methylethoxy]-N-(1-methyl-1H-pyrazol-3-yl)benzamide;

3-[4-(cyclopropylsulfonyl)phenoxy]-5-[(1S)-2-hydroxy-1-methylethoxy]-N-(1-methyl-1H-pyrazol-3-yl)benzamide;

3-[4-(azetidin-1-ylcarbonyl)phenoxy]-N-(1,5-dimethyl-1H-pyrazol-3-yl)-5-[(1S)-2-hydroxy-1-methylethoxy]benzamide; and 3-[4-(azetidin-1-ylcarbonyl)-2-fluorophenoxy]-N-(1,5-dimethyl-1H-pyrazol-3-yl)-5-[(1S)-2-hydroxy-1-methylethoxy]benzamide;

or a salt, pro-drug or solvate thereof.

In another aspect, particular compounds of the invention comprise any one or more of:

3-{2-fluoro-4-[(2-methylazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-methoxyazetidin-1-yl)carbonyl]phenoxy}-5-[(1S)-2-hydroxy-1-methylethoxy]-N-(1-methyl-1H-pyrazol-3-yl)benzamide;

3-{2-fluoro-4-[(3-isopropoxyazetidin-1-yl)carbonyl]phenoxy}-5-[(1S)-2-hydroxy-1-methylethoxy]-N-(1-methyl-1H-pyrazol-3-yl)benzamide;

3-[(1S)-2-hydroxy-1-methylethoxy]-5-{4-[(2-methylazetidin-1-yl)carbonyl]phenoxy}-N-(5-methylpyrazin-2-yl)benzamide;

3-[(1S)-2-hydroxy-1-methylethoxy]-5-{4-[(3-methoxyazetidin-1-yl)carbonyl]phenoxy}-N-(5-methylpyrazin-2-yl)benzamide;

or a salt, pro-drug or solvate thereof.

In another aspect, particular compounds of the invention comprise any one or more of:

3-[(1S)-2-hydroxy-1-methylethoxy]-N-(1-methyl-1H-pyrazol-3-yl)-5-[4-(methylsulfonyl)phenoxy]benzamide;

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)phenoxy]-5-[(1S)-2-hydroxy-1-methylethoxy]-N-(5-methylpyrazin-2-yl)benzamide;

3-[4-(azetidin-1-ylcarbonyl)phenoxy]-N-(1,5-dimethyl-1H-pyrazol-3-yl)-5-[(1S)-2-hydroxy-1-methylethoxy]benzamide; and 3-[4-(azetidin-1-ylcarbonyl)-2-fluorophenoxy]-N-(1,5-dimethyl-1H-pyrazol-3-yl)-5-[(1S)-2-hydroxy-1-methylethoxy]benzamide;

or a salt, pro-drug or solvate thereof.

In another aspect, particular compounds of the invention comprise any one or more of:

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)phenoxy]-5-[(1S)-2-hydroxy-1-methylethoxy]-N-(5-methylpyrazin-2-yl)benzamide;

or a salt, pro-drug or solvate thereof.

In another aspect, particular compounds of the invention comprise any one or more of:

3-[(1S)-2-hydroxy-1-methylethoxy]-5-[4-(methylsulfonyl)phenoxy]-N-(3-methyl-1,2,4-thiadiazol-5-yl)benzamide;

3-({4-[(dimethylamino)carbonyl]phenyl}oxy)-5-{[(1S)-2-hydroxy-1-methylethyl]oxy}-N-(1-methyl-1H-pyrazol-3-yl)benzamide;

3-[4-(azetidin-1-ylcarbonyl)-2-chlorophenoxy]-N-(1-ethyl-1H-pyrazol-3-yl)-5-[(1S)-2-hydroxy-1-methylethoxy]benzamide;

N-(1-ethyl-1H-pyrazol-3-yl)-3-[4-(ethylsulfonyl)-2-fluorophenoxy]-5-[(1S)-2-hydroxy-1-methylethoxy]benzamide;

3-(3,4-dimethoxyphenoxy)-5-[(1S)-2-hydroxy-1-methylethoxy]-N-(1-methyl-1H-pyrazol-3-yl)benzamide;

3-[4-(azetidin-1-ylcarbonyl)-2-fluorophenoxy]-5-[(1S)-2-hydroxy-1-methylethoxy]-N-(3-methyl-1,2,4-thiadiazol-5-yl)benzamide;

3-[4-(azetidin-1-ylcarbonyl)phenoxy]-5-[(1S)-2-hydroxy-1-methylethoxy]-N-(3-methyl-1,2,4-thiadiazol-5-yl)benzamide;

3-[4-(cyclobutylsulfonyl)phenoxy]-5-[(1S)-2-hydroxy-1-methylethoxy]-N-(1-methyl-1H-pyrazol-3-yl)benzamide;

3-[4-(cyclopropylsulfonyl)phenoxy]-5-[(1S)-2-hydroxy-1-methylethoxy]-N-(1-methyl-1H-pyrazol-3-yl)benzamide;

or a salt, pro-drug or solvate thereof.

In another aspect, particular compounds of the invention comprise any one or more of:

3-[4-(azetidin-1-ylcarbonyl)-2-fluorophenoxy]-5-[(1S)-2-hydroxy-1-methylethoxy]-N-(1-methyl-1H-pyrazol-3-yl)benzamide;

3-{[4-(azetidin-1-ylcarbonyl)-2-chlorophenyl]oxy}-5-{[(1S)-2-hydroxy-1-methylethyl]oxy}-N-(1-methyl-1H-pyrazol-3-yl)benzamide;

3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide;

or a salt, pro-drug or solvate thereof.

In another aspect, particular compounds of the invention comprise any one or more of:

3-{[4-(azetidin-1-ylcarbonyl)-2-fluorophenyl]oxy}-5-{[(1S)-2-hydroxy-1-methylethyl]oxy}-N-(5-methylpyrazin-2-yl)benzamide;

3-[4-(azetidin-1-ylcarbonyl)-2-chlorophenoxy]-5-[(1S)-2-hydroxy-1-methylethoxy]-N-(5-methylpyrazin-2-yl)benzamide;

3-{[4-(azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide;

3-[4-(azetidin-1-ylcarbonyl)-2-chlorophenoxy]-N-(1-ethyl-1H-pyrazol-3-yl)-5-[(1S)-2-hydroxy-1-methylethoxy]benzamide;

3-{[4-(azetidin-1-ylcarbonyl)phenyl]oxy}-N-(1-ethyl-1H-pyrazol-3-yl)-5-{[(1S)-2-hydroxy-1-methylethyl]oxy}benzamide;

3-[2-fluoro-4-(pyrrolidin-1-ylcarbonyl)phenoxy]-5-[(1S)-2-hydroxy-1-methylethoxy]-N-(1-methyl-1H-pyrazol-3-yl)benzamide;

3-[4-(azetidin 1-ylcarbonyl)-2-chlorophenoxy]-5-[(1S)-2-hydroxy-1-methylethoxy]-N-(1-isopropyl-1H-pyrazol-3-yl)benzamide;

3-[4-(azetidin-1-ylcarbonyl)-2-fluorophenoxy]-5-[(1S)-2-hydroxy-1-methyl ethoxy]-N-(1-isopropyl-1H-pyrazol-3-yl)benzamide;

3-[4-(azetidin-1-ylcarbonyl)phenoxy]-5-[(1S)-2-hydroxy-1-methylethoxy]-N-(1-isopropyl-1H-pyrazol-3-yl)benzamide;

3-[2-chloro-4-(pyrrolidin-1-ylcarbonyl)phenoxy]-N-(1-ethyl-1H-pyrazol-3-yl)-5-[(1S)-2-hydroxy-1-methylethoxy]benzamide;

3-[4-(azetidin-1-ylcarbonyl)phenoxy]-5-[(1S)-2-hydroxy-1-methylethoxy]-N-1H-pyrazol-3-ylbenzamide; and 3-[4-(azetidin-1-ylcarbonyl)phenoxy]-5-[(1S)-2-hydroxy-1-methylethoxy]-N-(5-methylpyrazin-2-yl)benzamide;

or a salt, pro-drug or solvate thereof.

In a further aspect of the invention there is provided
3-[(1S)-2-hydroxy-1-methylethoxy]-N-(1-methyl-1H-pyrazol-3-yl)-5-[4-(1,2,4-oxadiazol-3-yl)phenoxy]benzamide;

or a salt, pro-drug or solvate thereof.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988); and
f) N. Kakeya, et al., Chem Pharm Bull; 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$alkanoyloxymethyl esters for example pivaloyloxymethyl, phthalidyl esters, $C_3$ to $C_8$cycloalkoxycarbonyloxy$C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. It will be understood that an acid addition salt may be formed with any sufficiently basic group which may for example be in HET-1 or may for example be a substituent $R^2$. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

A further feature of the invention is a pharmaceutical composition comprising a compound of Formula (I) as defined above, or a salt, solvate or prodrug thereof, together with a pharmaceutically-acceptable diluent or carrier.

According to another aspect of the invention there is provided a compound of Formula (I) as defined above for use as a medicament.

Further according to the invention there is provided a compound of Formula (I) for use in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (I) or salt, solvate or pro-drug thereof, to a mammal in need of such treatment.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X, impaired glucose tolerance.

As discussed above, thus the GLK/GLKRP system can be described as a potential "Diabesity" target (of benefit in both Diabetes and Obesity). Thus, according to another aspect of the invention there if provided the use of a compound of Formula (I) or salt, solvate or pro-drug thereof, in the preparation of a medicament for use in the combined treatment or prevention of diabetes and obesity.

According to another aspect of the invention there is provided the use of a compound of Formula (I) or salt, solvate or pro-drug thereof, in the preparation of a medicament for use in the treatment or prevention of obesity.

According to a further aspect of the invention there is provided a method for the combined treatment of obesity and diabetes by administering an effective amount of a compound of Formula (I) or salt, solvate or pro-drug thereof, to a mammal in need of such treatment.

According to a further aspect of the invention there is provided a method for the treatment of obesity by administering an effective amount of a compound of Formula (I) or salt, solvate or pro-drug thereof, to a mammal in need of such treatment.

Compounds of the invention may be particularly suitable for use as pharmaceuticals, for example because of favourable physical and/or pharmacokinetic properties and/or toxicity profile.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants, (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above.

Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene-glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:

1) Insulin and insulin analogues;

2) Insulin secretagogues including sulphonylureas (for example glibenclamide, glipizide), prandial glucose regulators (for example repaglinide, nateglinide);

3) Agents that improve incretin action (for example dipeptidyl peptidase IV inhibitors, and GLP-1 agonists);

4) Insulin sensitising agents including PPARgamma agonists (for example pioglitazone and rosiglitazone), and agents with combined PPARalpha and gamma activity;

5) Agents that modulate hepatic glucose balance (for example metformin, fructose 1,6 bisphosphatase inhibitors, glycogen phopsphorylase inhibitors, glycogen synthase kinase inhibitors);

6) Agents designed to reduce the absorption of glucose from the intestine (for example acarbose);

7) Agents that prevent the reabsorption of glucose by the kidney (SGLT inhibitors);

8) Agents designed to treat the complications of prolonged hyperglycaemia (for example aldose reductase inhibitors);

9) Anti-obesity agents (for example sibutramine and orlistat);

10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);

11) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);

12) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;

13) Agents which antagonise the actions of glucagon; and

14) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts, solvates and prodrugs thereof.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of compounds of Formula (I) are provided as a further feature of the invention. Thus, according to a further aspect of the invention there is provided a process for the preparation of a compound of Formula (I), which comprises a process a) to d) (wherein the variables are as defined hereinbefore for compounds of Formula (I) unless otherwise defined):

(a) reaction of an acid of Formula (III) or activated derivative thereof with a compound of Formula (IV), wherein $R^1$ is hydroxymethyl or a protected version thereof;

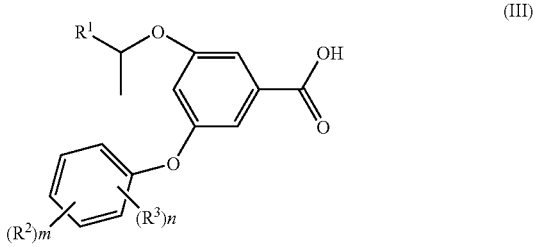

or (b) reaction of a compound of Formula (V) with a compound of Formula (VI),

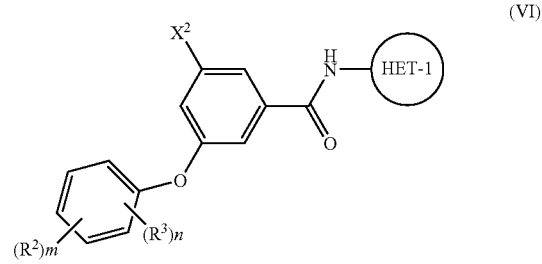

wherein $X^1$ is a leaving group and $X^2$ is a hydroxyl group or $X^1$ is a hydroxyl group and $X^2$ is a leaving group, and wherein $R^1$ is hydroxymethyl or a protected version thereof; process (b) could also be accomplished using the intermediate ester Formula (VII), wherein $P^1$ is a protecting group as hereinafter described, followed by ester hydrolysis and amide formation by procedures described elsewhere and well known to those skilled in the art;

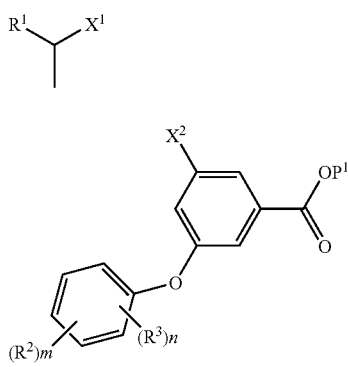

(c) reaction of a compound of Formula (VIII) with a compound of Formula (IX)

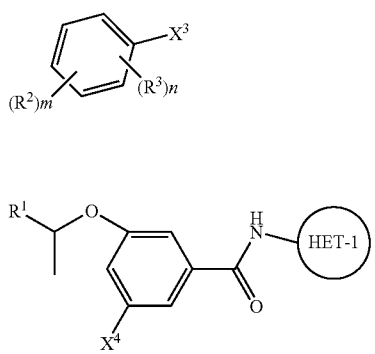

wherein $X^3$ is a leaving group or an organometallic reagent and $X^4$ is a hydroxyl group or $X^3$ is a hydroxyl group and $X^4$ is a leaving group or an organometallic reagent, and wherein $R^1$ is hydroxymethyl or a protected version thereof;

process (c) could also be accomplished using the intermediate ester Formula (X), followed by ester hydrolysis and amide formation by procedures described elsewhere and well known to those skilled in the art;

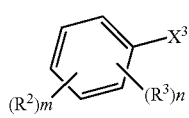

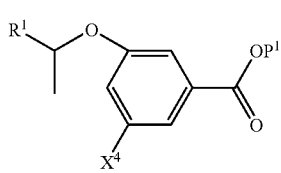

or (d) reaction of a compound of Formula (XI) with a compound of Formula (XII),

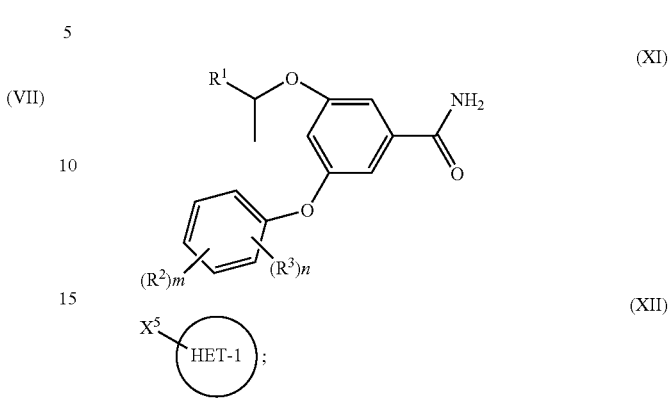

wherein $X^5$ is a leaving group; and wherein $R^1$ is hydroxymethyl or a protected version thereof;

and thereafter, if necessary:

i) converting a compound of Formula (I) into another compound of Formula (I);

ii) removing any protecting groups; and/or iii) forming a salt, pro-drug or solvate thereof.

Suitable leaving groups $X^1$ to $X^5$ for processes b) to d) are any leaving group known in the art for these types of reactions, for example halo, alkoxy, trifluoromethanesulfonyloxy, methanesulfonyloxy, or p-toluenesulfonyloxy; or a group (such as a hydroxy group) that may be converted into a leaving group (such as an oxytriphenylphosphonium group) in situ.

Suitable values for $R^1$ as a protected hydroxy group are any suitable protected hydroxy group known in the art, for example simple ethers such as a methyl ether, or silylethers such as —OSi[(1-4C)alkyl]$_3$ (wherein each (1-4C)alkyl group is independently selected from methyl, ethyl, propyl, isopropyl, and tertbutyl). Examples of such trialkylsilyl groups are trimethylsilyl, triethylsilyl, triisopropylsilyl and tert-butyldimethylsilyl. Further suitable silyl ethers are those containing phenyl and substituted phenyl groups, such as —Si(PhMe$_2$) and —Si(TolMe$_2$) (wherein Tol=methylbenzene). Further suitable values for hydroxy protecting groups are given hereinafter.

Compounds of Formulae (III) to (XII) are commercially available, or are known in the art, or may be made by processes known in the art, for example as shown in the accompanying Examples. For further information on processes for making such compounds, we refer to our PCT publications WO 03/000267, WO 03/015774 and WO 03/000262 and references therein. In general it will be appreciated that any aryl-O or alkyl-O bond may be formed by nucleophilic substitution or metal catalysed processes, optionally in the presence of a suitable base.

Examples of conversions of a compound of Formula (I) into another compound of Formula (I), well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions. An example would be removal of an $R^3$=chloro substituent, for example by reaction with hydrogen at atmospheric or elevated pressure, in a suitable solvent such as THF/methanol or ethanol.

Specific reaction conditions for the above reactions are as follows, wherein when $P^1$ is a protecting group $P^1$ is preferably (1-4C)alkyl, for example methyl or ethyl:

Process a)—coupling reactions of amino groups with carboxylic acids to form an amide are well known in the art. For example, (i) using an appropriate coupling reaction, such as a carbodiimide coupling reaction performed with EDAC (1-(3-dimethylaminopropyl)-3-ethylcarbodiimide hydrochloride) in the presence of dimethylaminopyridine (DMAP) in a suitable solvent such as dichloromethane (DCM), chloroform or dimethylformamide (DMF) at room temperature; or (ii) reaction in which the carboxylic group is activated to an acid chloride by reaction with oxalyl chloride in the presence of a suitable solvent such as DCM. The acid chloride can then be reacted with a compound of Formula (IV) in the presence of a base, such as triethylamine or pyridine, in a suitable solvent such as chloroform or DCM at a temperature between 0° C. and 80° C.

Process b)—compounds of Formula (V) and (VI) can be reacted together in a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II)acetate, palladium on carbon, copper (II)acetate or copper(I)iodide; alternatively, compounds of Formula (V) and (VI) can be reacted together in a suitable solvent, such as THF or DCM, with a suitable phosphine such as triphenylphosphine, and azodicarboxylate such as diethylazodicarboxylate; process b) could also be carried out using a precursor to the ester of formula (VII) such as an aryl-nitrile or trifluoromethyl derivative, followed by conversion to a carboxylic acid and amide formation as previously described;

Process c)—compounds of Formula (VIII) and (IX) can be reacted together in a suitable solvent, such as DMF or THF, with a base such as sodium hydride or potassium tert-butoxide, at a temperature in the range 0 to 200° C., optionally using microwave heating or metal catalysis such as palladium(II) acetate, palladium on carbon, copper(II)acetate or copper(I) iodide; process c) could also be carried out using a precursor to the ester of formula (X) such as an aryl-nitrile or trifluoromethyl derivative, followed by conversion to a carboxylic acid and amide formation as previously described;

Process d)—reaction of a compound of Formula (XI) with a compound of Formula (XII) can be performed in a polar solvent, such as DMF or a non-polar solvent such as THF with a strong base, such as sodium hydride or potassium tert-butoxide at a temperature between 0 and 200° C., optionally using microwave heating or metal catalysis, such as palladium(II)acetate, palladium on carbon, copper(II)acetate or copper(I)iodide.

Certain intermediates of formula (III), (VI), (VII), (IX) and/or (XI) are believed to be novel and comprise an independent aspect of the invention.

Certain intermediates of formula (III), (IX) and/or (XI) wherein $R^1$ is hydroxymethyl, methoxymethyl or a trialkylsilylether are believed to be novel and comprise an independent aspect of the invention.

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, nucleophilic displacement, acid-, base, metal- or enzymically-catalysed hydrolysis, catalytic hydrogenolysis/hydrogenation or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. 1-butyldimethylsilyloxymethyl, 1-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) with a field strength (for proton) of 300 MHz (generally using a Varian Gemini 2000) or 400 MHz (generally using a Bruker Avance DPX400), unless otherwise stated, and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) Purification by chromatography generally refers to flash column chromatography, on silica unless otherwise stated. Column chromatography was generally carried out using prepacked silica cartridges (from 4 g up to 400 g) such as Redisep™ (available, for example, from Presearch Ltd, Hitchin, Herts, UK) or Biotage (Biotage UK Ltd, Hertford, Herts, UK), eluted using a pump and fraction collector system;

(vii) Mass spectra (MS) data was generated on an LCMS system where the HPLC component comprised generally either a Agilent 1100 or Waters Alliance HT (2790 & 2795) equipment and was run on a Phemonenex Gemini C18 5 μm, 50×2 mm column (or similar) eluting with either acidic eluent (for example, using a gradient between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient between 0-95% water/acetonitrile with 5% of a 0.1% 880 Ammonia in acetonitrile mixture); and the MS component comprised generally a Waters ZQ spectrometer. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is $(M-H)^-$;

(viii) Suitable microwave reactors include "Smith Creator", "CEM Explorer", "Biotage Initiator sixty" and "Biotage Initiator eight".

| | Abbreviations |
|---|---|
| DCM | dichloromethane; |
| DEAD | diethylazodicarboxylate; |
| DIAD | diisopropylazodicarboxylate; |
| DIPEA | N,N-Diisopropylethylamine; |
| DMSO | dimethyl sulphoxide; |
| DMF | dimethylformamide; |
| EDAC | 1-(3-dimethylaminopropyl)-3-ethylcarbodiimide hydrochloride; |
| HATU | O-(7-Azabenzotriazol-1-yl)-N,N,N',N'-tetramethyluronium hexofluorophosphate |
| HPLC | high pressure liquid chromatography |
| HPMC | Hydroxypropylmethylcellulose; |
| LCMS | liquid chromatography/mass spectroscopy; |
| NMP | N-methyl-2-pyrrolidone; |
| NMR | nuclear magnetic resonance spectroscopy; |
| RT | room temperature; |
| THF | tetrahydrofuran; |
| TFA | trifluoroacetic acid; |
| $CDCl_3$ | deuterochloroform. |
| Mpt/mpt | melting point |
| $MgSO_4$ | magnesium sulfate |

All compound names were derived using ACD NAME computer package.

REFERENCE EXAMPLE 1

3-[(1S)-2-Hydroxy-1-methylethoxy]-5-[4-(methylsulfonyl)phenoxy]-N-1,3-thiazol-2-ylbenzamide

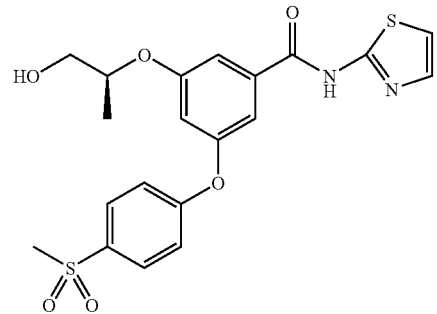

Tetra-n-butyl ammonium fluoride (1.0M in THF, 0.832 mL, 0.832 mmol) was added to a solution of 3-((1S)-2-{[tert-Butyl(dimethyl)silyl]oxy}-1-methylethoxy)-5-[4-(methylsulfonyl)phenoxy]-N-1,3-thiazol-2-ylbenzamide (425 mg, 0.756 mmol) in THF (5 mL) and the reaction stirred for 1.5 h. A further portion of tetra-n-butyl ammonium fluoride (0.83 mL) in THF was added and the reaction was stirred for a further 1.5 h. The reaction was then diluted with diethyl ether (40 mL) and 1M aqueous hydrochloric acid (20 mL) and the aqueous layer was re-extracted with diethyl ether (20 mL). The combined organic layers were dried (MgSO$_4$), filtered and evaporated. Purification by column chromatography, eluting with 50% to 100% ethyl acetate in hexanes, afforded the title compound as a foam (200 mg, 60%). $^1$H NMR δ (CDCl$_3$): 1.30 (d, 3H), 3.08 (s, 3H), 3.77 (m, 2H), 4.47 (m, 1H), 6.85 (s, 1H), 7.00 (d, 1H), 7.13 (d, 2H), 7.20 (s, 1H), 7.32 (d, 1H), 7.37 (s, 1H), 7.92 (d, 2H). m/z 467 (M–H)$^-$ 3-((1S)-2-{[tert-Butyl(dimethyl)silyl]oxy}-1-methylethoxy)-5-[4-(methylsulfonyl)phenoxy]-N-1,3-thiazol-2-ylbenzamide

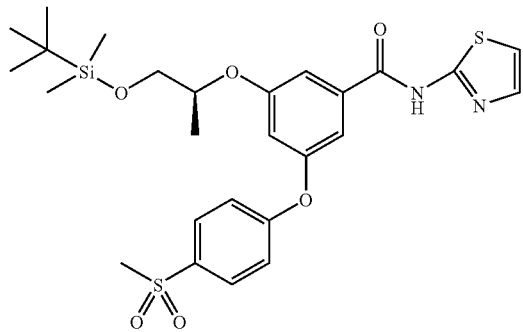

HATU (513 mg, 1.35 mmol) was added to 3-((1S)-2-{[tert-Butyl(dimethyl)silyl]oxy}-1-methylethoxy)-5-[4-(methylsulfonyl)phenoxy]benzoic acid (520 mg, 1.08 mmol) followed by addition of DMF (5 mL), disopropylethylamine (0.48 mL) and 2-aminothiazole (135 mg, 1.35 mmol) and the reaction was stirred under argon for 4 h. The solvent was evaporated and the residue was dissolved in saturated aqueous sodium hydrogencarbonate (30 mL) and ethyl acetate (50 mL). The organic layer was separated, washed with saturated aqueous ammonium chloride (30 mL) then dried (MgSO$_4$), filtered and evaporated. Purification by column chromatography, eluting with 1:2 to 2:1 ethyl acetate:hexanes, afforded the title compound as a colourless oil (425 mg, 70%).

$^1$H NMR δ (CDCl$_3$): 0.02 (s, 3H), 0.04 (s, 3H), 0.84 (s, 9H), 1.30 (d, 3H), 3.08 (s, 3H), 3.76 (m, 2H), 4.50 (m, 1H), 6.89 (s, 1H), 7.00 (d, 1H), 7.18 (m, 3H), 7.37 (m, 2H), 7.94 (d, 2H). m/z 561 (M–H)$^-$ 3-((1S)-2-{[tert-Butyl(dimethyl)silyl]oxy}-1-methylethoxy)-5-[4-(methylsulfonyl)phenoxy]benzoic acid

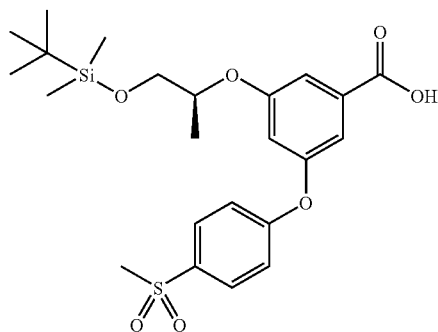

Lithium hydroxide monohydrate (346 mg, 8.24 mmol) was added to a solution of methyl 3-((1S)-2-{[tert-butyl(dimethyl)silyl]oxy}-1-methylethoxy)-5-[4-(methylsulfonyl)phenoxy]benzoate (3.70 g, 7.49 mmol) in THF (50 mL) and water (10 mL) and the reaction stirred for 2 h. A further portion of lithium hydroxide monohydrate (346 mg, 8.24 mmol) was then added and the reaction was heated at 45° C. for 1.5 h. The THF was then evaporated and water layer was extracted with diethyl ether (10 mL). The remaining aqueous layer was acidified with 5% w/v aqueous citric acid and extracted (2×50 mL) with ethyl acetate and the combined organic layers were dried (MgSO$_4$), filtered and evaporated to afford the title compound as a gum (2.54 g, 71%).

$^1$H NMR δ (d$_6$-DMSO): 0.00 (s, 3H), 0.02 (s, 3H), 0.80 (s, 9H), 1.22 (d, 3H), 3.20 (s, 3H), 3.71 (m, 2H), 4.60 (m, 1H), 7.00 (s, 1H), 7.12 (s, 1H), 7.22 (d, 2H), 7.36 (s, 1H), 7.94 (d, 2H).

m/z 479 (M–H)$^-$

Methyl 3-((1S)-2-{[tert-butyl(dimethyl)silyl]oxy}-1-methylethoxy)-5-[4-(methylsulfonyl)phenoxy]benzoate

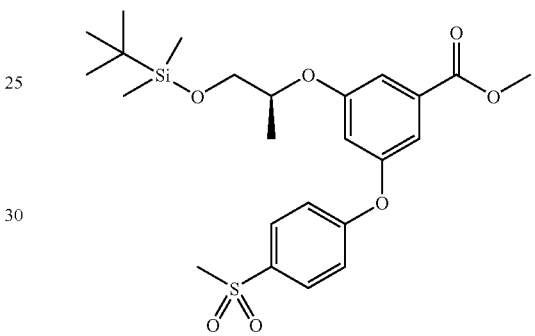

(2R)-1-{[tert-Butyl(dimethyl)silyl]oxy}propan-2-ol (2.18 g, 11.47 mmol) was added to a solution of methyl 3-hydroxy-5-[4-(methylsulfonyl)phenoxy]benzoate (2.76 g, 8.57 mmol) in dry DCM (100 mL) followed by addition of polymer-supported triphenylphosphine (3.0 mmol/g (Fluka), 8.57 g, 25.71 mmol) and DIAD (3.37 mL, 17.1 mmol) at RT. The reaction was stirred for 3 h before filtration through diatomaceous earth and evaporation. Purification by column chromatography, eluting with 1:4 to 1:2 ethyl acetate:hexanes, afforded the title compound as a colourless oil (3.70 g, 87%).

$^1$H NMR δ (CDCl$_3$): 0.03 (m, 6H), 0.84 (s, 9H), 1.33 (d, 3H), 3.07 (s, 3H), 3.48 (dd, 1H), 3.79 (dd, 1H), 3.92 (s, 1H), 4.50 (m, 1H), 6.92 (s, 1H), 7.11 (d, 2H), 7.29 (s, 1H), 7.47 (s, 1H), 7.92 (d, 2H). m/z 493 (M–H)$^-$

Methyl 3-hydroxy-5-[4-(methylsulfonyl)phenoxy]benzoate

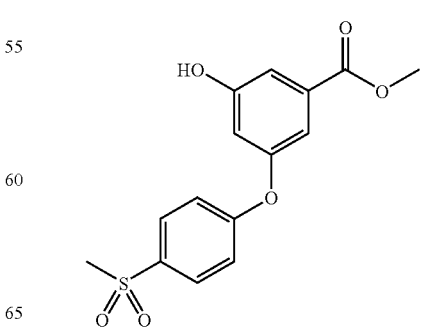

Methyl 3-(phenylmethyl)oxy-5-[4-(methylsulfonyl)phenoxy]benzoate (3.50 g, 8.50 mmol) was dissolved in THF (60 mL) followed by 10% palladium on carbon (500 mg). The reaction was then placed under a hydrogen atmosphere by an evacuation-backfill technique. The reaction was then stirred vigorously for 4 h followed by filtration and evaporation which afforded the title compound as an colourless oil (2.75 g, 100%).

$^1$H NMR δ (CDCl$_3$): 3.07 (s, 3H), 3.93 (s, 3H), 6.90 (s, 1H), 7.13 (d, 2H), 7.31 (s, 1H), 7.40 (s, 1H), 7.96 (d, 2H). m/z 321 (M−H)$^-$

Methyl 3-(phenylmethyl)oxy-5-[4-(methylsulfonyl)phenoxy]benzoate

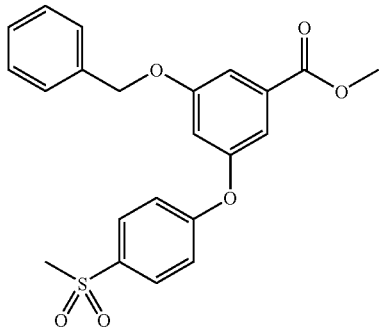

Potassium carbonate (3.21 g, 23.2 mmol) was added to a solution of methyl 3-hydroxy-5-{[phenylmethyl]oxy}benzoate (3.00 g, 11.6 mmol) in DMF (30 mL) followed by addition of 1-fluoro-4-(methylsulfonyl)benzene (2.02 g, 11.6 mmol) and the reaction was heated at 120° C. for 3 h. The solvent was then removed in vacuo and the residue was taken up in saturated aqueous sodium hydrogencarbonate (50 mL) and ethyl acetate (150 mL). The organic layer was separated, washed with 1M aqueous hydrochloric acid (50 mL) then dried (MgSO$_4$), filtered and evaporated. Purification by column chromatography, eluting with 1:4 to 1:1 ethyl acetate:hexanes, afforded the title compound as a colourless oil (3.50 g, 73%).

$^1$H NMR δ (CDCl$_3$): 3.07 (s, 3H), 3.92 (s, 3H), 5.13 (s, 2H), 6.87 (m, 1H), 7.10 (d, 2H), 7.38 (m, 6H), 7.56 (s, 1H), 7.90 (d, 2H). m/z 411 (M−H)$^-$

Methyl 3-hydroxy-5{[phenylmethyl]oxy}benzoate

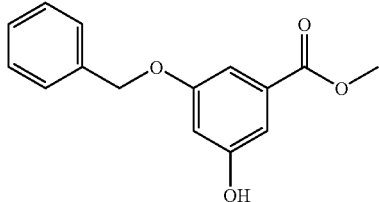

To a stirred solution of methyl 3,5-dihydroxybenzoate (5.95 mol) in DMF (6 L) was added potassium carbonate (9 mol), and the suspension stirred at ambient temperature under argon. To this was added benzyl bromide (8.42 mol) slowly over 1 hour, with a slight exotherm, and the reaction mixture stirred overnight at ambient temperature. The reaction was quenched cautiously with ammonium chloride solution (5 L) followed by water (35 L). The aqueous suspension was extracted with DCM (1×3 L and 2×5 L). The combined extracts were washed with water (10 L) and dried overnight (MgSO$_4$). The solution was evaporated in vacuo, and the crude product chromatographed in 3 batches (flash column, 3×2 kg silica, eluting with a gradient consisting of hexane containing 10% DCM, to neat DCM, to DCM containing 50% ethyl acetate) to eliminate starting material. The crude eluant was further chromatographed in 175 g batches (Amicon HPLC, 5 kg normal-phase silica, eluting with isohexane containing 20% v/v of ethyl acetate) to give the desired compound (21% yield); $^1$H $^1$H NMR δ (d$_6$-DMSO): 3.8 (s, 3H), 5.1 (s, 2H), 6.65 (m, 1H), 7.0 (m, 1H), 7.05 (m, 1H), 7.3-7.5 (m, 5H), 9.85 (br s, 1H).

(2R)-1-{[tert-Butyl(dimethyl)silyl]oxy}propan-2-ol

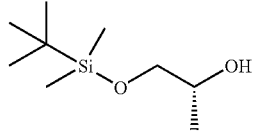

tert-Butyl(dimethyl)silyl chloride (5.90 g, 39-5 mmol) was added to a solution of (2R)-propane-1,2-diol (3.00 g, 39.5 mmol) in DCM (100 mL) followed by diisopropylethylamine (7.10 g, 55.3 mmol) and the reaction was stirred under argon for 72 h. The reaction was diluted with diethyl ether (500 mL) and water (140 mL) and the organic layer was separated then dried (MgSO$_4$), filtered and evaporated. Purification by column chromatography, eluting with 1:15 to 1:10 ethyl acetate:hexane, afforded the title compound as a colourless oil (6.00 g, 80%).

$^1$H NMR δ (CDCl$_3$): 0.10 (m, 6H), 0.92 (s, 9H), 1.14 (d, 3H), 2.42 (d, 1H), 3.38 (dd, 1H), 3.60 (dd, 1H), 3.82 (m, 1H).

The data matched that reported in the literature (*J. Org. Chem.*, 1998, 53, 2300).

REFERENCE EXAMPLE 2

3-[(1S)-2-Hydroxy-1-methylethoxy]-N-[4-(methoxymethyl)-1,3-thiazol-2-yl]-5-[4-(methylsulfonyl)phenoxy]benzamide

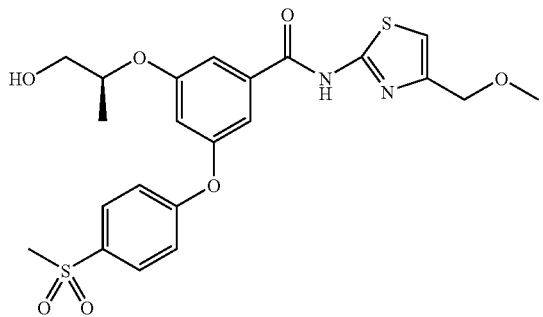

TFA (2 mL) was added to a solution of 3-((1S)-2-{[tert-butyl(dimethyl)silyl]oxy}-1-methylethoxy)-N-[4-(methoxymethyl)-1,3-thiazol-2-yl]-5-[4-(methylsulfonyl)phenoxy]benzamide (325 mg, 0.536 mmol) in DCM (4 mL) and water (1 mL) and the reaction was stirred for 1 h. The reaction was basified to pH7-8 with saturated aqueous sodium hydrogencarbonate and then extracted with DCM (2×20 mL). The combined organic layers were dried (MgSO$_4$), filtered and evaporated and purified by column chromatography, eluting with 50% to 100% ethyl acetate in hexanes, to afford the title compound as a white foam (147 mg, 56%).

$^1$H NMR δ (CDCl$_3$): 1.15 (d, 3H), 2.12 (br s, 1H), 2.95 (s, 3H), 3.28 (s, 3H), 3.63 (m, 2H), 4.28 (s, 2H), 4.44 (m, 1H), 6.70 (s, 1H), 6.75 (s, 1H), 6.97 (d, 2H), 7.17 (s, 1H), 7.80 (d, 2H), 9.63 (br s, 1H). m/z 491 (M−H)$^-$

The following compounds were synthesised in an analogous fashion from the appropriate protected ethers:

| Example | Structure | m/z | NMR |
|---|---|---|---|
| 2a | 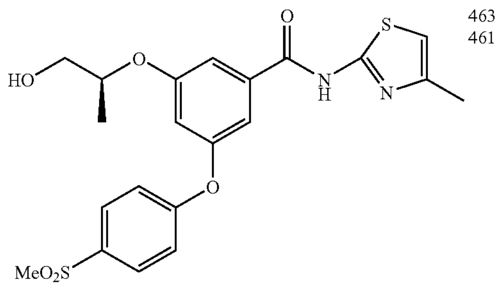 | 463 (M + H)+<br>461 (M − H)− | 1H NMR δ (CDCl3): 1.29 (d, 3H), 2.28 (s, 3H), 3.09 (s, 3H), 3.77 (m, 2H), 4.55 (m, 1H), 6.58 (s, 1H), 6.80 (s, 1H), 7.13 (m, 3H), 7.30 (s, 1H), 7.92 (d, 2H), 10.40 (br s, 1H) |
| Ref Eg 2b | 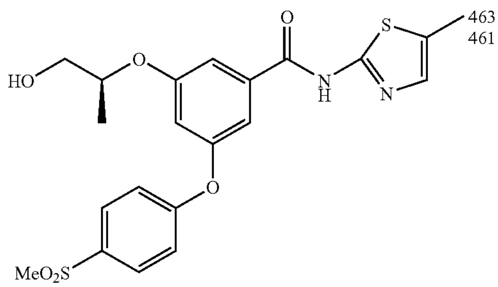 | 463 (M + H)+<br>461 (M − H)− | 1H NMR δ (CDCl3): 1.30 (d, 3H), 2.38 (s, 3H), 3.08 (s, 3H), 3.77 (m, 2H), 4.56 (m, 1H), 6.82 (s, 1H), 6.95 (s, 1H), 7.13 (d, 2H), 7.20 (s, 1H), 7.32 (s, 1H), 7.92 (d, 2H), 10.95 (br s, 1H) |
| 2c$ | 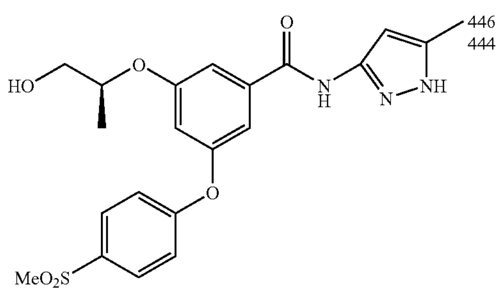 | 446 (M + H)+<br>444 (M − H)− | 1H NMR δ (CDCl3): 1.29 (d, 3H), 2.31 (s, 3H), 3.06 (s, 3H), 4.75 (m, 2H), 4.54 (m, 1H), 6.60 (br s, 1H), 6.79 (s, 1H), 7.12 (d, 2H), 7.14 (s, 1H), 7.31 (s, 1H), 7.91 (d, 2H), 9.04 (br s, 1H) |

$TFA:DCM:water (2:2:1, 5 mL total volume) was used, and the product purified by column chromatography eluting with 1:20 to 1:10 methanol:DCM The precursor for Reference Example 2 was prepared as described below:

3-((1S)-2-{[tert-Butyl(dimethyl)silyl]oxy}-1-methylethoxy)-N-[4-(methoxymethyl)-1,3-thiazol-2-yl]-5-[4-(methylsulfonyl)phenoxy]benzamide

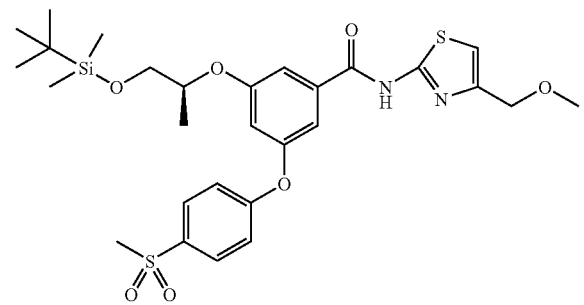

HATU (446 mg, 1.17 mmol) was added to 3-((1S)-2-{[tert-Butyl(dimethyl)silyl]oxy}-1-methylethoxy)-5-[4-(methylsulfonyl)phenoxy]benzoic acid (450 mg, 0.94 mmol) followed by addition of DMF (4.5 mL), DIPEA (0.42 mL) and 4-(methoxymethyl)-1,3-thiazol-2-amine (160 mg, 1.11 mmol) and the reaction was stirred under argon for 4 h. The solvent was evaporated and the residue was dissolved in saturated aqueous sodium hydrogencarbonate (30 mL) and ethyl acetate (50 mL). The organic layer was separated, washed with saturated aqueous ammonium chloride (30 mL) then dried (MgSO4), filtered and evaporated. Purification by column chromatography, eluting with 1:2 to 2:1 ethyl acetate:hexanes, afforded the title compound as a colourless oil (325 mg, 56%).

m/z 607 (M+H)+, 605 (M−H)−

The synthesis of 3-((1S)-2-{[tert-butyl(dimethyl)silyl]oxy}-1-methylethoxy)-5-[4-(methylsulfonyl)phenoxy]benzoic acid is described above in Example 1.

In a similar manner, the precursors for Examples 2a-2c were prepared using the appropriate amine:

| Structure | m/z | NMR |
|---|---|---|
| 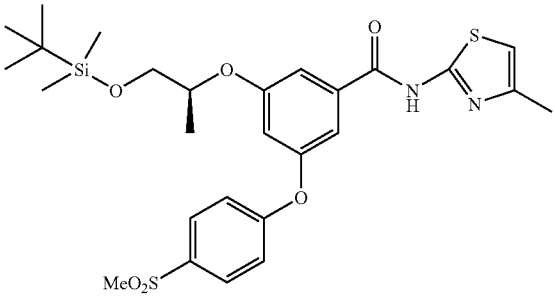 | 577 (M + H)⁺<br>575 (M − H)⁻ | |
| 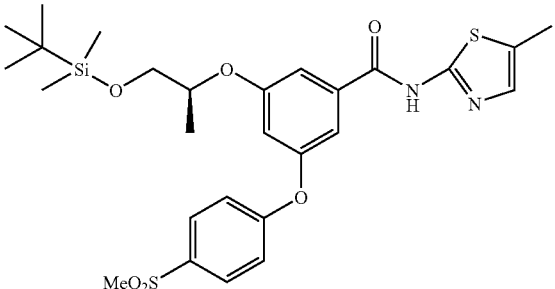 | 577 (M + H)⁺<br>575 (M − H)⁻ | |
| 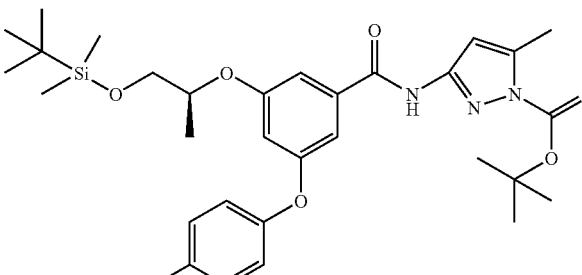 | 660 (M + H)⁺<br>658 (M − H)⁻ | |

The required amine for Reference Example 2 was prepared as follows:

4-(Methoxymethyl)-1,3-thiazol-2-amine

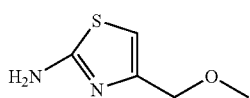

Sodium hexamethyldisilazide (10M in THF, 0.67 mL, 0.67 mmol) was added to a solution of 4-(chloromethyl)-1,3-thiazol-2-amine (*J. Indian Chem. Soc.* 1960, 37, 241; 100 mg, 0.67 mmol) in methanol (5 mL) followed by stirring under argon at ambient temperature for 72 h. The solvent was then removed under reduced pressure and the residue was taken up in saturated aqueous sodium hydrogencarbonate (20 mL) and ethyl acetate (50 mL). The organic layer was separated then dried ($MgSO_4$); filtered and evaporated. Purification by column chromatography, eluting with 80% to 100% ethyl acetate in hexanes, afforded the title compound as a colourless oil (20 mg, 21%).

$^1$H NMR δ ($CDCl_3$): 3.42 (s, 3H), 4.31 (s, 2H), 5.05 (br s, 2H), 6.42 (s, 1H).

The required amine for Example 2c was prepared as follows:

tert-Butyl 3-amino-5-methyl-1H-pyrazole-1-carboxylate

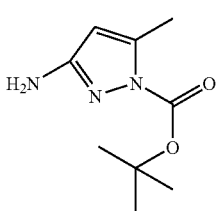

5-Methyl-1H-pyrazol-3-amine (800 mg, 8.25 mmol) was dissolved in DMF (10 mL) at 0° C. and treated with sodium hydride (336 mg, 8.25 mmol) followed by stirring for a further 30 min. Warmed di-tert-butyl dicarbonate (1.80 g, 8.25 mmol) was then slowly added via syringe over 5 min and the reaction was allowed to warm to RT and stirred for a further 1 h. The reaction was taken up in saturated aqueous sodium hydrogencarbonate (50 mL) and ethyl acetate (100 mL). The organic layer was separated then dried ($MgSO_4$), filtered and evaporated. Purification by column chromatography, eluting with 50% to 100% ethyl acetate in hexanes, afforded the title compound as a colourless oil (380 mg, 23%).

¹H NMR δ (CDCl₃): 1.62 (s, 9H), 2.43 (s, 3H), 3.87 (br s, 2H), 5.60 (s, 1H).

REFERENCE EXAMPLE 3

3-[(1S)-2-Hydroxy-1-methylethoxy]-N-(1-methyl-1H-pyrazol-3-yl)-5-[4-(methylsulfonyl)phenoxy]benzamide

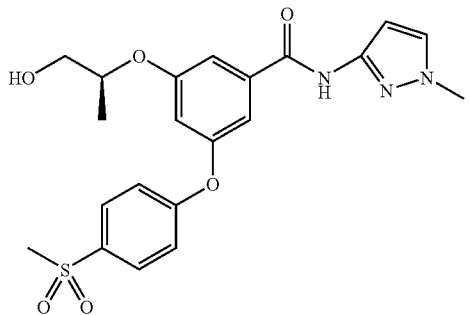

Trimethylsilyl iodide (11.1 mL, 76.3 mmol) was added to a solution of 3-[(1S)-2-methoxy-1-methylethoxy]-N-(1-methyl-1H-pyrazol-3-yl)-5-[4-(methylsulfonyl)phenoxy]benzamide (7.00 g, 15.3 mmol) in dry acetonitrile (100 mL) under argon for 21 h. Water (40 mL) was added to quench the reaction and the acetonitrile was removed in vacuo. The residue was diluted with ethyl acetate-(200 mL) and 1M aqueous hydrochloric acid. The organic layer was separated and further washed with 10% w/v aqueous sodium thiosulfate pentahydrate to remove residual iodine. The organic layer Was separated, dried (MgSO₄), filtered and evaporated and purified by column chromatography, eluting with 3% to 5% methanol in DCM, to give the title compound as a white foam (5.70 g, 84%). Recrystallisation from hot ethanol (125 mg/mL) afforded the title compound as colourless needles (87% recovery). Mpt 126-132° C.

¹H NMR δ (CDCl₃): 1.33 (d, 3H), 2.10 (t, 1H), 3.08 (s, 3H), 3.78 (m, 2H), 3.82 (s, 3H), 4.57 (m, 1H), 6.80 (m, 2H), 7.15 (m, 3H), 7.25 (m, 2H), 7.93 (d, 2H), 8.43 (s, 1H). m/z 444 (M−H)⁻

The following compounds were prepared in a similar manner:

| Ref Example | Structure | m/z | NMR |
|---|---|---|---|
| 3a$ | 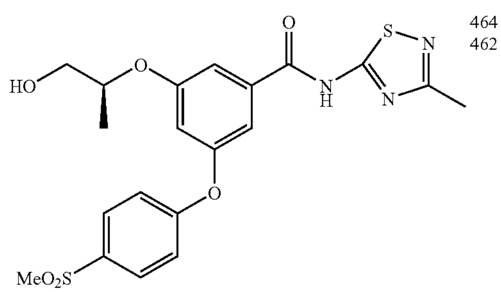 | 464 (M + H)⁺<br>462 (M − H)⁻ | ¹H NMR δ (CDCl₃): 1.31 (d, 3H), 2.52 (s, 3H), 3.12 (s, 3H), 3.80 (m, 2H), 4.49 (m, 1H), 6.90 (s, 1H), 7.18 (m, 3H), 7.30 (s, 1H), 7.97 (d, 2H), 10.35 (br s, 1H) |
| 3b$$ | 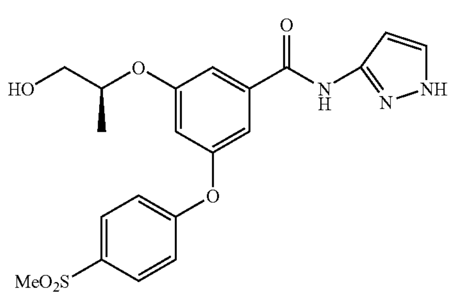 | 432 (M + H)⁺<br>430 (M − H)⁻ | ¹H NMR δ (D6-DMSO): 1.23 (d, 2H), 3.20 (s, 3H, obscured by water), 3.45-3.58 (m, 2H), 4.57 (m, 1H), 6.58 (br s, 1H), 6.90 (m, 1H), 7.12 (d, 2H), 7.29 (s, 1H), 7.47 (s, 1H), 7.62 (s, 1H), 7.92 (d, 2H), 10.84 (br s, 1H) |

$Purification by column chromatography eluting with 7:3 ethyl acetate:hexanes to neat ethyl acetate $$Purification by column chromatography eluting with 0-15% methanol in ethyl acetate The starting materials required for the preparation of Reference Examples 3 & 3a were prepared as follows:

3-[(1S)-2-Methoxy-1-methylethoxy]-N-(1-methyl-1H-pyrazol-3-yl)-5-[4-(methylsulfonyl)phenoxy]benzamide & 3-[(1S)-2-methoxy-(1-methylethyl)oxy]-5-[4-(methylsulfonyl)phenoxy]-N-(3-methyl-1,2,4-thiadiazol-5-yl)benzamide DIPEA (2.5 equivalents) was added to a suspension of 3-{(1S)-2-methoxy-(1-methylethyl)oxy}-5-{[4-(methylsulfonyl)phenyl]oxy}benzoic acid (1 equivalent), HATU (1.25 equivalents) and the appropriate amine (1.25 equivalents) in DMF (20 mL). The initial suspension dissolved into a dark orange solution. The resulting mixture was stirred at ambient temperature for 2 hours. The DMF was removed in vacuo, and the residue azeotroped with toluene. Water was added and the mixture extracted with ethyl acetate. The extracts were combined and washed sequentially with 1M hydrochloric acid, saturated sodium hydrogen carbonate solution and brine. The solution was dried (MgSO$_4$), filtered, and evaporated in vacuo to give the crude product which was chromatographed (50% ethyl acetate in isohexane) to give desired compound (40-70% yield).

3-{(1S)-2-Methoxy-(1-methylethyl)oxy}-5-{[4-(methylsulfonyl)phenyl]oxy}benzoic acid

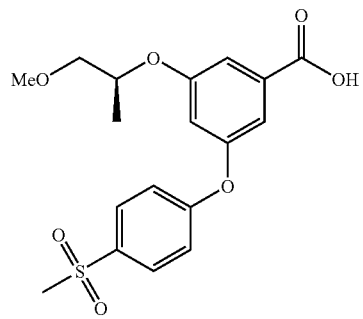

A solution of methyl 3-[(1S)-2-methoxy-(1-methylethyl)oxy]-5-{[4-(methylsulfonyl)phenyl]oxy}benzoate (60.9 mmol) in THF (400 mL) was treated with a solution of 1M sodium hydroxide (125 mmol), and the reaction mixture stirred for 13 hours at ambient temperature. Most of the organic solvent was removed in vacuo, and the remaining solution was diluted with water (150 mL). The resulting aqueous solution was acidified to pH4 with 1M citric acid solution, and extracted with ethyl acetate (2×100 mL). The extracts

| Structure | m/z | NMR |
|---|---|---|
|  | 460 (M + H)⁺ | $^1$H NMR δ (d$_6$-DMSO): 1.2 (d, 3H), 3.2 (s, 3H), 3.25 (s, 3H), 3.5 (m, 2H), 3.8 (s, 3H), 4.75 (m, 1H), 6.55 (s, 1H), 6.9 (s, 1H), 7.2 (d, 2H), 7.3 (s, 1H), 7.45 (s, 1H), 7.6 (s, 1H), 7.9 (d, 2H), 10.85 (br s, 1H) |
|  | 478 (M + H)⁺<br>476 (M − H)⁻ | $^1$H NMR δ (d$_6$-DMSO): 1.2 (d, 3H), 2.5 (s, 3H), 3.2 (s, 3H), 3.25 (s, 3H), 3.5 (m, 2H), 4.75 (m, 1H), 7.0 (s, 1H), 7.2 (d, 2H), 7.4 (s, 1H), 7.6 (s, 1H), 7.95 (d, 2H), 13.5 (br s, 1H) | were combined, washed with brine, dried (MgSO$_4$), and evaporated to give the desired compound (83% yield).

$^1$H NMR δ (d$_6$-DMSO): 1.2 (d, 3H), 3.2 (s, 3H), 3.26 (s, 3H), 3.44 (m, 2H), 4.63 (m, 1H), 7.05 (s, 1H), 7.11 (s, 1H), 7.2 (d, 2H), 7.3 (s, 1H), 7.9 (d, 2H). m/z 479 (M–H)$^-$

Methyl 3-[(1S)-2-methoxy-(1-methylethyl)oxy]-5-{[4-(methylsulfonyl)phenyl]oxy}benzoate

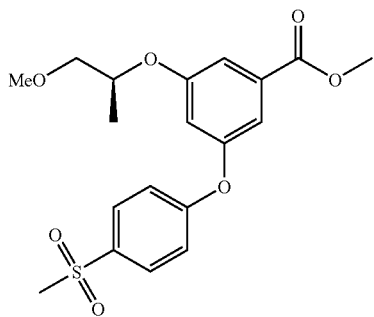

A suspension of methyl 3-hydroxy-5-[(1S)-2-methoxy-(1-methylethyl)oxy]benzoate (154 mmol), boronic acid (1.1 equivalents), copper (II) acetate (1.1 equivalents), triethylamine (5 equivalents) and freshly activated 4 Å molecular sieves (200 g) in DCM (500 mL) was stirred at ambient temperature and under ambient atmosphere for 2 days. The reaction mixture was filtered, the DCM removed in vacuo and the residual oil partitioned between ethyl acetate and 1-2M hydrochloric acid. The ethyl acetate layer was separated, washed with aqueous sodium hydrogen carbonate and brine, dried (MgSO$_4$), and evaporated to a residue which was chromatographed on silica (with 20-60% ethyl acetate in isohexane as eluant) to give the desired ester (58% yield).

$^1$H NMR δ (d$_6$-DMSO): 1.2 (d, 3H), 3.2 (s, 3H), 3.26 (s, 3H), 3.44 (m, 2H), 3.8 (s, 3H), 4.65 (m, 1H), 7.05 (s, 1H), 7.11 (s, 1H), 7.2 (d, 2H), 7.3 (s, 1H), 7.9 (d, 2H)

Methyl 3-Hydroxy-5-[(1S)-2-methoxy-(1-methylethyl)oxy]benzoate

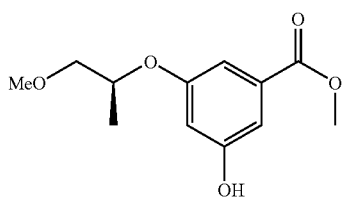

Methyl 3-[(1S)-2-methoxy-(1-methylethyl)oxy]-5-{[phenylmethyl]oxy}benzoate (50.0 g, 0.152 mmol) was dissolved in a mixture of THF:ethanol (600 mL) and the flask evacuated and purged with nitrogen (3 times). 10% Palladium on carbon (5.0 g) was added and the flask further evacuated and finally purged with hydrogen gas. The reaction mixture was stirred at ambient temperature for 20 hours until completion. The reaction mixture was evacuated and purged with nitrogen (3 times). The catalyst was filtered off, and the filtrate concentrated in vacuo to give the desired compound (36.7 g).

$^1$H NMR δ (d$_6$-DMSO): 1.2 (d, 3H), 3.25 (s, 3H), 3.44 (m, 2H), 3.82 (s, 3H), 4.55 (m, 1H), 6.6 (s, 1H), 6.9 (s, 1H), 6.95 (s, 1H), 9.8 (s, 1H).

Methyl 3-[(1S)-2-methoxy-(1-methylethyl)oxy]-5-{[phenylmethyl]oxy}benzoate

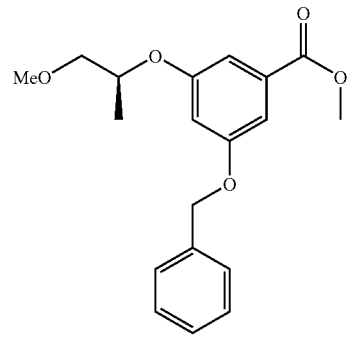

To a solution of methyl 3-hydroxy-5-{[phenylmethyl]oxy}benzoate (77.4 mmol) in THF was added polymer-supported triphenylphosphine (51.7 g of 3 mmol/g loading, 155 mmol) and (R)-(–)-1-methoxy-2-propanol (102 mmol). The stirred solution was blanketed with argon and cooled in an ice bath. A solution of DIAD (116 mmol) was added dropwise by syringe over 10 minutes. The solution was stirred for 20 minutes and filtered, washing the residue with THF (500 mL). The filtrate and washings were combined, and evaporated to give the desired compound which was used without further purification.

$^1$H NMR δ (d$_6$-DMSO): 3.26 (s, 3H), 3.44 (m, 2H), 3.82 (s, 3H), 4.63 (m, 1H), 5.14 (s, 2H), 6.85 (s, 1H), 7.05 (s, 1H), 7.11 (s, 1H), 7.30-7.47 (m, 5H). The $^1$H NMR spectrum also contained signals consistent with a small amount of bis(1-methylethyl)hydrazine-1,2-dicarboxylate.

The synthesis of methyl 3-hydroxy-5-{[phenylmethyl]oxy}benzoate is described above in Reference Example 1.

The starting material required for the preparation of Example 3b was prepared as follows:

3-[(1S)-2-Methoxy-1-methylethoxy]-5-[4-(methylsulfonyl)phenoxy]-N-1H-pyrazol-3-ylbenzamide

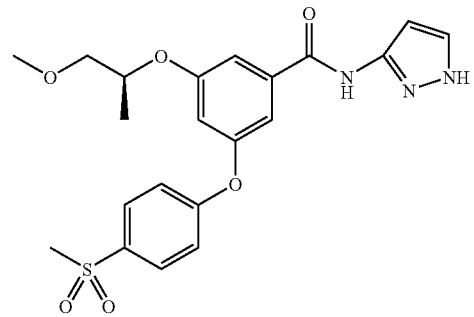

TFA (0.5 mL) was added to a solution of tert-butyl 3-({3-[(1S)-2-methoxy-1-methylethoxy]-5-[4-(methylsulfonyl)phenoxy]benzoyl}amino)-1H-pyrazole-1-carboxylate (180 mg, 0.330 mmol) in dry DCM (3 mL) and the reaction was stirred under argon for 3 h. A further portion of TFA (0.2 mL) was then added and the reaction was stirred for 30 min before all the solvent was removed in vacuo. The residue was taken up in ethyl acetate (30 mL) and saturated aqueous sodium hydrogencarbonate (15 mL) and the residue was evaporated then re-evaporated with DCM/hexanes to produce the title compound as a colourless foam (145 mg, 100%).

¹H NMR δ (d₆-DMSO): 1.27 (d, 3H), 3.22 (s, 3H), 3.31 (s, 3H), 3.60 (m, 2H, partially obscured by HOD), 4.78 (m, 1H), 6.62 (s, 1H), 6.93 (s, 1H), 7.27 (d, 2H), 7.32 (s, 1H), 7.53 (s, 1H), 7.65 (s, 1H), 7.96 (d, 2H), 10.86 (s, 1H). m/z 444 (M−H)⁻ tert-Butyl 3-({3-[(1S)-2-methoxy-1-methylethoxy]-5-[4-(methylsulfonyl)phenoxy]benzoyl}amino)-1H-pyrazole-1-carboxylate,

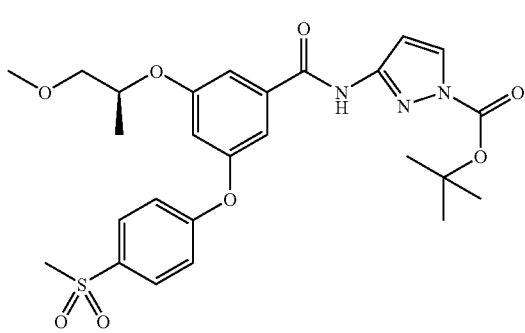

HATU (375 mg, 1.17 mmol) was added to 3-{(1S)-2-methoxy-(1-methylethyl)oxy}-5-{[4-(methylsulfonyl)phenyl]oxy}benzoic acid (300 mg, 0.79 mmol) followed by addition of DMF (5 mL), DIPEA (0.35 mL) and tert-butyl 3-amino-1H-pyrazole-1-carboxylate (155 mg, 0.85 mmol) and the reaction was stirred under argon for 4 h. The solvent was evaporated and the residue was dissolved in saturated aqueous sodium hydrogencarbonate (30 mL) and ethyl acetate (50 mL). The organic layer was separated, washed with saturated aqueous ammonium chloride (30 mL) then dried (MgSO₄), filtered and evaporated. Purification by column chromatography, eluting with 50% ethyl acetate in hexanes, afforded the title compound as a colourless oil (185 mg, 43%).

¹H NMR δ (CDCl₃): 1.37 (d, 3H), 1.63 (s, 9H), 3.09 (s, 3H), 3.40 (s, 3H), 3.58 (m, 2H), 4.61 (m, 1H), 6.85 (s, 1H), 7.08 (m, 2H), 7.15 (d, 2H), 7.30 (s, 1H), 7.92 (d, 2H), 8.01 (d, 1H), 8.58 (br s, 1H). m/z 544 (M−H)⁻ tert-Butyl 3-amino-1H-pyrazole-1-carboxylate

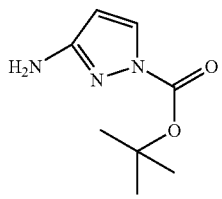

1H-Pyrazol-3-amine (428 mg, 5.15 mmol) was dissolved in DMF (5 mL) at 0° C. and treated with sodium hydride (206 mg, 5.15 mmol) followed by stirring for a further 30 min. Warmed di-tert-butyl dicarbonate (1.12 g, 5.15 mmol) was then slowly added via syringe over 5 min and the reaction was allowed to warm to RT and stirred for a further 2 h. The reaction was taken up in saturated aqueous sodium hydrogencarbonate (50 mL) and ethyl acetate (100 mL). The organic layer was separated then dried (MgSO₄), filtered and evaporated. Purification by column chromatography (eluting with 1:1 ethyl acetate:hexanes to neat ethyl acetate) afforded the title compound as a white solid (117 mg, 18%).

¹H NMR δ (CDCl₃): 1.62 (s, 9H), 4.00 (br s, 2H), 5.81 (d, 1H), 7.82 (d, 1H).

EXAMPLE 4

3-[4-(Azetidin-1-ylcarbonyl)-2-fluorophenoxy]-5-[(1S)-2-hydroxy-1-methylethoxy]-N-(1-methyl-1H-pyrazol-3-yl)benzamide

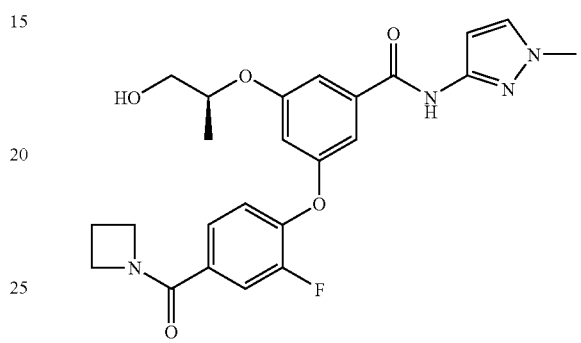

DIPEA (93 mg, 0.72 mmol; 4.0 equivalents) was added to a suspension of 3-[4-(azetidin-1-ylcarbonyl)-2-fluorophenoxy]-5-[(1S)-2-hydroxy-1-methylethoxy]benzoic acid (70 mg), HATU-(144 mmol; 2.1 equivalents) and 1-methyl-1-H-pyrazole-3-amine (26 mg, 0.27 mmol, 1.5 equivalents) in DMF (2 mL). The resulting mixture was stirred at ambient temperature for 16 hours. The DMF was removed in vacuo, water was added and the mixture extracted with ethyl acetate. The extracts were combined, washed with brine, dried (MgSO₄), filtered, and evaporated in vacuo to give the crude product which was chromatographed, eluting with 0-100% ethyl acetate in isohexane, to give desired compound (45 mg).

¹H NMR δ (d₆-DMSO): 1.22 (d, 3H), 2.24 (m, 2H), 3.51 (m, 2H), 3.76 (s, 3H), 4.03 (m, 2H), 4.34 (m, 2H), 4.56 (m, 1H), 4.83 (t, 1H), 6.54 (s, 1H), 6.78 (m, 1H), 7.14 (s, 1H), 7.21 (t, 1H), 7.41 (s, 1H), 7.48 (d, 1H), 7.56 (s, 1H), 7.62 (d, 1H), 10.83 (br s, 1H). m/z 469 (M+H)⁺ The material can be crystallised from ethylacetate, toluene and isohexane mixture after purification by chromatography (on silica and then/or on neutral alumina) and, where necessary, treatment with activated charcoal; mpt 142° C.

3-[4-(Azetidin-1-ylcarbonyl)-2-fluorophenoxy]-5-[(1S)-2-hydroxy-1-methylethoxy]benzoic acid

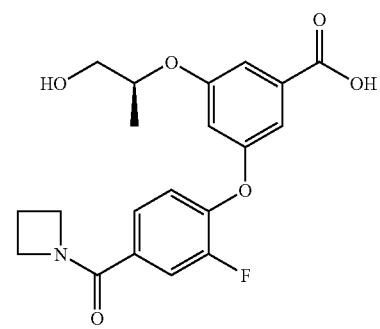

Methyl 3-[4-(azetidin-1-ylcarbonyl)-2-fluorophenoxy]-5-[(1S)-2-hydroxy-1-methylethoxy]benzoate (100 mg, 0.25 mmol) was dissolved in THF (2.0 mL and water (0.2 mL) and solid lithium hydroxide (21 mg, 0.5 mmol) added. The resultant mixture was stirred at ambient temperature for 16 hours. Water (10 mL) was added and the mixture partially reduced in vacuo and then extracted with ethyl acetate. The aqueous liquors were acidified with 1M hydrochloric acid and re-extracted with ethyl acetate (2×10 mL). The extracts were combined, washed with brine, dried (MgSO$_4$), filtered, and evaporated in vacuo to give the crude product which was used without further purification (70 mg).

$^1$H NMR δ (d$_6$-DMSO): 1.16 (d, 3H), 2.24 (m, 2H), 3.46 (m, 2H), 4.02 (m, 2H), 4.33 (m, 2H), 4.45 (m, 1H), 4.82 (t, 1H), 6.89 (s, 1H), 7.00 (m, 1H), 7.23 (m, 2H), 7.48 (d, 1H), 7.61 (d, 1H), COOH not seen. m/z 390 (M+H)$^+$ Methyl 3-[4-(azetidin-1-ylcarbonyl)-2-fluorophenoxy]-5-[(1S)-2-hydroxy-1-methylethoxy]benzoate

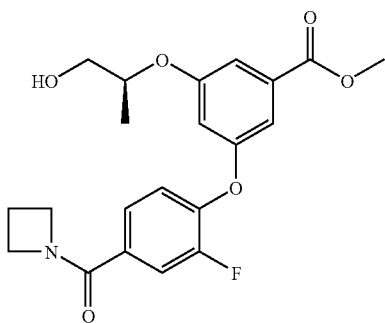

To a portion of methyl 3-((1S)-2-{[tert-butyl(dimethyl)silyl]oxy}-1-methylethoxy)-5-hydroxybenzoate (102 mg, 0.3 mmol) and 1-(3,4-difluorobenzoyl)azetidine (71 mg, 0.36 mmol) in DMF (2.0 mL) was added potassium carbonate (207 mg, 1.5 mmol) and the stirred mixture heated at 160° C. in a 'Smith Creator Microwave' for 120 minutes. The mixture was allowed to reach ambient temperature and pressure then partitioned between ethyl acetate (2×25 mL) and water (25 mL). The organic layer was separated, washed with brine, dried (MgSO$_4$), and evaporated in vacuo to give the crude product which was used without further purification (100 mg).
m/z 404 (M+H)$^+$ Methyl 3-((1S)-2-{[tert-butyl(dimethyl)silyl]oxy}-1-methylethoxy)-5-hydroxybenzoate

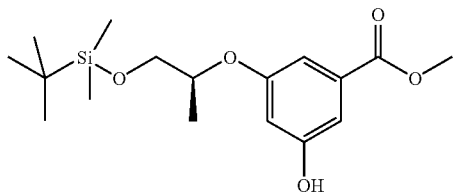

Methyl 3-((1S)-2-{[tert-butyl(dimethyl)silyl]oxy}-1-methylethoxy)-5-[(phenylmethyl)oxy]benzoate (1000 mg, 2.33 mmol) was dissolved in methanol (30 mL) and 10% palladium on charcoal (100 mg) added. The mixture was stirred at ambient temperature for 36 h, filtered, evaporated in vacuo and chromatographed, 0-100% ethyl acetate in isohexane, to give methyl 3-((1S)-2-{[tert-butyl(dimethyl)silyl]oxy}-1-methylethoxy)-5-hydroxybenzoate (750 mg). The material was used without further purification.
m/z 341 (M+H)$^+$ Methyl 3-((1S)-2-{[tert-butyl(dimethyl)silyl]oxy}-1-methylethoxy)-5-[(phenylmethyl)oxy]benzoate

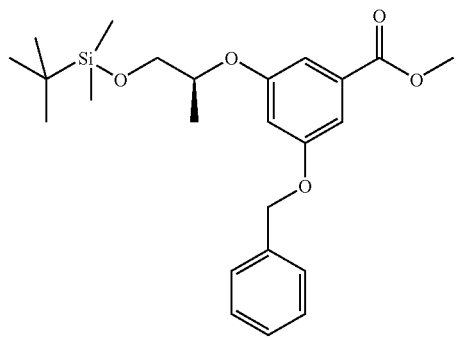

(2R)-1-{[tert-Butyl(dimethyl)silyl]oxy}propan-2-ol (3.31 g, 17.4 mmol) was added to a solution of methyl 3-hydroxy-5-{[phenylmethyl]oxy}benzoate (3.00 g, 11.6 mmol) in THF (50 mL) at 0° C. followed by addition of triphenylphosphine (4.57 g, 17.4 mmol) then DIAD (3.43 mL, 17.4 mmol) and the reaction was warmed to RT and stirred for 16 h. The reaction was quenched with water (100 mL) and diethyl ether (400 mL) and the organic layer was separated then dried (MgSO$_4$) and evaporated. Purification by column chromatography, eluting with 1:15 to 1:5 ethyl acetate:hexane, afforded the title compound as a colourless oil (4.00 g, 80%).

$^1$H NMR δ (CDCl$_3$): 0.03 (s, 3H), 0.05 (s, 3H), 0.89 (s, 9H), 1.29 (d, 3H), 3.63 (dd, 1H), 3.78 (dd, 1H), 3.92 (s, 3H), 4.44 (m, 1H), 5.08 (s, 2H), 6.77 (m, 1H), 7.40 (m, 7H)

EXAMPLE 5

3-[(3,5-Difluorophenyl)oxy]-5-{[(1S)-2-hydroxy-1-methylethyl]oxy}-N-(1-methyl-1H-pyrazol-3-yl)benzamide

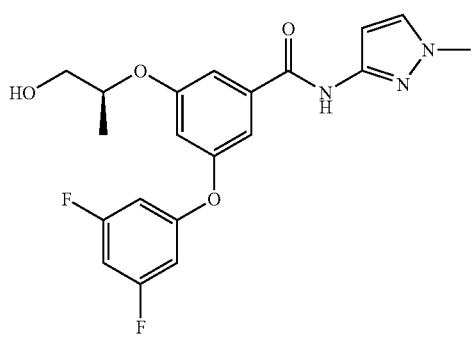

A solution of 3-((1S)-2-{[tert-butyl(dimethyl)silyl]oxy}-1-methylethyloxy)-5-hydroxy-N-(1-methyl-1H-pyrazol-3-yl)benzamide (202 mg, 0.5 mmol), 3,5-difluorophenylboronic acid (156 mg, 1.0 mmol), copper (II) acetate (182 mg, 1.0 mmol), triethylamine (252 mg, 2.5 mmol) and freshly activated 4 Å molecular sieves (1.5 g) in DCM (10 mL) was stirred at ambient temperature and under ambient atmosphere for 64 hours. The reaction mixture was filtered, washed with DCM (2×10 mL), evaporated in vacuo and the residual oil partitioned between ethyl acetate (25 mL) and 1M hydrochloric acid (10 mL). The ethyl acetate layer was separated, washed sequentially with aqueous sodium hydrogen carbonate solution and brine, dried (MgSO₄), and evaporated to a residue which was chromatographed by preparative HPLC on C18 reversed phase using 5-95% acetonitrile (+0.2% TFA) in water (+0.2% TFA) as eluant to give the title compound (45 mg).

¹H NMR δ (d₆-DMSO): 1.27 (d, 3H), 3.56 (m, 2H), 3.82 (s, 3H), 4.61 (m, 1H), 5.06 (br s, 1H), 6.58 (m, 1H), 6.85 (dd, 2H), 6.89, (m, 1H), 7.07 (m, 1H), 7.28 (m, 1H), 7.51 (m, 1H), 7.63 (m, 1H), 10.89, (br s, 1H). m/z 404 (M+H)⁺, 402 (M−H)⁻

The starting material for Example 5 was prepared as described below:

3-((1S)-2-{[tert-Butyl(dimethyl)silyl]oxy}-1-methylethyloxy)-5-hydroxy-N-(1-methyl-1H-pyrazol-3-yl)benzamide

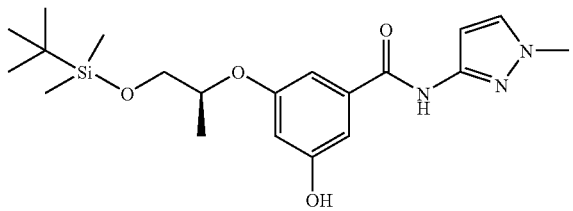

3-((1S)-2-{[tert-Butyl(dimethyl)silyl]oxy}-1-methylethyloxy)-5-(phenylmethyl)oxy-N-(1-methyl-1H-pyrazol-3-yl)benzamide (1.8 g, 3.64 mmol) was dissolved in methanol (50 mL) and the flask evacuated and purged with nitrogen (3 times). 10% Palladium on carbon (0.2 g) was added and the flask further evacuated and finally purged with hydrogen gas. The reaction mixture was stirred at ambient temperature for 16 hours until completion. The reaction mixture was evacuated and purged with nitrogen (3 times). The catalyst was filtered off, and the filtrate concentrated in vacuo to give the desired compound (1.45 g).

¹H NMR δ (d₆-DMSO): 0.02 (d, 6H), 0.83 (s, 9H), 1.18 (d, 3H), 3.66 (m, 2H), 3.72 (s, 3H), 4.51 (m, 1H), 6.42 (m, 1H), 6.52 (m, 1H), 6.90 (s, 1H), 7.02 (s, 1H), 7.55 (m, 1H), 9.58 (br s, 1H), 10.59 (br s, 1H). m/z 406 (M+H)⁺

3-((1S)-2-{[tert-Butyl(dimethyl)silyl]oxy}-1-methylethyloxy)-5-(phenylmethyl)oxy-N-(1-methyl-1H-pyrazol-3-yl)benzamide

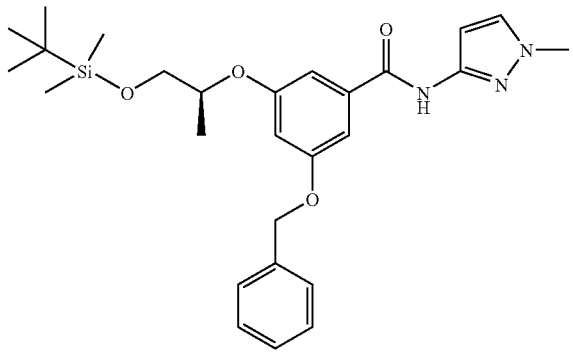

DIPEA (4.06 g, 23.4 mmol) was added to a suspension of 3-{(phenylmethyl)oxy}-5-((1S)-2-{[tert-butyl(dimethyl)silyl]oxy}-1-methylethoxy)benzoic acid (2.43 g, 5.84 mmol), 1-methyl-1H-pyrazole-3-amine (0.85 g, 8.76 mmol) and HATU (4.66 g, 12.3 mmol) in DMF (50 mL) and stirred at ambient temperature for 16 hours. The resultant mixture was partially reduced in vacuo, poured onto water (100 mL) and extracted with diethyl ether (2×50 mL). The extracts were washed with water and brine then dried (MgSO₄), filtered and reduced to an opaque gum which partially crystallized. The crude product was purified by column chromatography, eluting with 0-100% ethyl acetate in isohexane, to give the title compound as a colourless oil (1.87 g).

¹H NMR δ (d₆-DMSO): 0.02 (d, 6H), 0.84 (s, 9H), 1.21 (d, 3H), 3.68 (d, 2H), 3.76 (s, 3H), 4.58 (m, 1H), 5.13 (s, 2H), 6.56 (m, 1H), 6.70 (m, 1H), 7.18 (s, 1H), 7.24 (s, 1H), 7.29-7.46 (m, 5H), 7.57 (m, 1H), 10.74 (br s, 1H). m/z 496 (M+H)⁺

3-{(Phenylmethyl)oxy}-5-((1S)-2-{[tert-butyl(dimethyl)silyl]oxy}-1-methylethoxy)benzoic acid

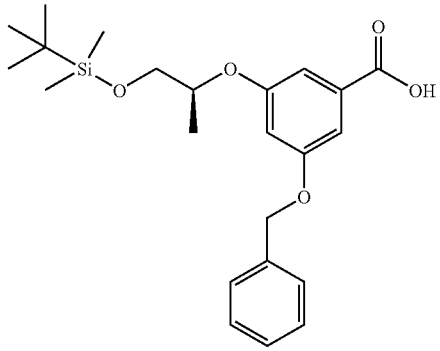

Methyl 3-((1S)-2-{[tert-butyl(dimethyl)silyl]oxy}-1-methylethoxy)-5-[(phenylmethyl)oxy]benzoate (3.0 g, 6.98 mmol) was dissolved in THF (50 mL) and water (10 mL) and lithium hydroxide monohydrate (586 mg, 13.95 mmol) added. The resultant mixture was heated with stirring at 45° C. for 2 hours, then at ambient temperature for 16 hours, and at 45° C. for a further 4 hours. Water (40 mL) was added and the solvent removed in vacuo. The resultant solution was acidified carefully with 1M citric acid (2 equivalents), washed with water and brine then dried (MgSO₄), filtered and evaporated in vacuo to give the title compound as a colourless gum (2.58 g).

¹H NMR δ (d₆-DMSO): 0.02 (d, 6H), 0.84 (s, 9H), 1.17 (d, 3H), 3.66 (m, 2H), 4.43 (m, 1H), 5.05 (s, 2H), 6.56 (br s, 1H), 7.10 (br s, 1H), 7.17 (br s, 1H), 7.25-7.44 (m, 5H), 7.60 (br s, 1H).

The synthesis of methyl 3-((1S)-2-{[tert-butyl(dimethyl)silyl]oxy}-1-methylethoxy)-5-[(phenylmethyl)oxy]benzoate is described above in Example 4.

EXAMPLE 6

3-{[4-(Azetidin-1-ylcarbonyl)-2-chlorophenyl]oxy}-5-{[(1S)-2-hydroxy-1-methylethyl]oxy}-N-(1-methyl-1H-pyrazol-3-yl)benzamide

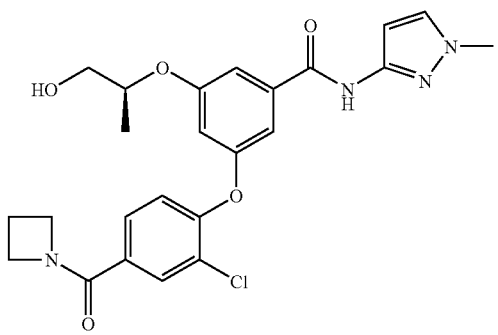

To a mixture of 3-((1S)-2-{[tert-butyl(dimethyl)silyl]oxy}-1-methylethyloxy)-5-hydroxy-N-(1-methyl-1H-pyrazol-3-yl)benzamide (215 mg, 0.53 mmol) and 1-(3-chloro-4-fluorobenzoyl)azetidine (135 mg, 0.63 mmol) in DMF (2.0 mL) was added potassium carbonate (146 mg, 1.06 mmol) and the stirred mixture heated at 160° C. in a 'Smith Creator Microwave' for 120 minutes. The mixture was allowed to reach ambient temperature and pressure then reduced in volume. Purification by column chromatography, eluting with 0-20% methanol in DCM, afforded the title compound (130 mg).

$^1$H NMR δ (CDCl$_3$): 1.22 (d, 3H), 2.14 (m, 2H), 3.50 (m, 2H), 3.76 (s, 3H), 4.05 (m, 2H), 4.33 (m, 2H), 4.56 (m, 1H), 4.84 (t, 1H), 6.53 (d, 1H), 6.78 (m, 1H), 7.12 (m, 2H), 7.42 (s, 1H), 7.59 (m, 2H), 7.80 (m, 1H), 10.84 (br s, 1H). m/z 485/487 (M+H)$^+$

In a similar manner, Example 6a was prepared using 3-((1S)-2-{[tert-butyl(dimethyl)silyl]oxy}-1-methylethyloxy)-5-hydroxy-N-(1-methyl-1H-pyrazol-3-yl)benzamide and the appropriate amide:

rated. The residue was crystallized from ethyl acetate/isohexane to give the title compound (1.64 g).

$^1$H NMR δ (CDCl$_3$): 2.4 (m, 2H), 4.2-4.4 (m, 4H), 7.2 (m, 1H), 7.55 (m, 1H), 7.7 (m, 1H).

In a similar manner, the amide required for Example 6a was also prepared:

| Structure | m/z | NMR |
|---|---|---|
| 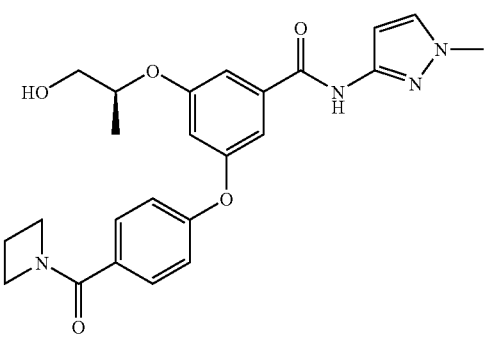 | 202, 204 (M + H)$^+$ | $^1$H NMR δ (d$_6$-DMSO): 2.90 (s, 3H), 2.96 (s, 3H), 7.42 (m, 2H), 7.62 (dd, 1H) |

| Example | Structure | m/z | NMR |
|---|---|---|---|
| 6a | 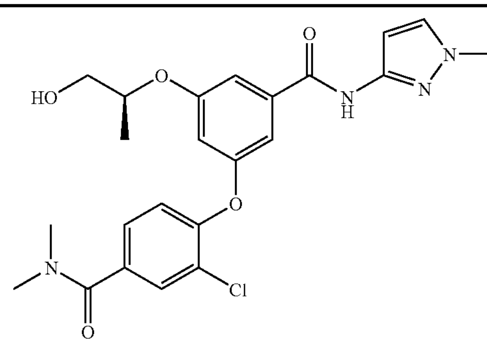 | 473, 475 (M + H)$^+$ | $^1$H NMR δ (d$_6$-DMSO): 1.22 (d, 3H), 2.94 (s, 6H), 3.52 (m, 2H), 3.76 (s, 3H), 4.56 (m, 1H), 4.84 (t, 1H), 6.53 (m, 1H), 6.75 (m, 1H), 7.12 (m, 2H), 7.40 (m, 2H), 7.58 (m, 1H), 7.65 (m, 1H), 10.84 (brs, 1H) |

The required amides for the synthesis of Examples 6 and 6a were prepared from 3-chloro-4-fluorobenzoic acid as follows:

1-(3-Chloro-4-fluorobenzoyl)azetidine

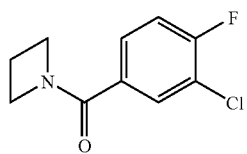

To a solution of 3-chloro-4-fluorobenzoic acid (1.74 g, 10.0 mmol) in DCM (50 mL) was added oxalyl chloride (1.05 mL, 12.0 mmol) and DMF (1 drop). The mixture was stirred at ambient temperature for 16 hours and the DCM and excess oxalyl chloride evaporated in vacuo. The residual acid chloride and azetidine hydrochloride (1.12 g, 12 mmol) were taken up in DCM (25 mL) and triethylamine (4.18 mL, 30 mmol) added to the mixture, which was stirred at ambient temperature for 2 hours. The DCM was evaporated in vacuo, and the residue partitioned between ethyl acetate (100 mL) and 1N hydrochloric acid (50 mL). The ethyl acetate layer was washed sequentially with saturated aqueous sodium hydrogen carbonate and brine, dried (MgSO$_4$), and evapo- The synthesis of 3-((1S)-2-{[tert-butyl(dimethyl)silyl]oxy}-1-methylethyloxy)-5-hydroxy-N-(1-methyl-1H-pyrazol-3-yl)benzamide is described above in Example 5.

EXAMPLE 7

3-{[4-(Azetidin-1-ylcarbonyl)phenyl]oxy}-5-{[(1S)-2-hydroxy-1-methylethyl]oxy}-N-(1-methyl-1H-pyrazol-3-yl)benzamide 3-{[4-(Azetidin-1-ylcarbonyl)-2-chlorophenyl]oxy}-5-{[(1S)-2-hydroxy-1-methylethyl]oxy}-N-(1-methyl-1H-pyrazol-3-yl)benzamide (104 mg, 0.215 mmol) was dissolved in methanol (3 mL) and THF (3 mL). Triethylamine (65 mg, 0.644 mmol) was added and the flask evacuated and purged with nitrogen (3 times). 10% Palladium on carbon (25 mg) was added and the flask further evacuated and finally purged with hydrogen gas. The reaction mixture was stirred at ambient temperature for 16 hours until completion. The reaction mixture was evacuated and purged with nitrogen (3 times). The catalyst was filtered off, the filtrate concentrated in vacuo and dissolved in ethyl acetate (10 mL), washed with water (2×10 mL, saturated aqueous sodium chloride solution (10 mL) and dried (MgSO$_4$) to give the title compound (95 mg).

$^1$H NMR δ (d$_6$-DMSO): 1.22 (d, 3H), 2.24 (m, 2H), 3.51 (m, 2H), 3.76 (s, 3H), 4.02 (m, 2H), 4.30 (br s, 2H), 4.56 (m, 1H), 4.84 (t, 1H), 6.53 (d, 1H), 6.80 (m, 1H), 7.06 (d, 2H), 7.21 (m, 1H), 7.43 (m, 1H), 7.57 (m, 1H), 7.66 (d, 2H), 10.83 (br s, 1H). m/z 451 (M+H)$^+$

The material can be crystallised from an ethylacetate and toluene mixture after purification by chromatography (on silica and then/or on neutral alumina) and, where necessary, treatment with activated charcoal; mpt 131° C.

In a similar manner, Reference Example 7a was prepared from 3-chloro-4-[(3-{[(1S)-2-hydroxy-1-methylethyl]oxy}-5-{[(1-methyl-1H-pyrazol-3-yl)amino]carbonyl}phenyl)oxy]-N,N-dimethylbenzamide:

| Ref Example | Structure | m/z | NMR |
| --- | --- | --- | --- |
| 7a | 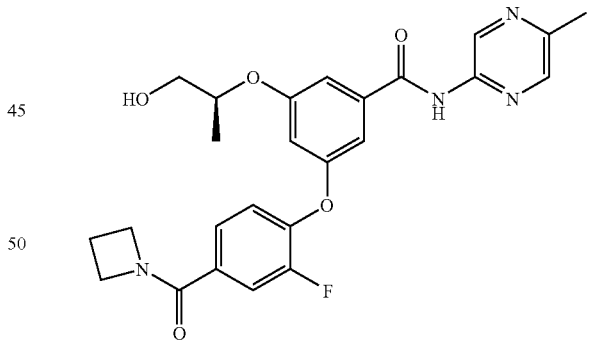 | 439 (M + H)$^+$ | $^1$H NMR δ (d$_6$-DMSO): 1.22 (d, 3H), 2.95 (s, 6H), 3.51 (m, 2H), 3.76 (s, 3H), 4.56 (m, 1H), 4.83 (t, 1H), 6.54 (m, 1H), 6.77 (m, 1H), 7.06 (d, 2H), 7.21 (m, 1H), 7.41 (s, 1H), 7.44 (d, 2H), 7.56 (m, 1H), 10.82 (br s, 1H) |

The syntheses of the chloro precursors are described above in Example 6 and 6a.

EXAMPLE 8

3-{[4-(Azetidin-1-ylcarbonyl)-2-fluorophenyl]oxy}-5-{[(1S)-2-hydroxy-1-methylethyl]oxy}-N-(5-methylpyrazin-2-yl)benzamide Potassium carbonate (182 mg, 1.32 mmol) was added to a mixture of 3-hydroxy-5-{[(1S)-2-hydroxy-1-methylethyl]oxy}-N-(5-methylpyrazin-2-yl)benzamide (200 mg, 0.66 mmol) and 1-(3,4-difluorobenzoyl)azetidine (137 mg, 0.69 mmol) in acetonitrile (5.0 mL) and the stirred mixture heated at 160° C. in a 'Smith Creator Microwave' for 4 hours. The mixture was allowed to reach ambient temperature and pressure and reduced in vacuo. The residual oil was partitioned between ethyl acetate (50 mL) and water (50 mL). The ethyl acetate layer was separated, washed with brine, dried (MgSO$_4$), and evaporated to a residue which was chromatographed on silica, eluting with a gradient of 50-100% ethyl acetate in isohexane, to give the desired compound (34 mg).

¹H NMR δ (CDCl₃): 1.31 (d, 3H), 2.36 (quin, 2H), 2.57 (s, 3H), 3.76 (m, 2H), 3.20-4.40 (brm, 4H), 4.56 (m, 1H), 6.75 (m, 1H), 7.07 (m, 2H), 7.27 (m, 2H), 7.41 (d, 1H), 7.5.1 (d, 1H), 8.11 (s, 1H), 8.43 (s, 1H), 9.50 (s, 1H). m/z 481 (M+H)⁺

The following compound was made in an analogous fashion.

| Example | Structure | m/z | NMR |
|---|---|---|---|
| 8a | 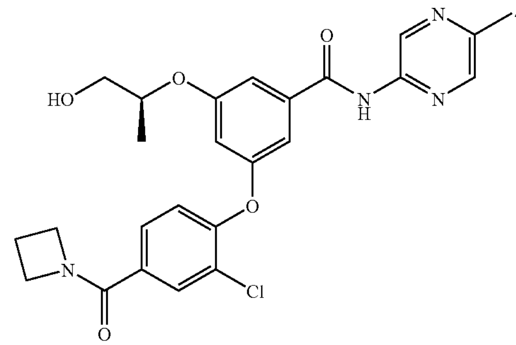 | 497, 499 (M + H)⁺ | ¹H NMR δ (CDCl₃): 1.30 (d, 3H), 2.38 (quin, 2H), 2.53 (s, 3H), 3.74 (m, 2H), 4.20-4.40 (brm, 4H), 4.58 (m, 1H), 6.74 (m, 2H), 7.04 (m, 2H), 7.28 (m, 1H), 7.51 (m, 1H) 7.78 (m, 1H), 8.11 (s, 1H), 8.40 (brs, 1H), 9.50 (s, 1H). |

3-Hydroxy-5-{[(1S)-2-hydroxy-1-methylethyl]oxy}-N-(5-methylpyrazin-2-yl)benzamide 3-Hydroxy-5-{[(1S)-1-methyl-2-(methyloxy)ethyl]oxy}-N-(5-methylpyrazin-2-yl)benzamide

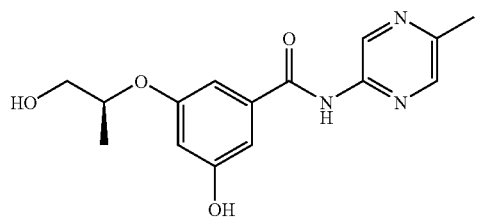

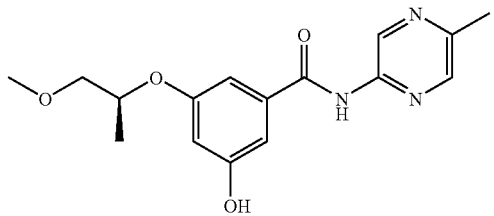

Trimethylsilyl iodide (6.06 mL, 42.75 mmol) was added to a solution of 3-hydroxy-5-{[(1S)-1-methyl-2-(methyloxy)ethyl]oxy}-N-(5-methylpyrazin-2-yl)benzamide (2.71 g, 8.55 mmol) in dry acetonitrile (150 mL) and stirred for 24 h. Methanol (30 mL) was added to quench the reaction and stirred for 10 mins. 10% w/v Aqueous sodium thiosulfate pentahydrate (20 mL) was added to the mixture and the organic solvents removed in vacuo. The residue was brought to pH5 with 1M hydrochloric acid and ethyl acetate (80 mL) added. A yellow solid (1.4 g) was separated by filtration. The aqueous filtrate was reextracted into ethyl acetate (2×80 mL) and the combined organic layers dried (MgSO₄), filtered and the solvents removed in vacuo. This residue was combined with the yellow solid obtained above and purified by column chromatography, eluting with 5% to 10% methanol in DCM, to give the title compound (1.70 g)

¹H NMR δ (d₆-DMSO): 1.21 (d, 3H), 2.50 (s, 3H), 3.40-3.60 (m, 2H), 4.45 (sex, 1H), 4.80 (t, 1H), 6.50 (s, 1H), 6.97 (s, 1H), 7.08 (s, 1H), 8.32 (s, 1H), 9.21 (s, 2H), 9.63 (s, 1H), 10.80 (br s, 1H). m/z 304 (M+H)⁺

3-{[(1S)-1-Methyl-2-(methyloxy)ethyl]oxy}-N-(5-methylpyrazin-2-yl)-5-[(phenylmethyl)oxy]benzamide (4.5 g, 11 mmol) was dissolved in ethanol (35 mL) and THF (35 mL) and the flask evacuated and purged with argon (3 times). 10% Palladium on carbon (0.45 g) was added and the flask further evacuated and finally purged with hydrogen gas. The reaction mixture was stirred at ambient temperature for 20 hours until completion. The reaction mixture was evacuated and purged with nitrogen (3 times). The catalyst was filtered off through celite, and the filtrate concentrated in vacuo to give the desired compound (3.21 g).

¹H NMR δ (d₆-DMSO): 1.23 (d, 3H), 2.45 (s, 3H), 3.28 (s, 3H), 3.48 (m, 2H), 4.65 (m, 1H), 6.51 (s, 1H), 6.97 (s, 1H), 7.10 (s, 1H), 8.34 (s, 1H), 9.22 (s, 1H), 9.70 (s, 1H), 10.89 (br s, 1H). m/z 318 (M+H)⁺

3-{[(1S)-1-Methyl-2-(methyloxy)ethyl]oxy}-N-(5-methylpyrazin-2-yl)-5-[(phenylmethyl)oxy]benzamide

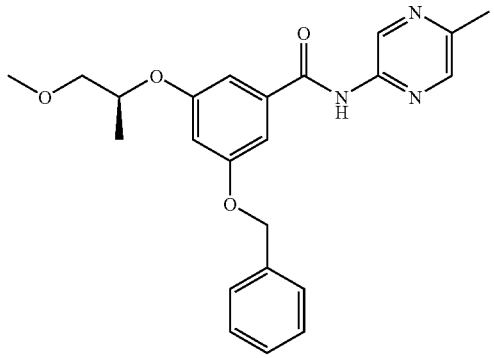

DMF (2 drops) was added to a solution of 3-{[(1S)-1-methyl-2-(methyloxy)ethyl]oxy}-5-[(phenylmethyl)oxy]benzoic acid (6.0 g, 19.0 mmol) and oxalyl chloride (1.99 mL, 22.8 mmol) in DCM (40 mL) The mixture was stirred at ambient temperature for 2 hours and the DCM and excess oxalyl chloride evaporated in vacuo. The residual acid chloride was dissolved in DCM and added dropwise to 2-amino-5 methylpyrazine [*Tett lett.* 2002, 9287-90] (2.28 g, 19.8 mmol) and pyridine (2.56 mL, 38 mmol) in DCM (40 mL), at 0° C. Stirred at ambient temperature for 24 hours. The DCM was evaporated in vacuo, and the residue partitioned between ethyl acetate (100 mL) and 1N hydrochloric acid (50 mL). The ethyl acetate layer was washed sequentially with saturated aqueous sodium hydrogen carbonate (50 mL) and brine (50 mL), dried (MgSO$_4$), and evaporated in vacuo. The residue was chromatographed on silica, eluting with a gradient of 30-100% ethyl acetate in isohexane, to give the desired compound (7.6 g)

$^1$H NMR δ (CDCl$_3$): 1.32 (d, 3H), 2.55 (s, 3H), 3.40 (s, 3H), 3.50-3.62 (m, 2H), 4.60 (m, 1H), 5.10 (s, 2H), 6.75 (s, 1H), 7.09 (m, 1H), 7.13 (m, 1H), 7.32-7.46 (m, 5H), 8.13 (s, 1H), 8.38 (s, 1H), 9.55 (s, 1H). m/z 408 (M+H)$^+$

The aryl fluoride used to prepare Example 8 was prepared as described below:

1-(3,4-Difluorobenzoyl)azetidine

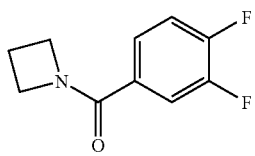

Oxalyl chloride (1.05 mL, 12.0 mmol) was added to a solution of 3,4-difluorobenzoic acid (1.58 g, 10 mmol) in DCM (50 mL) containing DMF (1 drop). The reaction was stirred at ambient temperature for 16 h then evaporated to dryness. The residue was redissolved in DCM (25 mL) and azetidine hydrochloride (1.12 g, 12.0 mmol) added followed by triethylamine (4.18 mL, 30.0 mmol). The mixture was stirred at ambient temperature for 2 h then concentrated in vacuo. The residue was partitioned between ethyl acetate and 1N hydrochloric acid, the organic phase washed with a saturated aqueous solution of sodium bicarbonate followed by brine, dried (MgSO$_4$), and concentrated in vacuo. The title compound was crystallized from an ethyl acetate/hexane mixture to give a white crystalline solid (1.0 g).

$^1$H NMR δ (CDCl$_3$): 2.4 (m, 2H), 4.3 (m, 4H), 7.2 (m, 1H), 7.4 (m, 1H), 7.5 (t, 1H).

The aryl fluoride used to prepare Example 8a was described in Example 6a

Alternatively Example 8 can be prepared in the following manner:

EXAMPLE 8

3-{[4-(Azetidin-1-ylcarbonyl)-2-fluorophenyl]oxy}-5-{[(1S)-2-hydroxy-1-methylethyl]oxy}-N-(5-methylpyrazin-2-yl)benzamide

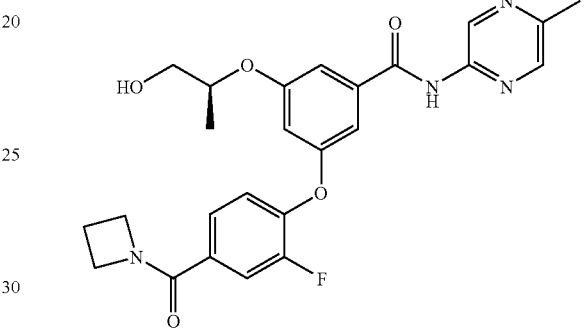

A mixture of 3-[4-(azetidin-1-ylcarbonyl)-2-fluorophenoxy]-5-((1S)-2-{[tert-butyl(dimethyl)silyl]oxy}-1-methylethoxy)-N-(5-methylpyrazin-2-yl)benzamide (3.6 g, 5.96 mmol) in methanol (60 mL) and 1M hydrochloric acid (60 mL) was stirred for 30 mins at RT. The volatiles were removed in vacuo and the residue adjusted to pH6 with saturated aqueous sodium bicarbonate solution then extracted into ethyl acetate (3×100 mL). The combined organic layers were washed with water (100 mL), brine (100 mL), dried (MgSO$_4$), filtered and the solvents removed in vacuo. 10% Methanol in ethyl acetate was added and a white solid filtered off. This was crystallised from ethyl acetate/methanol to give the desired compound. (1.24 g), mpt 172° C. The data was in agreement with samples prepared through alternative routes.

3-[4-(Azetidin-1-ylcarbonyl)-2-fluorophenoxy]-5-((1S)-2-{[tert-butyl(dimethyl)silyl]oxy}-1-methylethoxy)-N-(5-methylpyrazin-2-yl)benzamide

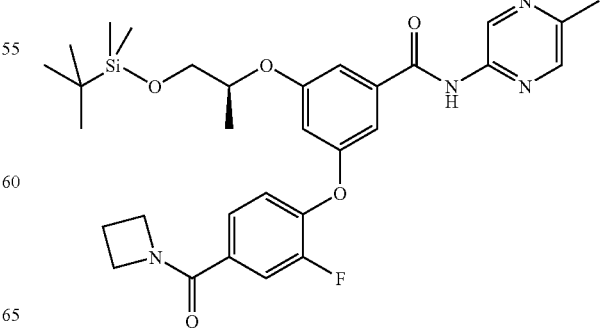

1-Chloro-N,N,2-trimethyl-1-propenylamine (0.86 g, 6.56 mmol) was added to a solution of 3-[4-(azetidin-1-ylcarbonyl)-2-fluorophenoxy]-5-((1S)-2-{[tert-butyl(dimethyl)silyl]oxy}-1-methylethoxy)benzoic acid (3 g, 5.96 mmol) in DCM (100 mL) and stirred at RT for 11 hour. 2-Amino-5-methylpyrazine (1.3 g, 11.9 mmol) and pyridine (0.94 mL, 11.9 mmol) were added and the reaction stirred for a further 30 mins. The solvent was removed in vacuo. Water (100 mL) was added and the mixture extracted with ethyl acetate (3×50 mL). The extracts were combined and washed with water (1100 mL), brine (100 mL), dried (MgSO$_4$), filtered, and evaporated in vacuo to give the crude product which was chromatographed on silica, eluting with a gradient of 50-100% ethyl acetate in isohexane, to give the desired compound (3.6 g).

$^1$H NMR δ (CDCl$_3$): 0.00 (s, 3H), 0.03 (s, 3H), 0.81 (s, 9H), 1.30 (d, 3H), 2.32 (quin, 2H), 2.51 (s, 3H), 3.60-3.80 (m, 2H), 4.20-4.39 (brm, 4H), 4.45 (m, 1H), 6.75 (m, 1H), 7.03 (d, 2H), 7.21 (s, 1H), 7.40 (d, 1H), 7.50 (d, 1H), 8.10 (s, 1H), 8.27 (s, 1H), 9.48 (s, 1H). m/z 595 (M+H)$^+$ 3-[4-(Azetidin-1-ylcarbonyl)-2-fluorophenoxy]-5-((1S)-2-{[tert-butyl(dimethyl)silyl]oxy}-1-methylethoxy)benzoic acid

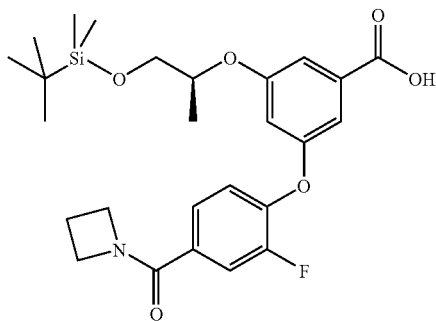

A mixture of 3-[4-(azetidin-1-ylcarbonyl)-2-fluorophenoxy]-5-[(1S)-2-hydroxy-1-methylethoxy]benzoic acid (9.8 g, 0.025 mol), t-butyldimethylsilylchloride (11.3 g, 0.075 mol) and imidazole (17.08 g, 0.25 mol) in DMF (100 mL) was stirred at RT for 24 hours. Water (100 mL) was added and the mixture extracted into diethyl ether (3×100 mL). The extracts were combined and washed with water (3×100 mL), brine (100 mL), dried (MgSO$_4$), filtered, and evaporated in vacuo to give a golden oil. Saturated aqueous sodium bicarbonate (100 mL) and diethyl ether (100 mL) were added and stirred for 30 mins. The aqueous layer was acidified with 1M citric acid solution and extracted into diethyl ether (3×100 mL). The extracts were combined, dried (MgSO$_4$), filtered, and evaporated in vacuo and the crude product chromatographed on silica, eluting with ethyl acetate, to give the desired compound. (6.32 g).

$^1$H NMR δ (CDCl$_3$): 0.00 (s, 3H), 0.03 (s, 3H), 0.84 (s, 9H), 1.27 (d, 3H), 2.35 (quin, 2H), 3.60-3.80 (m, 2H), 4.20-4.38 (brm, 4H), 4.46 (m, 1H), 6.78 (s, 1H), 7.03 (t, 1H), 7.25 (m, 1H), 7.38 (m, 2H), 7.47 (d, 1H). m/z 504 (M+H)$^+$ 3-[4-(Azetidin-1-ylcarbonyl)-2-fluorophenoxy]-5-[(1S)-2-hydroxy-1-methylethoxy]benzoic acid

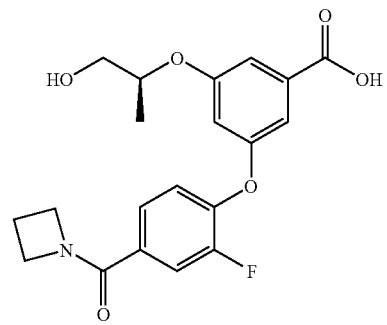

A suspension of methyl 3-hydroxy-5-[(1S)-2-hydroxy-1-methylethoxy]benzoate (10.65 g, 0.047 mmol), cesium carbonate (30.71 g, 0.094 mol) and 1-(3,4-difluorobenzoyl)azetidine (9.28 g, 0.047 mol) in dimethylacetamide (80 mL) was heated at 120° C. for 22 hours. The reaction mixture was cooled and water (60 mL) added followed by lithium hydroxide monohydrate (1.97 g, 0.047 mol) in water (45 mL). The reaction was stirred for a further 24 hours. Water (100 mL) was added and the mixture extracted with ethyl acetate (3×50 mL) to remove any ester. The aqueous layer was acidified and extracted into ethyl acetate (5×50 mL). The extracts were combined and washed with water (100 mL), brine (100 mL), dried (MgSO$_4$), filtered, and evaporated in vacuo to give a yellow liquid. A diethyl ether/ethyl acetate mixture (3:1) was added and the solution washed with water (100 mL), brine (100 mL), dried (MgSO$_4$), filtered and evaporated in vacuo to give the desired compound. (9.8 g)

$^1$H NMR δ (CDCl$_3$): 1.28 (d, 3H), 2.35 (quin, 2H), 3.71 (m, 2H), 4.30 (brm, 4H), 4.54 (m, 1H), 6.80 (m, 1H), 7.05 (t, 1H), 7.25 (m, 1H), 7.40 (m, 2H), 7.48 (dd, 1H).
m/z 390 (M+H)$^+$ Methyl 3-hydroxy-5-[(1S)-2-hydroxy-1-methylethoxy]benzoate

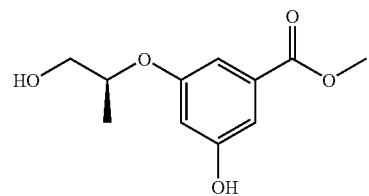

Trimethylsilyl iodide (115 mL, 0.79 mol) was added to a solution of methyl 3-hydroxy-5-[(1S)-2-methoxy-(1-methylethyl)oxy]benzoate (38.01 g, 0.158 mol) in acetonitrile (500 mL) and stirred for 24 hours. Methanol (300 mL) was added and the reaction stirred for 10 mins. 10% w/v Aqueous sodium thiosulfate pentahydrate (100 mL) was added to the mixture and stirred for 20 mins. The reaction mixture was neutralised with saturated aqueous sodium bicarbonate solution, the organic solvents removed in vacuo, and the product extracted into ethyl acetate (4×100 mL). The combined organic layers were dried (MgSO$_4$), filtered and the solvents removed in vacuo. The crude material was crystallised from ethyl acetate to give the title compound (16.80 g)

¹H NMR δ (d₆-DMSO): 1.18 (d, 3H), 3.40-3.55 (m, 2H), 3.80 (s, 3H), 4.35 (sex, 1H), 4.80 (t, 1H), 6.57 (m, 1H), 6.90 (m, 2H), 9.75 (s, 1H); m/z 304 (M+H)⁺

The preparation of methyl 3-hydroxy-5-[(1S)-2-methoxy-(1-methylethyl)oxy]benzoate was described in Example 3.

An analogous procedure can be employed in the preparation of Example 8a from 3-[4-(azetidin-1-ylcarbonyl)-2-chlorophenoxy]-5-((1S)-2-{[tert-butyl(dimethyl)silyl]oxy}-1-methylethoxy)-N-(5-methylpyrazin-2-yl)benzamide. The desired product can then be isolated following purification on silica, eluting with 5% methanol in ethyl acetate, and crystallization from ethyl acetate/isohexane, mpt 133° C.

3-[4-(Azetidin-1-ylcarbonyl)-2-chlorophenoxy]-5-((1S)-2-{[tert-butyl(dimethyl)silyl]oxy}-1-methylethoxy)-N-(5-methylpyrazin-2-yl)benzamide was prepared from methyl 3-hydroxy-5-[(1S)-2-hydroxy-1-methylethoxy]benzoate in an analogous fashion to 3-[4-(azetidin-1-ylcarbonyl)-2-fluorophenoxy]-5-((1S)-2-{[tert-butyl(dimethyl)silyl]oxy}-1-methylethoxy)-N-(5-methylpyrazin-2-yl)benzamide but replacing 1-(3,4-difluorobenzoyl)azetidine with 1-(3-chloro-4-fluorobenzoyl)azetidine.

| Structure | m/z | NMR |
|---|---|---|
| | 609 (M − H)⁻ | ¹H NMR δ (CDCl₃): 0.00 (s, 3H), 0.03 (s, 3H), 0.81 (s, 9H), 1.30 (d, 3H), 2.35 (quin, 2H), 2.55 (s, 3H), 3.60-3.80 (m, 2H), 4.25 (brm, 4H), 4.50 (m, 1H), 6.76 (m, 1H), 6.98 (m, 2H), 7.25 (m, 1H), 7.51 (dd, 1H), 7.75 (d, 1H), 8.12 (s, 1H), 8.43 (brs, 1H), 9.51 (s, 1H). |
| | 520 (M + H)⁺ | ¹H NMR δ (CDCl₃): 0.00 (s, 3H), 0.03 (s, 3H), 0.94 (s, 9H), 1.28 (d, 3H), 2.35 (quin, 2H), 3.60-3.80 (m, 2H), 4.20-4.38 (brm, 4H), 4.46 (m, 1H), 6.75 (s, 1H), 6.92 (d, 1H), 7.21 (m, 1H), 7.38 (m, 1H), 7.44 (m, 1H), 7.70 (s, 1H). |
| | 406 (M + H)⁺ | ¹H NMR δ (CDCl₃): 1.35 (d, 3H), 2.38 (quin, 2H), 3.75 (m, 2H), 4.30 (brm, 4H), 4.52 (m, 1H), 6.79 (m, 1H), 6.98 (d, 1H), 7.24 (m, 1H), 7.41 (m, 1H), 7.50 (dd, 1H), 7.78 (m, 1H). |

EXAMPLE 9

3-{[4-(Azetidin-1-ylcarbonyl)-2-fluorophenyl]oxy}-N-(1-ethyl-1H-pyrazol-3-yl)-5-{[(1S)-2-hydroxy-1-methylethyl]oxy}benzamide

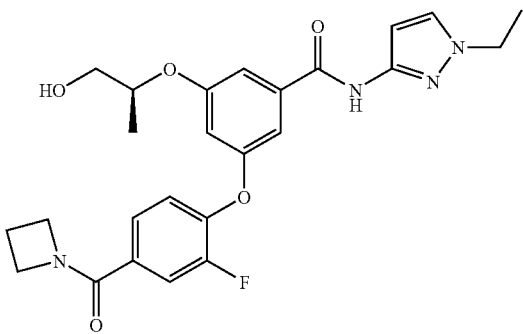

A suspension of 3-[((1S)-2-{[(1,1-dimethylethyl)(dimethyl)silyl]oxy}-1-methylethyl)oxy]-N-(1-ethyl-1H-pyrazol-3-yl)-5-hydroxybenzamide (200 mg, 0.477 mmol), potassium carbonate (132 mg, 2.0 equiv) and 1-(3,4-difluorobenzoyl)azetidine (113 mg, 1.2 equiv) in acetonitrile (2 mL) was heated in a microwave reactor at 160° C. for 15 hours. Reaction mixture was quenched with ethyl acetate/aqueous ammonium chloride solution and the aqueous phase extracted (×2) with ethyl acetate. The organic layer was dried (MgSO$_4$), filtered and concentrated in vacuo. The residue was then chromatographed, eluting with ethyl acetate, to give product as a white foam (135 mg, 59%).

The title compound may be crystallised by the following method:

The sample was dissolved in ethyl acetate, the vial containing this solution was allowed to stand inside another sealed vial containing toluene until crystals formed. The crystals were filtered and washed with toluene and then isohexane. Mpt 124° C.

$^1$H NMR δ (CDCl$_3$): 1.3 (d, 3H), 1.45 (t, 3H), 1.95 (t, 1H), 2.4 (m, 2H), 3.7 (m, 2H), 4.1 (m, 2H), 4.25 (s, br, 2H), 4.35 (s, br, 2H), 4.55 (m, 1H), 6.75 (d, 2H), 7.1 (s, 1H), 7.15 (t, 1H), 7.25 (s, 1H), 7.35 (s, 1H), 7.4 (d, 1H), 7.55 (d, 1H), 8.3 (s, 1H). m/z 481 (M–H)$^-$ 80%

The following compounds were made in an analogous fashion from 3-[((1S)-2-{[(1,1-dimethylethyl)(dimethyl)silyl]oxy}-1-methylethyl)oxy]-N-(1-ethyl-1H-pyrazol-3-yl)-5-hydroxybenzamide and the appropriate aryl fluoride.

| Example | Structure | m/z | NMR |
|---|---|---|---|
| 9a | 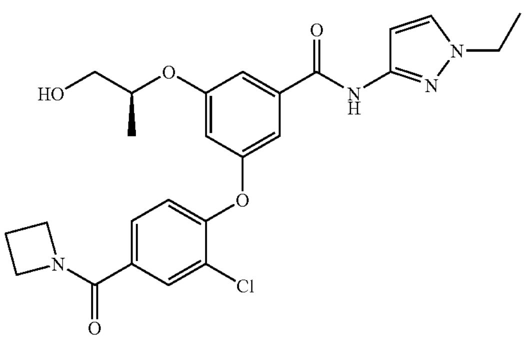 | 499 (M + H)$^+$, 497 (M – H)$^-$ | $^1$H NMR δ (CDCl$_3$): 1.29 (d, 3H), 1.45 (t, 3H), 2.01 (br. s, 1H), 2.38 (m, 2H), 3.75 (m, 2H), 4.07 (q, 2H), 4.26 (br. s, 2H), 4.36 (br. s, 2H), 4.55 (m, 1H), 6.72 (s, 1H), 6.78 (s, 1H), 7.02 (d, 2H), 7.25 (s, 1H), 7.33 (s, 1H), 7.52 (d, 1H), 7.80 (s, 1H), 8.38 (br. s, 1H) |
| 9b | 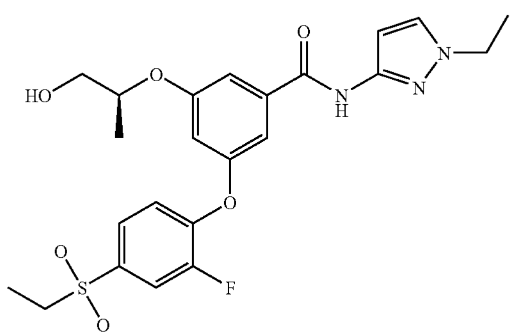 | 491 (M + H)$^+$ | $^1$H NMR δ (CDCl$_3$): 1.3 (d, 3H), 1.35 (t, 3H), 1.45 (t, 3H), 1.95 (t, 1H), 3.15 (q, 2H), 3.75 (m, 2H), 4.1 (m, 2H), 4.55 (m, 1H), 6.75 (s, 1H), 6.8 (t, 1H), 7.1 (s, 1H), 7.15 (t, 1H), 7.3 (s, 1H), 7.35 (d, 1H), 7.65 (d, 1H), 7.75 (dd, 1H), 8.3 (br, s 1H) |

-continued

| Example | Structure | m/z | NMR |
|---|---|---|---|
| 9c | 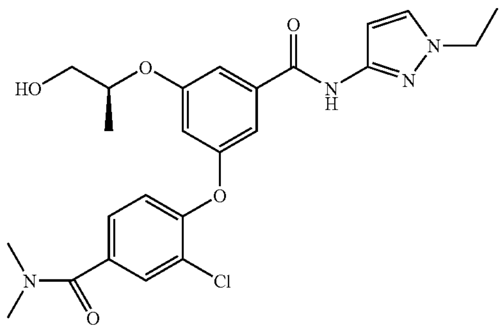 | 487 (M + H)⁺ | ¹H NMR δ (CDCl₃): 1.30 (d, 3H), 1.45 (t, 3H), 1.99 (t, 1H), 3.10 (br. s, 6H), 3.75 (m, 2H), 4.08 (q, 2H), 4.55 (m, 1H), 6.7 (s, 1H), 6.77 (s, 1H), 7.03 (m, 2H), 7.23 (s, 1H), 7.31 (m, 2H), 7.60 (s, 1H), 8.35 (br. s, 1H). |
| 9d | 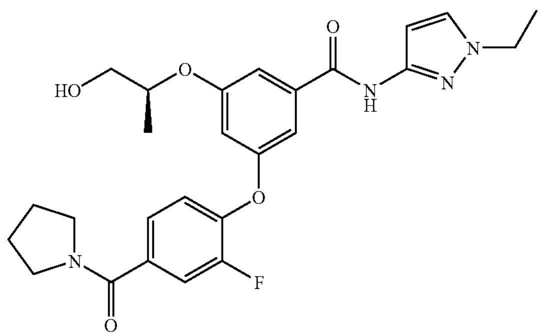 | 497 (M + H)⁺, 495 (M − H)⁻ | ¹H NMR δ (CDCl₃): 1.28 (d, 3H), 1.47 (t, 3H), 1.89-2.00 (brm, 4H), 3.50 (m, 2H), 3.67 (m, 2H), 3.76 (brm, 2H), 4.07 (m, 2H), 4.55 (m, 1H), 6.76 (m, 2H), 7.05 (m, 1H), 7.11 (m, 1H), 7.22 (s, 1H), 7.34 (m, 2H), 7.43 (d, 1H), 8.35 (brs, 1H). |
| 9e | 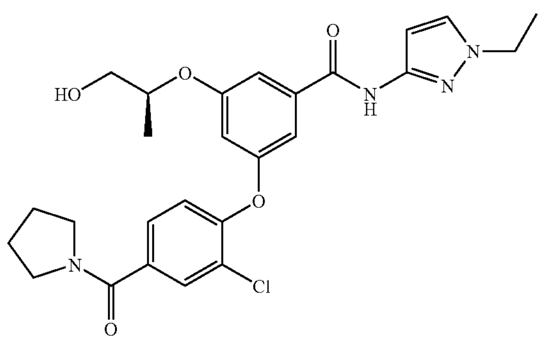 | 513, 515 (M + H)⁺, 511, 513 (M − H)⁻ | ¹H NMR δ (CDCl₃): 1.29 (d, 3H), 1.47 (t, 3H), 1.87-1.99 (brm, 4H), 3.48 (m, 2H), 3.64 (m, 2H), 3.75 (brm, 2H), 4.07 (m, 2H), 4.55 (m, 1H), 6.75 (m, 2H), 7.05 (m, 2H), 7.22 (s, 1H), 7.33 (m, 1H), 7.44 (m, 1H), 7.68 (s, 1H), 8.33 (brs, 1H). |

3-[((1S)-2-{[(1,1-Dimethylethyl)(dimethyl)silyl]oxy}-1-methylethyl)oxy]-N-(1-ethyl-1H-pyrazol-3-yl)-5-hydroxybenzamide A solution of 3-[((1S)-2-{[(1,1-dimethylethyl)(dimethyl)silyl]oxy}-1-methylethyl)oxy]-N-(1-ethyl-1H-pyrazol-3-yl)-5-[(phenylmethyl)oxy]benzamide (2.40 g, 4.71 mmol) and THF (80 mL) was evacuated and purged with Argon (×3). Palladium on carbon (10%, 422 mg) was added and reaction mixture was evacuated and finally purged with hydrogen gas. Reaction mixture was left to stir at ambient temperature under hydrogen for 16 hours. Pd/C was filtered off and concentrated in vacuo to give the product as a colourless oil (1.87 g, 95%).

¹H NMR δ (CDCl₃): 0.01 (s, 3H), 0.03 (s, 3H), 0.88 (s, 9H), 1.27 (d, 3H), 1.49 (t, 3H), 3.64 (dd, 1H), 3.78 (dd, 1H), 4.10 (q, 2H), 4.43 (m, 1H), 6.60 (s, 1H), 6.81 (s, 1H), 6.98 (s, 1H), 7.00 (s, 1H), 7.37 (s, 1H), 8.61 (br. s, 1H). m/z 420 (M+H)⁺, 418 (M−H)⁻.

3-[((1S)-2-{[(1,1-Dimethylethyl)(dimethyl)silyl]oxy}-1-methylethyl)oxy]-N-(1-ethyl-1H-pyrazol-3-yl)-5-[(phenylmethyl)oxy]benzamide DIPEA (3.11 mL, 18.03 mmol) was added to a solution of 3-{(phenylmethyl)oxy}-5-((1S)-2-{[tert-butyl(dimethyl)silyl]oxy}-1-methylethoxy)benzoic acid (3.00 g, 7.21 mmol), HATU (3.41 g, 9.01 mmol) and 1-ethyl-1H-pyrazol-3-amine [*Chem. Heterocycl. Compd. (Engl. Transl.)*, 11, 1975, 212] (1.20 g, 10.8 mmol) in DMF (10 mL). The resulting mixture was stirred at ambient temperature for 3 hours. The DMF was removed in vacuo. The solvent was evaporated and the residue was dissolved in 5% w/v citric acid (50 mL), ethyl acetate (30 mL) and diethyl ether (30 mL) and the organic layer was further washed with sat. aqueous NaHCO$_3$ (30 mL) and brine (30 mL). The organic layer was separated, then dried (MgSO$_4$), filtered and evaporated. Purification by column chromatography, eluting with 1:5 to 1:2 ethyl acetate:hexanes, afforded the title compound as a colourless oil (2.40 g, 65%).

$^1$H NMR δ (CDCl$_3$): 0.01 (s, 3H), 0.03 (s, 3H), 0.83 (s, 9H), 1.24 (d, 3H), 1.42 (t, 3H), 3.62 (dd, 1H), 3.75 (dd, 1H), 4.01 (q, 2H), 4.40 (m, 1H), 5.03 (s, 2H), 6.67 (s, 1H), 6.78 (s, 1H), 6.97 (s, 1H), 7.04 (s, 1H), 7.33 (m, 6H), 8.38 (br. s, 1H). m/z 510 (M+H)$^+$, 508 (M−H)$^−$.

The aryl fluorides used in the preparation of Examples 9, 9a and 9c were described in previous examples. The aryl fluoride used in the preparation of Example 9b was prepared as described below:

3,4-Difluorophenyl ethyl sulfone

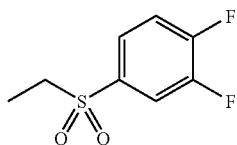

To a solution of 4-ethylsulphanyl-1,2-difluorobenzene (1.50 g) in DCM (50 mL) was added 75% m-chloroperbenzoic acid (2.97 g) and the mixture stirred at ambient temperature for 16 h. The mixture was washed successively with saturated potassium carbonate (20 mL) and brine (30 mL) then dried with magnesium sulphate, filtered and reduced in vacuo. The resultant clear oil was chromatographed on silica, eluting with 0-50% ethyl acetate in isohexane, and the faster running product isolated (0.90 g). The required 3,4-difluorophenyl ethyl sulfone was used without further characterisation.

The aryl fluorides used in the preparation of Examples 9d-e were prepared in an analogous manner to 1-(3,4-difluorobenzoyl)azetidine described in Example 8 using the appropriate amine.

1-(3,4-Difluorobenzoyl)pyrrolidine

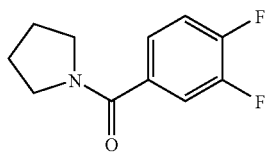

$^1$H NMR δ (CDCl$_3$): 1.8-2.1 (m, 4H), 3.4 (t, 2H), 3.7 (t, 2H), 7.2 (m, 1H), 7.3 (m, 1H), 7.4 (t, 1H).

1-(3-Chloro-4-fluorobenzoyl)pyrrolidine

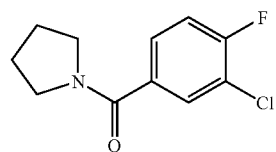

$^1$H NMR δ (d$_6$-DMSO): 1.8 (m, 4H), 3.4 (t, 2H), 3.5 (t, 2H), 7.4 (t, 1H), 7.5 (m, 1H), 7.7 (d, 1H). m/z 228, 230 (M+H)$^+$.

EXAMPLE 10

3-{[4-(Azetidin-1-ylcarbonyl)phenyl]oxy}-N-(1-ethyl-1H-pyrazol-3-yl)-5-{[(1S)-2-hydroxy-1-methylethyl]oxy}benzamide

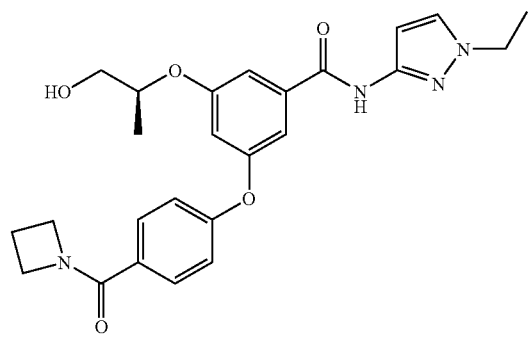

A solution of 3-{[4-(azetidin-1-ylcarbonyl)-2-chlorophenyl]oxy}-N-(1-ethyl-1H-pyrazol-3-yl)-5-{[(1S)-2-hydroxy-1-methylethyl]oxy}benzamide (246 mg, 0.504 mmol) and triethylamine (0.42 mL, 3.02 mmol) in THF (6 mL) and methanol (6 mL) was evacuated and purged with argon (×3). Palladium on carbon (10% w/w, 52 mg) was added and reaction mixture was evacuated and finally filled with hydrogen gas. The reaction mixture was left to stir at ambient temperature under hydrogen for 2 hours. The Pd/C was filtered off and mixture partitioned between ethyl acetate and 1M hydrochloric acid solution. The organic phase was dried (MgSO$_4$) and the filtrate concentrated in vacuo to give the product (170 mg, 73%).

$^1$H NMR δ (CDCl$_3$): 1.25 (d, 3H), 1.45 (t, 3H), 2.35 (m, 2H), 3.75 (m, 2H), 4.1 (q, 2H), 4.3 (m, 4H), 4.6 (m, 1H), 6.8 (m, 2H), 7.0 (d, 2H), 7.1 (s, 1H), 7.3: (s, 1H), 7.35 (s, 1H), 7.65 (d, 2H), 8.6 (s, 1H). m/z 464 (M+H)$^+$

The following compound was synthesised in an analogous fashion from the corresponding aryl chloride.

| Example | Structure | m/z | NMR |
|---|---|---|---|
| 10a | 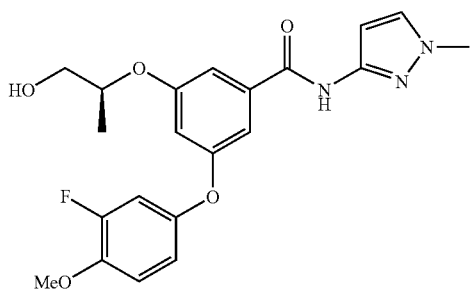 | 453 (M + H)+ | ¹H NMR δ (CDCl₃): 1.30 (d, 3H), 1.45 (t, 3H), 3.10 (br. s, 6H), 3.73 (m, 2H), 4.08 (q, 2H), 4.55 (m, 1H), 6.78 (m, 2H), 7.03 (d, 2H), 7.12 (s, 1H), 7.23 (s, 1H), 7.32 (s, 1H), 7.45 (d, 2H), 8.60 (br. s, 1H). |

EXAMPLE 11

3-(3-Fluoro-4-methoxyphenoxy)-5-[(1S)-2-hydroxy-1-methylethoxy]-N-(1-methyl-1H-pyrazol-3-yl)benzamide A solution of 3-((1S)-2-{[tert-butyl(dimethyl)silyl]oxy}-1-methylethyloxy)-5-hydroxy-N-(1-methyl-1H-pyrazol-3-yl)benzamide (0.30 g, 0.74 mmol), 3-fluoro-4-methoxyphenylboronic acid (255 mg, 1.5 mmol), copper (II) acetate (0.202 g, 1.11 mmol), triethylamine (0.517 mL, 3.71 mmol) and freshly activated 4 Å molecular sieves (1 g) in DCM (40 mL) was stirred at ambient temperature and under ambient atmosphere for 2 days. The reaction mixture was filtered through celite, washed with DCM (2×10 mL), the DCM removed in vacuo. The residue was partitioned between ethyl acetate and a saturated solution of sodium bicarbonate, the organic layer washed with brine, dried (MgSO₄) and concentrated in vacuo. 3.5M Hydrochloric acid (0.5 mL) was added to a solution of the residual oil dissolved in methanol (5 mL) and stirred at RT for 20 minutes, then the solution neutralised with saturated sodium bicarbonate. The reaction mixture was diluted with water (10 mL) and extracted with ethyl acetate (20 mL). The organic layer was washed with brine, dried (MgSO₄), and concentrated in vacuo. The residue was chromatographed on silica, eluting with ethyl acetate, to give the desired compound (95 mg).

¹H NMR δ (CDCl₃): 1.24 (d, 3H), 2.2 (brs, 1H), 3.6-3.8 (m, 5H), 3.9 (s, 3H), 4.4-4.6 (m, 1H), 6.7 (s, 1H), 6.8 (m, 3H), 6.95 (m, 2H), 7.15 (s, 1H), 7.2 (s, 1H), 8.6 (brs, 1H); m/z 416 (M+H)+

In a similar manner to that described above, the following compound was also prepared from 3-((1S)-2-{[tert-butyl(dimethyl)silyl]oxy}-1-methylethyloxy)-5-hydroxy-N-(1-methyl-1H-pyrazol-3-yl)benzamide and the appropriate boronic acid:

| | | | |
|---|---|---|---|
| 11a | | 428 (M + H)+ | ¹H NMR δ (CDCl3): 1.25 (d, 3H), 3.7-3.8 (m, 2H), 3.8 (s, 3H), 3.85 (s, 3H), 3.9 (s, 3H), 4.5 (sex, 1H), 6.6 (m, 1H), 6.64 (m, 1H), 6.7 (m, 1H), 6.78 (d, 1H), 6.8 (d, 1H), 6.95 (s, 1H), 7.1 (m, 1H), 7.3 (m, 1H), 8.5 (brs, 1H) |

EXAMPLE 12

3-Fluoro-4-[(3-{[(1S)-2-hydroxy-1-methylethyl]oxy}-5-{[(1-methyl-1H-pyrazol-3-yl)amino]carbonyl}phenyl)oxy]-N,N-dimethylbenzamide

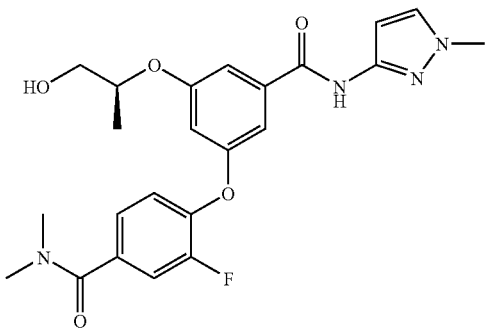

Potassium carbonate (276 mg) was added to a solution of 3-hydroxy-5-{[(1S)-2-hydroxy-1-methylethyl]oxy}-N-(1-methyl-1H-pyrazol-3-yl)benzamide (291 mg) and 3,4-difluoro-N,N-dimethylbenzamide (204 mg) in acetonitrile (3.5 mL) and the stirred mixture heated at 160° C. in a 'Smith Creator Microwave' for 15 h. The mixture was allowed to return to ambient temperature and pressure, the acetonitrile evaporated, and the residue chromatographed on silica, eluting with 0-5% methanol in ethyl acetate, to give the desired compound (63 mg). $^1$H NMR δ (d$_6$-DMSO): 1.22 (d, 3H), 2.94 (s, 6H), 3.49 (m, 2H), 3.76 (s, 3H), 4.54 (m, 1H), 4.83 (t, 1H), 6.53 (m, 1H), 6.76 (m, 1H), 7.14 (s, 1H), 7.24 (m, 2H), 7.40 (s, 1H), 7.47 (d, 1H), 7.57 (m, 1H), 10.83 (br s, 1H). m/z 457 (M+H)$^+$ The following compounds were prepared in a similar manner from 3-hydroxy-5-{[(1S)-2-hydroxy-1-methylethyl]oxy}-N-(1-methyl-1H-pyrazol-3-yl)benzamide and the appropriate aryl fluoride.

| Example | Structure | m/z | NMR |
|---|---|---|---|
| 12a | (structure) | 478 (M + H)$^+$ | $^1$H NMR δ (d$_6$-DMSO): 1.04 (t, 3H), 1.22 (d, 3H), 2.81 (m, 1H), 3.06 (m, 1H), 3.49 (m, 2H), 3.75 (s, 3H), 4.56 (m, 1H), 4.87 (t, 1H), 6.53 (m, 1H), 6.78 (m, 1H), 7.11 (m, 1H), 7.29 (d, 1H), 7.42 (m, 1H), 7.57 (dd, 1H), 7.62 (m, 1H), 7.84 (d, 1H), 10.87 (br s, 1H) |
| 12b | (structure) | 483 (M + H)$^+$ | $^1$H NMR δ (d$_6$-DMSO): 1.22 (d, 3H), 1.83 (s, br, 4H), 3.44 (m, 4H), 3.53 (m, 2H), 3.75 (s, 3H), 4.56 (m, 1H), 4.83 (t, 1H), 6.53 (m, 1H), 6.77 (m, 1H), 7.14 (s, 1H), 7.22 (m, 1H), 7.40 (d, 2H), 7.56 (m, 2H), 10.84 (s, br, 1H) |
| 12c* | (structure) Isomer 1 | | |

-continued

| Example | Structure | m/z | NMR |
|---|---|---|---|
| 12d* | 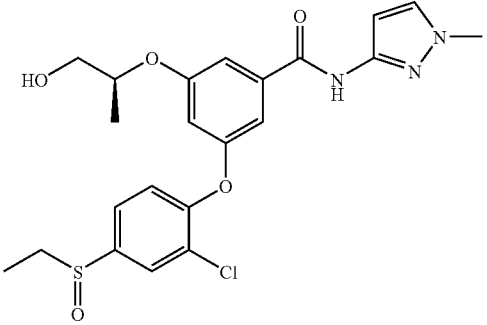 Isomer 2 | | |

*Examples 12c and 12d resulted from a chiral separation of the diastereomeric mixture in Example 12a. The separation was achieved on a Gilson semi prep system (200 mL heads) using a Merck 50 mm 16 um Chirose Bond C2 NCB column and eluting with tert-butylmethyl ether/ethanol (85/15) at a flow rate of 80 mL/min. Example 12c was the first isomer to elute (retention time 16.08 mins) and Example 12d the second (retention time 20.88 mins).

3-Hydroxy-5-{[(S)-2-hydroxy-1-methylethyl]oxy}-N-(1-methyl-1H-pyrazol-3-yl)benzamide

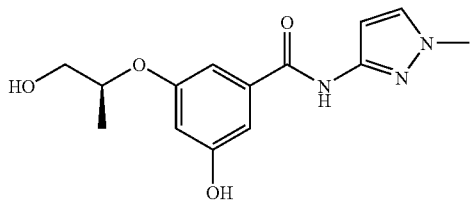

To a solution of 3-hydroxy-5-[(1S)-2-methoxy-(1-methylethyl)oxy]-N-(1-methyl-1H-pyrazol-3-yl)benzamide (10.0 g) in acetonitrile (200 mL), under an atmosphere of argon, was added iodotrimethylsilane (23.8 mL) and the resultant mixture stirred for 16 hours. Methanol (30 mL) was then added and the mixture stirred for 15 minutes, saturated potassium carbonate (30 mL) and sodium thiosulphate (0.5 g) were then added and the mixture stirred for 2 hours. The acetonitrile was removed in vacuo, the residue dissolved in water (150 mL) and continuously extracted with ethyl acetate for 16 hours. The ethyl acetate was removed in vacuo and the residue chromatographed on silica (eluting with 0-5% methanol in ethyl acetate) to give the desired compound (7.1 g).

$^1$H NMR δ (d$_6$-DMSO): 1.20 (d, 3H), 3.44 (m, 1H), 3.53 (m, 1H), 3.75 (s, 3H), 4.45 (m, 1H), 4.79 (t, 1H), 6.44 (m, 1H), 6.52 (m, 1H), 6.92 (m, 1H), 7.02 (m, 1H), 7.56 (m, 1H), 9.58 (s, 1H), 10.60 (br s, 1H). m/z 292 (M+H)$^+$

3-Hydroxy-5-[(1S)-2-methoxy-(1-methylethyl)oxy]-N-(1-methyl-1H-pyrazol-3-yl)benzamide

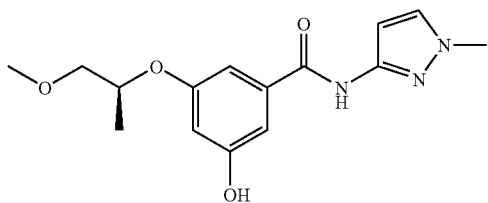

To a solution of 3-[(1S)-2-methoxy-(1-methylethyl)oxy]-N-(1-methyl-1H-pyrazol-3-yl)-5-[(phenylmethyl)oxy]benzamide (7.07 g) in THF (50 mL) and methanol (50 mL) was added 10% palladium on carbon (727 mg) as a slurry in THF (1 mL) and methanol (1 mL). The mixture was placed under vacuum and stirred under an atmosphere of hydrogen for 70 hours. The mixture was filtered through diatomaceous earth, and the diatomaceous earth washed with methanol (2×100 mL), followed by evaporation in vacuo. The residues were dissolved in ethyl acetate (10 mL), treated with isohexane (40 mL), the solid filtered off and washed with isohexane (50 mL) to afford the desired compound (5.17 g) which was used without further purification.

$^1$H NMR δ (d$_6$-DMSO): 1.22 (d, 3H), 3.28 (s, 3H, obscured by water), 3.38-3.53 (m, 2H), 3.76 (s, 3H), 4.65 (m, 1H), 6.44 (m, 1H), 6.54 (m, 1H), 6.93 (s, 1H), 7.04 (s, 1H), 7.57 (m, 1H), 9.63 (br s, 1H), 10.60 (s, 1H). m/z 306 (M+H)$^+$, 304 (M-H)$^-$

3-[(1S)-2-Methoxy-(1-methylethyl)oxy]-N-(1-methyl-1H-pyrazol-3-yl)-5-[(phenylmethyl)oxy]benzamide

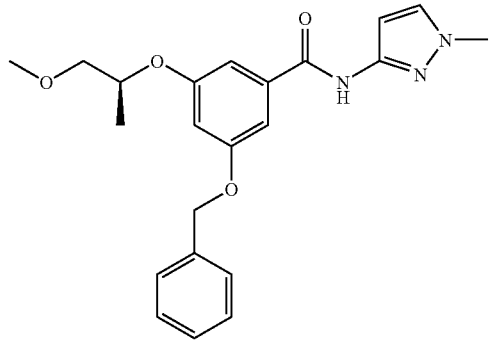

A solution of 3-[(1S)-2-methoxy-(1-methylethyl)oxy]-5-{[phenylmethyl]oxy}benzoic acid (8.73 g) in DCM (150 mL) was cooled to 0° C. Oxalyl chloride (4.81 mL) and DMF (0.15 mL) were slowly added with stirring. The mixture was allowed to warm to ambient temperature and stirred for 16-hours, following which the organics were removed in vacuo, and the residues azeotroped with toluene (75 mL). The crude material was dissolved in DCM (75 mL) and slowly added to a stirred suspension of 1-methyl-1H-pyrazol-3- amine (3.35 g) and DIPEA (14.4 mL) in DCM (75 mL). The mixture was stirred at ambient temperature for 18 hours, before the organics were evaporated in vacuo and the residue dissolved in ethyl acetate (150 mL). The organics were washed with 1M aqueous hydrochloric acid (100 mL) and brine (50 mL); and dried (MgSO$_4$), before evaporation in vacuo to give crude material. This was chromatographed on a 200 g Biotage Flash 75 SiO$_2$ column (eluting with 30 to 90% ethyl acetate in isohexane), and evaporated in vacuo to afford the desired compound (7.07 g).

$^1$H NMR δ (d$_6$-DMSO): 1.23 (d, 3H), 3.28 (s, 3H, obscured by water), 3.40-3.52 (m, 2H), 3.77 (s, 3H), 4.70 (m, 1H), 5.03 (s, 2H), 6.56 (m, 1H), 6.71 (m, 1H), 7.18 (s, 1H), 7.24 (s, 1H), 7.32-7.47 (brm, 5H), 7.58 (m, 1H), 10.73 (s, 1H). m/z 396 (M+H)$^+$.

3-[(1S)-2-Methoxy-(1-methylethyl)oxy]-5-{[phenylmethyl]oxy}benzoic acid

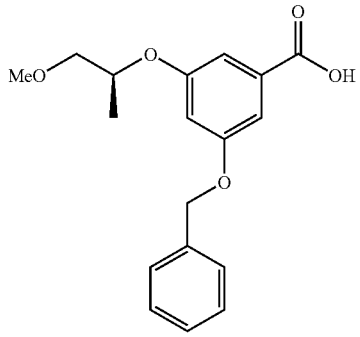

A solution of methyl 3-[(1S)-2-methoxy-(1-methylethyl)oxy]-5-{[phenylmethyl]oxy}benzoate (77.4 mmol) in a mixture of THF (232 mL) and methanol (232 mL) was treated with a solution of 2M sodium hydroxide (232 mmol), and the reaction mixture stirred for 4 hours at ambient temperature. The resulting solution was diluted with water (250 mL) and most of the organic solvent removed in vacuo. The resulting suspension was washed with diethyl ether (3×200 mL) and the organic washings discarded. The resulting aqueous solution was acidified to pH4 with 2M hydrochloric acid solution and extracted with ethyl acetate (2×200 mL). The extracts were combined, washed with brine, dried (MgSO$_4$), and evaporated to give the desired compound (99% yield).

$^1$H NMR δ (d$_6$-DMSO): 1.20 (d, 3H), 3.46 (m, 2H), 4.64 (m, 1H), 5.15 (s, 2H), 6.83 (app t, 1H), 7.06 (s, 1H), 7.13 (s, 1H), 7.30-7.49 (m, 5H), 12.67 (br s, 1H)

Methyl 3-[(1S)-2-methoxy-(1-methylethyl)oxy]-5-{[phenylmethyl]oxy}benzoate

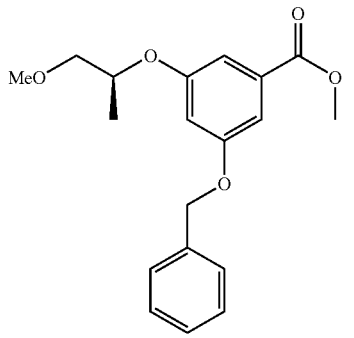

To a solution of methyl 3-hydroxy-5-{[phenylmethyl]oxy}benzoate (77.4 mmol) in THF was added polymer-supported triphenylphosphine (51.7 g of 3 mmol/g loading, 155 mmol) and (R)-(−)-1-methoxy-2-propanol (102 mmol). The stirred solution was blanketed with argon and cooled in an ice bath. A solution of DIAD (116 mmol) was added dropwise by syringe over 10 minutes. The solution was stirred for 20 minutes and filtered, washing the residue with THF (500 mL). The filtrate and washings were combined, and evaporated to give the desired compound which was used without further purification.

$^1$H NMR δ (d$_6$-DMSO): 3.26 (s, 3H), 3.44 (m, 2H), 3.82 (s, 3H), 4.63 (m, 1H), 5.14 (s, 2H); 6.85 (s, 1H), 7.05 (s, 1H), 7.11 (s, 1H), 7.30-7.47 (m, 5H). The $^1$H NMR spectrum also contained signals consistent with a small amount of bis(1-methylethyl)hydrazine-1,2-dicarboxylate.

Methyl 3-hydroxy-5-{[phenylmethyl]oxy}benzoate

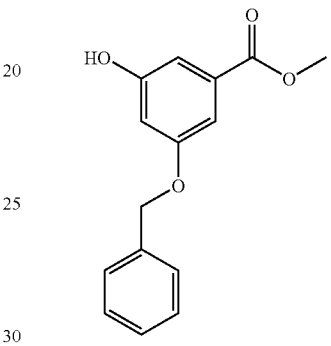

To a stirred solution of methyl 3,5-dihydroxybenzoate (5.95 mol) in DMF (6 L) was added potassium carbonate (9 mol), and the suspension stirred at ambient temperature under argon. To this was added benzyl bromide (8.42 mol) slowly over 1 hour, with a slight exotherm, and the reaction mixture stirred overnight at ambient temperature. The reaction was quenched cautiously with ammonium chloride solution (5 L) followed by water (35 L). The aqueous suspension was extracted with DCM (1×3 L and 2×5 L). The combined extracts were washed with water (10 L) and dried overnight (MgSO$_4$). The solution was evaporated in vacuo, and the crude product chromatographed in 3 batches (flash column, 3×2 kg silica, eluting with a gradient consisting of hexane containing 10% DCM, to neat DCM, to DCM containing 50% ethyl acetate) to eliminate starting material. The crude eluant was further chromatographed in 175 g batches (Amicon HPLC, 5 kg normal-phase silica, eluting with isohexane containing 20% v/v of ethyl acetate) to give the desired compound (21% yield).

$^1$H NMR δ (d$_6$-DMSO): 3.8 (s, 3H), 5.1 (s, 2H), 6.65 (m, 1H), 7.0 (m, 1H), 7.05 (m, 1H), 7.3-7.5 (m, 5H), 9.85 (br s, 1H).

The aryl fluorides used in the preparation of Examples 12, 12b were prepared in an analogous fashion to 1-(3,4-difluorobenzoyl)azetidine described in Example 8 by reaction of the appropriate benzoic acid with the appropriate amine.

3,4-Difluoro-N,N-dimethylbenzamide

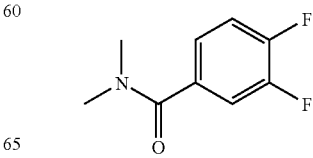

¹H NMR δ (CDCl₃): 2.9-3.2 (m, 6H), 7.2 (m, 2H), 7.3 (m, 1H). m/z 186 (M+H)⁺.

1-(3,4-Difluorobenzoyl)pyrrolidine

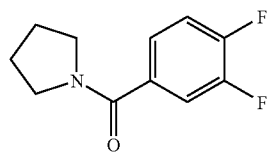

¹H NMR δ (CDCl₃): 1.8-2.1 (m, 4H), 3.4 (t, 2H), 3.7 (t, 2H), 7.2 (m, 1H), 7.3 (m, 1H), 7.4 (t, 1H).

The aryl fluoride used in the preparation of Example 12a was prepared as described below.

2-Chloro-4-(ethylsulfinyl)-1-fluorobenzene

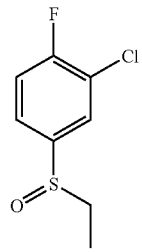

To a solution of 2-chloro-4-ethanesulphanyl-1-fluorobenzene (2.40 g) in DCM (100 mL) was added 75% m-chloroperbenzoic acid (4.35 g) and the mixture stirred at ambient temperature for 16 h. The mixture was washed successively with saturated potassium carbonate (30 mL) and brine (30 mL) then dried (MgSO₄), filtered and reduced in vacuo. The resultant residue was chromatographed on silica (eluting with 0-50% ethyl acetate in iso-hexane) and the slower running product isolated (1.26 g).

¹H NMR δ (d₆-DMSO): 1.01 (t, 3H), 2.80 (m, 1H), 3.06 (m, 1H), 7.64 (m, 2H), 7.84 (dd, 1H)

EXAMPLE 13

3-[4-(Azetidin-1-ylcarbonyl)-2-chlorophenoxy]-5-[(1S)-2-hydroxy-1-methylethoxy]-N-(1-isopropyl-1H-pyrazol-3-yl)benzamide

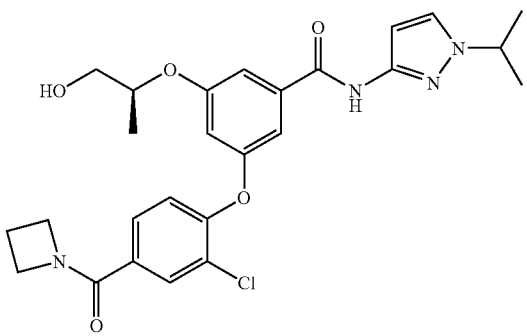

Potassium carbonate (182 mg, 1.32 mmol) was added to a mixture of 3-((1S)-2-{[tert-butyl(dimethyl)silyl]oxy}-1-methylethoxy)-5-hydroxy-N-(1-isopropyl-1H-pyrazol-3-yl)benzamide (350 mg, 0.81 mmol) and 1-(3-Chloro-4-fluorobenzoyl)azetidine (181 mg, 0.85 mmol) in acetonitrile (5 mL) and the stirred mixture heated at 160° C. in a 'Smith Creator Microwave' for 15 hours. The mixture was allowed to reach ambient temperature and pressure and reduced in vacuo. The residual oil was partitioned between ethyl acetate (50 mL) and water (50 mL). The ethyl acetate layer was separated, washed with brine, dried (MgSO₄), and evaporated to a residue which was chromatographed on silica, eluting with a gradient of 50-100% ethyl acetate in isohexane, to give the desired compound (331 mg)

¹H NMR δ (CDCl₃): 1.28 (d, 3H), 1.46 (d, 6H), 2.05 (brs, 1H), 2.38 (quin, 2H), 3.75 (m, 2H), 4.20-4.40 (brm, 5H), 4.55 (m, 1H), 6.71 (m, 1H), 7.01 (m, 2H), 7.25 (m, 2H), 7.31 (m, 1H), 7.51 (d, 1H), 7.79 (d, 1H), 8.39 (brs, 1H). m/z 513, 515 (M+H)⁺

In a similar manner to that described above, the following compounds were also prepared:

| Example | Structure | m/z | NMR |
|---|---|---|---|
| 13a | 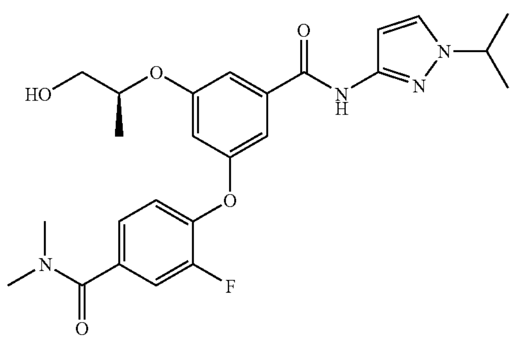 | 485 (M + H)⁺ | ¹H NMR δ (CDCl₃): 1.30 (d, 3H), 1.46 (d, 6H), 2.49 (t, 1H), 3.06 (s, 6H), 3.71 (m, 2H), 4.36 (sept, 1H), 4.55 (m, 1H), 6.70 (m, 1H), 6.78 (m, 1H), 7.07 (m, 2H), 7.21 (m, 2H), 7.30 (dd, 1H), 7.36 (d, 1H), 8.69 (brs, 1H). |

| Example | Structure | m/z | NMR |
|---|---|---|---|
| 13b | 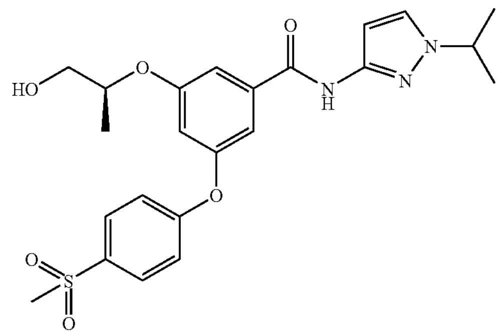 | 474 (M + H)+ | ¹H NMR δ (CDCl₃): 1.31 (d, 3H), 1.46 (d, 6H), 2.15 (brs, 1H), 3.07 (s, 3H), 3.78 (m, 2H), 4.35 (sept, 1H), 4.55 (sex, 1H), 6.79 (m, 2H), 7.12 (m, 3H), 7.30 (m, 1H), 7.35 (d, 1H), 7.91 (d, 2H), 8.41 (brs, 1H). |
| 13c | 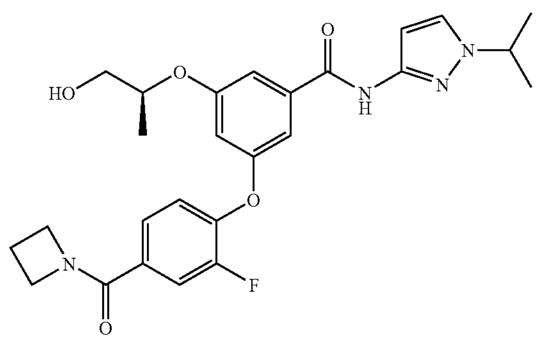 | 497 (M + H)+ | ¹H NMR δ (CDCl₃): 1.28 (d, 3H), 1.46 (d, 6H), 2.08 (brt, 1H), 2.38 (quin, 2H), 3.75 (m, 2H), 4.20-4.40 (brm, 5H), 4.54 (m, 1H), 6.73 (m, 2H), 7.08 (m, 2H), 7.21 (m, 1H), 7.33 (m, 1H), 7.41 (d, 1H) 7.51 (dd, 1H), 8.38 (brs, 1H). |
| 13d | 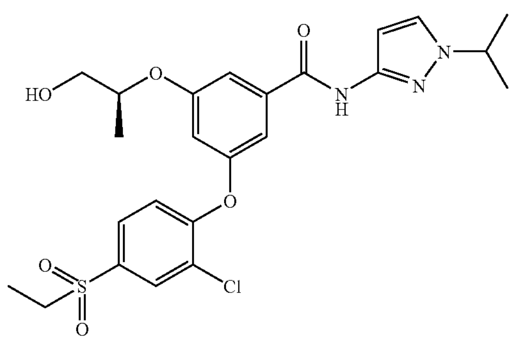 | 522, 524 (M + H)+ | ¹H NMR δ (CDCl₃): 1.30 (m, 6H), 1.45 (d, 6H), 2.86 (t, 1H), 3.15 (q, 2H), 3.75 (m, 2H), 4.35 (sept, 1H), 4.56 (sex, 1H), 6.75 (m, 2H), 7.04 (d, 1H), 7.10 (m, 1H), 7.28 (m, 1H), 7.35 (m, 1H) 7.70 (dd, 1H), 8.00 (d, 1H), 8.78 (brs, 1H). |

3-((1S)-2-{[tert-Butyl(dimethyl)silyl]oxy}-1-methylethoxy)-5-hydroxy-N-(1-isopropyl-1H-pyrazol-3-yl)benzamide

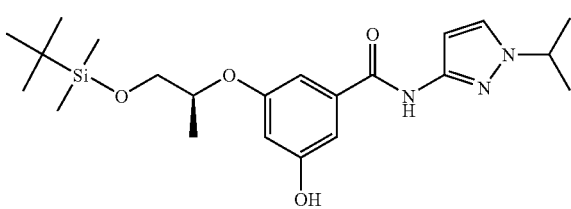

A solution of 3-(benzyloxy)-5-((1S)-2-{[tert-butyl(dimethyl)silyl]oxy}-1-methylethoxy)-N-(1-isopropyl-1H-pyrazol-3-yl)benzamide (1.97 g, 3.77 mmol) and THF (70 mL) was evacuated and purged with, Argon (×3). Palladium on carbon (10% w/w, 400 mg) was added and reaction mixture was evacuated and finally purged with hydrogen gas. Reaction mixture was left to stir at ambient temperature under hydrogen for 16 hours. Pd/C was filtered off and concentrated in vacuo to give the product as a colourless oil (1.58 g, 97%).

¹H NMR δ (CDCl₃): 0.02 (s, 3H), 0.04 (s, 3H), 0.85 (s, 9H), 1.27 (d, 3H), 1.53 (s, 3H), 1.55 (s, 3H), 3.63 (dd, 1H), 3.77 (dd, 1H), 4.41 (m, 1H), 6.60 (s, 1H), 6.81 (s, 1H), 7.00 (s, 1H), 7.07 (s, 1H), 7.38 (s, 1H), 8.78 (br. s, 1H). m/z 434 (M+H)+, 432 (M–H)⁻.

3-(Benzyloxy)-5-((1S)-2-{[tert-butyl(dimethyl)silyl]oxy}-1-methylethoxy)-N-(1-isopropyl-1H-pyrazol-3-yl)benzamide

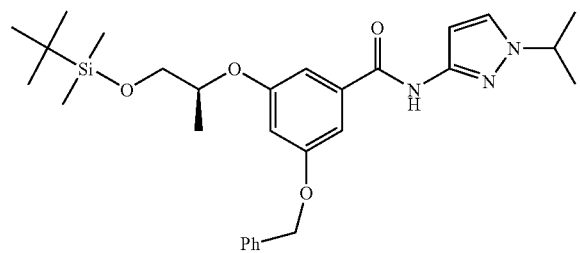

DIPEA (3.11 mL, 18.03 mmol) was added to a solution of 3-{(phenylmethyl)oxy}-5-((1S)-2-{[tert-butyl(dimethyl)silyl]oxy}-1-methylethoxy)benzoic acid (3.00 g, 7.21 mmol), HATU (3.12 g, 8.21 mmol) and 1-isopropyl-1H-pyrazol-3-amine (1.13 g, 9.01 mmol) in DMF (10 mL). The resulting mixture was stirred at ambient temperature for 16 hours. The DMF was removed in vacuo. The solvent was evaporated and the residue was dissolved in 5% w/v citric acid (50 mL) and ethyl acetate (30 mL) and diethyl ether (30 mL) and the organic layer was further washed with sat. aqueous sodium bicarbonate solution (30 mL) and brine (30 mL). The organic layer was separated, then dried (MgSO$_4$), filtered and evaporated. Purification by column chromatography, eluting with 1:4 to 1:3 ethyl acetate:hexanes, afforded the title compound as a colourless oil (2.40 g, 65%).

$^1$H NMR δ (CDCl$_3$): 0.01 (s, 3H), 0.03 (s, 3H), 0.86 (s, 9H), 1.24 (d, 3H), 1.49 (s, 3H), 1.51 (s, 3H), 3.64 (dd, 1H), 3.78 (dd, 1H), 4.39 (m, 1H), 4.46 (m, 1H), 5.09 (s, 2H), 6.70 (s, 1H), 6.78 (s, 1H), 7.02 (s, 1H), 7.08 (s, 1H), 7.35 (m, 6H), 8.32 (br. s, 1H). m/z 524 (M+H)$^+$, 522 (M−H)$^-$.

1-Isopropyl-1H-pyrazol-3-amine

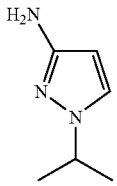

2-Chloroacrylonitrile (3.41 mL, 42.59 mmol) was added at RT to a stirring solution of N-isopropylhydrazine hydrochloride (4.71 g, 42.6 mmol), potassium carbonate (11.8 g, 85.2 mmol) in water (50 mL). The reaction was warmed to 45° C. for 4 hours before cooling back to RT. The aqueous layer was then extracted with ethyl acetate (5×30 mL) and the combined organic layers were dried (MgSO$_4$), treated with activated charcoal, filtered and evaporated. The residue was purified by chromatography, eluting with 67%-100% ethyl acetate in hexanes, to afford the title compound (3.08 g, 58%) as a 6:1 mixture of authentic product to regioisomeric product as an oil. The material was used without further purification.

$^1$H NMR δ (CDCl$_3$): 1.42 (m, 6H), 3.58 (br. s, 2H), 4.25 (sept, 1H), 5.58 (d, 1H), 7.15 (d, 1H).

The aryl fluorides used to prepare Example 13, 13a, 13b are described in previous examples. 4-Fluorophenyl methyl sulphone used in the preparation of Example 13c is commercially available. The aryl fluoride used to prepare Example 13d was prepared as described below.

2-Chloro-4-(ethylsulfonyl)-1-fluorobenzene

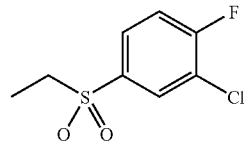

To a solution of 2-chloro-4-ethanesulphanyl-1-fluorobenzene (2.40 g) in DCM (100 mL) was added 75% m-chloroperbenzoic acid (4.35 g) and the mixture stirred at ambient temperature for 16 h. The mixture was washed successively with saturated potassium carbonate (30 mL) and brine (30 mL) then dried (MgSO$_4$), filtered and reduced in vacuo. The resultant residue was chromatographed on silica (eluting with 0-50% ethyl acetate in iso-hexane) and the faster running product isolated (0.99 g). $^1$H NMR δ (d$_6$-DMSO): 1.08 (t, 3H), 3.36 (q, 2H), 7.69 (t, 1H), 7.90 (m, 1H), 8.10 (dd, 1H)

EXAMPLE 14

3-[4-(Azetidin-1-ylcarbonyl)phenoxy]-5-[(1S)-2-hydroxy-1-methylethoxy]-N-(1-isopropyl-1H-pyrazol-3-yl)benzamide

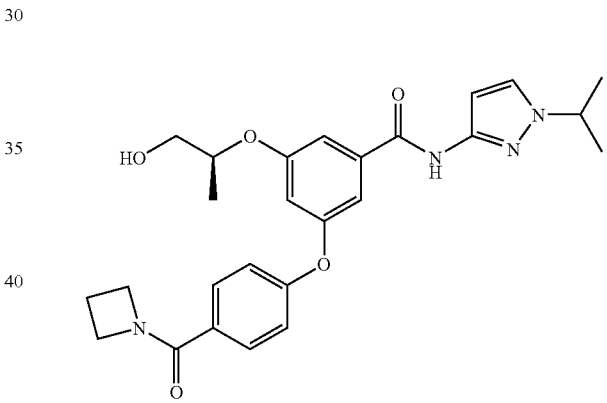

3-[4-(Azetidin-1-ylcarbonyl)-2-chlorophenoxy]-5-[(1S)-2-hydroxy-1-methylethoxy]-N-(1-isopropyl-1H-pyrazol-3-yl)benzamide (0.33 g, 0.644 mmol) was dissolved in methanol (4 mL) and THF (4 mL) and the flask evacuated and purged with argon (3 times). 10% Palladium on carbon (0.033 g) was added and the flask further evacuated and finally purged with hydrogen gas. The reaction mixture was stirred at ambient temperature for 20 hours. The reaction mixture was evacuated and purged with nitrogen (3 times). The catalyst was filtered off through celite, and the filtrate concentrated in vacuo. The residue was chromatographed on silica eluting with a gradient of 0-100% ethyl acetate in isohexane to give the desired compound (0.15 g);

$^1$H NMR δ (CDCl$_3$): 1.30 (d, 3H), 1.45 (d, 6H), 2.20 (brs, 1H), 2.35 (quin, 2H), 3.71 (m, 2H), 4.20-4.40 (brm, 5H), 4.54 (m, 1H), 6.77 (m, 2H), 7.00 (d, 2H), 7.08 (m, 1H), 7.23 (m, 1H), 7.34 (m, 1H), 7.63 (d, 2H), 8.49 (brs, 1H); m/z 479 (M+H)$^+$ In a similar manner to that described above, the following compound was also prepared:

| Example | Structure | m/z | NMR |
|---|---|---|---|
| 14a | 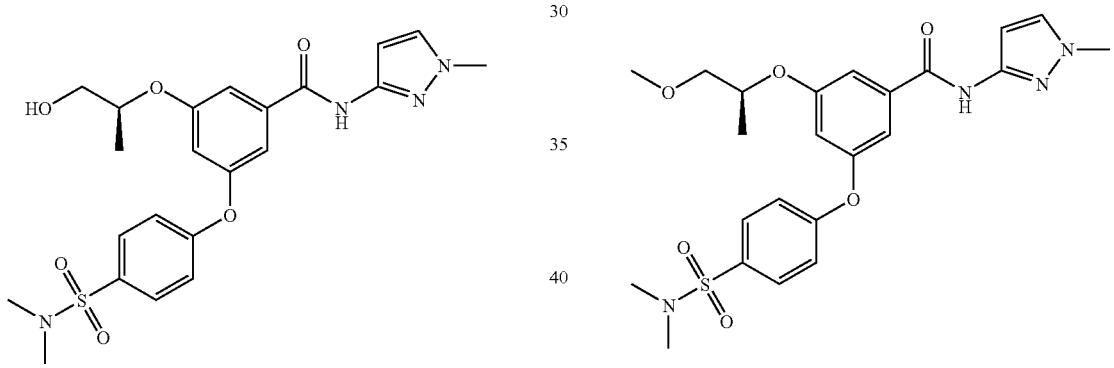 | 488 (M + H)+ | $^1$H NMR δ (CDCl$_3$): 1:30 (m, 6H), 1.45 (d, 6H), 2.15 (brs, 1H), 3.11 (q, 2H), 3.75 (m, 2H), 4.37 (sept, 1H), 4.56 (m, 1H), 6.78 (m, 2H), 7.11 (m, 3H), 7.30 (m, 1H), 7.35 (m, 1H), 7.86 (d, 2H), 8.40 (brs, 1H). |

EXAMPLE 15

3-{4-[(Dimethylamino)sulfonyl]phenoxy}-5-[(1S)-2-hydroxy-1-methylethoxy]-N-(1-methyl-1H-pyrazol-3-yl)benzamide 3-{-4-[(Dimethylamino)sulfonyl]phenoxy}-5-[(1S)-2-methoxy-1-methylethoxy]-N-(1-methyl-1H-pyrazol-3-yl)benzamide To a solution of 3-{4-[(dimethylamino)sulfonyl]phenoxy}-5-[(1S)-2-methoxy-1-methylethoxy]-N-(1-methyl-1H-pyrazol-3-yl)benzamide (500 mg, 1.0 mmol) in acetonitrile (30 mL) was added iodotrimethylsilane (0.73 mL, 1.0 g, 5.1 mmol) dropwise. The resulting mixture was stirred at RT for 20 hours. Aqueous sodium hydrogen carbonate solution (saturated, 5 mL) was added slowly and the resulting mixture was concentrated under reduced pressure. Water (50 mL) was added and the mixture was extracted with ethyl acetate (50 mL). The organic layers was washed with brine (50 mL), dried (MgSO$_4$) and evaporated to afford the crude product. This was purified by flash chromatography (eluting with an increasing gradient of 60 to 100% ethyl acetate in isohexane) to afford the pure title compound (216 mg, 45%).

$^1$H NMR δ (d$_6$-DMSO): 1.23 (s, 3H), 2.61 (s, 6H), 3.53 (m, 2H), 3.76 (s, 3H), 4.57 (m, 1H), 4.84 (t, 1H), 6.55 (s, 1H), 6.90 (s, 1H), 7.21 (d, 2H), 7.30 (t, 1H), 7.48 (t, 1H), 7.58 (d, 1H), 7.75 (d, 2H), 10.85 (br s, 1H); m/z 475 (M+H)+.

To a solution of 3-{2-chloro-4-[(dimethylamino)sulfonyl]phenoxy}-5-[(1S)-2-methoxy-1-methylethoxy]-N-(1-methyl-1H-pyrazol-3-yl)benzamide (1.0 g, 1.9 mmol) in methanol (20 mL) and THF (20 mL) was added triethylamine (1.5 mL) and 10% palladium on carbon (100 mg). The resulting mixture was stirred under an atmosphere of hydrogen for 20 hours. The mixture was filtered through Celite® and evaporated under reduced pressure. The residue was dissolved in DCM (100 mL) and washed with 2M hydrochloric acid (100 mL). The organic phase was separated and the aqueous reextracted with DCM (100 mL). The combined organic extracts were dried (MgSO$_4$) and evaporated to afford the title compound (300 mg, 32%).

$^1$H NMR δ (d$_6$-DMSO): 1.23 (d, 3H), 2.60 (s, 6H), 3.27 (s, 3H, obscured by water), 3.43-3.54 (m, 2H), 3.75 (s, 3H), 4.75 (m, 1H), 6.54 (m, 1H), 6.91 (m, 1H), 7.21 (d, 2H), 7.29 (s, 1H), 7.48 (s, 1H), 7.58 (m, 1H), 7.75 (d, 2H), 10.84 (s, 1H); m/z 489 (M+H)+

3-{2-Chloro-4-[(dimethylamino)sulfonyl]phenoxy}-5-[(1S)-2-methoxy-1-methylethoxy]-N-(1-methyl-1H-pyrazol-3-yl)benzamide

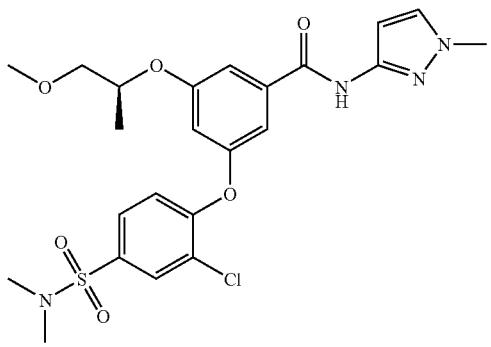

To a solution of 3-hydroxy-5-[(1S)-2-methoxy-(1-methylethyl)oxy]-N-(1-methyl-1H-pyrazol-3-yl)benzamide (152 mg, 0.50 mmol) in acetonitrile (3.5 mL) was added potassium carbonate (345 mg, 2.5 mmol) and 3-chloro-4-fluoro-N,N-dimethylbenzenesulfonamide (237 mg, 1.0 mmol) and the mixture was heated under microwave conditions at 160° C. for 2 hours. The mixtures were filtered and evaporated. The residue was purified by flash chromatography (eluting with an increasing gradient of 60 to 100% ethyl acetate in isohexane) to afford the title compound (1.8 g, 98%).

$^1$H NMR δ (d$_6$-DMSO): 1.24 (d, 3H), 2.65 (s, 6H), 3.27 (s, 3H, obscured by water), 3.42-3.54 (m, 2H), 3.76 (s, 3H), 4.72-4.81 (m, 1H), 6.55 (m, 1H), 6.93 (m, 1H), 7.20 (d, 1H), 7.26 (s, 1H), 7.48 (s, 1H), 7.58 (m, 1H), 7.70 (dd, 1H), 7.91 (m, 1H), 10.84 (s, 1H); m/z 523, 525 (M+H)$^+$

3-Chloro-4-fluoro-N,N-dimethylbenzenesulfonamide

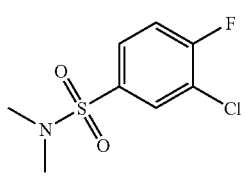

A solution of 2M dimethylamine in THF (5.9 mL, 12 mmol) was diluted with DCM (25 mL) and cooled to 0° C. DIPEA (2.8 mL) was added, followed by and 3-chloro-4-fluorobenzenesulfonyl chloride (2.5 g, 11 mmol) in DCM (25 mL). The resulting mixture was allowed to warm to rt and stirred for 3 hours. Water (5 mL) and 1M hydrochloric acid (16 mL) was added. The organic phase was separated and evaporated under reduced pressure to afford the title compound (2.4 g, 94%).

$^1$H NMR δ (d$_6$-DMSO): 2.64 (s, 6H), 7.68 (t, 1H), 7.78 (m, 1H), 7.94 (m, 1H).

EXAMPLE 16

3-[4-(Azetidin-1-ylcarbonyl)phenoxy]-5-[(1S)-2-hydroxy-1-methylethoxy]-N-1H-pyrazol-3-ylbenzamide

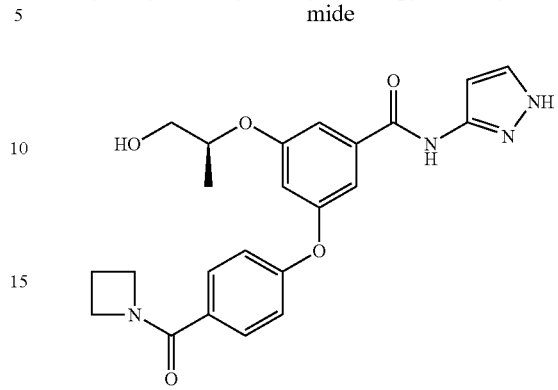

A suspension of 4-{3-[(1S)-2-hydroxy-1-methylethoxy]-5-[(1H-pyrazol-3-ylamino)carbonyl]phenoxy}benzoic acid (130 mg, 0.327 mmol), HATU (156 mg, 0.41 mmol), azetidine hydrochloride (38 mg, 0.41 mmol) and DIPEA (0.143 mL; 0.82 mmol) in DMF (2 mL) was stirred at ambient temperature for 16 hours. Water was added to the reaction mixture and it was extracted into ethyl acetate (3×30 mL). The organic phases were combined, washed with brine solution and dried (MgSO$_4$). The filtrate was concentrated in vacuo and the residue chromatographed, eluting with 0-50% methanol in DCM, to give a clear oil which gave a foam under high vacuum (65 mg, 46%).

$^1$H NMR δ (d$_6$-DMSO): 1.2 (d, 3H), 2.2 (s, 2H), 2.95 (s, 6H), 3.2 (s, 3H), 3.5 (m, 2H), 4.0 (m, 2H), 4.3 (m, 2H), 4.6 (m, 1H), 4.80 (t, 1H), 6.6 (s, 1H), 6.8 (s, 1H), 7.05 (d, 2H), 7.2 (s, 1H), 7.4 (s, 1H), 7.6 (s, 1H), 7.65 (d, 2H), 10.8 (s, 1H). m/z 437 (M+H)$^+$, 435 (M−H)$^+$.

4-{3-[(1S)-2-Hydroxy-1-methylethoxy]-5-[(1H-pyrazol-3-ylamino)carbonyl]phenoxy}benzoic acid was prepared as described below:

4-{3-[(1S)-2-Hydroxy-1-methylethoxy]-5-[(1H-pyrazol-3-ylamino)carbonyl]phenoxy}benzoic acid

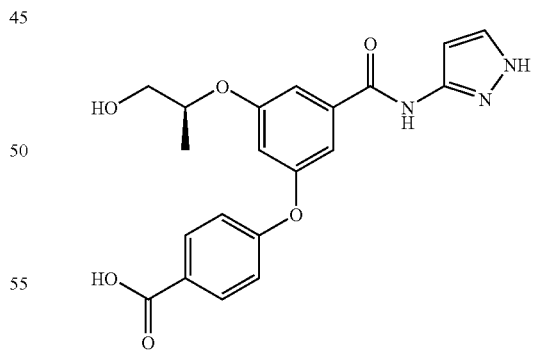

A solution of ethyl 4-{3-[(1S)-2-hydroxy-1-methylethoxy]-5-[(1H-pyrazol-3-ylamino)carbonyl]phenoxy}benzoate (175 mg, 0.4 mmol) in THF (5 mL) and water (1 mL) was treated with 1N sodium hydroxide solution (3 mL) and the reaction stirred at RT for 16 hours. On completion, the solvent was removed in vacuo and 1N citric acid added until pH 3-4. The white precipitate was collected by filtration and dried in vacuo to give the desired product as a white solid (138 mg, 85%).

¹H NMR δ (d₆-DMSO): 1.2 (d, 3H), 3.25 (s, 3H obscured by water peak), 3.5 (m, 2H), 4.55 (m, 1H), 4.80 (t, 1H), 6.6 (d 1H), 6.8 (app s, 1H), 7.1 (d, 2H), 7.2 (s, 1H), 7.4 (s, 1H), 7.6 (d, 1H), 8.0 (d, 2H), 10.8 (s, 1H). m/z 398 (M+H)⁺, 396 (M−H)⁺ 95%

Ethyl 4-{3-[(S)-2-hydroxy-1-methylethoxy]-5-[(1H-pyrazol-3-ylamino)carbonyl]phenoxy}benzoate

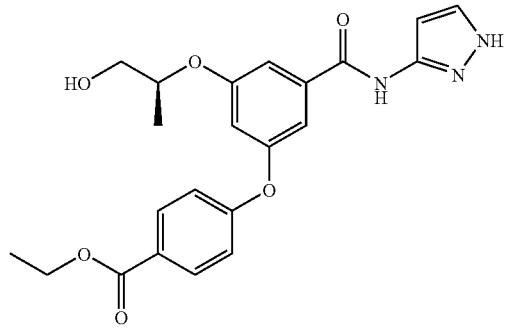

Trimethylsilyl iodide (0.27 mL) was added dropwise under argon to a solution of tert-butyl 3-({3-[4-(ethoxycarbonyl)phenoxy]-5-[(1S)-2-methoxy-1-methylethoxy]benzoyl}amino)-1H-pyrazole-1-carboxylate (167 mg, 0.38 mmol) in acetonitrile (5 mL) and stirred at ambient temperature for 16 hours. Sodium thiosulfate solution was added to quench the reaction and the reaction mixture was extracted into ethyl acetate (3×25 mL). Organic phases were combined and dried (MgSO₄) and the filtrate was concentrated in vacuo to give a clear oil (180 mg), which was not purified further. m/z 426 (M+H)⁺, 424 (M−H)⁺ 88% tert-Butyl 3-({3-[4-(ethoxycarbonyl)phenoxy]-5-[(1S)-2-methoxy-1-methylethoxy]benzoyl}amino)-1H-pyrazole-1-carboxylate

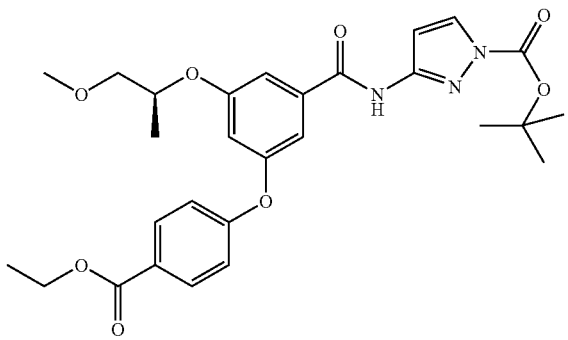

tert-Butyl 3-({3-hydroxy-5-[(1S)-2-methoxy-1-methylethoxy]benzoyl}amino)-1H-pyrazole-1-carboxylate (391 mg, 1 mmol), ethyl-4-boronic acid benzoate (388 mg, 2.0 equiv), copper (II) acetate (363 mg, 2.0 equiv) and triethylamine (0.7 mL; 5.0 equiv) were suspended in dry DCM over freshly activated powdered 4A molecular sieves (ca. 1 g) for 7 hours under an ambient atmosphere. Reaction mixture filtered through diatomaceous earth was washed with DCM (×3). Filtrate concentrated in vacuo, taken up in ethyl acetate and washed with 1M hydrochloric acid, saturated sodium hydrogen carbonate, saturated brine and dried (MgSO₄). Filtered, filtrate concentrated in vacuo and chromatographed (0-50% ethyl acetate/isohexane) to give a brown oil (210 mg, 39%).

¹H NMR δ (CDCl₃): 1.3 (d, 3H), 1.4 (t, 3H), 1.6 (s, 9H), 3.4 (s, 3H), 3.5 (m, 2H), 4.35 (q, 2H), 4.5 (m, 1H), 6.8 (s, 1H), 7.0 (d, 2H), 7.05 (s, 2H), 7.2 (s, 1H), 8.0 (s, 1H), 8.05 (d, 2H), 9.2 (s, br, 1H); m/z 440 (M+H)⁺.

tert-Butyl 3-({3-hydroxy-5-[(1S)-2-methoxy-1-methylethoxy]benzoyl}amino)-1H-pyrazole-1-carboxylate

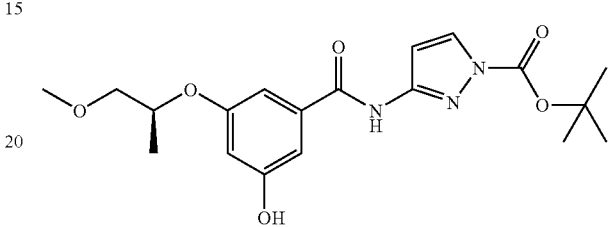

A solution of tert-butyl 3-({3-(benzyloxy)-5-[(1S)-2-methoxy-1-methylethoxy]benzoyl}amino)-1H-pyrazole-1-carboxylate (23 g, 47.8 mmol) in THF (140 mL) and ethanol (140 mL) was evacuated and purged with nitrogen (×3). 10% Palladium on carbon (2.3 g, 10% w/w) was added and reaction mixture was evacuated and finally purged with hydrogen gas. Reaction mixture was left to stir at ambient temperature under a hydrogen balloon for 16-hours. Pd/C was filtered through diatomaceous earth and the filtrate concentrated in vacuo to give a white, foam (18 g, 97%).

¹H NMR δ (d₆-DMSO): 1.2 (d, 3H), 1.55 (s, 9H), 3.25 (s, 3H obscured by water peak), 3.4-3.5 (m, 2H), 4.7 (m, 1H), 6.5 (s, 1H), 6.95 (d, 1H), 7.0 (s, 1H), 7.1 (s, 1H), 8.2 (d, 1H), 9.65 (s, 1H), 11.2 (s, br, 1H); m/z 392 (M+H)⁺ tert-Butyl 3-({3-(benzyloxy)-5-[(1S)-2-methoxy-1-methylethoxy]benzoyl}amino-1H-pyrazole-1-carboxylate

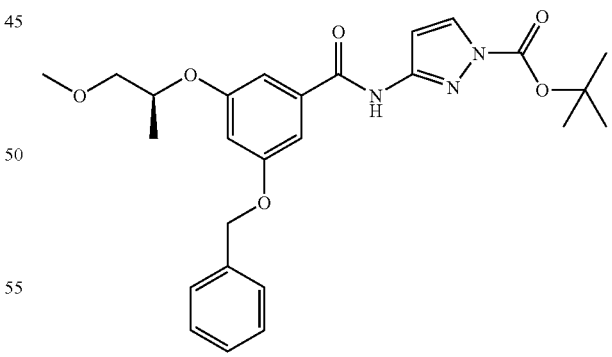

To a suspension of 3-[(1S)-2-methoxy-(1-methylethyl)oxy]-5-{[phenylmethyl]oxy}benzoic acid (20.7 g, 65.6 mmol), HATU (31.2 g, 82.0 mmol) and tert-butyl 3-amino-1H-pyrazole-1-carboxylate (15.0 g, 82.0 mmol) in DMF (30 mL) was added DIPEA (28.5 mL, 164 mmol) and reaction mixture stirred for 16 hours at ambient temperature. Water (250 mL) was then added to reaction mixture and extracted into diethyl ether (3×150 mL). Organic layer was washed with saturated brine solution and dried (MgSO₄). Filtrate was concentrated in vacuo and residue crystallised on standing. Washed with isohexane to give yellow crystals (23.4 g, 73%). m/z 482 (M+H)+.

The preparation of tert-butyl 3-amino-1H-pyrazole-1-carboxylate was described in Example 3.

The preparation of 3-[(1S)-2-methoxy-(1-methylethyl)oxy]-5-{[phenylmethyl]oxy}benzoic acid was described in Example 12.

EXAMPLE 17

3-[5-Chloro-2-fluoro-4-(methylsulfonyl)phenoxy]-5-[(1S)-2-hydroxy-1-methylethoxy]-N-(1-methyl-1H-pyrazol-3-yl)benzamide

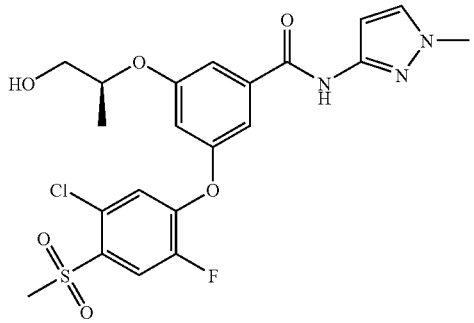

Potassium carbonate (1.00 g) was added to a solution of 3-hydroxy-5-{[(1S)-2-hydroxy-1-methylethyl]oxy}-N-(1-methyl-1H-pyrazol-3-yl)benzamide (1.41 g) and 1-chloro-4,5-difluoro-2-(methylsulfonyl)benzene (0.79 g) in NMP (20 mL). The mixture was heated to 115° C. for 3.5 hours and left to cool before being poured into water (300 mL) and extracted with ethyl acetate (2×150 mL). The combined organics were washed with water, brine and dried (MgSO4) before evaporation in vacuo. Chromatography on silica, eluting with 0 to 10% methanol in ethyl acetate, afforded the desired compound (0.86 g)

$^1$H NMR δ (d$_6$-DMSO): 1.23 (d, 3H), 3.27 (s, 3H), 3.45-3.60 (brm, 2H), 3.76 (s, 3H), 4.58 (m, 1H), 4.85 (t, 1H), 6.55 (m, 1H), 6.95 (m, 1H), 7.27 (s, 1H), 7.47 (m, 2H), 7.58 (d, 1H), 7.97 (d, 1H), 10.84 (brs, 1H); m/z 498, 500 (M+H)+, 496, 498 (M−H)−.

The preparation of 3-hydroxy-5-{[(1S)-2-hydroxy-1-methylethyl]oxy}-N-(1-methyl-1H-pyrazol-3-yl)benzamide was described in Example 12.

The preparation of 1-chloro-4,5-difluoro-2-(methylsulfonyl)benzene is described below:

1-Chloro-4,5-difluoro-2-(methylsulfonyl)benzene

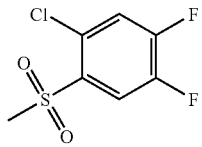

2-Chloro-4,5-difluorobenzenesulfonyl chloride (300 mg) was added to a solution of sodium sulfite (306 mg) and sodium bicarbonate (153 mg) in water (4 mL). The mixture was heated to 150° C. in a sealed microwave vial for 400 seconds and allowed to cool. The mixture was treated with bromoacetic acid (253 mg) in water (1 mL), and heated to 150° C. for 300 seconds then allowed to cool, following which the precipitate was removed by filtration and dried in vacuo to give the desired compound (132 mg). The material was used without further purification.

$^1$H NMR δ (d$_6$-DMSO): 3.38 (s, 3H), 7.99-8.12 (m, 2H).

EXAMPLE 18

3-[2,5-Difluoro-4-(methylsulfonyl)phenoxy]-5-[(1S)-2-hydroxy-1-methylethoxy]-N-(1-methyl-1H-pyrazol-3-yl)benzamide

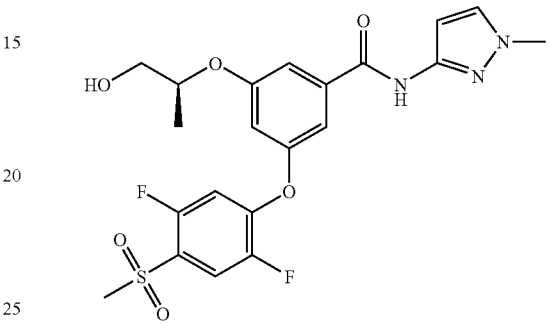

Caesium carbonate (523 mg) was added to a solution of 3-hydroxy-5-{[(1S)-2-hydroxy-1-methylethyl]oxy}-N-(1-methyl-1H-pyrazol-3-yl)benzamide (234 mg) and 1,2,4-trifluoro-5-(methylsulfonyl)benzene (169 mg) in acetonitrile (5 mL) was added. The mixture was heated in a sealed microwave vial to 160° C. for 7000 seconds and left to cool before being filtered and washed with acetonitrile (10 mL). The filtrate was evaporated in vacuo and chromatographed on silica, eluting with 0 to 10% methanol in ethyl acetate. This gave incomplete resolution so the mixture was purified by preparatory HPLC using a gradient of 5 to 95% acetonitrile in water to afford the desired compound (5.1 mg)

$^1$H NMR δ (d$_6$-DMSO): 1.24 (d, 3H), 3.33 (s, 3H), 3.45-3.59 (brm, 2H), 3.77 (s, 3H), 4.58 (m, 1H), 4.85 (m, 1H), 6.55 (m, 1H), 6.95 (m, 1H), 7.28 (m, 1H), 7.36 (m, 1H), 7.48 (m, 1H), 7.58 (m, 1H), 7.83 (m, 1H), 10.84 (brs, 1H); m/z 482 (M+H)+, 480 (M−H)−

The preparation of 3-hydroxy-5-{[(1S)-2-hydroxy-1-methylethyl]oxy}-N-(1-methyl-1H-pyrazol-3-yl)benzamide was described in Example 12.

The preparation of 1,2,4-trifluoro-5-(methylsulfonyl)benzene is described below:

1,2,4-Trifluoro-5-(methylsulfonyl)benzene

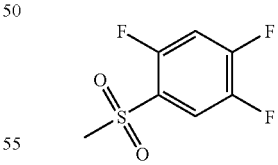

2,4,5-Trifluorophenyl sulfonyl chloride (279 mg) was added to a solution of sodium sulfite (306 mg) and sodium bicarbonate (153 mg) in water (4 mL). The mixture was heated to 150° C. in a sealed microwave vial for 400 seconds and allowed to cool. The mixture was treated with bromoacetic acid (253 mg) in water (1 mL), and heated to 150° C. for 300 seconds then allowed to cool, following which the precipitate was removed by filtration and dried in vacuo to give the desired compound (169 mg). The material was used without further purification. $^1$H NMR δ (d$_6$-DMSO): 3.35 (s, 3H), 7.87-8.01 (m, 2H).

EXAMPLE 19

3-[(1S)-2-Hydroxy-1-methylethoxy]-N-(1-methyl-1H-pyrazol-3-yl)-5-[4-(1,2,4-oxadiazol-3-yl)phenoxy]benzamide

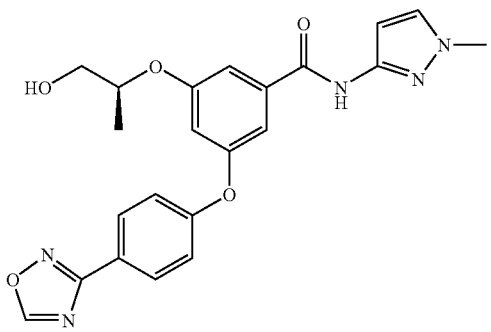

Trimethylsilyl iodide (0.062 mL, 0.434 mmol) was added to a solution of 3-[(1S)-2-methoxy-1-methylethoxy]-N-(1-methyl-1H-pyrazol-3-yl)-5-[4-(1,2,4-oxadiazol-3-yl)phenoxy]benzamide (78 mg, 0.174 mmol) in acetonitrile (2 mL) and the reaction mixture allowed to stir at RT for 18 hours. The reaction was diluted with ethyl acetate (15 mL) and quenched by the addition of saturated aqueous sodium bicarbonate (20 mL). The organic phase was washed with saturated aqueous thiosulphate solution (20 mL) and dried (MgSO$_4$). The volatiles were removed under reduced pressure and the resulting oil purified by chromatography on silica, eluting with 0-100% ethyl acetate in iso-hexane, to give the title compound as a colourless solid (64 mg).

$^1$H NMR δ (d$_6$-DMSO): 1.22 (d, 3H), 3.52 (m, 2H), 3.75 (s, 3H), 4.56 (q, 1H), 4.83 (t, 1H), 6.54 (d, 1H), 6.85 (d, 1H), 7.23 (m, 3H), 7.44 (s, 1H), 7.57 (d, 1H), 8.06 (d, 2H), 9.65 (s, 1H), 10.82 (s, 1H); m/z 436 (M+H)$^+$.

3-[(1S)-2-Methoxy-1-methylethoxy]-N-(1-methyl-1H-pyrazol-3-yl)-5-[4-(1,2,4-oxadiazol-3-yl)phenoxy]benzamide

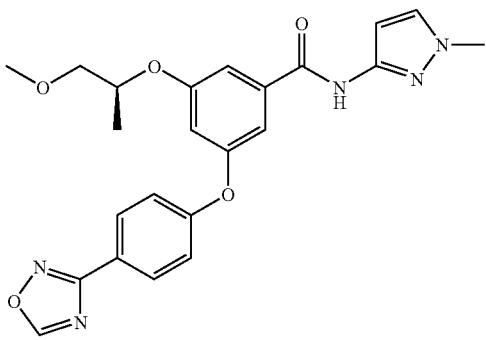

3-{4-[(Hydroxyamino)(imino)methyl]phenoxy}-5-[(1S)-2-methoxy-1-methylethoxy]-N-(1-methyl-1H-pyrazol-3-yl)benzamide was taken up in trimethyl orthoformate (3 mL) and 2 drops of borontrifluoroetherate added. The resulting solution was heated to 55° C. in a CEM explorer microwave for 80 mins. The volatiles were removed under reduced pressure and the resulting oil chromatographed on silica, eluting with 0-100% ethyl acetate in iso-hexane, to give the desired compound as a white foam (295 mg)

$^1$H NMR δ (d$_6$-DMSO) δ 1.23 (d, 3H), 3.40-3.58 (m, 2H), 3.75 (s, 3H), 4.71 m, 1H), 6.54 (s, 1H), 6.86 (s, 1H), 7.18-7.28 (m, 3H), 7.44 (s, 1H); 7.57 (s, 1H), 8.06 (d, 2H), 9.65 (s, 1H), 10.82 (s, 1H); m/z 450 (M+H)$^+$.

3-{-4-[(Hydroxyamino)(imino)methyl]phenoxy}-5-[(1S)-2-methoxy-1-methylethoxy]-N-(1-methyl-1H-pyrazol-3-yl)benzamide

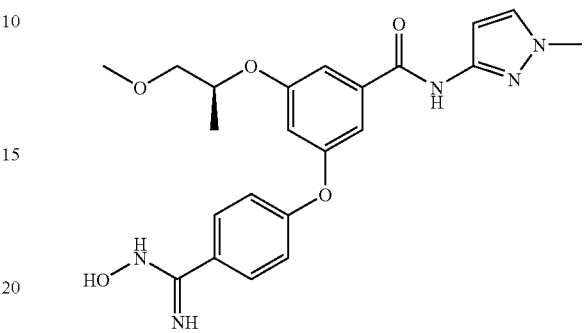

Hydroxylamine (50% w/w solution, 1 mL) was added to absolution of 3-(4-cyanophenoxy)-5-[(1S)-2-methoxy-(1-methylethyl)oxy]-N-(1-methyl-1H-pyrazol-3-yl)benzamide (300 mg, 0.74 mmol) in ethanol (3 mL) and the reaction mixture allowed to stir at RT for 18 hours. The volatiles were removed in vacuo to give the desired compound as a colourless foam (325 mg).

m/z 440 (M+H)$^+$

3-(4-Cyanophenoxy)-5-[(1S)-2-methoxy-(1-methylethyl)oxy]-N-(1-methyl-1H-pyrazol-3-yl)benzamide

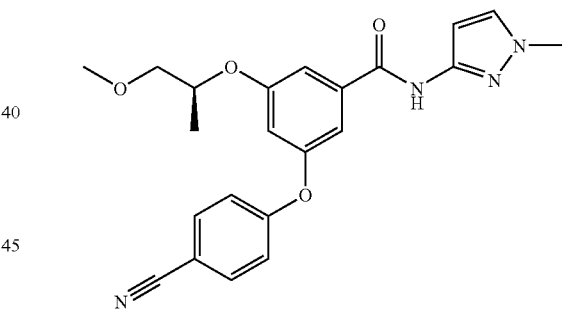

To a stirred solution of 3-hydroxy-5-[(1S)-2-methoxy-(1-methylethyl)oxy]-N-(1-methyl-1H-pyrazol-3-yl)benzamide (0.164 mmol) in DMF (1 mL) was added a 1M solution of sodium hexamethyldisilazide in THF (0.164 mmol). The reaction was stirred at RT for 10 minutes before adding 4-fluorobenzonitrile (0.164 mmol) The reaction was stirred overnight at RT, then heated to 60° C. and stirred for a further 4 hours. The reaction was allowed to cool to RT, and treated with a further 0.2 equivalents of 4-fluorobenzonitrile and sodium hexamethyldisilazide, heated to 70° C. and stirred at this temperature for 3 hours. The reaction was cooled to RT, and treated with a further 0.2 equivalents of sodium hexamethyldisilazide, warmed to 70° C., and stirred at this temperature overnight. The solvent was removed in vacuo and the residual oil partitioned between ethyl acetate and water. The water layer was separated and re-extracted with ethyl acetate. The combined organic layers were washed with brine, dried (MgSO$_4$), filtered and evaporated to a residue which was chromatographed on silica, using 0-1% methanol in DCM as the eluent, to give the desired product (60% yield).

¹H NMR δ (CDCl₃): 1.35 (d, 3H), 3.40 (s, 3H), 3.55 (m, 2H), 3.78 (s, 3H), 4.60 (m, 1H), 6.80 (m, 2H), 7.10 (m, 3H), 7.30 (m, 2H), 7.62 (d, 2H), 8.55 (br s, 1H); m/z 407 (M+H)⁺, 405 (M−H)⁻

The synthesis of 3-hydroxy-5-[(1S)-2-methoxy-(1-methylethyl)oxy]-N-(1-methyl-1H-pyrazol-3-yl)benzamide is described in Example 12.

EXAMPLE 20

3-[4-(Azetidin-1-ylcarbonyl)phenoxy]-5-[(1S)-2-hydroxy-1-methylethoxy]-N-(5-methylpyrazin-2-yl)benzamide

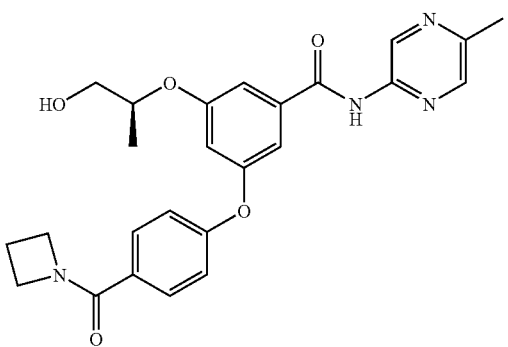

DIPEA (0.4 mL, 2.08 mmol) was added to a suspension of 4-(3-[(1S)-2-hydroxy-1-methylethoxy]-5-{[(5-methylpyrazin-2-yl)amino]carbonyl}phenoxy)benzoic acid (110 mg, 0.26 mmol), HATU (210 mg, 0.55 mmol) and azetidine hydrochloride (49 mg, 0.52 mmol) in DMF (3 mL) and the mixture stirred at RT for 24 hours. Water (30 mL) was added and the mixture extracted with ethyl acetate (3×15 mL). The combined organic extracts were washed with brine, dried (MgSO₄), and evaporated to a residue which was chromatographed on silica, eluting with 5% methanol in ethyl acetate, to give the desired compound (55 mg).

¹H NMR δ (CDCl₃): 1.30 (d, 3H), 2.35 (m, 2H), 2.57 (s, 2H), 3.77 (m, 2H), 4.20-4.40 (brm, 4H), 4.57 (m, 1H), 6.80 (m, 1H), 7.03 (d, 2H), 7.12 (m, 1H), 7.30 (m, 1H), 7.64 (d, 2H), 8.11 (s, 1H), 8.42 (brs, 1H), 9.51 (s, 1H); m/z 463 (M+H)⁺

4-(3-[(1S)-2-Hydroxy-1-methylethoxy]-5-{[(5-methylpyrazin-2-yl)amino]carbonyl}phenoxy)benzoic acid

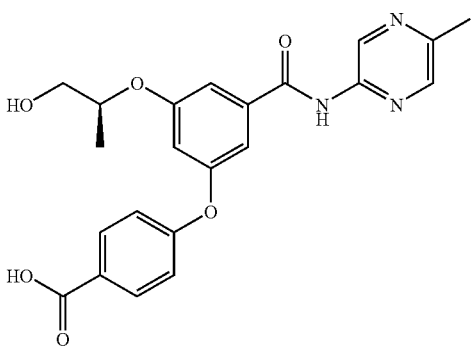

A solution of ethyl 4-(3-[(1S)-2-hydroxy-1-methylethoxy]-5-{[(5-methylpyrazin-2-yl)amino]carbonyl}phenoxy)benzoate (0.4 g, 0.88 mmol) in THF (16 mL) was added to a solution of lithium hydroxide monohydrate (0.19 g, 4.43 mmol) in water (8 mL). The mixture was stirred at RT for 72 hours and the THF removed in vacuo. The aqueous layer was acidified with 1M hydrochloric acid (10 mL), and the solid precipitate filtered off, washed with water and dried in vacuo to give the desired compound (0.22 g). The material was used without further purification.

m/z 424 (M+H)⁺

Ethyl 4-(3-[(1S)-2-hydroxy-1-methylethoxy]-5-{[(5-methylpyrazin-2-yl)amino]carbonyl}phenoxy)benzoate

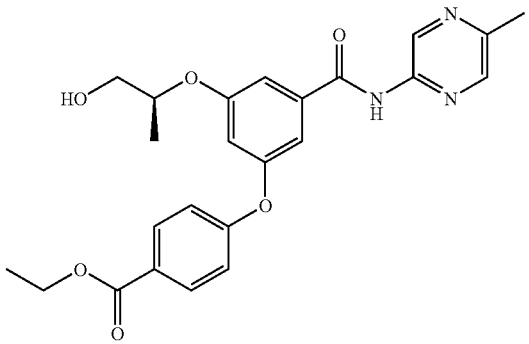

Caesium carbonate (8.45 g, 26 mmol) was added to a mixture of 3-hydroxy-5-{[(1S)-2-hydroxy-1-methylethyl]oxy}-N-(5-methylpyrazin-2-yl)benzamide (4 g, 13 mmol) and ethyl-4-fluorobenzoate (2.33 g, 13 mmol) in dimethylacetamide (70 mL) and the stirred mixture heated at 130° C. for 72 hours. The mixture was allowed to reach RT and ethyl acetate (100 mL) added. The mixture was washed with water (5×40 mL), brine (40 mL), dried (MgSO₄), filtered, and reduced in vacuo. The residue was chromatographed on silica, eluting with a gradient of 50% ethyl acetate in isohexane, to give the desired compound (0.18 g)

¹H NMR δ (CDCl₃): 1.33 (d, 3H), 1.40 (t, 3H), 2.62 (s, 3H), 3.75 (m, 2H), 4.39 (q, 2H), 4.60 (m, 1H), 6.83 (m, 1H), 7.05 (d, 2H), 7.19 (m, 1H), 7.27 (m, 1H), 7.39 (m, 1H), 8.05 (d, 2H), 8.18 (m, 1H), 8.98 (brs, 1H), 9.65 (m, 1H). m/z 452 (M+H)⁺

The preparation of 3-hydroxy-5-{[(1S)-2-hydroxy-1-methylethyl]oxy}-N-(5-methylpyrazin-2-yl)benzamide was described in Example 8.

Example 20 can also be prepared from 3-[4-(azetidin-1-ylcarbonyl)phenoxy]-5-((1S)-2-{[tert-butyl(dimethyl)silyl]oxy}-1-methylethoxy)-N-(5-methylpyrazin-2-yl)benzamide in an analogous fashion to the preparation of Example 8 from 3-[4-(azetidin-1-ylcarbonyl)-2-fluorophenoxy]-5-((1S)-2-{[tert-butyl(dimethyl)silyl]oxy}-1-methylethoxy)-N-(5-methylpyrazin-2-yl)benzamide, described earlier. The desired material was isolated following crystallization from ethyl acetate and isohexane (mpt 169° C.) and the spectroscopic data was in agreement with that previously reported.

3-[4-(Azetidin-1-ylcarbonyl)phenoxy]-5-((1S)-2-{[tert-butyl(dimethyl)silyl]oxy}-1-methylethoxy)-N-(5-methylpyrazin-2-yl)benzamide can be prepared from 3-[4-(azetidin-1-ylcarbonyl)phenoxy]-5-((1S)-2-{[tert-butyl(dimethyl)silyl]oxy}-1-methylethoxy)benzoic acid in an analogous fashion to the preparation of 3-[4-(azetidin-1-ylcarbonyl)-2-fluorophenoxy]-5-((1S)-2-{[tert-butyl(dimethyl)silyl]oxy}-1-methylethoxy)-N-(5-methylpyrazin-2-yl)benzamide from 3-[4-(azetidin-1-ylcarbonyl)-2-fluorophenoxy]-5-((1S)-2-{[tert-butyl(dimethyl)silyl]oxy}-1-methylethoxy)benzoic acid, described in Example 8.

| Structure | m/z | NMR |
|---|---|---|
| 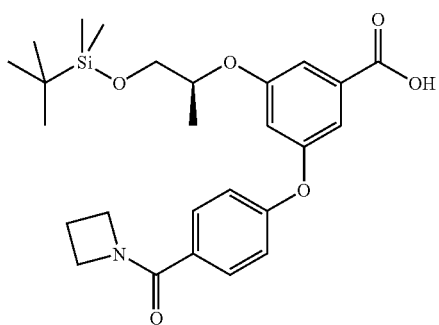 | 576 (M − H)⁻ | ¹H NMR δ (CDCl₃): 0.0 (d, 6H), 0.85 (s, 9H), 1.3 (d, 3H), 2.35 (m, 2H), 2.55 (s, 3H), 3.65-3.8 (m, 2H), 4.2-4.4 (d, 4H), 4.5 (m, 1H), 6.8 (s, 1H), 7.05 (2H, d), 7.1 (s, 1H), 7.25 (s, 1H), 7.65 (d, 2H), 8.15 (s, 1H), 8.3 (s, 1H), 9.55 (s, 1H). |

3-[4-(Azetidin-1-ylcarbonyl)phenoxy]-5-((1S)-2-{[tert-butyl(dimethyl)silyl]oxy}-1-methylethoxy)benzoic acid 3-[4-(Azetidin-1-ylcarbonyl)-2-chlorophenoxy]-5-((1S)-2-{[tert-butyl(dimethyl)silyl]oxy}-1-methylethoxy)benzoic acid (3.08 g, 5.93 mmol) was dissolved in methanol (30 mL) and THF (30 mL). Triethylamine (2 mL) was added and the flask evacuated and purged with nitrogen (3 times). 10% Palladium on carbon (200 mg) was added and the flask further evacuated and finally purged with hydrogen gas. The reaction mixture was stirred at ambient temperature for 16 hours LC-MS showed only 26% required product. The reaction mixture was evacuated and purged with nitrogen (3 times). The catalyst was filtered off, and the flask containing the filtrate evacuated and purged with nitrogen (3 times). Fresh 10% Palladium on carbon (200 mg) was added and the flask further evacuated and finally purged with hydrogen gas. The reaction mixture was stirred at ambient temperature for a further 16 hours LC-MS showed complete reaction. The reaction mixture was evacuated and purged with nitrogen (3 times). The catalyst was filtered off, the filtrate concentrated in vacuo and dissolved in diethylether (50 mL), washed with water (20 mL), 1N citric acid (20 mL), saturated aqueous sodium chloride solution (20 mL) and dried (MgSO₄) to give the title compound (2.16 g).

¹H NMR δ (CDCl₃): 0.0 (d, 6H), 0.85 (s, 9H), 1.25 (d, 3H), 2.35 (m, 2H), 3.6-3.8 (m, 2H), 4.15-4.4 (d, 4H), 4.45 (m, 1H), 6.8 (s, 1H), 7.0 (d, 2H), 7.25 (s, 1H), 7.4 (s, 1H), 7.65 (d, 2H); m/z 486 (M+H)⁺

The preparation of 3-[4-(azetidin-1-ylcarbonyl)-2-chlorophenoxy]-5-((1S)-2-{[tert-butyl(dimethyl)silyl]oxy}-1-methylethoxy)benzoic acid was described in Example 8a.

EXAMPLE 21

3-[4-(Azetidin-1-ylcarbonyl)-2-fluorophenoxy]-5-[(1S)-2-hydroxy-1-methylethoxy]-N-(5-methyl-1,3-thiazol-2-yl)benzamide

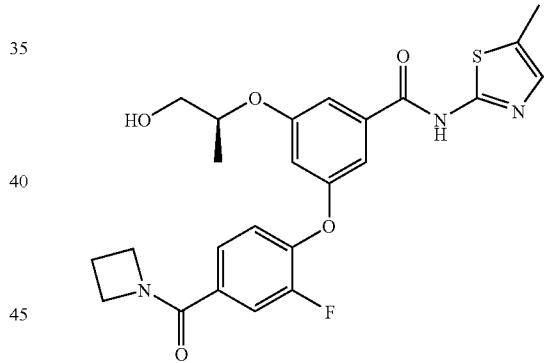

Potassium carbonate (143 mg, 1.04 mmol) was added to a mixture of 3-hydroxy-5-[(1S)-2-hydroxy-1-methylethoxy]-N-(5-methyl-1,3-thiazol-2-yl)benzamide (160 mg, 0.52 mmol) and 1-(3,4-difluorobenzoyl)azetidine (102 mg, 0.52 mmol) in acetonitrile (5.0 mL), and the stirred mixture heated at 160° C. in a 'Smith Creator Microwave' for 15 hours. The mixture was allowed to reach ambient temperature and pressure and reduced in vacuo. The residual oil was partitioned between ethyl acetate (50 mL) and water (50 mL). The ethyl acetate layer was separated, washed with brine, dried (MgSO₄), and evaporated to a residue which was chromatographed on silica, eluting with a gradient of 0-10% methanol in ethyl acetate, to give the desired compound (30 mg)

¹H NMR δ (CDCl₃): 1.25 (d, 3H), 2.35 (s & m, 5H), 3.75 (m, 2H), 4.20-4.40 (brm, 4H), 4.56 (m, 1H), 6.72 (s, 1H), 6.91 (s, 1H), 7.08 (t, 1H), 7.15 (s, 1H), 7.30 (m, 1H), 7.40 (d, 1H), 7.50 (d, 1H); m/z 486 (M+H)⁺

The following compounds were synthesised in an analogous fashion from the appropriate phenol:

| Example | Structure | m/z | NMR |
|---|---|---|---|
| 21a | 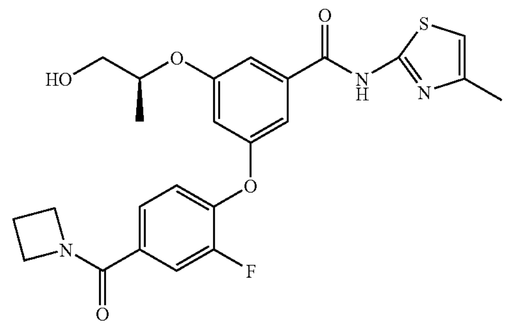 | 486 (M + H)⁺ | $^1$H NMR δ (CDCl$_3$): 1.25 (d, 3H), 2.22 (s, 3H), 2.32 (m, 2H), 3.72 (m, 2H), 4.20-4.40 (brm, 4H), 4.52 (m, 1H), 6.55 (s, 1H), 6.75 (s, 1H), 7.05 (m, 2H), 7.21 (s, 1H), 7.40 (d, 1H), 7.51 (dd, 1H) |
| 21b | 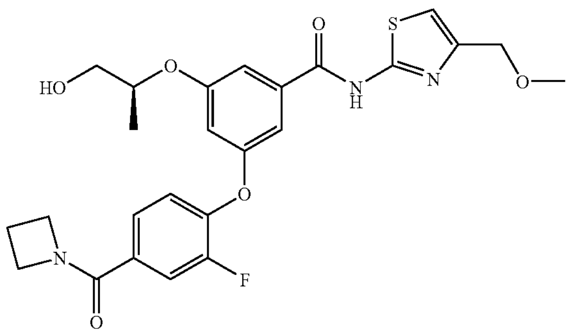 | 516 (M + H)⁺ | $^1$H NMR δ (CDCl$_3$): 1.30 (d, 3H), 2.38 (quin, 2H), 3.41 (s, 3H), 3.72 (m, 2H), 4.25 (m, 2H), 4.35 (m, 2H), 4.41 (s, 2H), 4.56 (m, 1H), 6.78 (m, 1H), 6.98 (s, 1H), 7.06 (m, 2H), 7.27 (m, 1H), 7.42 (d, 1H), 7.51 (m, 1H) |

The precursor for Example 21 was prepared as described below:

3-Hydroxy-5-[(1S)-2-hydroxy-1-methylethoxy]-N-(5-methyl-1,3-thiazol-2-yl)benzamide

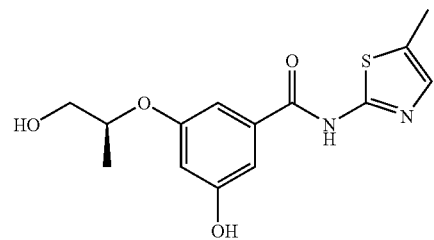

Triethylamine (0.11 mL, 0.79 mmol) and triethylsilane (4.88 mL, 27.3 mmol) were added to palladium (11) acetate (56 mg, 9 mol %) in DCM (14 mL) under an atmosphere of argon. The reaction was stirred for 15 mins then 3-(benzyloxy)-5-((1S)-2-{[tert-butyl(dimethyl)silyl]oxy}-1-methylethoxy)-N-(5-methyl-1,3-thiazol-2-yl)benzamide (1.4 g, 2.73 mmol) in DCM (14 mL) added dropwise and stirred for a further 48 hours. The reaction was filtered through celite and the filtrate concentrated in vacuo to give a residue which was chromatographed on silica, eluting with a gradient of 50-100% ethyl acetate in isohexane, to give the desired compound (0.18 g).

$^1$H NMR δ (d$_6$-DMSO): 1.21 (d, 3H), 2.38 (s, 3H), 3.50 (m, 2H), 4.46 (sex, 1H), 4.81 (t, 1H), 6.51 (m, 1H), 7.01 (s, 1H), 7.15 (s, 1H), 7.21 (s, 1H), 7.92 (s, 2H), 9.72 (s, 1H). m/z 309 (M+H)⁺

3-(Benzyloxy)-5-((1S)-2-{[tert-butyl(dimethyl)silyl]oxy}-1-methylethoxy)-N-(5-methyl-1,3-thiazol-2-yl)benzamide

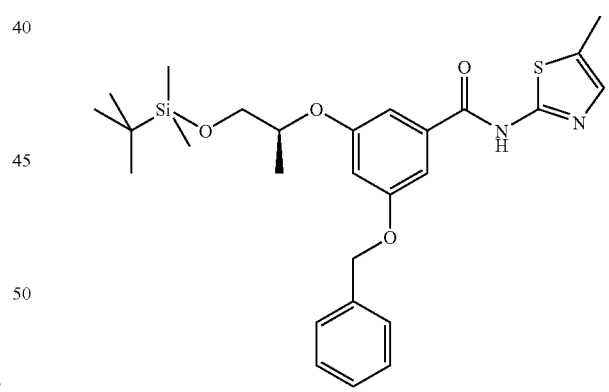

DIPEA (7.5 mL) was added to a suspension of 3-{(phenylmethyl)oxy}-5-((1S)-2-{[tert-butyl(dimethyl)silyl]oxy}-1-methylethoxy)benzoic acid (4.5 g, 0.011 mol), HATU (8.6 g, 0.023 mol) and 2-amino-5-methylthiazole (2.46 g, 0.022 mol) in DMF (70 mL). The resulting mixture was stirred at ambient temperature for 72 hours. The DMF was removed in vacuo. Water (100 mL) was added and the mixture extracted with ethyl acetate (3×50 mL). The extracts were combined and washed with brine (100 mL). The solution was dried (MgSO$_4$), filtered, and evaporated in vacuo to give the crude product which was chromatographed on silica, eluting with a gradient of 50-100% ethyl acetate in isohexane, to give the desired compound. (1.7 g).

$^1$H NMR δ (CDCl$_3$): 0.03 (s, 3H), 0.07 (s, 3H), 0.85 (s, 9H), 1.30 (d, 3H), 2.33 (s, 3H), 3.65 (m, 1H), 3.75 (m, 1H), 4.46 (m, 1H), 5.04 (s, 2H), 6.78 (m, 1H), 6.88 (m, 1H), 7.12 (d, 2H), 7.38 (m, 5H), 11.30 (brs, 1H); m/z 513 (M+H)$^+$ The preparation of 3-{(phenylmethyl)oxy}-5-((1S)-2-{[tert-butyl(dimethyl)silyl]oxy}-1-methylethoxy)benzoic acid was described in Example 5.

In a similar manner, the precursors for Examples 21a and 21b were prepared from deprotection of the appropriate benzyl ether:

| Structure | m/z | NMR |
|---|---|---|
| 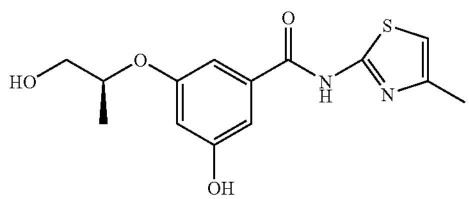 | 309 (M + H)$^+$ | $^1$H NMR δ (d$_6$-DMSO): 1.21 (d, 3H), 2.28 (s, 3H), 3.05 (m, 1H), 3.40-3.58 (m, 2H), 4.48 (m, 1H), 6.56 (s, 1H), 6.81 (s, 1H), 7.02 (s, 1H), 7.12 (s, 1H). |
| 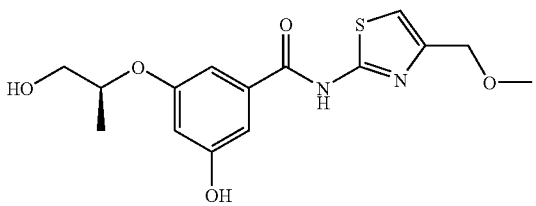 | 339 (M + H)$^+$ | $^1$H NMR δ (d$_6$-DMSO): 1.21 (d, 3H), 3.30 (s, 3H), 3.41-3.58 (m, 2H), 4.39 (s, 2H), 4.45 (m, 1H), 6.55 (s, 1H), 7.01 (s, 1H), 7.10 (s, 1H), 7.18 (s, 1H). |

The benzyl ethers used in the preparation of Examples 21a and 21b were prepared from 3-{(phenylmethyl)oxy}-5-((1S)-2-{[tert-butyl(dimethyl)silyl]oxy}-1-methylethoxy)benzoic acid using the appropriate amine:

| Structure | m/z | NMR |
|---|---|---|
| | | $^1$H NMR δ (CDCl$_3$): 0.05 (s, 3H), 0.08 (s, 3H), 0.95 (s, 9H), 1.26 (d, 3H), 2.19 (s, 3H), 3.68 (m, 1H), 3.73 (m, 1H), 4.41 (m, 1H), 5.01 (s, 2H), 6.54 (m, 1H), 6.72 (m, 1H), 7.08 (m, 2H), 7.35 (m, 6H). |
| 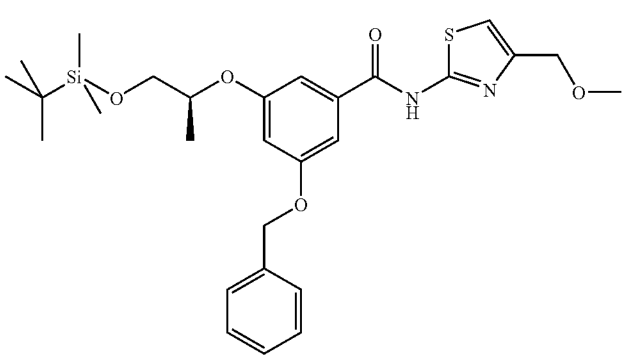 | 543 (M + H)$^+$ | $^1$H NMR δ (CDCl$_3$): 0.05 (s, 3H), 0.08 (s, 3H), 0.86 (s, 9H), 1.30 (d, 3H), 3.41 (s, 3H), 3.68 (m, 1H), 3.78 (m, 1H), 4.38 (s, 2H), 4.45 (m, 1H), 5.07 (s, 2H), 6.75 (m, 1H), 6.88 (s, 1H), 7.05 (m, 2H), 7.40 (m, 5H), 9.85 (brs, 1H). |

EXAMPLE 22

3-[(1S)-2-Hydroxy-1-methylethoxy]-N-(1-methyl-1H-pyrazol-3-yl)-5-[4-(piperidin-1-ylcarbonyl)phenoxy]benzamide

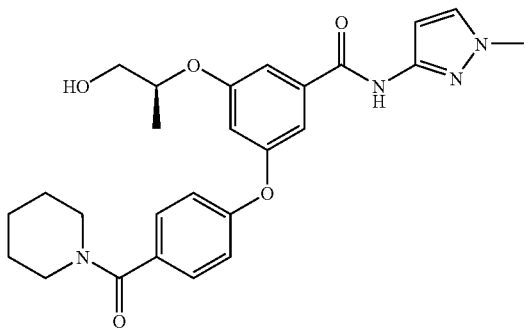

DIPEA (0.36 mL, 1.95 mmol) was added to a suspension of 4-(3-[(1S)-2-hydroxy-1-methylethoxy]-5-{[(1-methyl-1H-pyrazol-3-yl)amino]carbonyl}phenoxy)benzoic acid (200 mg, 0.49 mmol), HATU (390 mg, 1.02 mmol) and piperidine (0.19 mL, 1.95 mmol) in DMF (3 mL) and the mixture stirred at ambient temperature for 24 hours. The solvent was evaporated. Water (30 mL) was added and the mixture extracted with ethyl acetate (3×15 mL). The combined organic extracts were washed with brine (30 mL), dried, (MgSO$_4$), and evaporated to a residue which was chromatographed on silica, eluting with a gradient of 0-20% methanol in ethyl acetate, to give the desired compound (167 mg).

$^1$H NMR δ (CDCl$_3$): 1.28 (d, 3H), 1.58-1.78 (brm, 6H), 2.15 (brt, 1H), 3.25-3.75 (brm, 4H), 3.76 (m, 2H), 3.78 (s, 3H), 4.51 (m, 1H), 6.75 (m, 2H), 7.03 (d, 2H), 7.08 (m, 1H), 7.21 (m, 1H), 7.30 (m, 1H), 7.41 (d, 2H), 8.51 (brs, 1H); m/z 479 (M+H)$^+$ The following compounds were synthesised in an analogous-fashion from 4-(3-[(1S)-2-hydroxy-1-methylethoxy]-5-{[(1-methyl-1H-pyrazol-3-yl)amino]carbonyl}phenoxy)benzoic acid and the appropriate amine:

| Example | Structure | m/z | NMR |
|---|---|---|---|
| 22a | 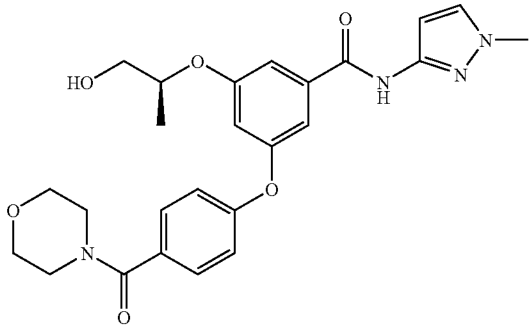 | 481 (M + H)$^+$ | $^1$H NMR δ (CDCl$_3$): 1.29 (d, 3H), 2.10 (brt, 1H), 3.60-3.80 (brm, 10 H), 3.80 (s, 3H), 4.51 (m, 1H), 6.76 (m, 2H), 7.05 (m, 3H), 7.22 (m, 1H), 7.29 (m, 1H), 7.43 (d, 2H), 8.45 (brs, 1H) |
| 22b | 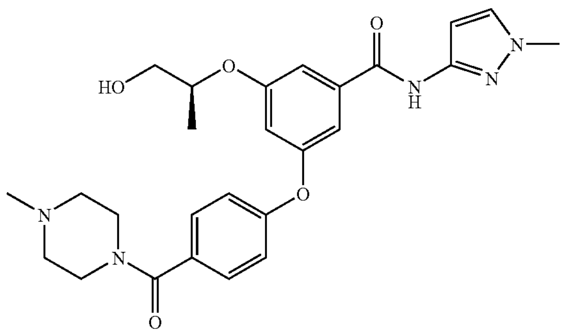 | 494 (M + H)$^+$ | $^1$H NMR δ (CDCl$_3$): 1.30 (d, 3H), 2.34 (s, 3H), 2.44 (brm, 4H), 3.50-3.80 (brm, 4H), 3.76 (m, 2H), 3.81 (s, 3H), 4.54 (m, 1H), 6.78 (m, 2H), 7.03 (d, 2H), 7.09 (m, 1H), 7.23 (m, 1H), 7.30 (m, 1H), 7.42 (d, 2H), 8.40 (brs, 1H) |
| 22c | 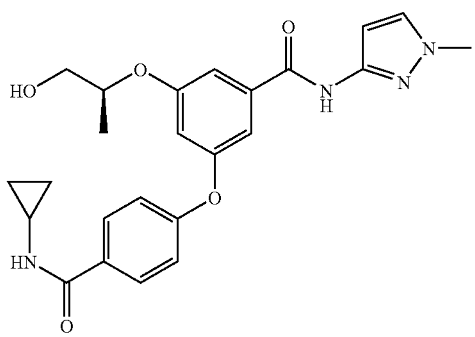 | 451 (M + H)$^+$ | $^1$H NMR δ (CDCl$_3$): 0.63 (m, 2H), 0.85 (m, 2H), 1.30 (d, 3H), 2.15 (t, 1H), 2.87 (m, 1H), 3.67 (s, 3H), 3.75 (m, 2H), 4.52 (m, 1H), 6.46 (brs, 1H), 6.75 (m, 2H), 6.94 (m, 3H), 7.22 (m, 1H), 7.27 (m, 1H), 7.70 (d, 2H), 9.01 (brs, 1H) |

| Example | Structure | m/z | NMR |
|---|---|---|---|
| 22d | 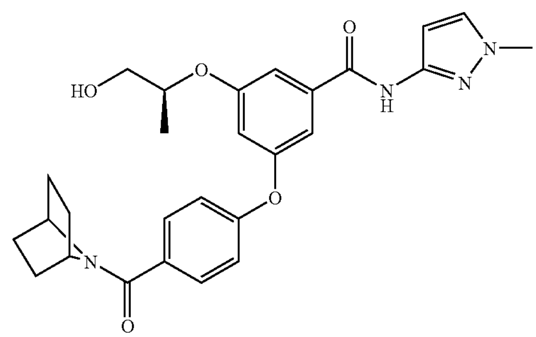 | 491 (M + H)⁺ | ¹H NMR δ (CDCl₃): 1.29 (d, 3H), 1.51 (d, 4H), 1.86 (brm, 4H), 2.80 (m, 2H), 3.75 (d, 2H), 3.81 (s, 3H), 4.55 (m, 1H), 6.75 (m, 1H), 6.81 (m, 1H), 7.01 (d, 2H), 7.10 (m, 1H), 7.23 (m, 1H), 7.30 (m, 1H), 7.55 (d, 2H), 8.90 (brs, 1H) |

4-(3-[(1S)-2-Hydroxy-1-methylethoxy]-5-{[(1-methyl-1H-pyrazol-3-yl)amino]carbonyl}phenoxy)benzoic acid was prepared as described below:

4-(3-[(1S)-2-Hydroxy-1-methylethoxy]-5-{[(1-methyl-1H-pyrazol-3-yl)amino]carbonyl}phenoxy)benzoic acid

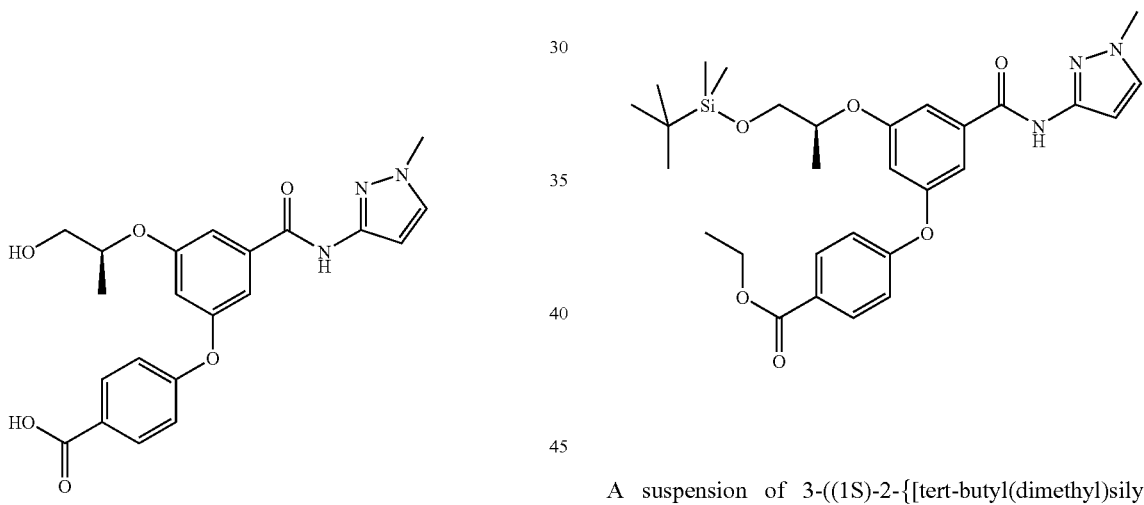

A solution of ethyl 4-(3-((1S)-2-{[tert-butyl(dimethyl)silyl]oxy}-1-methylethoxy)-5-{[(1-methyl-1H-pyrazol-3-yl)amino]carbonyl}phenoxy)benzoate (3.78 g, 6.84 mmol) in THF (100 mL) was added to a solution of lithium hydroxide monohydrate (1.44 g, 33 mmol) in water (50 mL). The mixture was stirred at ambient temperature for 72 hours. 1M Hydrochloric acid was added until pH=2 and the mixture stirred for a further 1 hour. The THF was removed in vacuo and the solid precipitate filtered off, washed with water and dried in vacuo to give the desired compound (3.06 g).

¹H NMR δ (d₆-DMSO): 1.28 (d, 3H), 3.58 (m, 2H), 3.81 (s, 3H), 4.61 (sex, 1H), 6.60 (m, 1H), 6.88 (m, 1H), 7.12 (d, 2H), 7.25 (m, 1H), 7.51 (m, 1H), 7.63 (d, 1H), 8.02 (d, 2H), 10.87 (brs, 1H);

Ethyl 4-(3-((1S)-2-{[tert-butyl(dimethyl)silyl]oxy}-1-methylethoxy)-5-{[(1-methyl-1H-pyrazol-3-yl)amino]carbonyl}phenoxy)benzoate A suspension of 3-((1S)-2-{[tert-butyl(dimethyl)silyl]oxy}-1-methylethyloxy)-5-hydroxy-N-(1-methyl-1H-pyrazol-3-yl)benzamide (4.5 g, 0.011 mol), 4-ethoxycarbonylphenylboronic acid (3.24 g, 0.016-mol), copper (II) acetate (3.06 g, 0.016 mol), triethylamine (7.74 mL, 0.055 mol) and freshly activated 4 Å molecular sieves (13 g) in DCM (180 mL) was stirred at ambient temperature and under ambient atmosphere for 3 days. The reaction mixture was filtered through celite, washed with DCM (2×50 mL). The DCM was removed in vacuo and the residual oil partitioned between ethyl acetate (100 mL) and water (100 mL), filtered and the ethyl acetate layer washed with brine (50 mL), dried (MgSO₄), and evaporated to a residue which was chromatographed on silica, eluting with a gradient of 50-100% ethyl acetate in isohexane, to give the desired compound (3.78 g).

¹H NMR δ (CDCl₃): 0.04 (s, 3H), 0.06 (s, 3H), 0.88 (s, 9H), 1.30 (d, 3H), 1.41 (t, 3H), 3.67 (m, 1H), 3.78 (m, 1H), 3.79 (s, 3H), 4.38 (q, 2H), 4.46 (m, 1H), 6.78 (m, 2H), 7.01 (m, 1H), 7.03 (m, 2H), 7.23 (m, 1H), 7.29 (m, 1H), 8.03 (d, 2H), 8.39 (brs, 1H).

m/z 554 (M+H)⁺

The preparation of 3-((1S)-2-{[tert-butyl(dimethyl)silyl]oxy}-1-methylethyloxy)-5-hydroxy-N-(1-methyl-1H-pyrazol-3-yl)benzamide was described in Example 5.

EXAMPLE 23

3-[2-Fluoro-4-(piperidin-1-ylcarbonyl)phenoxy]-5-[(1S)-2-hydroxy-1-methylethoxy]-N-(1-methyl-1H-pyrazol-3-yl)benzamide

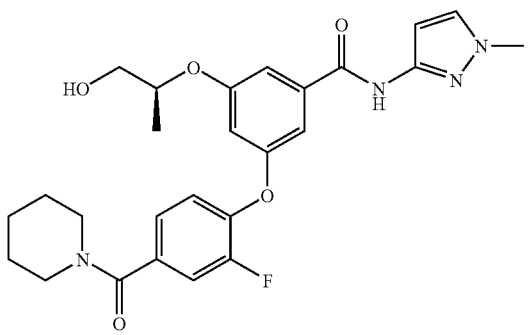

DIPEA (0.36 mL, 1.95 mmol) was added to a suspension of 3-fluoro-4-(3-[(1S)-2-hydroxy-1-methylethoxy]-5-{[(1-methyl-1H-pyrazol-3-yl)amino]carbonyl}phenoxy)benzoic acid (209 mg, 0.49 mmol), HATU (390 mg, 1.02 mmol) and piperidine (0.19 mL, 1.95 mmol) in DMF (3 mL), and the mixture stirred at ambient temperature for 24 hours. Water (30 mL) was added and the mixture extracted with diethyl ether/ethyl acetate 4:1 (3×20 mL). The combined organic extracts were washed with brine (30 mL), dried (MgSO$_4$), and evaporated to a residue which was chromatographed on silica, eluting with a gradient of 0-20% methanol in ethyl acetate, to give the desired compound (116 mg).

$^1$H NMR δ (CDCl$_3$): 1.31 (d, 3H), 1.55-1.78 (brm, 6H), 2.40 (brt, 1H), 3.40-3.90 (brm, 4H), 3.75 (m, 2H), 3.81 (s, 3H), 4.58 (m, 1H), 6.74 (m, 1H), 6.81 (m, 1H), 7.07 (m, 2H), 7.18 (m, 1H), 7.23 (m, 1H), 7.28 (m, 1H), 7.31 (m, 1H), 8.85 (brs, 1H); m/z 497 (M+H)$^+$ The following compounds were synthesised in an analogous fashion from 3-fluoro-4-(3-[(1S)-2-hydroxy-1-methylethoxy]-5-{[(1-methyl-1H-pyrazol-3-yl)amino]carbonyl}phenoxy)benzoic acid and the appropriate amine:

| Example | Structure | m/z | NMR |
|---|---|---|---|
| 23a | 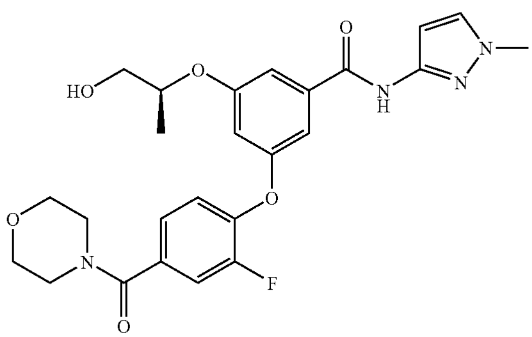 | 499 (M + H)$^+$ | $^1$H NMR δ (CDCl$_3$): 1.31 (d, 3H), 3.58-3.78 (brm, 10H), 3.81 (s, 3H), 4.55 (sex, 1H), 6.75 (m, 1H), 6.81 (m, 1H), 7.10 (m, 2H), 7.20 (m, 2H), 7.28 (m, 1H), 7.31 (d, 1H), 8.90 (brs, 1H) |
| 23b | 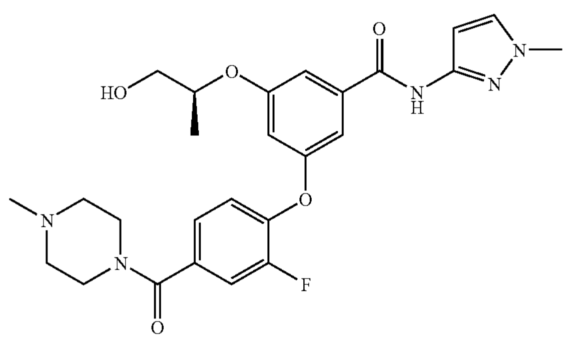 | 512 (M + H)$^+$ | $^1$H NMR δ (CDCl$_3$): 1.28 (d, 3H), 2.38 (s, 3H), 2.38 (m, 1H), 2.51 (brm, 4H), 3.71 (m, 9H), 4.51 (m, 1H), 6.71 (m, 2H), 7.05 (m, 2H), 7.19 (m, 2H), 7.28 (m, 2H), 8.78 (brs, 1H) |

-continued

| Example | Structure | m/z | NMR |
|---|---|---|---|
| 23c | 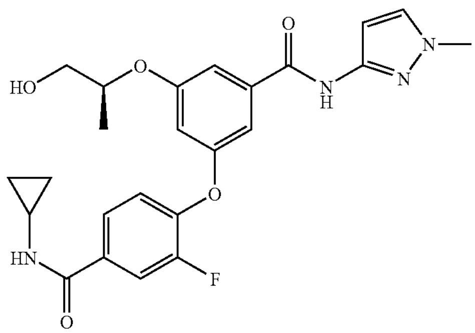 | 469 (M + H)+ | ¹H NMR δ (CDCl₃): 0.65 (m, 2H), 0.85 (m, 2H), 1.30 (m, 3H), 2.81 (m, 1H), 2.90 (m, 1H), 3.65 (s, 3H), 3.75 (m, 2H), 4.56 (m, 1H), 6.72 (m, 3H), 6.90 (m, 2H), 7.27 (m, 2H), 7.40 (m, 1H), 7.57 (m, 1H), 9.50 (brs, 1H) |
| 23d | 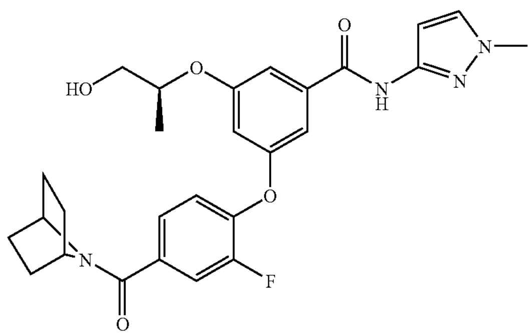 | 509 (M + H)+ | ¹H NMR δ (CDCl₃): 1.22 (d, 3H), 1.48 (d, 4H), 1.82 (m, 4H), 3.30 (brs, 1H), 3.65 (d, 2H), 3.70 (s, 3H), 4.20 (brm, 1H), 4.48 (sex, 1H), 4.60 (m, 1H), 6.65 (m, 1H), 6.71 (m, 1H), 7.01 (m, 2H), 7.15 (m, 1H), 7.27 (m, 2H), 7.35 (d, 1H), 9.11 (brs, 1H) |
| 23e | 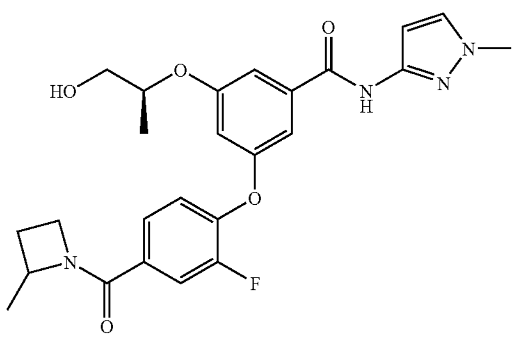 | 483 (M + H)+ | ¹H NMR δ (CDCl₃): 1.25 (d, 3H), 1.40 (brs, 3H), 1.87 (m, 1H), 2.45 (m, 1H), 2.91 (brs, 1H), 3.67 (d, 2H), 3.78 (s, 3H), 4.05 (m, 1H), 4.25 (m, 1H), 4.49 (sex, 1H), 4.62 (sex, 1H), 6.66 (m, 1H), 6.78 (m, 1H), 7.01 (m, 2H), 7.25 (m, 2H), 7.31 (m, 1H), 7.42 (d, 1H), 9.18 (brs, 1H) |
| 23f | 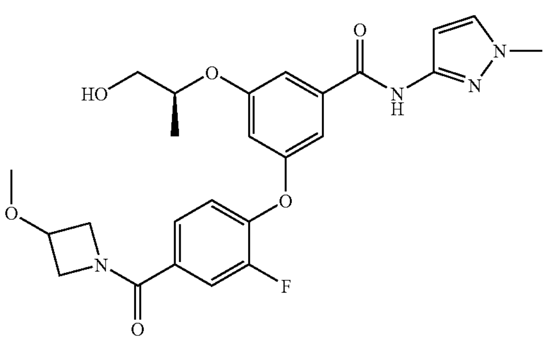 | 499 (M + H)+ | ¹H NMR δ (CDCl₃): 1.27 (d, 3H), 2.62 (brs, 1H), 3.32 (s, 3H), 3.74 (d, 2H), 3.78 (s, 3H), 4.12 (brm, 2H), 4.27 (m, 1H), 4.41 (brm, 2H), 4.54 (sex, 1H), 6.72 (m, 1H), 6.80 (m, 1H), 7.06 (m, 2H), 7.24 (m, 1H), 7.30 (m, 1H), 7.38 (m, 1H), 7.50 (m, 1H). |

| Example | Structure | m/z | NMR |
|---|---|---|---|
| 23g | 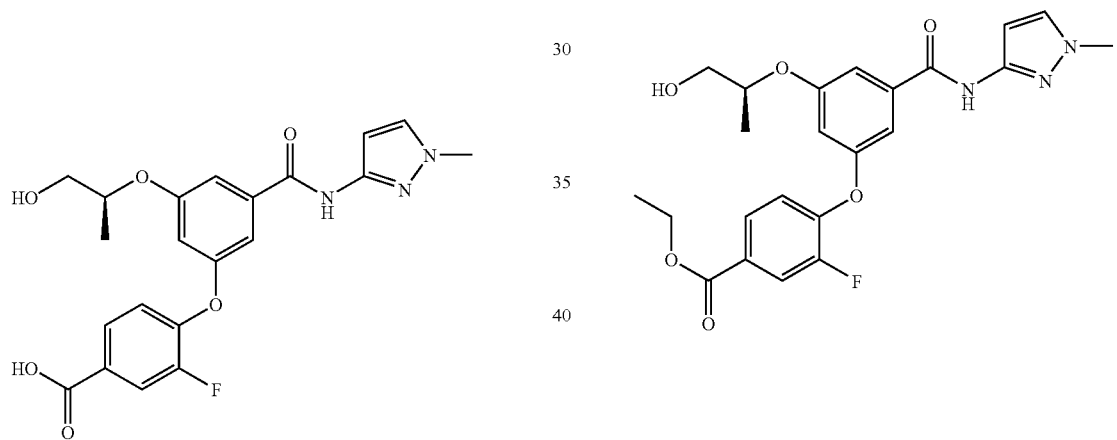 | 527 (M + H)+ | ¹H NMR δ (CDCl₃): 1.18 (d, 6H), 1.31 (d, 3H), 2.70 (brs, 1H), 3.64 (quin, 1H), 3.76 (m, 2H), 3.84 (s, 3H), 4.15 (brm, 2H), 4.41 (m, 3H), 4.58 (sex, 1H), 6.72 (m, 1H), 6.84 (m, 1H), 7.09 (m, 2H), 7.31 (m, 2H), 7.39 (m, 1H), 7.50 (d, 1H), 9.20 (brs, 1H). |

3-Fluoro-4-(3-[(1S)-2-hydroxy-1-methylethoxy]-5-{[(1-methyl-1H-pyrazol-3-yl)amino]carbonyl}phenoxy)benzoic acid was prepared as described below:

3-Fluoro-4-(3-[(1S)-2-hydroxy-1-methylethoxy]-5-{[(1-methyl-1H-pyrazol-3-yl)amino]carbonyl}phenoxy)benzoic acid A solution of ethyl 3-fluoro-4-(3-[(1S)-2-hydroxy-1-methylethoxy]-5-{[(1-methyl-1H-pyrazol-3-yl)amino]carbonyl}phenoxy)benzoate (1.8 g, 3.94 mmol) in THF (60 mL) was added to a solution of lithium hydroxide monohydrate (0.83 g, 19.7 mmol) in water (30 mL). The mixture was stirred at RT for 72 hours and the THF removed in vacuo. The aqueous layer was extracted into ethyl acetate (100 mL) to remove any impurities, then acidified with 1M hydrochloric acid and extracted into ethyl acetate (2×100 mL). The combined extracts were dried (MgSO₄) and the solvent removed in vacuo to give the desired compound (1.62 g).

¹H NMR δ (d₆-DMSO): 1.23 (d, 3H), 3.50 (m, 2H), 3.76 (s, 3H), 4.58 (sex, 1H), 4.82 (brs, 1H), 6.54 (d, 1H), 6.84 (m, 1H), 7.21 (m, 2H), 7.42 (m, 1H), 7.58 (d, 1H), 7.81 (m, 2H), 10.82 (brs, 1H); m/z 430 (M+H)+

Ethyl 3-fluoro-4-(3-[(1S)-2-hydroxy-1-methylethoxy]-5-{[(1-methyl-1H-pyrazol-3-yl)amino]carbonyl}phenoxy)benzoate Cesium carbonate (8.3 g, 25.4 mmol) was added to a mixture of 3-hydroxy-5-{[(1S)-2-hydroxy-1-methylethyl]oxy}-N-(1-methyl-1H-pyrazol-3-yl)benzamide (3.7 g, 12.7 mmol) and ethyl-3,4-difluorobenzoate (2.36 g, 12.7 mmol) in dimethylacetamide (60 mL) and the stirred mixture heated at 115° C. for 3 hours. The mixture was allowed to cool to RT and ethyl acetate (100 mL) added. The mixture was washed with water (5×40 mL), brine (40 mL), dried (MgSO₄), filtered, and reduced in vacuo. The residue was chromatographed on silica, eluting with 50% ethyl acetate in isohexane, to give the desired compound (1.8 g).

¹H NMR δ (CDCl₃): 1.31 (d, 3H), 1.41 (t, 3H), 3.72 (d, 2H), 3.83 (s, 3H), 4.39 (q, 2H), 4.57 (sex, 1H), 6.75 (m, 1H), 6.83 (m, 1H), 7.09 (m, 2H), 7.30 (d, 2H), 7.83 (m, 2H), 8.91 (brs, 1H). m/z 458 (M+H)+

The preparation of 3-hydroxy-5-{[(1S)-2-hydroxy-1-methylethyl]oxy}-N-(1-methyl-1H-pyrazol-3-yl)benzamide was described in Example 12.

2-Methylazetidine required for the preparation of Example 23e was prepared as described in JOC, 26, 1961 138.

3-Methoxyazetidine hydrochloride required for the preparation of Example 23f was prepared as follows:

3-Methoxyazetidine hydrochloride

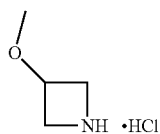

A solution of tert-butyl 3-methoxyazetidine-1-carboxylate (0.32 g, 1.71 mmol) in 3M hydrogen chloride in ethyl acetate (10 mL) was stirred at RT for 3 hours. The volatiles were removed in vacuo, ethyl acetate was added to the residue then decanted off and the residue dried in vacuo to give the desired compound. (0.16 g)
$^1$H NMR δ (d$_6$-DMSO): 3.21 (s, 3H), 3.75 (m, 2H), 4.07 (m, 2H), 4.23 (m, 1H), 9.08 (brs. 1H).

tert-Butyl 3-methoxyazetidine-1-carboxylate

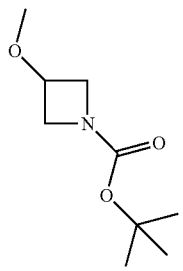

Sodium hydride (60% dispersion in oil) (83 mg, 3.46 mmol) was added to tert-butyl 3-hydroxyazetidine-1-carboxylate (*J Med chem.*, 44(1), 2001, 94) (0.3 g, 1.73 mmol) in THF (10 mL), at 0° C., under argon. The reaction was stirred for 30 mins then iodomethane (0.13 mL, 4.15 mmol) added. After stirring at 0° C. for 30 mins and at RT for 3 hours the volatiles were removed in vacuo. Ethyl acetate (40 mL) was added and the mixture washed with brine (40 mL), dried (MgSO$_4$), filtered, and reduced in vacuo to give the desired compound. (0.32 g). $^1$H NMR δ (CDCl$_3$): 1.42 (s, 9H), 3.27 (s, 3H), 3.81 (m, 2H), 4.06 (m, 2H), 4.11 (m, 1H).

3-Isopropoxyazetidine hydrochloride used in the preparation of Example 23g was prepared from tert-butyl 3-hydroxyazetidine-1-carboxylate in an analogous fashion to 3-methoxyazetidine hydrochloride:

| Structure | m/z | NMR |
|---|---|---|
| 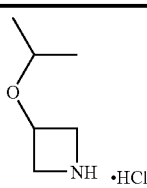 | | $^1$H NMR δ (CDCl$_3$): 1.12 (d, 6H), 2.03 (brs, 1H), 3.60 (m, 1H), 4.01 (m, 2H), 4.20 (m, 2H), 4.50 (m, 1H). |

-continued

| Structure | m/z | NMR |
|---|---|---|
| 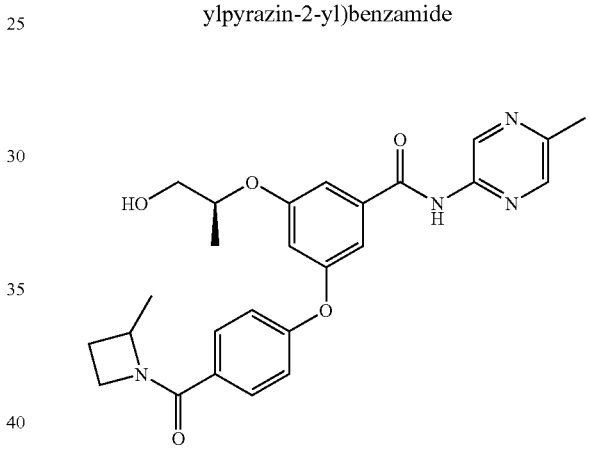 | | $^1$H NMR δ (CDCl$_3$): 1.11 (d, 6H), 1.41 (s, 9H), 3.56 (quin, 1H), 3.81 (m, 2H), 4.07 (t, 2H), 4.27 (m, 1H). |

EXAMPLE 24

3-[(1S)-2-Hydroxy-1-methylethoxy]-5-{4-[(2-methylazetidin-1-yl)carbonyl]phenoxy}-N-(5-methylpyrazin-2-yl)benzamide

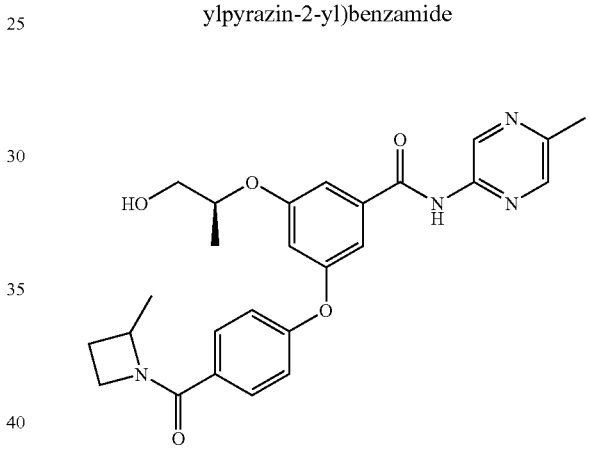

DIPEA (0.20 mL, 1.04 mmol) was added to a suspension of 4-(3-[(1S)-2-hydroxy-1-methylethoxy]-5-{[(5-methylpyrazin-2-yl)amino]carbonyl}phenoxy)benzoic acid (0.11 g, 0.26 mmol), HATU (210 mg, 0.55 mmol) and 2-methylazetidine (37 mg, 0.52 mmol) in DMF (3 mL) and the mixture stirred at ambient temperature for 24 hours. Ethyl acetate (30 mL) was added and washed with water (3×20 mL), brine (20 mL), dried (MgSO$_4$), filtered and evaporated to a residue which was chromatographed on silica, eluting with a gradient of 0-20% methanol in ethyl acetate, to give the desired compound (54 mg).

$^1$H NMR δ (CDCl$_3$): 1.23 (d, 3H), 1.40 (brs, 3H), 1.81 (brm, 1H), 2.42 (m, 1H), 2.45 (s, 3H), 2.70 (m, 1H), 3.65 (d, 2H), 4.01 (m, 1H), 4.46 (sex, 1H), 4.61 (m, 1H), 6.68 (m, 1H), 6.91 (d, 2H), 7.05 (m, 1H), 7.11 (m, 1H), 7.56 (d, 2H), 8.05 (s, 1H), 8.60 (s, 1H), 9.41 (s, 1H); m/z 477 (M+H)$^+$ The following compound was synthesised in an analogous fashion from 4-(3-[(1S)-2-hydroxy-1-methylethoxy]-5-{[(5-methylpyrazin-2-yl)amino]carbonyl}phenoxy)benzoic acid and the appropriate amine:

| Example | Structure | m/z | NMR |
|---|---|---|---|
| 24a | 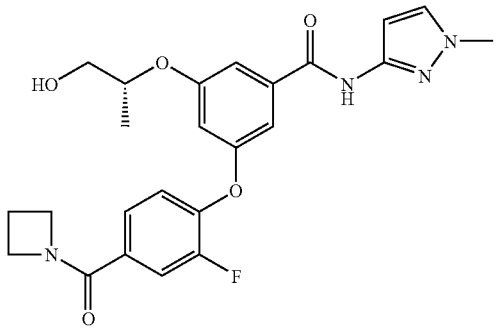 | 493 (M + H)⁺ | $^1$H NMR δ (CDCl$_3$): 1.31 (d, 3H), 2.07 (brs, 1H), 2.58 (s, 3H), 3.31 (s, 3H), 3.77 (m, 2H), 4.12 (m, 2H), 4.24 (m, 1H), 4.40 (m, 2H), 4.58 (m, 1H), 6.79 (m, 1H), 7.04 (d, 2H), 7.13 (m, 1H), 7.31 (m, 1H), 7.65 (d, 2H), 8.15 (s, 1H), 8.57 (brs, 1H), 9.55 (s, 1H); |

The preparation of 4-(3-[(1S)-2-hydroxy-1-methylethoxy]-5-{[(5-methylpyrazin-2-yl)amino]carbonyl}phenoxy)benzoic acid was described in Example 20.

EXAMPLE 25

3-[4-(azetidin-1-ylcarbonyl)-2-fluorophenoxy]-5-[(1R)-2-hydroxy-1-methylethoxy]-N-(1-methyl-1H-pyrazol-3-yl)benzamide Cesium carbonate (780 mg, 2.40 mmol) was added to a mixture of 3-hydroxy-5-[(1R)-2-hydroxy-1-methylethoxy]-N-(1-methyl-1H-pyrazol-3-yl)benzamide (350 mg, 1.2 mmol) and 1-(3,4-difluorobenzoyl)azetidine (235 mg, 1.2 mmol) in dimethylacetamide (5.0 mL) and the stirred-mixture heated at 160° C. in a 'Smith Creator Microwave' for 2 hours. The mixture was allowed to return to ambient temperature and pressure and was partitioned between ethyl acetate (50 mL) and water (50 mL). The ethyl acetate layer was separated, washed with water (5×50 mL) brine (50 mL), dried (MgSO$_4$) and evaporated to a residue which was chromatographed on silica, eluting with a gradient of 0-10% methanol in DCM, and then chromatographed by preparative HPLC on C18 reversed phase using 5-95% acetonitrile (+0.2% TFA) in water (+0.2% TFA) as eluant. A 10% impurity remained. This mixture (0.12 g, 0.26 mmol) was dissolved in DMF (3 mL) and imidazole (0.123 g, 1.79 mmol) and tert-butyldimethylsilylchloride (77 mg, 0.51 mmol) were added. After stirring at RT for 24 hours water (30 mL) was added and the material extracted into diethyl ether (2×50 mL). The combined extracts were washed with brine (50 mL), dried (MgSO$_4$) and evaporated to a residue which was chromatographed on silica, eluting with a gradient of 0-10% methanol in chloroform, and then chromatographed by preparative HPLC on C18 reversed phase using 5-95% acetonitrile (+0.2% TFA) in water (+0.2% TFA) as eluant. The chromatography fractions were allowed to stand overnight and the acetonitrile removed in vacuo. The aqueous residue was basified with saturated aqueous sodium bicarbonate solution and extracted into ethyl acetate (2×50 mL) and the combined extracts reduced in vacuo to give the desired compound. (30 mg)

$^1$H NMR δ (CDCl$_3$): 1.23 (d, 3H), 2.28 (quin, 2H), 2.80 (brs, 1H), 3.63 (d, 2H), 3.70 (s, 3H), 4.22 (brm, 4H), 4.46 (sex, 1H), 6.63 (m, 1H), 6.73 (m, 1H), 6.98 (m, 2H), 7.15 (m, 1H), 7.21 (m, 1H), 7.32 (d, 1H), 7.44 (dd, 1H), 8.99 (brs, 1H). m/z 469 (M+H)⁺

The preparation of 3-hydroxy-5-[(1R)-2-hydroxy-1-methylethoxy]-N-(1-methyl-1H-pyrazol-3-yl)benzamide is described below:

3-Hydroxy-5-[(1R)-2-hydroxy-1-methylethoxy]-N-(1-methyl-1H-pyrazol-3-yl)benzamide

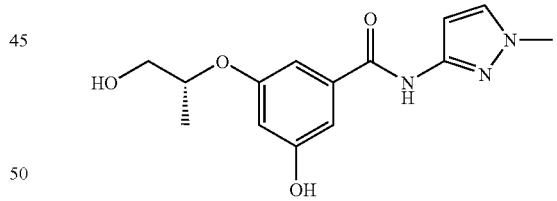

Iodotrimethylsilane (6.64 mL, 47 mmol) was added to a solution of 3-hydroxy-5-[(1R)-2-methoxy-1-methylethoxy]-N-(1-methyl-1H-pyrazol-3-yl)benzamide (2.86 g, 9.38 mmol) in acetonitrile (120 mL) and the resultant mixture stirred for 24 hours. Methanol (30 mL) was added and the mixture stirred for 30 minutes, saturated potassium carbonate (30 mL) and saturated sodium thiosulphate (30 mL) were then added and the mixture stirred for 20 mins. The acetonitrile was removed in vacuo and water (50 mL) added. The mixture was adjusted to pH4 with 1M hydrochloric acid, extracted into ethyl acetate (3×100 mL) and the combined extracts washed with brine (50 mL), dried (MgSO$_4$) and evaporated to a residue which was chromatographed on silica, eluting with a gradient of 0-50% methanol in ethyl acetate, to give the desired compound (1.75 g).

¹H NMR δ (d₆-DMSO): 1.21 (d, 3H), 3.41-3.58 (m, 2H), 3.77 (s, 3H), 4.45 (sex, 1H), 4.79 (t, 1H), 6.44 (m, 1H), 6.51 (m, 1H), 6.91 (s, 1H), 7.04 (s, 1H), 7.58 (m, 1H), 9.58 (s, 1H), 10.58 (brs, 1H). m/z 292 (M+H)⁺

3-Hydroxy-5-[(1R)-2-methoxy-1-methylethoxy]-N-(1-methyl-1H-pyrazol-3-yl)benzamide

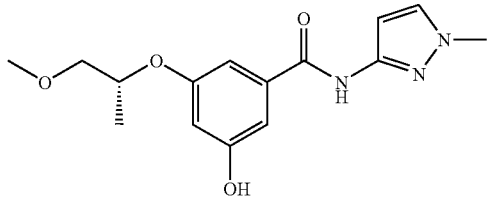

3-(Benzyloxy)-5-[(1R)-2-methoxy-1-methylethoxy]-N-(1-methyl-1H-pyrazol-3-yl)benzamide (4.23 g, 0.011 mol) was dissolved in ethanol (35 mL) and THF (35 mL) and the flask evacuated and purged with argon (3 times). 10% Palladium on carbon (0.42 g) was added and the flask further evacuated and finally purged with hydrogen gas. The reaction mixture was stirred at ambient temperature for 20 hours until completion. The reaction mixture was evacuated and purged with nitrogen (3 times). The catalyst was filtered off through celite and the filtrate concentrated in vacuo to give the desired compound (2.86 g)
¹H NMR δ (CDCl₃): 1.25 (d, 3H), 3.38 (s, 3H), 3.43-3.60 (m, 2H), 3.77 (s, 3H), 4.54 (m, 1H), 6.61 (m, 1H), 6.80 (m, 1H), 6.98 (m, 2H), 7.30 (m, 1H), 9.11 (brs, 1H). m/z 306 (M+H)⁺.

3-(Benzyloxy)-5-[(1R)-2-methoxy-1-methylethoxy]-N-(1-methyl-1H-pyrazol-3-yl)benzamide

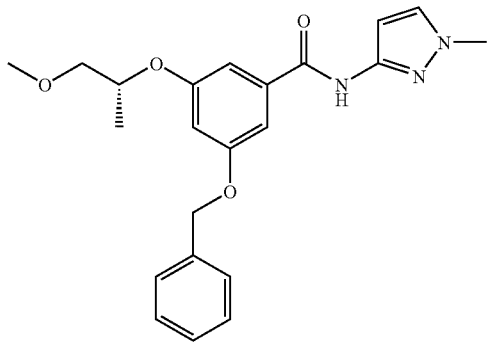

DMF (2 drops) was added to a solution of 3-(benzyloxy)-5-[(1R)-2-methoxy-1-methylethoxy]benzoic acid (3.79 g, 0.012 mol) and oxalyl chloride (1.25 mL, 0.015 mol) in DCM (60 mL) and stirred for 3 hours, following which the organics were removed in vacuo. The crude material was dissolved in DCM (30 mL) and slowly added, at 0° C., to a stirred suspension of 1-methyl-1H-pyrazol-3-amine (1.22 g, 0.013 mol) and triethylamine (3.5 mL, 0.025 mol) in DCM (30 mL). The mixture was stirred at ambient temperature for 24 hours and the organics evaporated in vacuo. The residue was dissolved in ethyl acetate (100 mL), washed with 1M aqueous hydrochloric acid (50 mL) and brine (50 mL), dried (MgSO₄), filtered and evaporated in vacuo to give the crude product which was chromatographed on silica, eluting with a 50% ethyl acetate in isohexane, to give the desired compound. (4.23 g).
¹H NMR δ (CDCl₃): 1.31 (d, 3H), 3.39 (s, 3H), 3.45-3.61 (m, 2H), 3.81 (s, 3H), 4.55 (m, 1H), 5.08 (s, 2H), 6.73 (m, 1H), 6.86 (m, 1H), 7.08 (s, 1H), 7.11 (s, 1H), 7.30-7.50 (m, 6H), 8.88 (brs, 1H). m/z 396 (M+H)⁺.

3-(Benzyloxy)-5-[(1R)-2-methoxy-1-methylethoxy] benzoic acid

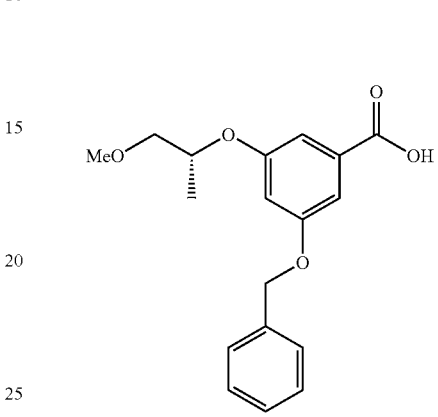

Lithium hydroxide monohydrate (1.30 g, 0.03 mol) in water (40 mL) was added to a solution of methyl 3-(benzyloxy)-5-[(1R)-2-methoxy-1-methylethoxy]benzoate (4.11 g, 0.012 mol) in THF (80 mL) and the reaction mixture stirred for 20 hours at ambient temperature. The THF was removed in vacuo. The aqueous residue was adjusted to pH3 with 1M hydrochloric acid and extracted with ethyl acetate (2×100 mL). The combined extracts were washed with brine (50 mL), dried (MgSO₄), filtered, and evaporated to give the desired compound (3.79 g).
¹H NMR δ (d₆-DMSO): 1.21 (d, 3H), 3.25 (s, 3H, obscured by water), 3.45 (m, 2H), 4.61 (m, 1H), 5.12 (s, 2H), 6.81 (s, 1H), 7.05 (s, 1H), 7.11 (s, 1H), 7.30-7.50 (m, 5H). m/z 315 (M−H)⁻

Methyl 3-(benzyloxy)-5-[(1R)-2-methoxy-1-methylethoxy]benzoate

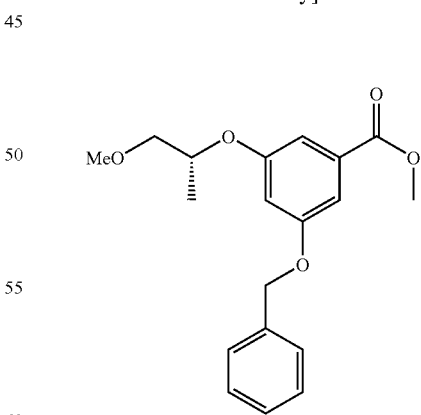

DIAD (4.6 g, 0.029 mol) was added dropwise to a solution of methyl 3-hydroxy-5-{[phenylmethyl]oxy}benzoate (6 g, 0.023 mol), (S)-(+)-1-methoxy-2-propanol (2.59 g, 0.029 mol) and triphenylphosphine (7.53 g, 0.029 mol) in THF (100 mL), under argon, at 0° C. The reaction was stirred at 0° C. for 1 hour and at RT for 20 hours. The volatiles were removed in vacuo and isohexane/ethyl acetate 2:1 added followed by stirring for 1 hour. A white solid was removed by filtration and the filtrate was evaporated to a residue which was chromatographed on silica, eluting with a gradient of 0-20% ethyl acetate in isohexane, to give the desired compound (5.11 g).

¹H NMR δ (CDCl₃): 1.31 (d, 3H), 3.40 (s, 3H), 3.45-3.60 (m, 2H), 3.88 (s, 3H), 4.57 (sex, 1H), 5.07 (s, 2H), 6.76 (m, 1H), 7.25 (m, 2H), 7.40 (m, 5H). m/z 331 (M+H)⁺.

The preparation of methyl 3-hydroxy-5-{[phenylmethyl] oxy}benzoate was described in Example 1.

EXAMPLE 26

3-[4-(Azetidin-1-ylcarbonyl)phenoxy]-5-[(1R)-2-hydroxy-1-methylethoxy]-N-(1-methyl-1H-pyrazol-3-yl)benzamide

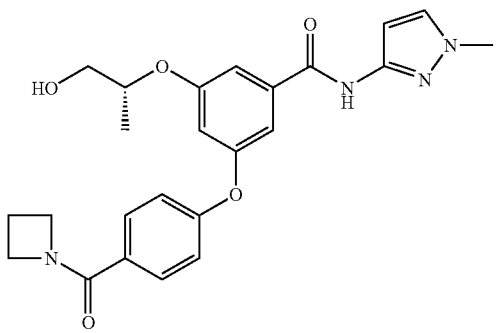

3-[4-(Azetidin-1-ylcarbonyl)-2-chlorophenoxy]-5-[(1R)-2-hydroxy-1-methylethoxy]-N-(1-methyl-1H-pyrazol-3-yl) benzamide (0.23 g, 0.48 mmol (60% pure)) and triethylamine (0.2 mL, 1.44 mmol) were dissolved in ethanol (8 mL) and the flask evacuated and purged with argon (3 times). 10% Palladium on carbon (23 mg) was added and the flask further evacuated and finally purged with hydrogen gas. The reaction mixture was stirred at ambient temperature for 6 days until completion. The reaction mixture was evacuated and purged with nitrogen (3 times). The catalyst was filtered off through celite and the filtrate concentrated in vacuo to a residue which was chromatographed on silica, eluting with a gradient of 0-10% methanol in ethyl acetate. An impurity remained at a level of 40%. This mixture (0.27 g, 0.6 mmol) was dissolved in DMF (5 mL) and imidazole (0.29 g, 4.2 mmol) and tert-butyldimethylsilylchloride (180 mg, 1.2 mmol) were added. After stirring at RT for 20 hours water (30 mL) was added and the mixture extracted into diethyl ether (2×50 mL). The combined extracts were washed with brine (50 mL) dried (MgSO₄) and evaporated to a residue which was chromatographed on silica, eluting with a gradient of 0-10% methanol in ethyl acetate, and then chromatographed by preparative HPLC on C18 reversed phase using 5-95% acetonitrile (+0.2% TFA) in water (+0.2% TFA) as eluant. The chromatography fractions were allowed to stand overnight and the acetonitrile removed in vacuo. The aqueous residue was basified with saturated aqueous sodium bicarbonate solution and extracted into ethyl acetate (2×50 mL) and the combined extracts reduced in vacuo to give the desired compound. (28 mg)

¹H NMR δ (CDCl₃): 1.32 (d, 3H), 2.38 (quin, 2H), 3.75 (m, 2H), 3.90 (s, 3H), 4.30 (t, 4H), 4.60 (m, 1H), 6.79 (m, 1H), 6.90 (m, 1H), 7.03 (d, 2H), 7.17 (m, 1H), 7.38 (m, 2H), 7.68 (d, 2H), 9.28 (brs, 1H). m/z 451 (M+H)⁺

The preparation of 3-[4-(azetidin-1-ylcarbonyl)-2-chlorophenoxy]-5-[(1R)-2-hydroxy-1-methylethoxy]-N-(1-methyl-1H-pyrazol-3-yl)benzamide is described below:

3-[4-(Azetidin-1-ylcarbonyl)-2-chlorophenoxy]-5-[(1R)-2-hydroxy-1-methylethoxy]-N-(1-methyl-1H-pyrazol-3-yl)benzamide

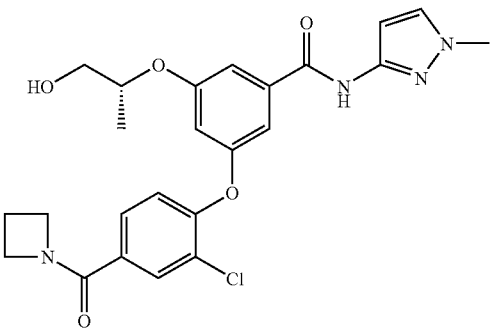

Cesium carbonate (1.12 g, 3.44 mmol) was added to a mixture of 3-hydroxy-5-[(1R)-2-hydroxy-1-methylethoxy]-N-(1-methyl-1H-pyrazol-3-yl)benzamide (500 mg, 1.72 mmol) and 1-(3-chloro-4-fluorobenzoyl)azetidine (367 mg, 1.72 mmol) in dimethylacetamide (5.0 mL) and the stirred mixture heated at 160° C. in a 'Smith Creator Microwave' for 2 hours. The mixture was allowed to return to ambient temperature and pressure and was partitioned between ethyl acetate (50 mL) and water (50 mL). The ethyl acetate layer was separated, washed with water (5×50 mL) brine (50 mL), dried (MgSO₄) and evaporated to a residue which was chromatographed on silica, eluting with a gradient of 0-10% methanol in ethyl acetate, and then chromatographed by preparative HPLC on C18 reversed phase using 5-95% acetonitrile (+0.2% TFA) in water (+0.2% TFA) as eluant. An impurity remained at the 40% level and this material was used crude in the next step (0.21 g).

m/z 485, 487 (M+H)⁺

The preparation of 3-hydroxy-5-[(1R)-2-hydroxy-1-methylethoxy]-N-(1-methyl-1H-pyrazol-3-yl)benzamide was described in Example 25.

EXAMPLE 27

3-[4-(Azetidin-1-ylcarbonyl)-2-fluorophenoxy]-5-[(1S)-2-hydroxy-1-methylethoxy]-N-(3-methyl-1,2,4-thiadiazol-5-yl)benzamide

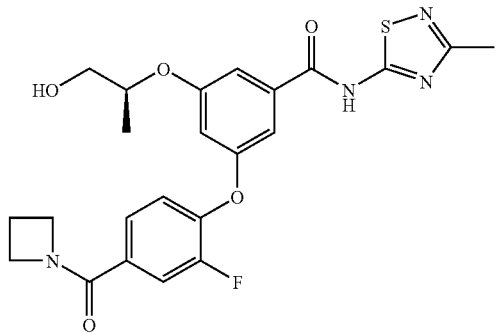

10% Hydrochloric acid (2 mL) was added to a solution of 3-[4-(azetidin-1-ylcarbonyl)-2-fluorophenoxy]-5-((1S)-2-{[tert-butyl(dimethyl)silyl]oxy}-1-methylethoxy)-N-(3-methyl-1,2,4-thiadiazol-5-yl)benzamide (950 mg, 1.58 mmol) in methanol (20 mL). The reaction was stirred at ambient temperature for 1 hour, saturated sodium bicarbonate solution added and the methanol evaporated. The aqueous residue was taken to pH2 and extracted with ethyl acetate. The extracts were combined, washed with brine, dried (MgSO₄), filtered and evaporated in vacuo to give the crude product which was chromatographed on silica, eluting with ethyl acetate, to give the desired compound (400 mg) which was recrystallised from ethyl acetate (mpt 173° C.-175° C.).

¹H NMR δ (CDCl₃): 1.3 (d, 3H), 2.4 (m, 2H), 2.5 (s, 3H), 3.75 (d, 2H), 4.2-4.4 (m, 4H), 4.6 (m, 1H), 6.85 (s, 1H), 7.1 (d, 1H), 7.15 (s, 1H), 7.20 (s, 1H), 7.4 (d, 1H), 7.5 (s, 1H). m/z 487 (M+H)+

The preparation of 3-[4-(azetidin-1-ylcarbonyl)-2-fluorophenoxy]-5-((1S)-2-{[tert-butyl(dimethyl)silyl]oxy}-1-methylethoxy)-N-(3-methyl-1,2,4-thiadiazol-5-yl)benzamide is described below:

3-[4-(Azetidin-1-ylcarbonyl)-2-fluorophenoxy]-5-((1S)-2-{[tert-butyl(dimethyl)silyl]oxy}-1-methylethoxy)-N-(3-methyl-1,2,4-thiadiazol-5-yl)benzamide

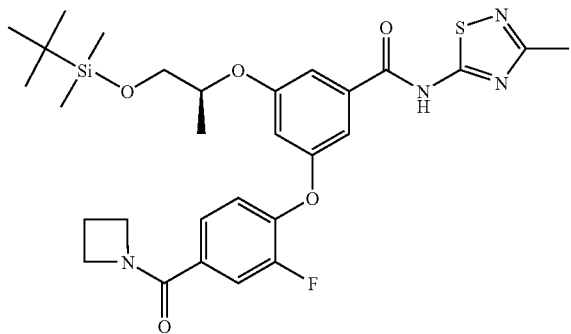

DIPEA (0.8 mL, 4.77 mmol) was added to a suspension of 3-[4-(azetidin-1-ylcarbonyl)-2-fluorophenoxy]-5-((1S)-2-{[tert-butyl(dimethyl)silyl]oxy}-1-methylethoxy)benzoic acid (800 mg, 1.59 mmol), HATU (787 mg, 2.07 mmol) and 5-amino-3-methyl-1,2,4 thiadiazole (549 mg, 4.77 mmol) in DMF (110 mL). The resulting mixture was stirred at ambient temperature for 16 hours, water (150 mL) was added and the mixture extracted with ethyl acetate. The extracts were combined, washed with brine, dried (MgSO₄), filtered and evaporated in vacuo to give the crude product which was chromatographed on silica, eluting with 75% ethyl acetate in isohexane, to give the desired compound (950 mg).

m/z 601 (M+H)⁺.

The preparation of 3-[4-(azetidin-1-ylcarbonyl)-2-fluorophenoxy]-5-((1S)-2-{[tert-butyl(dimethyl)silyl]oxy}-1-methyl ethoxy)benzoic acid was described in Example 8.

EXAMPLE 28

3-[4-(Azetidin-1-ylcarbonyl)phenoxy]-5-[(1S)-2-hydroxy-1-methylethoxy]-N-(3-methyl-1,2,4-thiadiazol-5-yl)benzamide

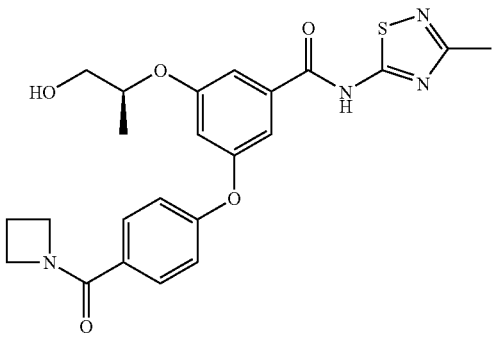

10% Hydrochloric acid (2 mL) was added to a solution of 3-[4-(azetidin-1-ylcarbonyl)phenoxy]-5-((1S)-2-{[tert-butyl(dimethyl)silyl]oxy}-1-methylethoxy)-N-(3-methyl-1,2,4-thiadiazol-5-yl)benzamide (580 mg, 1.0 mmol) in methanol (20 mL). The reaction was stirred at ambient temperature for 1 hour, saturated sodium bicarbonate solution added and the methanol evaporated. The aqueous residue was taken to pH2 and extracted with ethyl acetate. The extracts were combined, washed with brine, dried (MgSO₄), filtered, and evaporated in vacuo to give the crude product (275 mg) which was recrystallised from ethyl acetate (m pt 159° C.-160° C.).

¹H NMR δ (CDCl₃): 1.3 (d, 3H), 2.4 (m, 2H), 2.5 (s, 3H), 3.75 (d, 2H), 4.2-4.4 (m, 4H), 4.6 (m, 1H), 6.8 (s, 1H), 7.0 (d, 1H), 7.2 (s, 1H), 7.25 (s, 1H), 7.3 (s, 1H), 7.65 (d, 2H). m/z 468 (M+H)⁺.

The preparation of 3-[4-(azetidin-1-ylcarbonyl)phenoxy]-5-((1S)-2-{[tert-butyl(dimethyl)silyl]oxy}-1-methylethoxy)-N-(3-methyl-1,2,4-thiadiazol-5-yl)benzamide is described below:

3-[4-(Azetidin-1-ylcarbonyl)phenoxy]-5-((1S)-2-{[tert-butyl(dimethyl)silyl]oxy}-1-methylethoxy)-N-(3-methyl-1,2,4-thiadiazol-5-yl)benzamide

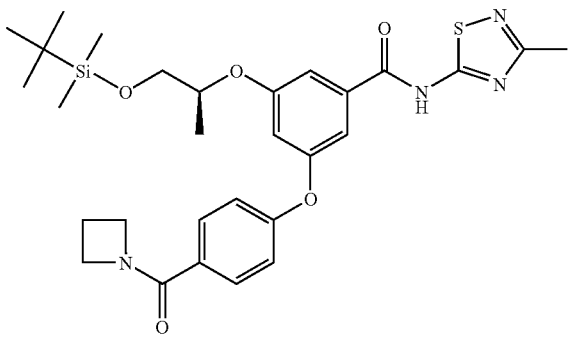

DIPEA (0.5 mL, 3.0 mmol) was added to a suspension of 3-[4-(azetidin-1-ylcarbonyl)phenoxy]-5-((1S)-2-{[tert-butyl(dimethyl)silyl]oxy}-1-methylethoxy)benzoic acid (485 mg, 1.0 mmol), HATU (4951 g, 1.3 mmol) and 5-amino-3-methyl-1,2,4 thiadiazole (345 mg, 3.0 mmol) in DMF (6 mL).

The resulting mixture was stirred at ambient temperature for 16 hours, water (90 mL) was added and the mixture extracted with ethyl acetate. The extracts were combined, washed with brine, dried (MgSO$_4$), filtered and evaporated in vacuo to give the crude product which was chromatographed on silica, eluting with 75% ethyl acetate in isohexane, to give the desired compound (580 mg).

m/z 583 (M+H)$^+$.

The preparation of 3-[4-(azetidin-1-ylcarbonyl)phenoxy]-5-((1S)-2-{[tert-butyl(dimethyl)silyl]oxy}-1-methylethoxy) benzoic acid was described in Example 20.

EXAMPLE 29

3-[4-(Azetidin-1-ylsulfonyl)phenoxy]-5-[(1S)-2-hydroxy-1-methylethoxy]-N-(1-methyl-1H-pyrazol-3-yl)benzamide

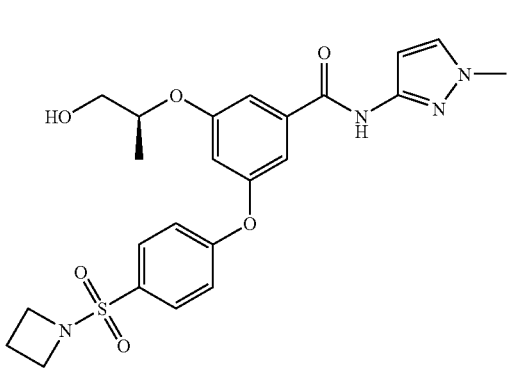

A suspension of 1-[(4-fluorophenyl)sulfonyl]azetidine (108 mg, 0.5 mmol), 3-((1S)-2-{[tert-butyl(dimethyl)silyl]oxy}-1-methylethyloxy)-5-hydroxy-N-(1-methyl-1H-pyrazol-3-yl)benzamide (202 mg, 0.5 mmol) and caesium carbonate (325 mg, 1.0 mmol) in dimethylacetamide (10 mL) was heated to 115° C. for 4-5 hours. Water was added to the reaction mixture and extracted with ethyl acetate (3×30 mL). Combined organic extracts were washed with saturated brine solution and dried (MgSO$_4$). Filtrate was concentrated in vacuo and the residue was chromatographed on silica, eluting with 20-80% ethyl acetate in iso hexane, to give a pale yellow oil which foamed up under high vacuum (122 mg).

$^1$H NMR δ (d$_6$-DMSO): 1.20 (d, 3H), 2.0 (m, 2H), 3.5 (m, 2H), 3.65 (m, 4H), 3.75 (s, 3H), 4.6 (m, 1H), 4.8 (m, 1H), 6.55 (d, 1H), 6.9 (app s, 1H), 7.25 (d, 2H), 7.3 (app s 1H), 7.5 (app s 1H), 7.6 (d, 1H), 7.8 (d, 2H); m/z 487 (M+H)$^+$, 485 (M–H)$^-$ The preparation of 3-((1S)-2-{[tert-butyl(dimethyl)silyl]oxy}-1-methylethyloxy)-5-hydroxy-N-(1-methyl-1H-pyrazol-3-yl)benzamide was described in Example 5.

The preparation of 1-[(4-fluorophenyl)sulfonyl]azetidine is described below:

1-[(4-Fluorophenyl)sulfonyl]azetidine

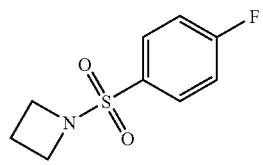

Azetidine (0.25 g, 4.35 mmol) was added to a solution of sodium hexamethyldisilylazide (0.85 g, 4.6 mmol) in THF (10 mL) at 0° C. and reaction mixture stirred for 10 minutes. 4-fluorobenzenesulfonyl chloride (0.85 g, 4.35 mmol) was subsequently added and the reaction mixture was allowed to warm up to ambient temperature overnight. The reaction mixture was concentrated in vacuo and the residue taken up in ethyl acetate and water. The organic layer was separated and then dried (MgSO$_4$), filtered and evaporated to give a waxy, yellow solid (75 mg).

$^1$H NMR δ (CDCl$_3$): 2.1 (m, 2H), 3.8 (t, 4H), 7.25 (app t, 2H), 7.85 (dd, 2H). m/z 216 (M+H)$^+$

EXAMPLE 30

3-[4-(Azetidin-1-ylcarbonyl)-2-fluorophenoxy]-5-[(1S)-2-hydroxy-1-methylethoxy]-N-1H-pyrazol-3-ylbenzamide

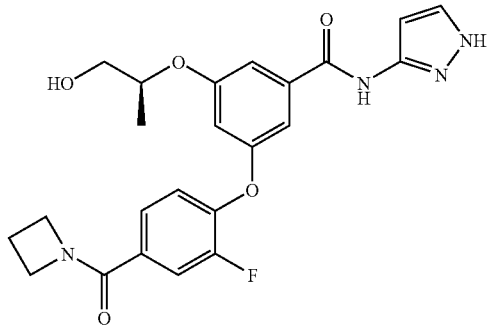

A suspension of tert-butyl 3-[(3-hydroxy-5-{(1S)-1-methyl-2-[(triisopropylsilyl)oxy]ethoxy}benzoyl)amino]-1H-pyrazole-1-carboxylate (66 mg, 0.12 mmol), 1-(3,4-difluorobenzoyl)azetidine (24 mg, 0.12 mmol) and cesium carbonate (59 mg, 0.18 mmol) in DMF (2 mL) was heated in the microwave at 150° C. for 2 hours. Water was added to the reaction mixture and extracted with ethyl acetate (3×30 mL). The combined organic layers were washed with water (3×25 mL) and saturated brine solution and subsequently dried (MgSO$_4$), filtered and evaporated to give yellow/orange oil. This was purified by preparative HPLC, eluting with 5-95% acetonitrile in water (0.2% TFA modifier), using a Phenomenex column Luna 10u C18(2) 100A (150×21.2 mm) column; to give a white foam (20 mg)

$^1$H NMR δ (CDCl$_3$): 1.05 (2H, m), 1.3 (d, 3H), 1.35 (m, 2H), 2.45 (m, 1H), 3.75 (m, 2H), 3.8 (s, 3H), 4.6 (m, 1H), 6.8 ( ), 7.1 ( ), 7.3 (d, 2H), 7.9 (d, 2H), 8.5 (s br, 1H); m/z 455 (M+H)$^+$, 453 (M–H)$^-$

The synthesis of 1-(3,4-difluorobenzoyl)azetidine is described in Example 8, the synthesis of tert-butyl 3-[(3-hydroxy-5-{(1S)-1-methyl-2-[(triisopropylsilyl)oxy]ethoxy}benzoyl)amino]-1H-pyrazole-1-carboxylate is described below:

tert-Butyl 3-[(3-hydroxy-5-{(1S)-1-methyl-2-[(triisopropylsilyl)oxy]ethoxy}benzoyl)amino]-1H-pyrazole-1-carboxylate

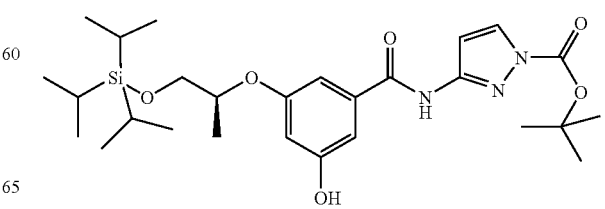

A solution of tert-butyl 3-[(3-(benzyloxy)-5-{(1S)-1-methyl-2-[(triisopropylsilyl)oxy]ethoxy}benzoyl)amino]-1H-pyrazole-1-carboxylate (90 mg, 0.144-mmol) in 1:1 mixture of THF/ethanol was evacuated and purged with nitrogen (×3). 10% Palladium on carbon was added and the reaction mixture was evacuated and purged with nitrogen and then evacuated and finally purged with hydrogen gas. The reaction mixture was left to stir at ambient temperature under an atmosphere of hydrogen for 6 hours. The Palladium catalyst was filtered through diatomaceous earth. The filtrate was evaporated to give a crude solid (70 mg)

m/z 534 (M+H)⁺, 532 (M−H)⁻ tert-Butyl 3-[(3-(benzyloxy)-5-{(1S)-1-methyl-2-[(triisopropylsilyl)oxy]ethoxy}benzoyl)amino]-1H-pyrazole-1-carboxylate

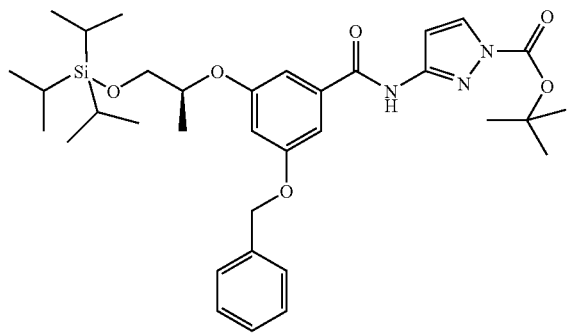

DIPEA (0.21 mL, 1.2 mmol) was added to a solution of 3-(benzyloxy)-5-{(1S)-1-methyl-2-[(triisopropylsilyl)oxy]ethoxy}benzoic acid (220 mg, 0.48 mmol), HATU (228 mg, 0.6 mmol), and tert-butyl 3-amino-1H-pyrazole-1-carboxylate (110 mg, 0.66 mmol) in DMF (2 mL) and the reaction mixture stirred at ambient temperature overnight. Water was added to the reaction mixture and extracted with ethyl acetate (3×25 mL). The combined organic extracts were separated and washed with 1M hydrochloric acid, saturated sodium hydrogen carbonate solution, saturated brine solution, dried (MgSO₄), filtered and evaporated. The residue was purified by column chromatography on silica, eluting with 0% to 50% ethyl acetate in hexanes, to give a clear oil (90 mg)

m/z 624 (M+H)⁺, 622 (M−H)⁻

3-(Benzyloxy)-5-{(1S)-1-methyl-2-[(triisopropylsilyl)oxy]ethoxy}benzoic acid

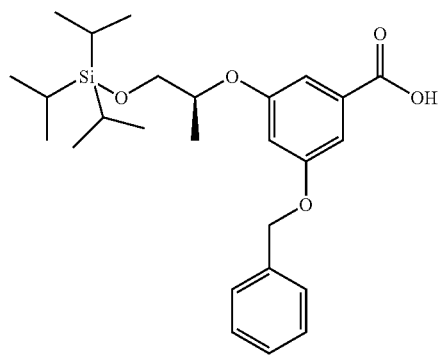

Lithium hydroxide monohydrate (12.14 g, 0.289 mol) in water (100 mL) was added to a solution of methyl 3-(benzyloxy)-5-{(1S)-1-methyl-2-[(triisopropylsilyl)oxy]ethoxy}benzoate (62 g, 0.131 mol) in THF (300 mL) and warmed to 43° C. The reaction was stirred for 16 hours, the THF removed in vacuo and the resultant mixture acidified to pH 5 with 10% w/v citric acid. This was extracted with ethyl acetate (2×300 mL) and the combined organic layers were dried (MgSO₄), filtered and evaporated to afford the title compound (60.2 g).

¹H NMR δ (CDCl₃): ¹H NMR δ (CDCl₃): 1.05 (s, 18H), 1.05-1.1 (m, 3H), 1.35 (d, 3H), 3.7 (m, 1H), 3.9 (m, 1H), 4.5 (m, 1H), 5.1 (s, 2H), 6.8 (s, 1H), 7.3-7.5 (m, 7H). m/z 457 (M−H)⁻

Methyl 3-(benzyloxy)-5-{(1S)-1-methyl-2-[(triisopropylsilyl)oxy]ethoxy}benzoate

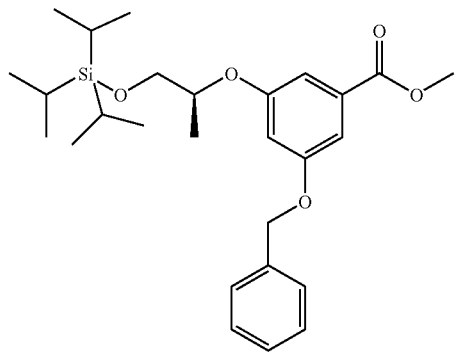

(2R)-1-[(Triisopropylsilyl)oxy]propan-2-ol (56.1 g, 242 mmol) was added to a solution of methyl 3-hydroxy-5-{[phenylmethyl]oxy}benzoate (50 g, 194 mmol) and triphenylphosphine (63.5 g, 242 mmol) in dry THF (500 mL), at to 0° C., followed by addition of DIAD (47.6 mL, 242 mmol) over 45 minutes under an argon atmosphere. The reaction was stirred at 0° C. for 1 hour and allowed to warm up to RT over an hour then stirred at RT for 1 hour. The THF was evaporated and a mixture of ethyl acetate (80 mL) and hexane (120 mL) was added. This mixture stirred for 2 hours and filtered. The precipitate was washed with a mixture of ethyl acetate (20 mL) and hexane (180 mL) and the filtrate evaporated. The residue was purified by column chromatography, eluting with 1:20 to 1:10 ethyl acetate:hexanes, to afford the title compound (65.5 g).

¹H NMR δ (CDCl₃): 1.05 (s, 18H), 1.05-1.1 (m, 3H), 1.35 (d, 3H), 3.7 (m, 1H), 3.9 (m, 1H), 3.9 (s, 3H), 4.5 (m, 1H), 5.05 (s, 2H), 6.75 (s, 1H), 7.2 (s, 1H). 7.3-7.5 (m, 6H). m/z 471 (M−H)⁻

(2R)-1-[(Triisopropylsilyl)oxy]propan-2-ol

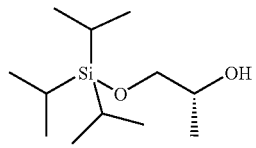

Triisopropylsilyl chloride (83.8 mL, 390 mmol) was added slowly over 15 minutes to a solution of (2R)-propane-1,2-diol (29.7 g, 390 mmol) in DMF at 0° C. (100 mL) keeping the internal temperature below 15° C. This was followed by addition of imidazole (66.4 g, 975 mmol) and the reaction mixture was allowed to warm to RT and stirred under argon for 20 hours. The reaction was quenched with 1M hydrochloric acid/diethyl ether (300 mL/800 mL). The organic layer was separated and washed with 1M hydrochloric acid followed by saturated brine solution. The organic layer was dried (MgSO₄), filtered and evaporated. Purification by distillation at 10 mmHg, 90-104° C., afforded the title compound as colourless oil (69.5 g).

¹H NMR δ (CDCl₃): 1.05 (s, 18H), 1.05-1.1 (m, 3H), 1.05 (d, 3H), 2.55 (s, 1H), 3.45 (dd, 1H), 3.7 (dd, 1H), 3.85 (m, 1H).

The preparation of methyl 3-hydroxy-5-{[phenylmethyl]oxy}benzoate was described in Example 1.

The preparation of tert-butyl 3-amino-1H-pyrazole-1-carboxylate was described in Example 3.

EXAMPLE 31

3-[4-(cyclobutylsulfonyl)phenoxy]-5-[(1S)-2-hydroxy-1-methylethoxy]-N-(1-methyl-1H-pyrazol-3-yl)benzamide

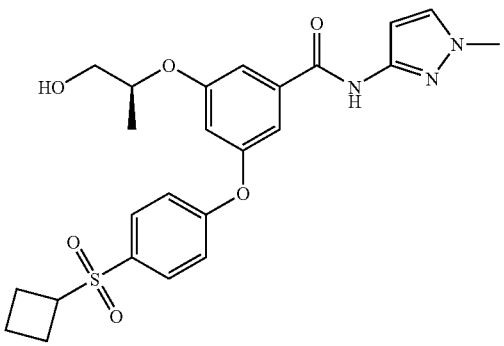

A suspension of 1-(cyclobutylsulfonyl)-4-fluorobenzene (100 mg, 0.47 mmol), cesium carbonate (162 mg, 0.5 mmol) and 3-hydroxy-N-(1-methyl-1H-pyrazol-3-yl)-5-{(1S)-1-methyl-2-[(triisopropylsilyl)oxy]ethoxy}benzamide (210 mg, 0.47 mmol) in dimethylacetamide (10 mL) was heated at 115° C. for approximately 6 hours. Water was added to the reaction mixture and extracted with ethyl acetate (3×40 mL). The organic phase was washed with water (3×30 mL), saturated brine solution and dried (MgSO₄). This was evaporated and the residue chromatographed on silica, eluting with 50-100% ethyl acetate in hexanes, to give clear oil, which foamed up under high vacuum (65 mg).

¹H NMR δ (d₆-DMSO): 1.20 (d, 3H), 1.9 (m, 2H), 2.1 (m, 2H), 2.3 (m, 2H), 3.5 (m, 2H), 3.75 (s, 3H), 4.05 (m, 1H), 4.6 (m, 1H), 4.85 (m, 1H), 6.55 (d, 1H), 6.9 (app s, 1H), 7.2 (d, 2H), 7.3 (app s 1H), 7.5 (app s 1H), 7.6 (d, 1H), 7.8 (d, 2H), 10.83 (br s, 1H); m/z 486 (M+H)⁺, 484 (M-H)⁻

The preparation of 1-(cyclobutylsulfonyl)-4-fluorobenzene is described below:

1-(Cyclobutylsulfonyl)-4-fluorobenzene

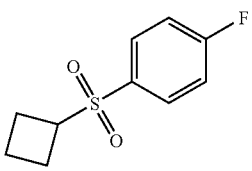

1-(Cyclobutylthio)-4-fluorobenzene (558 mg, 3.05 mmol) was dissolved in DCM (10 mL) and cooled to -15° C. m-Chloroperbenzoic acid (1.11 g, 6.44 mmol) was added portion wise keeping the temperature between -15° C. and -10° C. The cooling bath was removed and the mixture stirred at RT for 3-4 hours. The reaction mixture was partitioned between DCM (40 mL) and water (40 mL). The organic phase was washed with sodium hydrogen carbonate solution, saturated brine solution, dried (MgSO₄) and the resultant solution evaporated to give a white solid (578 mg).

¹H NMR δ (CDCl₃): 2.0 (m, 2H), 2.2 (m, 2H), 2.6 (m, 2H), 3.8 (m, 1H), 7.2 (t, 2H), 7.9 (m, 2H)

1-(Cyclobutylthio)-4-fluorobenzene

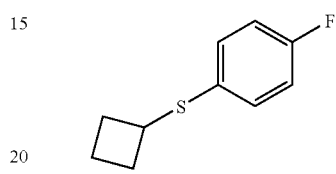

A suspension of 4-fluorothiophenol (0.5 g, 3.9 mmol), cesium carbonate (1.39 g, 4.3 mmol) and cyclobutylbromide (0.58 g, 4.3 mmol) in DMSO (10 mL) was heated to 70° C. overnight. Inorganic salts were filtered off and the filtrate partitioned between diethyl ether and water. The water layer was subsequently extracted with diethyl ether (3×35 mL). The combined extracts were washed with water (2×30 mL), saturated brine solution, dried (MgSO₄), filtered and evaporated to a pale yellow liquid (0.65 g).

¹H NMR δ (CDCl₃): 2.0 (m, 4H), 2.4 (m, 2H), 3.8 (m, 1H), 7.0 (t, 2H), 7.25 (m, 2H).

The synthesis of 3-hydroxy-N-(1-methyl-1H-pyrazol-3-yl)-5-{(1S)-1-methyl-2-[(triisopropylsilyl)oxy]ethoxy}benzamide is described below:

3-Hydroxy-N-(1-methyl-1H-pyrazol-3-yl)-5-{(1S)-1-methyl-2-[(triisopropylsilyl)oxy]ethoxy}benzamide

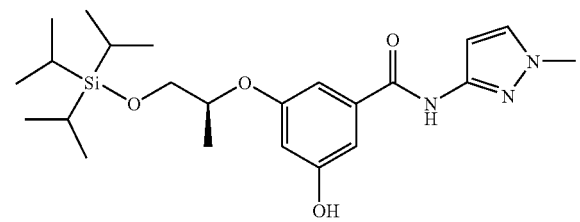

10% Palladium on carbon was added to 3-(benzyloxy)-N-(1-methyl-1H-pyrazol-3-yl)-5-{(1S)-1-methyl-2-[(triisopropylsilyl)oxy]ethoxy}benzamide (21.7 g, 40.4 mmol) in dry THF (480 mL) under argon. The reaction mixture was degassed and placed under a hydrogen balloon and stirred for 16 hours. The atmosphere was replaced with argon and mixture was filtered through diatomaceous earth then the filtrate evaporated and dried under high vacuum for 1 hour to give the title compound (18.2 g).

¹H NMR δ (CDCl₃): 1.05 (s, 18H), 1.05-1.1 (m, 3H), 1.3 (d, 3H), 3.7 (m, 1H), 3.8 (s, 3H), 3.9 (m, 1H), 4.5 (m, 1H), 6.6 (s, 1H), 6.8 (s, 1H), 7.0 (m, 2H), 7.20 (s, 1H), 7.3 (s, 1H), 8.7 (s, 1H). m/z 448 (M+H)⁺, 446 (M-H)⁻

3-(Benzyloxy)-N-(1-methyl-1H-pyrazol-3-yl)-5-{(1S)-1-methyl-2-[(triisopropylsilyl)oxy]ethoxy}benzamide

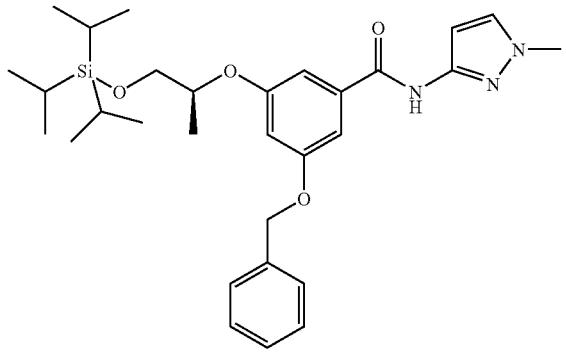

HATU (23.5 g, 61.8 mmol) was added to 3-(benzyloxy)-5-{(1S)-1-methyl-2-[(triisopropylsilyl)oxy]ethoxy}benzoic acid (23.6 g, 51.5 mmol), followed by addition of DMF (140 mL), and cooled to 0° C. 1-Methyl-1H-pyrazole-3-amine (6.00 g. 61.8 mmol) was added followed by DIPEA (21.3 mL) and the reaction was stirred under argon at 0° C. for 3 hours. The solvent was evaporated and the residue was dissolved in ethyl acetate (500 mL) and washed with citric acid solution (200 mL), sodium hydrogen carbonate solution (150 mL), and saturated brine solution (2×150 mL). The organic layer was separated and dried (MgSO$_4$), filtered and evaporated. Purification by column chromatography, eluting with 1:4 to 1:1 ethyl acetate:hexanes, afforded the title compound as a colourless oil (21.7 g).

$^1$H NMR δ (CDCl$_3$): $^1$H NMR δ (CDCl$_3$): 1.05 (s, 18H), 1.05-1.1 (m, 3H), 1.3 (d, 3H), 3.7 (m, 1H), 3.8 (s, 3H), 3.9 (m, 1H), 4.5 (m, 1H), 5.1 (s, 2H), 6.7 (s, 1H), 6.8 (s, 1H), 7.0 (m, 2H), 7.1 (s, 1H), 7.3 (s, 1H), 7.35-7.5 (m, 5H), 8.5 (s, 1H). m/z 538 (M+H)$^+$

The preparation of 3-(benzyloxy)-5-{(1S)-1-methyl-2-[(triisopropylsilyl)oxy]ethoxy}benzoic acid was described in Example 30.

The following compound was prepared in an analogous fashion to Example 31, from 3-hydroxy-N-(1-methyl-1H-pyrazol-3-yl)-5-{(1S)-1-methyl-2-[(triisopropylsilyl)oxy]ethoxy}benzamide and 1-(cyclopropylsulfonyl)-4-fluorobenzene 1-(Cyclopropylsulfonyl)-4-fluorobenzene was prepared in an analogous fashion to the preparation of 1-(cyclobutylsulfonyl)-4-fluorobenzene described in Example 31.

| Structure | m/z | NMR |
|---|---|---|
| 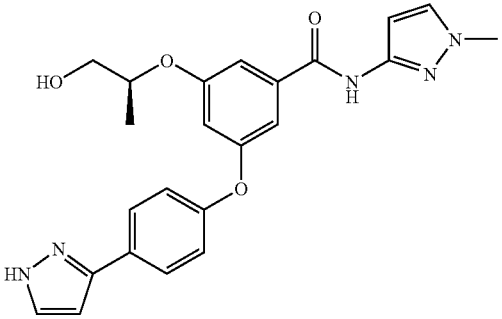 | | $^1$H NMR δ (CDCl$_3$): 1.05 (m, 2H), 1.35 (m, 2H), 2.45 (m, 1H), 7.2 (t, 2H), 7.9 (m, 2H) |
| | | $^1$H NMR δ (CDCl$_3$): 0.7 (m, 2H), 1.05 (m, 2H), 2.2 (m, 1H), 7.0 (t, 2H), 7.35 (m, 2H) |

EXAMPLE 32

3-[(1S)-2-Hydroxy-1-methylethoxy]-N-(1-methyl-1H-pyrazol-3-yl)-5-[4-(1H-pyrazol-3-yl)phenoxy]benzamide Trimethylsilyl iodide (0.080 mL, 0.559 mmol) was added to a solution of 3-[(1S)-2-methoxy-1-methylethoxy]-N-(1-methyl-1H-pyrazol-3-yl)-5-[4-(1H-pyrazol-3-yl)phenoxy]benzamide (50 mg, 0.112 mmol) in acetonitrile (2 mL) and

| Example | Structure | m/z | NMR |
|---|---|---|---|
| 31a | | 472 (M + H)$^+$, 470 (M − H)$^−$ | $^1$H NMR δ (CDCl$_3$): 1.05 (m, 2H), 1.3 (m, 3H), 1.35 (m, 2H), 2.45 (m, 1H), 3.75 (m, 2H), 3.8 (s, 3H), 4.55 (m, 1H), 6.8 (d, 1H), 6.85 (app s, 1H), 7.1 (d, 2H), 7.1 (s, 1H), 7.3 (d, 2H), 7.9 (d, 2H), 8.5 (brs, 1H) | the reaction mixture allowed to stir at RT for 18 hours. The reaction was diluted with ethyl acetate (15 mL) and quenched by the addition of saturated aqueous sodium bicarbonate solution (20 mL). The organic phase was washed with saturated aqueous thiosulphate solution (20 mL) and dried (MgSO$_4$). The volatiles were removed under reduced pressure and the resulting oil purified by chromatography on silica, eluting with 0-100% ethyl acetate in iso-hexane, to give the title compound as a colourless solid (40 mg).

$^1$H NMR δ (CDCl$_3$): 1.21 (d, 3H), 3.59-3.72 (m, 2H), 3.77 (s, 3H), 4.35-4.47 (m, 1H), 6.56 (d, 1H), 6.64 (t, 1H), 6.85 (d, 1H), 6.94 (d, 2H), 7.06-7.13 (m, 2H), 7.28 (d, 2H), 7.58-7.65 (m, 3H), 9.64 (s, 1H); m/z 434 (M+H)$^+$.

The preparation of 3-[(1S)-2-methoxy-1-methylethoxy]-N-(1-methyl-1H-pyrazol-3-yl)-5-[4-(1H-pyrazol-3-yl)phenoxy]benzamide is described below:

3-[(1S)-2-Methoxy-1-methylethoxy]-N-(1-methyl-1H-pyrazol-3-yl)-5-[4-(1H-pyrazol-3-yl)phenoxy]benzamide

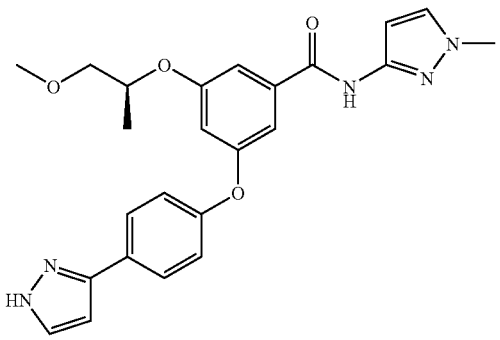

A mixture of 3-{4-[(2E)-3-(dimethylamino)prop-2-enoyl]phenoxy}-5-[(1S)-2-methoxy-1-methylethoxy]-N-(1-methyl-1H-pyrazol-3-yl)benzamide (100 mg, 0.209 mmol) and hydrazine hydrate (0.204 mL, 4.18 mmol) in ethanol (3 mL) was heated to 100° C. for 5 minutes in a 'Smith Creator' microwave. The volatiles were removed in vacuo to give the product as a colourless foam (92 mg).

$^1$H NMR δ (CDCl$_3$): 1.26 (d, 3H), 3.38 (s, 3H), 3.41-3.49 (m, 1H), 3.54 (dd, 1H), 3.74 (s, 3H), 4.48-4.60 (m, 1H), 6.55 (s, 1H), 6.74 (s, 1H), 6.83 (s, 1H), 6.99 (d, 2H), 7.09 (s, 1H), 7.21 (s, 1H), 7.57-7.72 (m, 3H), 9.42 (s, 1H); m/z 448 (M+H)$^+$.

3-{-4-[(2E)-3-(Dimethylamino)prop-2-enoyl]phenoxy}-5-[(1S)-2-methoxy-1-methylethoxy]-N-(1-methyl-1H-pyrazol-3-yl)benzamide

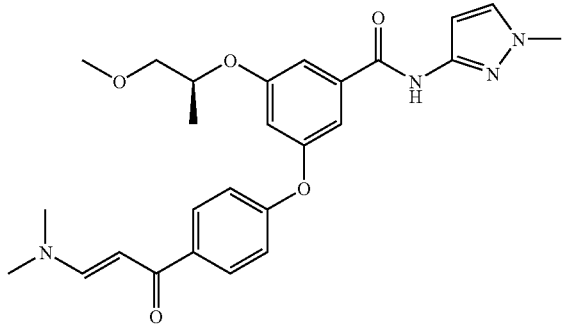

A mixture of 3-(4-acetylphenoxy)-5-[(1S)-2-methoxy-1-methylethoxy]-N-(1'-methyl-1H-pyrazol-3-yl)benzamide (812 mg, 1.92 mmol) and N,N-dimethylformamide dimethyl acetal (10.2 mL, 77 mmol) was heated to 100° C. in a 'Smith Creator' microwave for 140 mins. The volatiles were removed under reduced pressure and the resulting oil purified by chromatography on silica, eluting with 0-20% methanol in DCM, to give the desired product (765 mg).

m/z=479 (M+H)$^+$ 3-(4-Acetylphenoxy)-5-[(1S)-2-methoxy-1-methylethoxy]-N-(1-methyl-1H-pyrazol-3-yl)benzamide

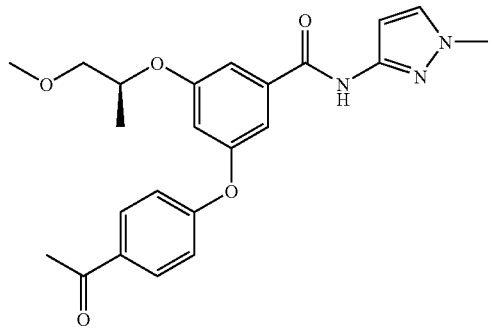

A mixture of 3-hydroxy-5-[(1S)-2-methoxy-(1-methylethyl)oxy]-N-(1-methyl-1H-pyrazol-3-yl)benzamide (400 mg, 1.31 mmol), PS-BEMP (2-tert-butylimino-2-diethylamino-1,3-dimethyl-perhydro-1,3,2-diaza-phosphorine, polymer-bound, loading 2.2 mmol/g) (894 mg, 1.97 mmol), potassium benzoate (210 mg, 1.31 mmol) and 4-fluoroacetophenone (0.160 mL, 1.31 mmol) in NMP (10 mL) was heated to 200° C. in a 'Smith Creator' microwave for 1 hour. The polymer supported base was filtered off and the resin washed with ethyl acetate (100 mL). The organic phase was partioned with water (100 mL) at which point brine had to be added to resolve the layers. The aqueous phase was washed twice with ethyl acetate (50 mL) and then discarded. The combined organic extracts were Washed with saturated aqueous lithium chloride solution (2×100 mL), 2M sodium hydroxide solution (2×100 mL), water (2×100 mL), brine (100 mL) and dried (MgSO$_4$). The volatiles were removed and the resulting oil purified by on silica, eluting with 0-100% ethyl acetate in iso-hexane, to give the desired product as a colourless foam (276 mg).

$^1$H NMR δ (CDCl$_3$): 1.28 (d, 3H), 2.58 (s, 3H), 3.40 (s, 3H), 3.52 (dd, 1H), 3.58 (dd, 1H), 3.78 (s, 3H), 4.56 (m, 1H), 6.80 (m, 2H), 6.98-7.08 (m, 3H), 7.24 (m, 2H), 7.96 (d, 2H), 8.58 (s, 1H); m/z 424 (M+H)$^+$

The preparation of 3-hydroxy-5-[(1S)-2-methoxy-(1-methylethyl)oxy]-N-(1-methyl-1H-pyrazol-3-yl)benzamide was described in Example 12.

EXAMPLE 33

2-Chloro-5-fluoro-4-(3-[(1S)-2-hydroxy-1-methylethoxy]-5-{[(1-methyl-1H-pyrazol-3-yl)amino]carbonyl}phenoxy)-N,N-dimethylbenzamide

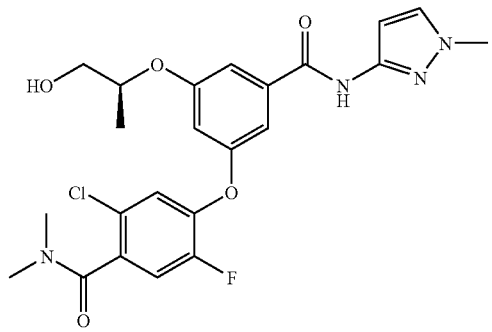

A suspension of 3-((1S)-2-{[tert-butyl(dimethyl)silyl]oxy}-1-methylethyloxy)-5-hydroxy-N-(1-methyl-1H-pyrazol-3-yl)benzamide (200 mg, 0.477 mmol), potassium carbonate (136 mg, 0.95 mmol) and 2-chloro-4,5-difluoro-N,N-dimethylbenzamide (106 mg, 0.45 mmol) in acetonitrile (3.5 mL) was heated in a microwave reactor at 160° C. for 2 hours. The reaction mixture was quenched with water and extracted with DCM (2×6 mL). The organic layer was dried (MgSO$_4$), filtered and concentrated in vacuo. The residue was then chromatographed by preparatory reverse phase HPLC using a

| Example | Structure | m/z | NMR |
|---|---|---|---|
| 33a | | 475 (M + H)$^+$, 473 (M − H)$^−$ | $^1$H NMR δ (d$_6$-DMSO): 1.22 (d, 3H), 2.88 (s, 3H), 2.98 (s, 3H), 3.44-3.59 (m, 2H), 3.77 (s, 3H), 4.56 (m, 1H), 4.83 (m, 1H), 6.54 (m, 1H), 6.83 (m, 1H), 7.17-7.26 (m, 2H), 7.42 (m, 1H), 7.52 (m, 1H), 7.58 (m, 1H), 10.83 (brs, 1H). | gradient of 5-95% acetonitrile in water (containing 0.2% TFA) on a Phenomenex Luna 10u C18 (2) 100A (150×21.2 mm) column to give the title compound (37 mg).

$^1$H NMR δ (d$_6$-DMSO): 1.22 (d, 3H), 2.76 (s, 3H), 2.83 (s, 3H), 3.44-3.58 (brm, 2H), 3.77 (s, 3H), 4.56 (m, 1H), 4.83 (t, 1H), 6.53 (m, 1H), 6.82 (m, 1H), 7.36-7.45 (m, 2H), 7.52-7.62 (m, 2H), 7.80 (m, 1H), 10.84 (brs, 1H). m/z 491, 493 (M+H)$^+$ 489, 49 (M−H)$^−$ The preparation of 3-((1S)-2-{[tert-butyl(dimethyl)silyl]oxy}-1-methylethyloxy)-5-hydroxy-N-(1-methyl-1H-pyrazol-3-yl)benzamide was described in Example 5.

The preparation of 2-chloro-4,5-difluoro-N,N-dimethylbenzamide is described below:

2-Chloro-4,5-difluoro-N,N-dimethylbenzamide

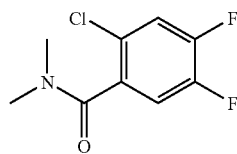

A solution of 2-chloro-4,5-difluorobenzoic acid (385 mg, 2.0 mmol) in DCM (5 mL) was treated with (1-chloro-2-methylprop-1-en-1-yl)dimethylamine (293 mg, 2.2 mmol) and stirred under argon for 1 hour. The mixture was then treated with triethylamine (0.56 mL, 4.0 mmol) and a 2M solution of dimethylamine in THF (1.2 mL, 2.4 mmol), and stirred for 18 hours. The mixture was diluted with DCM (5 mL) and 2M hydrochloric acid (4 mL) and separated. The organic layer was dried (MgSO$_4$), filtered and concentrated in vacuo to afford the title compound (425 mg). The residue was used without further purification.

$^1$H NMR δ (d$_6$-DMSO): 2.77 (s, 3H), 3.00 (s, 3H), 7.58 (m, 1H), 7.80 (m, 1H).

The following compound was prepared from 3-((1S)-2-{[tert-butyl(dimethyl)silyl]oxy}-1-methylethyloxy)-5-hydroxy-N-(1-methyl-1H-pyrazol-3-yl)benzamide and 2,4,5-trifluoro-N,N-dimethylbenzamide in an analogous fashion to that of Example 33.

2,4,5-Trifluoro-N,N-dimethylbenzamide was prepared in an analogous fashion to 2-chloro-4,5-difluoro-N,N-dimethylbenzamide.

| Structure | m/z | NMR |
|---|---|---|
| | | $^1$H NMR δ (d$_6$-DMSO): 2.83 (s, 3H), 2.97 (s, 3H), 7.53-7.68 (brm, 2H). |

EXAMPLE 34

3-[4-(Azetidin-1-ylcarbonyl)-2,5-difluorophenoxy]-5-[(1S)-2-hydroxy-1-methylethoxy]-N-(1-methyl-1H-pyrazol-3-yl)benzamide

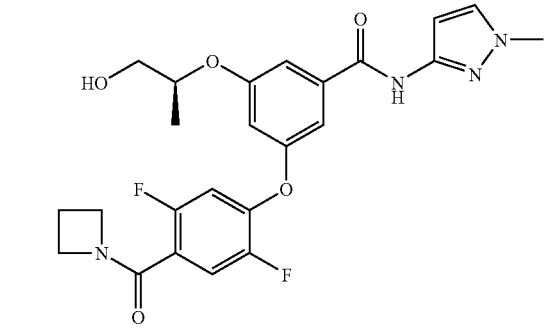

A solution of 2,4,5-trifluorobenzoic acid (123 mg, 0.7 mmol) in DCM (1.7 mL) was treated with (1-chloro-2-methylprop-1-en-1-yl)dimethylamine (103 mg, 0.77 mmol) and stirred under argon for 1 hour. The mixture was then treated with triethylamine (0.29 mL, 2.1 mmol) and azetidine hydrochloride (78 mg, 0.84 mmol), before being left to stir for 18 hours. The mixture was diluted with DCM (5 mL) and 2M hydrochloric acid (4 mL) and separated. The organic layer was dried (MgSO$_4$), filtered and concentrated in vacuo. The residue was treated with suspension of 3-hydroxy-5-{[(1S)-2-hydroxy-1-methylethyl]oxy}-N-(1-methyl-1H-pyrazol-3-yl)benzamide (200 mg, 0.477 mmol) and potassium carbonate (284 mg, 2.05 mmol) in acetonitrile (3.5 mL) was heated in a microwave reactor at 160° C. for 1.5 hours. The reaction mixture was filtered and concentrated in vacuo. The residue was then chromatographed on silica, eluting with 0-15% methanol in ethylacetate, to give the title compound (74 mg).

$^1$H NMR δ (d$_6$-DMSO): 1.23 (d, 3H), 2.18-2.30 (m, 2H), 3.44-3.58 (m, 2H), 3.77 (s, 3H), 3.98-4.11 (m, 4H), 4.57 (m, 1H), 4.83 (m, 1H), 6.54 (m, 1H), 6.84 (m, 1H), 7.19 (m, 2H), 7.43 (m, 1H), 7.53-7.58 (m, 2H), 10.83 (brs, 1H; m/z 487 (M+H)$^+$ The preparation of 3-hydroxy-5-{[(1S)-2-hydroxy-1-methylethyl]oxy}-N-(1-methyl-1H-pyrazol-3-yl)benzamide was described in Example 12.

The following compounds were made in an analogous fashion from 3-hydroxy-5-{[(1S)-2-hydroxy-1-methylethyl]oxy}-N-(1-methyl-1H-pyrazol-3-yl)benzamide and the appropriate benzoic acid.

EXAMPLE 35

3-[4-(Azetidin-1-ylcarbonyl)-2-fluorophenoxy]-5-[(1S)-2-hydroxy-1-methylethoxy]-N-1,3-thiazol-2-ylbenzamide

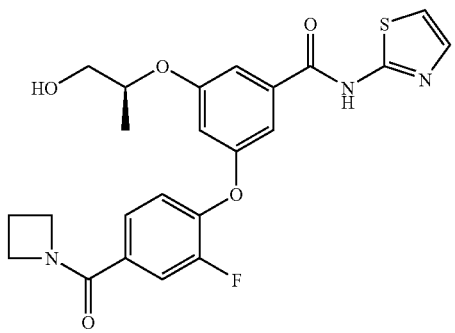

10% Hydrochloric acid (2 mL) was added to a solution of 3-[4-(azetidin-1-ylcarbonyl)-2-fluorophenoxy]-5-((1S)-2-{[tert-butyl(dimethyl)silyl]oxy}-1-methylethoxy)-NV-1,3-thiazol-2-ylbenzamide (585 mg, 1.0 mmol) in methanol (20

| Example | Structure | m/z | NMR |
|---|---|---|---|
| 34a | 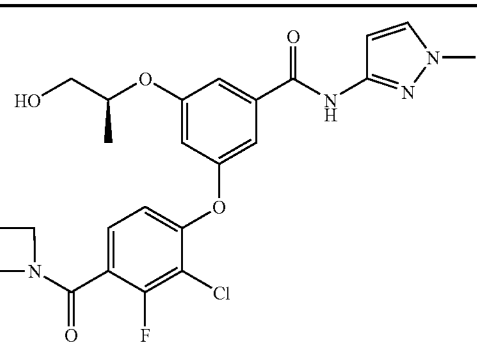 | 503, 505 (M + H)$^+$ 501, 503 (M − H)$^−$ | $^1$H NMR δ (d$_6$-DMSO): 1.23 (d, 3H), 2.19-2.29 (m, 2H), 3.44-3.58 (m, 2H), 3.77 (s, 3H), 4.02-4.09 (m, 4H), 4.56 (m, 1H), 4.84 (m, 1H), 6.54 (m, 1H), 6.86 (m, 1H), 6.94 (m, 1H), 7.21 (m, 1H), 7.47 (m, 2H), 7.58 (m, 1H), 10.82 (brs, 1H). |
| 34b | | 503, 505 (M + H)$^+$ 501, 503 (M − H)$^−$ | $^1$H NMR δ (d$_6$-DMSO): 1.22 (d, 3H), 2.18-2.28 (m, 2H), 3.44-3.57 (m, 2H), 3.76 (s, 3H), 3.94 (m, 2H), 4.04 (m, 2H), 4.56 (m, 1H), 4.83 (m, 1H), 6.54 (m, 1H), 6.82 (m, 1H), 7.18 (m, 1H), 7.35 (d, 1H), 7.42 (m, 1H), 7.58 (m, 2H), 10.83 (brs, 1H). | mL). The reaction was stirred at RT for 1 hour, saturated sodium bicarbonate solution added and the methanol evaporated. The aqueous residue was taken to pH 2 and extracted with ethyl acetate. The extracts were combined, washed with brine, dried (MgSO$_4$), filtered and evaporated in vacuo to give the crude product which was chromatographed on silica, eluting with 1% methanol in ethyl acetate, to give the desired compound (283 mg).

$^1$H NMR δ (CDCl$_3$): 1.3 (d, 3H), 2.4 (m, 2H), 3.75 (d, 2H), 4.2-4.4 (m, 4H), 4.6 (m, 1H), 6.75 (s, 1H), 7.0 (d, 1H), 7.1 (t, 1H), 7.2 (s, 1H), 7.3 (t, 1H), 7.35 (s, 1H), 7.4 (d, 1H), 7.5 (d, 1H). m/z 472 (M+H)$^+$

The preparation of 3-[4-(azetidin-1-ylcarbonyl)-2-fluorophenoxy]-5-((1S)-2-{[tert-butyl(dimethyl)silyl]oxy}-1-methylethoxy)-N-1,3-thiazol-2-ylbenzamide is described below:

3-[4-(Azetidin-1-ylcarbonyl)-2-fluorophenoxy]-5-((1S)-2-{[tert-butyl(dimethyl)silyl]oxy}-1-methylethoxy)-N-1,3-thiazol-2-ylbenzamide

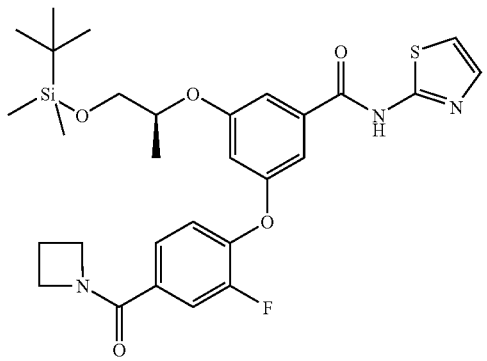

DIPEA (0.5 mL, 3.0 mmol) was added to a suspension of 3-[4-(azetidin-1-ylcarbonyl)-2-fluorophenoxy]-5-((1S)-2-{[tert-butyl(dimethyl)silyl]oxy}-1-methylethoxy)benzoic acid (503 mg, 1.0 mmol), HATU (495 mg, 1.3 mmol) and 2-amino-1,3 thiazole (300 mg, 3.0 mmol) in DMF (6 mL). The resulting mixture was stirred at RT for 16 hours, water (90 mL) was added and the mixture extracted with ethyl acetate. The extracts were combined, washed with brine, dried (MgSO$_4$), filtered and evaporated in vacuo to give the crude product which was chromatographed on silica, eluting with 75% ethyl acetate in isohexane, to give the desired compound (585 mg).

m/z 586 (M+H)$^+$.

The preparation of 3-[4-(azetidin-1-ylcarbonyl)-2-fluorophenoxy]-5-((1S)-2-{[tert-butyl(dimethyl)silyl]oxy}-1-methylethoxy)benzoic acid is described in Example 8.

EXAMPLE 36

3-[4-(Azetidin-1-ylcarbonyl)phenoxy]-5-[(1S)-2-hydroxy-1-methylethoxy]-N-1,3-thiazol-2-ylbenzamide

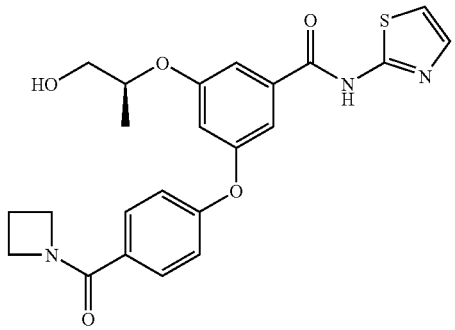

10% Hydrochloric acid (1 mL) was added to a solution of 3-[4-(azetidin-1-ylcarbonyl)phenoxy]-5-((1S)-2-{[tert-butyl(dimethyl)silyl]oxy}-1-methylethoxy)-N-1,3-thiazol-2-ylbenzamide (284 mg, 0.5 mmol) in methanol (10 mL). The reaction was stirred at RT for 1 hour, saturated sodium bicarbonate solution added and the methanol evaporated. The aqueous residue was taken to pH 2 and extracted with ethyl acetate. The extracts were combined, washed with brine, dried (MgSO$_4$), filtered, and evaporated in vacuo to give the crude product which was chromatographed on silica, eluting with 1% methanol in ethyl acetate, to give the desired compound (113 mg).

$^1$H NMR δ (CDCl$_3$): 1.3 (d, 3H), 2.4 (m, 2H), 3.75 (d, 2H), 4.2-4.4 (m, 4H), 4.6 (m, 1H), 6.8 (s, 1H), 7.0 (m, 3H), 7.2 (s, 1H), 7.3 (d, 1H), 7.4 (s, 1H), 7.65 (d, 2H). m/z 454 (M+H)$^+$.

The preparation of 3-[4-(azetidin-1-ylcarbonyl)phenoxy]-5-((1S)-2-{[tert-butyl(dimethyl)silyl]oxy}-1-methylethoxy)-N-1,3-thiazol-2-ylbenzamide is described below:

3-[4-(Azetidin-1-ylcarbonyl)phenoxy]-5-((1S)-2-{[tert-butyl(dimethyl)silyl]oxy}-1-methylethoxy)-N-1,3-thiazol-2-ylbenzamide

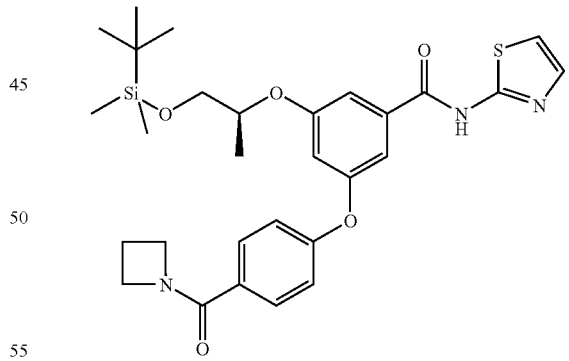

DIPEA (0.25 mL, 1.5 mmol) was added to a suspension of 3-[4-(azetidin-1-ylcarbonyl)phenoxy]-5-((1S)-2-{[tert-butyl(dimethyl)silyl]oxy}-1-methylethoxy)benzoic acid (243 mg, 0.5 mmol), HATU (248 mg, 0.65 mmol) and 2-amino-1,3 thiazole (150 mg, 1.5 mmol) in DMF (3 mL). The resulting mixture was stirred at RT for 16 hours, water (45 mL) was added and the mixture extracted with ethyl acetate. The extracts were combined, washed with brine, dried (MgSO$_4$), filtered and evaporated in vacuo to give the crude product which was chromatographed on silica, eluting with 75% ethyl acetate in isohexane, to give the desired compound (284 mg).

m/z 568 (M+H)$^+$

The preparation of 3-[4-(azetidin-1-ylcarbonyl)phenoxy]-5-((1S)-2-{[tert-butyl(dimethyl)silyl]oxy}-1-methylethoxy)benzoic acid is described in Example 20.

EXAMPLE 37

3-[4-(Azetidin-1-ylcarbonyl)-2-chlorophenoxy]-5-[(1S)-2-hydroxy-1-methylethoxy]-N-pyrazin-2-ylbenzamide

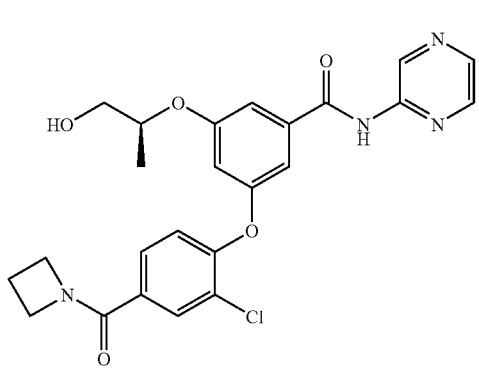

A mixture of 3-[4-(azetidin-1-ylcarbonyl)-2-chlorophenoxy]-5-((1S)-2-{[tert-butyl(dimethyl)silyl]oxy}-1-methylethoxy)-N-pyrazin-2-ylbenzamide (37 mg, 0.062 mmol) in methanol (0.5 mL) and 3.5M hydrochloric acid (0.018 mL) was stirred for 30 mins at RT. The solution was taken to pH 6 with saturated aqueous sodium bicarbonate solution and the volatiles were removed in vacuo. The residue was taken into ethyl acetate (10 mL) and washed with water (2 mL), brine (2 mL), dried ($MgSO_4$), filtered and the solvents removed in vacuo to give the crude product which was chromatographed on silica, eluting with 0-10% methanol in ethyl acetate, to give the desired compound as a white foam (21 mg).

$^1$H NMR δ ($CDCl_3$): 1.3 (d, 3H), 2.05 (b, 1H), 2.4 (m, 2H), 3.75 (s, 2H), 4.2-4.5 (bd, 4H), 4.55 (m, 1H), 6.8 (s, 1H), 7.0 (d, 1H), 7.1 (s, 1H), 7.25 (m, 1H), 7.55 (d, 1H), 7.8 (s, 1H), 8.3 (s, 1H), 8.4 (s, 1H), 8.5 (b, 1H), 9.60 (s, 1H). m/z 483 $(M+H)^+$

The following compound was synthesised in an analogous fashion from 3-[4-(azetidin-1-ylcarbonyl)phenoxy]-5-((1S)-2-{[tert-butyl(dimethyl)silyl]oxy}-1-methylethoxy)-N-pyrazin-2-ylbenzamide:

The preparation of 3-[4-(azetidin-1-ylcarbonyl)-2-chlorophenoxy]-5-((1S)-2-{[tert-butyl(dimethyl)silyl]oxy}-1-methylethoxy)-N-pyrazin-2-ylbenzamide is described below:

3-[4-(Azetidin-1-ylcarbonyl)-2-chlorophenoxy]-5-((1S)-2-{[tert-butyl(dimethyl)silyl]oxy}-1-methylethoxy)-N-pyrazin-2-ylbenzamide

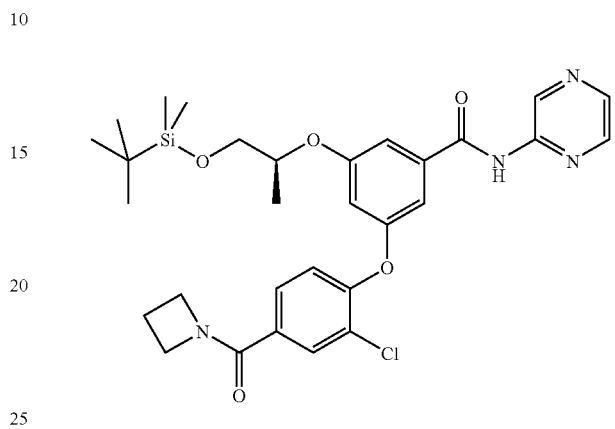

1-Chloro-N,N,2-trimethyl-1-propenylamine (0.073 mL, 0.55 mmol) was added to a solution of 3-[4-(azetidin-1-ylcarbonyl)-2-chlorophenoxy]-5-((1S)-2-{[tert-butyl(dimethyl)silyl]oxy}-1-methylethoxy)benzoic acid (260 mg, 0.5 mmol) in DCM (10 mL) and stirred at RT for 1 hour. 2-Amino-5-methylpyrazine (95 mg, 1 mmol) and pyridine (0.081 mL, 1.0 mmol) were added and the reaction stirred for a further 30 mins. The solvent was removed in vacuo. Water (10 mL) was added and the mixture extracted with ethyl acetate (2×10 mL). The extracts were combined and washed with 1N citric acid, water (10 mL) and brine (10 mL), dried ($MgSO_4$), filtered, and evaporated in vacuo to give the crude product which was chromatographed on silica, eluting with a gradient of 50-100% ethyl acetate in isohexane, to give the desired compound (37 mg).

m/z 597 $(M+H)^+$

3-[4-(Azetidin-1-ylcarbonyl)phenoxy]-5-((1S)-2-{[tert-butyl(dimethyl)silyl]oxy}-1-methylethoxy)-N-pyrazin-2-ylbenzamide was prepared in an analogous fashion from 3-[4-(azetidin-1-ylcarbonyl)phenoxy]-5-((1S)-2-{[tert-butyl(dimethyl)silyl]oxy}-1-methylethoxy)benzoic acid:

| Example | Structure | m/z | NMR |
|---|---|---|---|
| 37a | (structure shown) | 449 $(M + H)^+$ | $^1$H NMR δ ($CDCl_3$): 1.3 (d, 3H), 2.35 (quin, 2H), 3.75 (m, 2H), 4.20-4.40 (bd, 4H), 4.6 (m, 1H), 6.8 (s, 1H), 7.05 (d, 2H), 7.15 (s, 1H), 7.25 (s, 1H) 7.5 (d, 2H), 8.05 (s, 1H), 8.4 (s, 1H), 9.55 (s, 1H). |

| Structure | m/z | NMR |
|---|---|---|
| 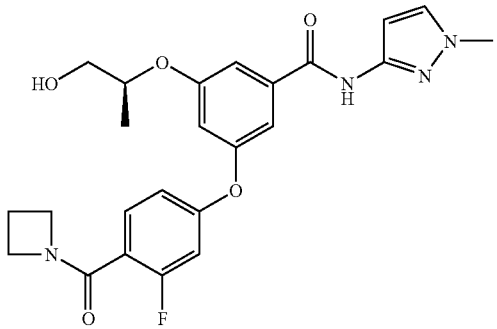 | 563 (M−H)− | |

The preparation of 3-[4-(azetidin-1-ylcarbonyl)-2-chlorophenoxy]-5-((1S)-2-{[tert-butyl(dimethyl)silyl]oxy}-1-methylethoxy)benzoic acid is described in Example 8a.

The preparation of 3-[4-(azetidin-1-ylcarbonyl)phenoxy]-5-((1S)-2-{[tert-butyl(dimethyl)silyl]oxy}-1-methylethoxy) benzoic acid is described in Example 20.

EXAMPLE 38

3-[4-(Azetidin-1-ylcarbonyl)-3-fluorophenoxy]-5-[(1S)-2-hydroxy-1-methylethoxy]-N-(1-methyl-1H-pyrazol-3-yl)benzamide 3-[4-(Azetidin-1-ylcarbonyl)-2-chloro-3-fluorophenoxy]-5-[(1S)-2-hydroxy-1-methylethoxy]-N-(1-methyl-1H-pyrazol-3-yl)benzamide (162 mg; 0.322 mmol) was dissolved in methanol (10 mL). Triethylamine (97 mg, 0.967 mmol) was added and the flask evacuated and purged with nitrogen (3 times). 10% Palladium on carbon (25 mg) was added and the flask further evacuated and finally purged with hydrogen gas. The reaction mixture was stirred at ambient temperature for 7 days until completion. The reaction mixture was evacuated and purged with nitrogen (3 times). The catalyst was filtered off, the filtrate concentrated in vacuo and purified by preparatory reverse phase HPLC using a gradient of 5-95% acetonitrile in water (containing 0.2% TFA) on a Phenomenex Luna 10u C18 (2) 100A column to give the title compound (60 mg).

$^1$H NMR δ (CDCl$_3$): 1.31 (d, 3H), 2.32 (m, 2H), 3.78 (m, 3H), 3.96 (s, 3H), 4.16 (t, 2H), 4.72 (t, 2H), 4.69 (m, 1H), 6.22 (d, 1H), 6.30 (s, 1H), 6.35 (d, 1H), 6.46 (s, 1H), 7.28 (s, 1H), 7.36 (s, 1H), 7.41 (s, 1H), 7.53 (t, 1H), 10.16 (br s, 1H). m/z 469 (M+H)$^+$

The preparation of 3-[4-(azetidin-1-ylcarbonyl)-2-chloro-3-fluorophenoxy]-5-[(1S)-2-hydroxy-1-methylethoxy]-N-(1-methyl-1H-pyrazol-3-yl)benzamide was described in Example 34a.

EXAMPLE 39

3-[4-(2-Azabicyclo[2.1.1]hex-2-ylcarbonyl)-2-fluorophenoxy]-5-[(1S)-2-hydroxy-1-methylethoxy]-N-(1-methyl-1H-pyrazol-3-yl)benzamide

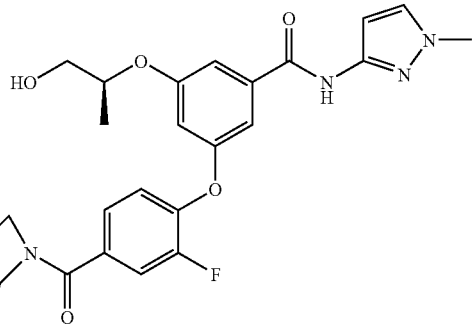

DIPEA (0.80 mL, 4.32 mmol) was added to a suspension of 3-fluoro-4-(3-[(1S)-2-hydroxy-1-methylethoxy]-5-{[(1-methyl-1H-pyrazol-3-yl)amino]carbonyl}phenoxy)benzoic acid (230 mg, 0.54 mmol), HATU (430 mg, 1.29 mmol) and 2-azabicyclo[2.1.1]hexane hydrochloride salt (96 mg, 0.81 mmol) in DMF (4 mL) and the mixture stirred at RT for 24 hours. Ethyl acetate was added and washed with water (3×30 mL), brine (30 mL), dried (MgSO$_4$), and evaporated to a residue which was chromatographed on silica, eluting with a gradient of 0-10% methanol in DCM, to give the desired compound (51 mg).

$^1$H NMR δ (CDCl$_3$): 1.21 (d, 3H), 1.40 (m, 1H), 1.51 (brm, 1H), 1.92 (m, 2H), 2.15 (t, 1H), 2.90 (m, 1H), 3.42 (m, 1H), 3.55 (m, 1H), 3.69 (m, 2H), 3.71 (s, 3H), 4.37 (m, 1H), 4.45 (m, 1H), 6.70 (m, 1H), 6.73 (s, 1H), 6.98 (m, 1H), 7.05 (t, 1H), 7.12 (s, 1H), 7.27 (m, 2H), 7.30-7.50 (brm, 1H), 8.61 (brs, 1H); m/z 495 (M+H)$^+$ The preparation of 3-fluoro-4-(3-[(1S)-2-hydroxy-1-methylethoxy]-5-{[(1-methyl-1H-pyrazol-3-yl)amino] carbonyl}phenoxy)benzoic acid was described in Example 23.

The preparation of 2-azabicyclo[2.1.1]hexane hydrochloride salt is described below:

2-Azabicyclo[2.1.1]hexane hydrochloride salt

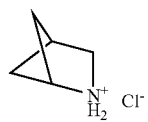

A mixture of ethyl 2-azabicyclo[2.1.1]hexane-2-carboxylate (0.35 g, 2.25 mmol) and concentrated hydrochloric acid (10 mL) was refluxed for 4 hours, cooled and the volatiles removed in vacuo. Toluene was added then removed in vacuo and the resultant product dried under reduced pressure to give the desired compound which was used without further purification (0.24 g).

Ethyl 2-azabicyclo[2.1.1]hexane-2-carboxylate was prepared in accordance with literature precedence (J. Org. chem. 1998, 63, 8558) and the spectroscopic data was in agreement with literature values.

EXAMPLE 40

3-[4-(Azetidin-1-ylcarbonyl)phenoxy]-N-(1,5-dimethyl-1H-pyrazol-3-yl)-5-[(1S)-2-hydroxy-1-methylethoxy]benzamide

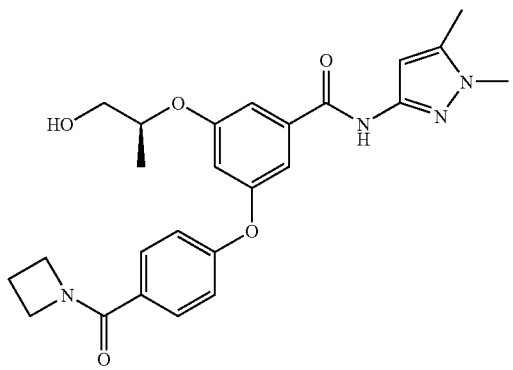

3-[4-(Azetidin-1-ylcarbonyl)phenoxy]-5-((1S)-2-{[tert-butyl(dimethyl)silyl]oxy}-1-methylethoxy)-N-(1,5-dimethyl-1H-pyrazol-3-yl)benzamide

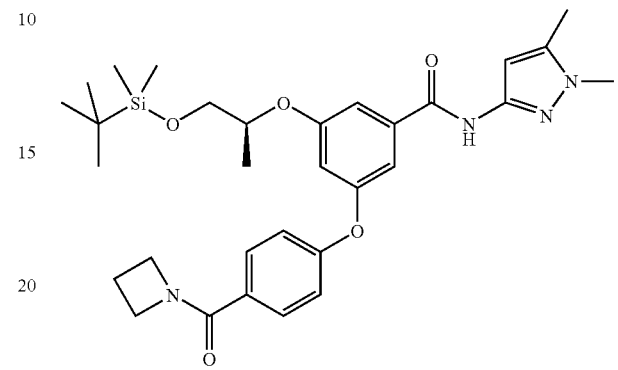

3.5M Hydrochloric acid (1.0 mL) was added to a solution of 3-[4-(azetidin-1-ylcarbonyl)phenoxy]-5-((1S)-2-{[tert-butyl(dimethyl)silyl]oxy}-1-methylethoxy)-N-(1,5-dimethyl-1H-pyrazol-3-yl)benzamide (232 mg, 0.4 mmol) in methanol (10 mL). The reaction mixture was stirred for 45 minutes then saturated sodium bicarbonate added until the pH was adjusted to 7. The mixture was reduced in vacuo. The residue was dissolved in ethyl acetate (50 mL), washed water (25 mL) and brine (25 mL). Dried (MgSO$_4$) and reduced to a white foam. The crude product was purified by chromatography on silica, eluting with 0-10% methanol in ethyl acetate, to obtain the required product as a white foam (123 mg).

$^1$H NMR δ (CDCl$_3$): 1.39 (d, 3H), 2.21 (br s, 1H), 2.27 (s, 3H), 2.34 (m, 2H), 3.64 (s, 3H), 3.73 (br s, 2H), 4.24 (br s, 2H), 4.34 (br s, 2H), 4.52 (m, 1H), 6.56 (s, 1H), 6.75 (s, 1H), 7.01 (d, 2H), 7.08 (d, 1H), 7.21 (s, 1H), 7.65 (d, 2H), 8.49 (s, 1H). m/z 465 (M+H)$^+$

The following example was prepared in an analogous fashion from 3-[4-(azetidin-1-ylcarbonyl)-2-fluorophenoxy]-5-((1S)-2-{[tert-butyl(dimethyl)silyl]oxy}-1-methylethoxy)-N-(1,5-dimethyl-1H-pyrazol-3-yl)benzamide DIPEA (517 mg, 3.00 mmol) was added to a solution of 3-[4-(azetidin-1-ylcarbonyl)phenoxy]-5-((1S)-2-{[tert-butyl (dimethyl)silyl]oxy}-1-methylethoxy)benzoic acid (364 mg, 0.75 mmol), 3-amino-1,5-dimethylpyrazole (109 mg, 0.90 mmol) and HATU (599 mg, 1.58 mmol) in DMF (3.0 mL) and the mixture stirred for 24 hours. Water (25 mL) was added and the mixture extracted with ethyl acetate (2×25 mL) dried (MgSO$_4$) and reduced to a brown oil. The crude product was purified by chromatography on silica, eluting with ethyl acetate, to give the required product as a clear oil. (232 mg).

m/z 480 (M+H)$^+$

3-[4-(Azetidin-1-ylcarbonyl)-2-fluorophenoxy]-5-((1S)-2-{[tert-butyl(dimethyl)silyl]oxy}-1-methylethoxy)-N-(1,5-dimethyl-1H-pyrazol-3-yl)benzamide used in the preparation of Example 40a was prepared in an analogous fashion from 3-[4-(azetidin-1-ylcarbonyl)-2-fluorophenoxy]-5-((1S)-2-{[tert-butyl(dimethyl)silyl]oxy}-1-methylethoxy) benzoic acid.

| Example | Structure | m/z | NMR |
|---|---|---|---|
| 40a | (structure shown) | 483 (M + H)$^+$ | $^1$H NMR δ (CDCl$_3$): 1.39 (d, 3H), 2.17 (br s, 1H), 2.26 (s, 3H), 2.49 (m, 2H), 3.63 (s, 3H), 3.73 (br s, 2H), 4.23 (br s, 2H), 4.35 (br s, 2H), 4.50 (m, 1H), 6.56 (s, 1H), 6.71 (s, 1H), 7.02 (m, 1H), 7.07 (d, 1H), 7.19 (s, 1H), 7.40 (d, 1H), 7.51 (s, 1H), 8.47 (s, 1H) |

| Structure | m/z | NMR |
|---|---|---|
| 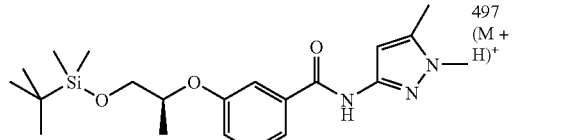 | 497 (M+H)+ | |

The preparation of 3-[4-(azetidin-1-ylcarbonyl)phenoxy]-5-((1S)-2-{[tert-butyl(dimethyl)silyl]oxy}-1-methylethoxy)benzoic acid was described in Example 20.

The preparation of 3-[4-(azetidin-1-ylcarbonyl)-2-fluorophenoxy]-5-((1S)-2-{[tert-butyl(dimethyl)silyl]oxy}-1-methylethoxy)benzoic acid was described in Example 8.

3-Amino-1,5-dimethylpyrazole is a compound whose preparation is described in the literature (J. Het. Chem. 1982, 19(6), 1267).

Biological

Tests:

The biological effects of the compounds of formula (I) may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm (Matschinsky et al 1993). Activation of GLK by compounds can be assessed using this assay in the presence or absence of GLKRP as described in Brocklehurst et al (Diabetes 2004, 53, 535-541).

Production of Recombinant GLK and GLKRP:

Human GLK and GLKRP cDNA was obtained by PCR from human pancreatic and hepatic mRNA respectively, using established techniques described in Sambrook J, Fritsch E F & Maniatis T, 1989. PCR primers were designed according to the GLK and GLKRP cDNA sequences shown in Tanizawa et al 1991 and Bonthron, D. T. et al 1994 (later corrected in Warner, J. P. 1995).

Cloning in Bluescript II Vectors

GLK and GLKRP cDNA was cloned in E. coli using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

E. Coli transformations were generally carried out by electroporation. 400 mL cultures of strains DH5a or BL21 (DE3) were grown in L-broth to an OD 600 of 0.5 and harvested by centrifugation at 2,000 g. The cells were washed twice in ice-cold deionised water, resuspended in 1 mL 10% glycerol and stored in aliquots at −70° C. Ligation mixes were desalted using Millipore V Series™ membranes (0.0025 mm) pore size). 40 mL of cells were incubated with 1 mL of ligation mix or plasmid DNA on ice for, 10 minutes in 0.2 cm electroporation cuvettes, and then pulsed using a Gene Pulser™ apparatus (BioRad) at 0.5 kVcm⁻¹, 250 mF. Transformants were selected on L-agar supplemented with tetracycline at 10 mg/mL or ampicillin at 100 mg/mL.

Expression

GLK was expressed from the vector pTB375NBSE in E. coli BL21 cells, producing a recombinant protein containing a 6-His tag immediately adjacent to the N-terminal methionine. Alternatively, another suitable vector is pET21 (+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in E. coli BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

(2) Oral Glucose Tolerance Test (OGTT)

Oral glucose tolerance tests were done on conscious Zucker obese fa/fa rats (age 12-13 weeks or older) fed a high fat diet (45% kcal fat) for at least two weeks prior to experimentation. The animals were fasted for 2 hours before use for experiments. A test compound or a vehicle was given orally 120 minutes before oral administration of a glucose solution at a dose of 2 g/kg body weight. Blood glucose levels were measured using a Accucheck glucometer from tail bled samples taken at different time points before and after administration of glucose (time course of 60 minutes). A time curve of the blood glucose levels was generated and the area-under-the-curve (AUC) for 120 minutes was calculated (the time of glucose administration being time zero). Percent reduction in glucose excursion was determined using the AUC in the vehicle-control group as zero percent reduction.

Example 3a

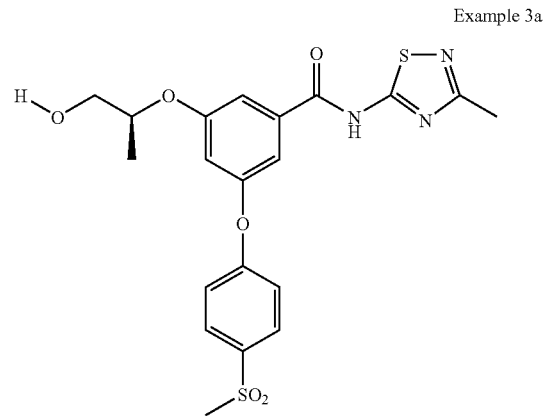

Example II107

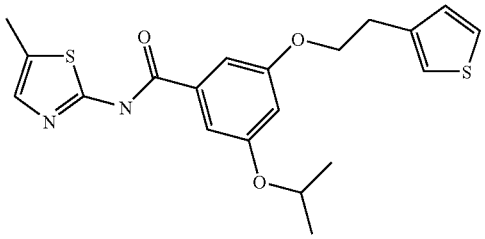

Compounds of the invention generally activate glucokinase with an $EC_{50}$ of less than about 500 nM. For example, Example 3a has an $EC_{50}$ of 50 nM.

Example 3a and Example II107 in WO 03/015774 have broadly similar $EC_{50}$ values. However Example 3a has superior oral exposure and exhibits 17% OGTT activity at 3 mg/kg whereas Example II107 in WO 03/015774 is not active at 10 mg/kg.

REFERENCES

1 Printz, R. L., Magnuson, M. A. and Granner, D. K. (1993) Annual Review of Nutrition 13, 463-96
2 DeFronzo, R. A. (1988) Diabetes 37, 667-87
3 Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702
4 Bell, G. I., Pilkis, S. J., Weber, I. T. and Polonsky, K. S. (1996) Annual Review of Physiology 58, 171-86
5 Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61
6 Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6
6a Gloyn, A. L., Noordam, K., Willemsen, M. A. A. P., Ellard, S., Lam, W. W. K., Campbell, I. W., Midgley, P., Shiota, C., Buettger, C., Magnuson, M. A., Matschinsky, F. M., and Hattersley, A. T.; Diabetes 52: 2433-2440
7 Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (11998) New England Journal of Medicine 338, 226-30
8 Caro, J. F., Triester, S., Patel, V. K., Tapscott, E. B., Frazier, N. L. and Dohm, G. L. (1995) Hormone & Metabolic Research 27, 19-22
9 Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95
10 Shiota, M., Postic, C., Fujimoto, Y., Jetton, T. L., Dixon, K., Pan, D., Grimsby, J., Grippo, J. F., Magnuson, M. A. and Cherrington, A. D. (2001) Diabetes 50, 622-9
11 Ferre, T., Pujol, A., Riu, E., Bosch, F. and Valera, A. (1996) Proceedings of the National Academy of Sciences of the United States of America 93, 7225-30
12 Seoane, J., Barbera, A., Telemaque-Potts, S., Newgard, C. B. and Guinovart, J., J. (1999) Journal of Biological Chemistry 274, 31833-8
13 Moore, M. C., Davis, S, N., Mann, S. L. and Cherrington, A. D. (2001) Diabetes Care 24, 1882-7
14 Alvarez, E., Roncero, I., Chowen, J. A., Vazquez, P. and Blazquez, E. (2002) Journal of Neurochemistry 80, 45-53
15 Lynch, R. M., Tompkins, L. S., Brooks, H. L., Dunn-Meynell, A. A. and Levin, B. E. (2000) Diabetes 49, 693-700
16 Roncero, I., Alvarez, E., Vazquez, P. and Blazquez, E. (2000) Journal of Neurochemistry 74, 1848-57
17 Yang, X. J., Kow, L. M., Funabashi, T. and Mobbs, C. V. (1999) Diabetes 48, 1763-1772
18 Schuit, F. C., Huypens, P., Heimberg, H. and Pipeleers, D. G. (2001) Diabetes 50, 1-11
19 Levin, B. E. (2001) International Journal of Obesity 25, supplement 5, S68-S72.
20 Alvarez, E., Roncero, I., Chowen, J. A., Thorens, B. and Blazquez, E. (1996) Journal of Neurochemistry 66, 920-7
21 Mobbs, C. V., Kow, L. M. and Yang, X. J. (2001) American Journal of Physiology-Endocrinology & Metabolism 281, E649-54
22 Levin, B. E., Dunn-Meynell, A. A. and Routh, V. H. (1999) American Journal of Physiology 276, R1223-31
23 Spanswick, D., Smith, M. A., Groppi, V. E., Logan, S. D. and Ashford, M. L. (1997) Nature 390, 521-5
24 Spanswick, D., Smith, M. A., Mirshamsi, S., Routh, V. H. and Ashford, M. L. (2000) Nature Neuroscience 3, 757-8
25 Levin, B. E. and Dunn-Meynell, A. A. (1997) Brain Research 776, 146-53
26 Levin, B. E., Govek, E. K. and Dunn-Meynell, A. A. (1998) Brain Research 808, 317-9
27 Levin, B. E., Brown, K. L. and Dunn-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20
32 Jetton T. L., Liang Y., Pettepher C. C., Zimmerman E. C., Cox F. G., Horvath K., Matschinsky F. M., and Magnuson M. A., J. Biol. Chem., February 1994; 269: 3641-3654.
33 Reimann F. and Gribble F. M., Diabetes 2002 51: 2757-2763
34 Cheung A. T., Dayanandan B., Lewis J. T., Korbutt G. S., Rajotte R. V., Bryer-Ash M., Boylan M. O., Wolfe M. M., Kieffer T. J., Science, Vol 290, Issue 5498, 1959-1962, 8 Dec. 2000

The invention claimed is:
1. The compound 3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide or a salt thereof.
2. A pharmaceutical composition comprising the compound of claim 1, or a salt thereof, together with a pharmaceutically acceptable diluent or carrier.
3. A process for the preparation of a compound of claim 1 or a salt thereof comprising reacting 3-{[4-(Azetidin-1-ylcarbonyl)-2-chlorophenyl]oxy}-5-{[(1S)-2-hydroxy-1-methylethyl]oxy}-N-(1-methyl-1H-pyrazol-3-yl)benzamide with hydrogen in the presence of 10% palladium on carbon to form 3-{[4-(azetidin-1-ylcarbonyl)phenyl]oxy}-5-{[(1S)-2-hydroxy-1-methylethyl]oxy}-N-(1-methyl-1H-pyrazol-3-yl)benzamide, and thereafter optionally forming a salt thereof.

* * * * *